(12) United States Patent
Slade et al.

(10) Patent No.: US 7,678,823 B2
(45) Date of Patent: Mar. 16, 2010

(54) COMPOUNDS FOR ALZHEIMER'S DISEASE

(75) Inventors: Rachel Slade, Salt Lake City, UT (US); Yevgeniya Klimova, Sandy, UT (US); Robert J. Halter, Salt Lake City, UT (US); Ashantai J. Yungai, Salt Lake City, UT (US); Warren S. Weiner, Salt Lake City, UT (US); Ruth J. Walton, Bountiful, UT (US); Jon Adam Willardsen, Sandy, UT (US); Mark B. Anderson, Salt Lake City, UT (US); Kenton Zavitz, Salt Lake City, UT (US)

(73) Assignee: Myriad Pharmaceticals, Inc., Salt Lake City, UT (US)

( * ) Notice: Subject to any disclaimer, the term of this patent is extended or adjusted under 35 U.S.C. 154(b) by 0 days.

(21) Appl. No.: 11/696,526

(22) Filed: Apr. 4, 2007

(65) Prior Publication Data

US 2008/0249135 A1    Oct. 9, 2008

Related U.S. Application Data

(63) Continuation of application No. PCT/US2005/035747, filed on Oct. 4, 2005, now abandoned.

(60) Provisional application No. 60/615,914, filed on Oct. 4, 2004, provisional application No. 60/616,162, filed on Oct. 4, 2004, provisional application No. 60/660,479, filed on Mar. 9, 2005, provisional application No. 60/660,278, filed on Mar. 10, 2005.

(51) Int. Cl.
  *A61K 31/416* (2006.01)
  *C07D 209/04* (2006.01)
(52) U.S. Cl. .................................... 514/412; 548/516
(58) Field of Classification Search ............... 514/412; 548/516
  See application file for complete search history.

(56) References Cited

U.S. PATENT DOCUMENTS

| 3,904,761 A | * | 9/1975 | Novick et al. ............... 514/411 |
| 6,790,848 B2 | | 9/2004 | Briggs et al. |
| 7,057,052 B2 | | 6/2006 | Pirrung et al. |

FOREIGN PATENT DOCUMENTS

| EP | 1 224 932 | 7/2002 |
| EP | 1 275 646 | 1/2003 |
| WO | WO 98/27972 | 7/1998 |

* cited by examiner

*Primary Examiner*—Yong Chu

(57) ABSTRACT

The invention provides novel compounds useful for the treatment of neurodegenerative disorders including Alzheimer's disease and dementia. The compounds have a substituents chosen from -L-C(=O)OH, -L-CH=CHC(=O)OH, -L-C(=O)$NH_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$$NH_2$, -L-S(=O)$_2$N($C_{1-3}$ alkyl)$_2$, -L-S(=O)$_2$NH($C_{1-3}$ alkyl), -L-C(=O)NHOH, -L-C(=O)$CH_2$$NH_2$, -L-C(=O)$CH_2$OH, -L-C(=O)$CH_2$SH, -L-C(=O)NHCN, -L-NHC(=O)$OR_o$, -L-C(=O)$NHR_o$, -L-NH(C=O)$NHR_o$, -L-C(=O)N($R_o$)$_2$, -L-NH(C=O)N($R_o$)$_2$, -L-sulfo, -L-(2,6 difluorophenol), -L-phosphono, and -L-tetrazolyl, where L is a linker.

12 Claims, No Drawings

COMPOUNDS FOR ALZHEIMER'S DISEASE

CROSS-REFERENCE TO RELATED APPLICATIONS

This is a continuation of International Application PCT/US2005/035747 filed Oct. 4, 2005, now abandoned; which claims priority to U.S. Provisional Application Ser. Nos. 60/615,914 filed on Oct. 4, 2004; 60/616,162 filed on Oct. 4, 2004; 60/660,479 filed Mar. 9, 2005; and 60/660,278 filed on Mar. 10, 2005, each of which are incorporated herein by reference in their entireties.

TECHNICAL FIELD OF THE INVENTION

The invention provides a method for the therapeutic treatment of neurodegenerative disorders. The invention further provides a method for prophylaxis against neurodegenerative disorders. The invention further provides pharmaceutical composition for use in the methods of the invention. The invention has utility for treating and preventing neurodegenerative disorders such as Alzheimer's disease, dementia, and mild cognitive impairment.

BACKGROUND OF THE INVENTION

Dementia is a brain disorder that seriously affects a person's ability to carry out normal daily activities. Among older people, Alzheimer's disease (AD) is the most common form of dementia and involves parts of the brain that control thought, memory, and language. Despite intensive research throughout the world, the causes of AD are still unknown and there is no cure. AD most commonly begins after the age of 60 with the risk increasing with age. Younger people can also get AD, but it is much less common. It is estimated that 3 percent of men and women ages 65 to 74 have AD. Almost half of those ages 85 and older may have the disease. AD is not a normal part of aging. Alzheimer's disease is a complex disease that can be caused by genetic and environmental factors. In the United States alone, four million adults suffer from Alzheimer's disease (AD). Not only does Alzheimer's disease significantly impact the lives of countless families today, it threatens to become even more of a problem as the baby boom generation matures. The economic burden of AD in the United States is estimated to cost over $100 billion a year and the average lifetime cost per patient is estimated to be $174,000. Unfortunately, there is no cure available for AD.

In 1906, Dr. Alois Alzheimer, noticed changes in the brain tissue of a woman who had died of an unusual mental illness. In her brain tissue, he found abnormal clumps (now known as amyloid plaques) and tangled bundles of fibers (now known as neurofibrillary tangles) which, today, are considered the pathological hallmarks of AD. Other brain changes in people with AD have been discovered. For example, with AD, there is a loss of nerve cells in areas of the brain that are vital to memory and other mental abilities. Scientists have also found that there are lower levels of chemicals in the brain that carry complex messages back and forth between nerve cells. AD may disrupt normal thinking and memory by blocking these messages between nerve cells.

Plaques and tangles are found in the same brain regions that are affected by neuronal and synaptic loss. Neuronal and synaptic loss is universally recognized as the primary cause in decline of cognitive function. The number of tangles is more highly correlated with the cognitive decline than amyloid load in patients with AD (Albert *Proc. Natl. Acad. Sci. U.S.A.* 93:13547-13551 (1996)). The cellular, biochemical, and molecular events responsible for neuronal and synaptic loss in AD are not known. A number of studies have demonstrated that amyloid can be directly toxic to neurons (Iversen et al. *Biochem. J.* 311:1-16 (1995); Weiss et al. *J. Neurochem.* 62:372-375 (1994); Lorenzo et al. *Ann. N.Y. Acad. Sci.* 777: 89-95 (1996); Storey et al. *Neuropathol. Appl. Neurobiol.* 2:81-97 (1999), resulting in behavioral impairment. The toxicity of amyloid or tangles is potentially aggravated by activation of the complement cascade (Rogers et al. *Proc. Natl. Acad. Sci. U.S.A.* 21:10016-10020 (1992); Rozemuller et al. *Res. Immunol.* 6:646-9 (1992); Rogers et al. *Res. Immunol.* 6:624-30 (1992); Webster et al. *J. Neurochem.* 69(1):388-98 (1997)). This suggests involvement of an inflammatory process in AD and neuronal death seen in AD (Fagarasan et al. *Brain Res.* 723 (1-2):231-4. (1996); Kalaria et al. *Neurodegeneration* 5(4):497-503 (1996); Kalaria et al. *Neurobiol Aging.* 17(5):687-93 (1996); Farlow *Am. J. Health Syst. Pharm.* 55 Suppl. 2:S5-10 (1998).

Evidence that amyloid β protein (Aβ) deposition causes some forms of AD was provided by genetic and molecular studies of some familial forms of AD (FAD). (See, e.g., Ii *Drugs Aging* 7(2):97-109 (1995); Hardy *Proc. Natl. Acad. Sci. U.S.A.* 94(6):2095-7 (1997); Selkoe *J. Biol. Chem.* 271 (31):18295-8 (1996)). The amyloid plaque buildup in AD patients suggests that abnormal processing of Aβ may be a cause of AD. Aβ is a peptide of 39 to 42 amino acids and forms the core of senile plaques observed in all Alzheimer cases. If abnormal processing is the primary cause of AD, then familial Alzheimer's disease (FAD) mutations that are linked (genetically) to FAD may induce changes that, in one way or another, foster Aβ deposition. There are 3 FAD genes known so far (Hardy et al. *Science* 282:1075-9 (1998); Ray et al. (1998)). Mutations in these FAD genes can result in increased Aβ deposition.

The first of the 3 FAD genes codes for the Aβ precursor, amyloid precursor protein (APP) (Selkoe *J. Biol. Chem.* 271 (31):18295-8 (1996)). Mutations in the APP gene are very rare, but all of them cause AD with 100% penetrance and result in elevated production of either total Aβ or Aβ$_{42}$, both in model transfected cells and transgenic animals. The other two FAD genes code for presenilin 1 and 2 (PS1, PS2) (Hardy *Proc. Natl. Acad. Sci. U.S.A.* 94(6):2095-7 (1997)). The presenilins contain 8 transmembrane domains and several lines of evidence suggest that they are involved in intracellular protein trafficking. Other studies suggest that the presenilins function as proteases. Mutations in the presenilin genes are more common than in the APP gene, and all of them also cause FAD with 100% penetrance. Similar to APP mutants, studies have demonstrated that PS1 and PS2 mutations shift APP metabolism, resulting in elevated Aβ$_{42}$ production (in vitro and in vivo).

Cyclooxygenases (COX) are major Alzheimer's disease drug targets due to the epidemiological association of NSAID use, whose primary target are cycloxygenases, with a reduced risk of developing Alzheimer's disease (see, e.g., Hoozemans et al. *Curr. Drug Targets* 4(6):461-8 (2003) and Pasinetti et al. *J. Neurosci. Res.* 54(1):1-6 (1998)). The epidemiological studies have indicated that chronic NSAID use appears to reduce the risk of acquiring Alzheimer's disease and/or delay the onset of the disease (see e.g., McGeer et al. *Neurology* 47(2):425-432 (1996); and Etminan et al. *BMJ.* 327(7407): 128 (2003)). COX-2 selective inhibitors are attractive candidates for long-term drug use since they do not inhibit COX-1 and appear to be less toxic. In support of COX-2 as a target for the treatment for AD, a recent study was published reporting that in mouse models of AD, COX-2 overexpression was related to the neuropathology of AD (Xiang et al. *Neurobiol. Aging* 23:327-34 (2002)). However, recent clinical trials of specific NSAIDs have called into question the hypothesis the hypothesis that anti-inflammatory drugs are useful for the treatment or prevention of Alzheimer's disease. It was reported that rofecoxib, a COX-2 selective NSAID, at 25 mg daily, failed to show efficacy for treating AD. Naproxen, another NSAID, in the same trial failed to show efficacy in Alzheimer's treatment. See Aisen et al. *JAMA* 289:2819-26 (2003) and Reines et al. *Neurology* 62(1):66-71 (2004). These authors concluded that the results with naproxen and rofecoxib do not support the use of NSAIDs for the treatment of AD. Celecoxib, a COX-2-selective NSAID, failed to show efficacy in several recent clinical trials for the treatment of AD. See Jhee et al., "A Double-Blind, Placebo-Controlled Pharmacokinetic (PK), Pharmacodynamic (PD) and Safety Study of Celecoxib Treatment for Four Weeks in Patients with Alzheimer's Disease (AD)," Abstract from 7$^{th}$ International Geneva/Springfield Symposium on Advances in Alzheimer's Therapy (2002); also published in *Clinical Research and Regulatory Affairs* 21 (1): 49-66 (2004)) and Sainati et al. (Abstract from 6$^{th}$ International Stockholm/Springfield Symposium on Advances on Alzheimer's Therapy, Abstract Book 2000; 180). Conversely, it was reported recently that rofecoxib provides neuroprotection in an in vivo Alzheimer's disease excitotoxic model system (Scali et al. Neuroscience 117:909-919 (2003). However, rofecoxib, in a large prevention clinical trial, failed to prevent the development of Alzheimer's disease in patients having mild cognitive impairment. In fact, the results of this trial showed that 6.4% of patients taking rofecoxib developed AD as compared to 4.5% for those taking placebo (see e.g., Visser et al., abstract from Annual meeting of the American College of Neuropsychopharmacology San Juan, Puerto Rico, 2003; and Landers, *Wall Street Journal* 10 Dec. 2003). Thus, clinical trials have indicated that NSAIDs, as a general class of drugs, are not likely to be useful for treating and/or preventing Alzheimer's disease.

Of the five drugs currently being used in the US for the treatment of AD, four of them—tacrine (Cognex®), donepezil (Aricept®), rivastigmine (Exelon®), and galantamine (Reminyl®)—are inhibitors of acetylcholinesterase. Another drug, memantine, was recently approved for treating moderate-to-severe AD. More recently it was reported that memantine showed efficacy in treating mild-to-moderate AD. Memantine is a NMDA receptor antagonist.

The drugs currently used for treating AD, including memantine and the acetylcholine esterase inhibitors, are marginally efficacious and have undesirable side-effects. Thus, there is a large unmet need for better and safer drugs.

SUMMARY OF THE INVENTION

In general, the invention relates to compounds of Formulae I-XIV, pharmaceutically acceptable salts thereof, and pharmaceutical compositions containing the compounds and salts. The compounds of the invention can be used for the treatment and prophylaxis of neurodegenerative disorders, including Alzheimer's disease.

In a first aspect, the invention provides compounds of Formula I and II, pharmaceutically acceptable salts thereof, and pharmaceutical compositions having such compounds.

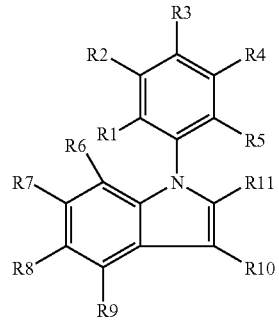

FORMULA I

According to the first aspect of the invention, compounds of Formula I have one or more of R1-R5 independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, and wherein each carbon can be optionally substituted with one or more C$_{1-3}$ alkyl or C$_{3-6}$ cycloalkyl.

The first aspect of the invention also includes compounds of Formula II.

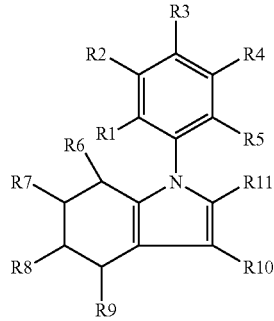

FORMULA II

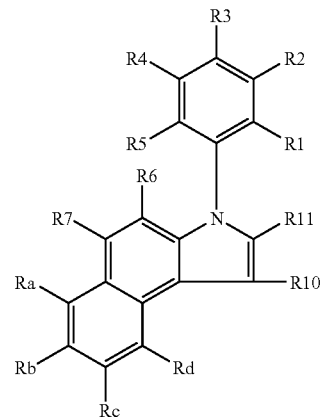

FORMULA III

In the first aspect of the invention, compounds of Formula II are provided having one or more of R1-R5 independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -LC(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; with the provision when R2 is —C(=O)OH, then R3 is not hydroxyl (or —O—C(=O)CH$_3$), —SH, —Cl, —NH$_2$, methoxy, and —NHC(=O)CH$_3$;

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group; and

R$_o$ is chosen from haloalkyl and alkyl.

According to one embodiment of the first aspect of the invention, R8 and R9 in the compounds of Formula I are taken together to form a 6 member aryl ring as in Formula III.

According to one embodiment of the first aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the first aspect of the invention.

According to one embodiment of the first aspect of the invention, R8 and R9 in the compounds of Formula II are taken together to form a 6 member aryl ring as in Formula IV.

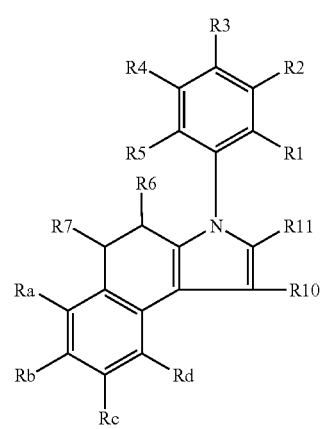

FORMULA IV

According to one embodiment of the first aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); and the other variables can be defined as in one of the other embodiments of the first aspect of the invention.

In a second aspect, the invention provides compounds of Formula I and II, wherein R1-R5 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 are chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$ alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl; or two adjacent of R6-R9 can be taken together to form a 4-7 member substituted aryl or cycloalkyl ring wherein the substituent is chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$ alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R10 is chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R11 is an optionally substituted phenyl group; and

L is as defined above.

In a third aspect, the invention provides compounds of Formula I and II, wherein R1-R9 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

In a fourth aspect, the invention provides compounds of Formula I and II, wherein R1-R10 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is a phenyl ring substituted with one or more substituents independently chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$ alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl and the others are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and

L is as defined above.

In a fifth aspect, the invention provides compounds of Formula I and II, wherein R1-R9 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is a phenyl ring substituted with one or more substituents independently chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$ alkyl), -L-S(═O)$_2$NH$_2$, -L-S(═O)$_2$N(C$_{1-3}$ alkyl)$_2$, -L-S (=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR₀, -L-C(=O)NHR₀, -L-NH(C=O)NHR₀, -L-C(=O)N(R₀)₂, -L-NH(C=O)N(R₀)₂, -L-sulfo, -L-(2,6 difluorophenol), -L-phosphono, and -L-tetrazolyl;

R₀ is chosen from alkyl and haloalkyl; and

L is as defined above.

In a sixth aspect, the invention provides compounds of Formula I and II, wherein R1-R9 and R11 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl or cycloalkyl ring;

R10 is -L-R12 wherein L is as defined above; and

R12 is a phenyl ring substituted with one or more substituents independently chosen from of -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR₀, -L-C(=O)NHR₀, -L-NH(C=O)NHR₀, -L-C(=O)N(R₀)₂, -L-NH(C=O)N(R₀)₂, -L-sulfo, -L-(2,6 difluorophenol), -L-phosphono, and -L-tetrazolyl;

R₀ is chosen from alkyl and haloalkyl; and

L is as defined above.

In a seventh embodiment, the invention provides compounds of Formula I and II, wherein R1-R10 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl or cycloalkyl ring;

R11 is -L-R12 wherein L is as defined above; and

R12 is a phenyl ring substituted with one or more substituents independently chosen from -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR₀, -L-C(=O)NHR₀, -L-NH(C=O)NHR₀, -L-C(=O)N(R₀)₂, -L-NH(C=O)N(R₀)₂, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R₀ is chosen from alkyl and haloalkyl; and

L is as defined above.

In an eighth embodiment, the invention provides compounds of Formula I and II, wherein R1-R9 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl ring;

R10 and R11 are independently chosen from hydro, hydroxyl, halo, alkyl, alkoxy, haloalkyl, haloalkoxy, —N(C₁₋₃ alkyl)₂, —NH(C₁₋₃ alkyl), —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, and -L-R12; and R12 is a phenyl ring substituted with one or more substituents independently chosen from -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR₀, -L-C(=O)NHR₀, -L-NH(C=O)NHR₀, -L-C(=O)N(R₀)₂, -L-NH(C=O)N(R₀)₂, -L-sulfo, -L-(2,6 difluorophenol), -L-phosphono, and -L-tetrazolyl;

R₀ is chosen from alkyl and haloalkyl; and

L is as defined above.

In a ninth aspect, the invention provides compounds of Formula V and VI,

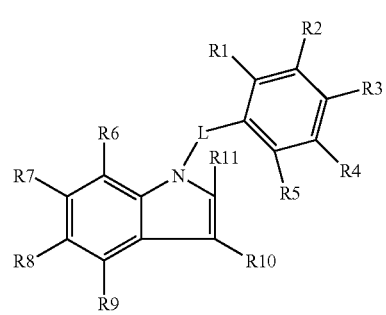

FORMULA V

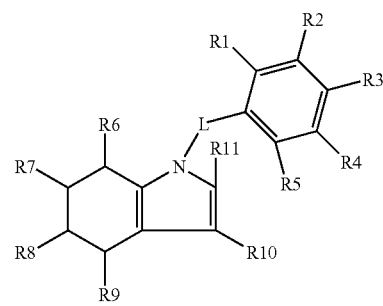

FORMULA VI wherein one or more of R1-R5 is independently chosen from -L-C(=O)OH, -L-CH=CHC(=O)

NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

L is as defined above;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring; and R11 is an optionally substituted phenyl group.

In one embodiment of the ninth aspect of the invention, R8 and R9 in the compound of Formula V are taken together to form a 6 member aryl ring as in Formula VII.

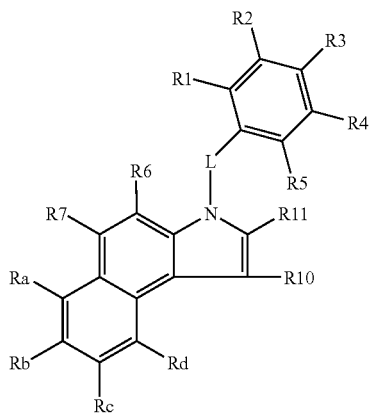

FORMULA VII

According to one embodiment of the ninth aspect of the invention, compounds of Formula VII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the ninth aspect of the invention.

In one embodiment of the ninth aspect of the invention, R8 and R9 in the compounds of Formula VI are taken together to form a 6 member aryl ring as in Formula VIII.

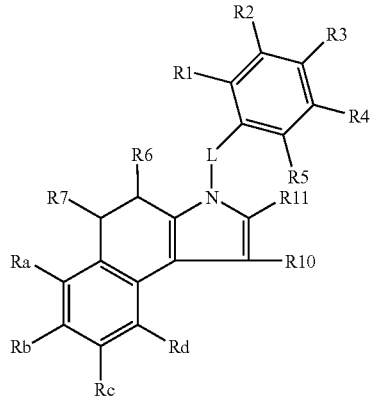

FORMULA VIII

According to one embodiment of the ninth aspect of the invention, compounds of Formula VIII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the ninth aspect of the invention.

(10)

In a tenth aspect, the invention provides compounds of Formula IX and X:

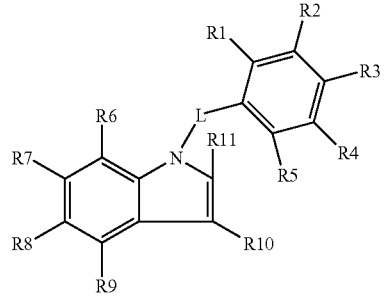

FORMULA IX

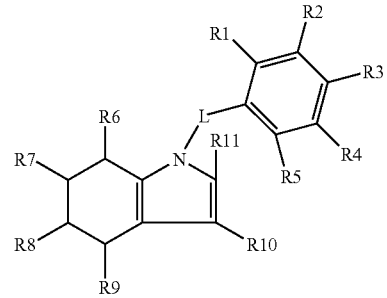

FORMULA X wherein one or more of R1-R11 are chosen from -L-R12,

-L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; wherein R12 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

L is as defined above; and the others of R1-R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; and two adjacent of R6-R9 can be taken together to form a 4-7 member optionally substituted aryl or cycloalkyl ring.

In one embodiment of the tenth aspect of the invention, R8 and R9 in the compounds of Formula IX are taken together to form a 6 member aryl ring as in Formula XI

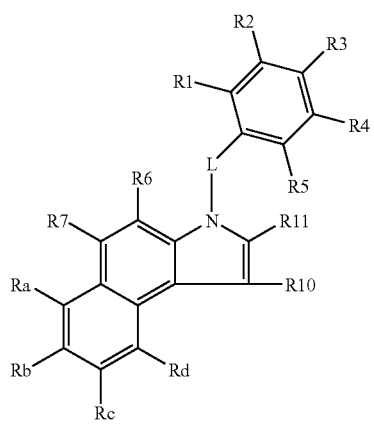

FORMULA XI

According to one embodiment of the tenth aspect of the invention, compounds of Formula XI are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In one embodiment of the tenth aspect of the invention, R8 and R9 in the compounds of Formula X are taken together to form a 6 member aryl ring as in Formula XII.

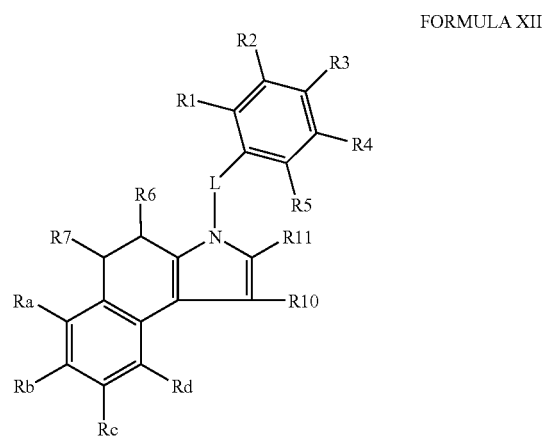

FORMULA XII

According to one embodiment of the tenth aspect of the invention, compounds of Formula XII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In an eleventh aspect, the invention provides compounds of Formula XIII and XIV:

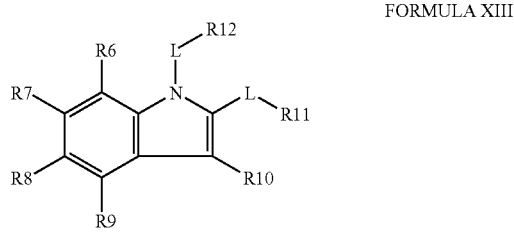

FORMULA XIII

-continued

FORMULA XIV

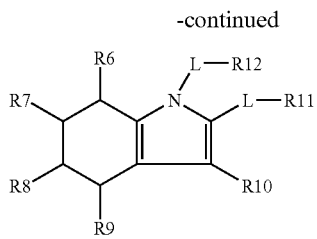

wherein L is as defined above or is selected from an optionally substituted, saturated or partially saturated cyclopropyl, cyclobutyl, cyclopentyl, cyclohexyl, cycloheptyl, and $C_{1-12}$ alkyl;

R1-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O))$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

R12 is chosen from optionally substituted $C_{1-12}$ alkyl, phenyl, and $C_{3-7}$ cycloalkyl.

In one embodiment of the eleventh aspect of the invention, R8 and R9 in the compounds of Formula XI are taken together to form a 6 member aryl ring as in Formula XIII.

FORMULA XIII

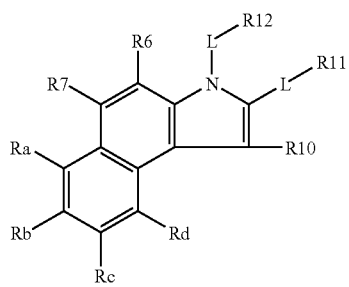

According to one embodiment of the eleventh aspect of the invention, compounds of Formula XIII are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In one embodiment of the eleventh aspect of the invention, R8 and R9 in the compounds of Formula XII are taken together to form a 6 member aryl ring as in Formula XIV.

FORMULA XIV

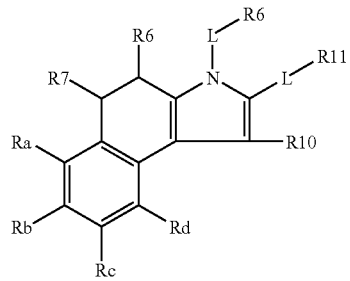

According to one embodiment of the eleventh aspect of the invention, compounds of Formula XIV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In a twelfth aspect, the invention provides compounds of Formula I and II, wherein one or more of R1-R5 is chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a thirteenth aspect, the invention provides compounds of Formula I and II, wherein R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$NH$_2$, —S(=O)$_2$(C$_{1-3}$alkyl), —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 is independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; or two adjacent of R6-R9 can be taken together to form an optionally substituted 4-7 member aryl, heterocyclic, or cycloalkyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl.

In a fourteenth aspect, the invention provides compounds of Formula I and II, wherein R1-R9 are independently chosen hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form an optionally substituted C$_{4-7}$ member aryl, heterocyclic, or cycloalkyl ring;

R10 is chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a fifteenth aspect, the invention provides compounds of Formula I and II, wherein R1-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is a heterocyclic group with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a sixteenth aspect, the invention provides compounds of Formula I and II, wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In a seventeenth aspect, the invention provides compounds of Formula I and II, wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is -L-R12;

R12 is a heterocyclic group with one or more substituents chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In an eighteenth embodiment, the invention provides compounds of Formula I and II, wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In a nineteenth aspect, the invention provides compounds of Formula I and II, wherein R1-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 and R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$NH$_2$, —S(=O)$_2$($C_{1-3}$alkyl), —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, and -L-R12;

R12 is a heterocyclic group with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a twentieth aspect, the invention provides compounds of Formula V and VI,

FORMULA V

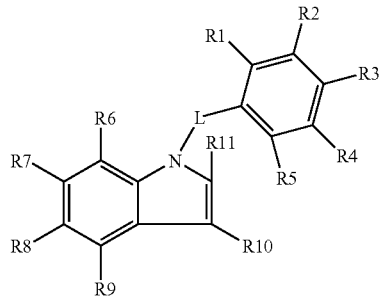

FORMULA VI

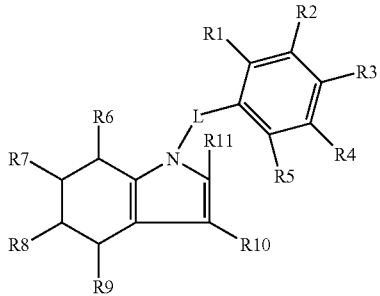

wherein one or more of R1-R5 is independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In a twenty-first aspect, the invention provides compounds of Formula V and VI,

FORMULA V

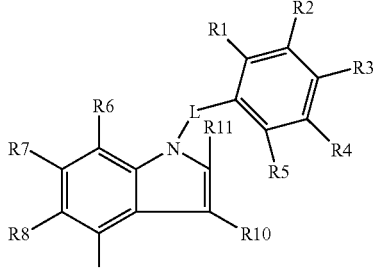

FORMULA VI

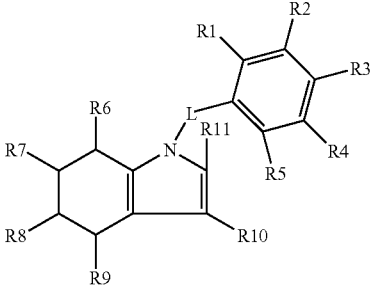

wherein R1-R11, independent of one another, are chosen from -L-R12, -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl;

R12 is a heterocyclic group with one or more substituents independently chosen -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R1-R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring; and L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of this twenty-first aspect, the invention includes analogs where the ring to which R1-R5 are attached is a 4-7 member heterocyclic ring instead a phenyl ring.

In another aspect of the invention, one or more of the carbon atoms of the indole core are replaced by a heteroatom independently —N—, —O—, and —S—.

In some embodiments of the invention, R$_o$ is independently chosen from methyl or ethyl.

Optionally substituted, when used herein without reference to further definition, refers to a substituent independently chosen from the group consisting of hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

Furthermore, the invention provides derivatives or analog of the compounds defined in first through twenty-first aspects of the invention, where the derivative or analog is chosen from an ester (e.g., methyl or ethyl ester), an amide, a carbamate, a urea, an amadine, or a combination thereof. Methods for generating an ester, an amide, a carbamate, a urea, an amadine, or a combination thereof, of the compounds of the first aspect through the twenty-first aspects are known to an ordinary artisan skilled in organic chemical synthesis.

As the skilled artisan readily recognizes, in some of the embodiments of the first twenty-one aspects of the invention, some of the compounds can have more than one -L-group, each of which is independent chosen.

In a twenty-second aspect, the invention provides a method of treating a neurodegenerative disorder, by identifying a patient in need of such treatment, and administering to the patient a therapeutically effective amount of a pharmaceutical composition having one or more compounds of Formulae I-XVI. Administration of a compound of Formulae I-XVI for at least 4 weeks, preferably at least 4 months, and more desirably at least 8 months, can provide an improvement or lessening in decline of cognitive function as characterized by cognition tests, biochemical disease marker progression, and/or plaque pathology. Cognition tests are those which are capable of measuring cognitive decline in a patient or group of patients. Examples of such cognition tests include the ADAS-cog (Alzheimer's Disease Assessment Scale, cognitive subscale) NPI (Neuropsychiatric Inventory), ADCS-ADL (Alzheimer's Disease Cooperative Study-Activities of Daily Living), CIBIC-plus (Clinician Interview Based Impression of Change), and CDR sum of boxes (Clinical Dementia Rating). It is preferred that the lessening in decline in cognitive function is at least 25% as compared to individuals treated with placebo, more preferably at least 40%, and even more desirably at least 60%. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. Desirably, the oral dose is provided in capsule or tablet form. The pharmaceutical composition for use in the invention is formulated with one or more pharmaceutically acceptable excipients, salts, or carriers. The pharmaceutical composition for use in the invention is delivered orally, preferably in a tablet or capsule dosage form.

In a twenty-third aspect, the invention provides a method for prophylaxis against a neurodegenerative disorder, by identifying a patient in need of or desiring such treatment, and administering to the patient a prophylactically effective amount of a pharmaceutical composition having one or more compounds of Formulae I-XVI. Administration of a compound of Formulae I-XVI for at least 4 weeks, preferably at least 4 months, and more desirably at least 8 months, can delay the onset of the neurodegenerative disorder or slow the rate of onset of symptoms of the disorder. Patients having a predisposition to a neurodegenerative disorder or suspected of needing prophylaxis can be identified by any method known to the skilled artisan for diagnosis such neurodegenerative disorders.

In a twenty-fourth aspect, the invention provides a method of treating a disease characterized by abnormal amyloid precursor protein processing by (1) identifying a patient in need of such treatment, and (2) administering to the patient a therapeutically effective amount of a pharmaceutical composition having one or more compounds of Formulae I-XVI. Oral administration of the pharmaceutical composition for use in the method of this aspect the invention for at least 4 weeks, preferably at least 4 months, and more desirably at least 8 months, provides an improvement or lessening in decline of cognitive function as characterized by cognition tests, biochemical disease marker progression, and/or plaque pathology. Examples of biochemical disease markers include, for example, amyloid beta peptide (Aβ), Aβ$_{42}$, and tau. It is preferred that the lessening in decline in biochemical disease marker progression is at least 10% as compared to individuals treated with placebo, more preferably at least 20%, and more desirably at least 40%. It is preferred that the lessening in decline in cognitive function is at least 25% as compared to individuals treated with placebo, more preferably at least 40%, and even more desirably at least 60%. Desirably, the composition is provided as an oral dose, preferably in capsule or tablet form.

In a twenty-fifth aspect, the invention provides a method of prophylaxis or delaying the onset of a disease (or one or more symptoms thereof) characterized by abnormal amyloid precursor protein processing, by identifying a patient in need of such treatment and administering to the patient a prophylactically effective amount of a pharmaceutical composition having one or more compounds of Formulae I-XVI. Oral administration of the pharmaceutical composition for use in the method of this aspect the invention for at least 4 weeks, preferably at least 4 months, and more desirably at least 8 months, prevents or delays the onset of the disease (or symptoms thereof) characterized by abnormal amyloid precursor protein processing.

In a twenty-sixth aspect, the invention provides a method of treating Alzheimer's disease comprising administering to a patient in need of such treatment, a pharmaceutical composition having one or more compounds of Formulae I-XVI. Oral administration of the pharmaceutical composition for use in the method of this aspect of the invention for at least 4 weeks, preferably at least 4 months, and more desirably at least 8 months, provides an improvement or lessening in decline of cognitive function as characterized by cognition tests, biochemical disease marker progression, and/or plaque pathology. Desirably, the oral dose is provided in capsule or tablet form. According to this aspect of the invention, a patient in need of treatment is administered an Alzheimer's disease treating effective amount of a pharmaceutical composition having one or more compounds of Formulae I-XVI and one or more pharmaceutically acceptable salts, excipients and carriers. The method of this aspect of the invention involves identifying an individual likely to have mild-to-moderate Alzheimer's disease. An individual having probable mild-to-moderate Alzheimer's disease can be diagnosed by any method available to the ordinary artisan skilled in such diagnoses. For example, diagnosis can be according to DSM IV (TR) and/or meets NINCDS-ADRDA criteria for probable AD. According to this aspect of the invention, individuals with probable mild-to-moderate AD take an oral dose of a pharmaceutical composition for a specified period of time. Individuals undergoing such treatment are likely to see an improvement or lessening in decline of cognitive function, an improvement or lessening in decline in biochemical disease marker progression, and/or an improvement or lessening decline in plaque pathology. A lessening in decline in cognitive function can be assessed using a test of cognitive function like the ADAS-cog. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. In a related aspect, the method involves identifying a patient having moderate-to-severe AD and administering to the patient an Alzheimer's disease treating effective amount of a compound of Formulae I-XVI.

In a twenty-seventh aspect, the invention provides a method of preventing the onset of Alzheimer's disease comprising administering to a patient in need of or desiring such treatment, a pharmaceutical composition having one or more compounds of Formulae I-XVI. Oral administration of the pharmaceutical composition for use in the method of this aspect of the invention for at least 4 weeks, preferably at least 4 months, and more desirably at least 8 months, delays the onset of decline of cognitive function, biochemical disease marker progression, and/or plaque pathology. According to this embodiment, an individual desiring or needing preventative treatment against the onset of AD is administered a pharmaceutical composition having one or more compounds of Formulae I-XVI. Desirably, the oral dose is provided in capsule or tablet form. The preventive treatment is preferably maintained as long as the individual continues to desire or need the treatment. Individuals needing or desiring preventative treatment against AD can be those having risk factors for developing AD. For example, risk factors for developing AD can be genetic factors or environmental factors. In one embodiment, the risk factor is age. Genetic risk factors can be assessed in a variety of ways, such as ascertaining the family medical history of the individual, or performing a genetic test to identify genes that confer a predisposition for developing AD. Additionally, risk factors can be assessed by monitoring genetic and biochemical markers.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

BRIEF DESCRIPTION OF THE DRAWINGS

N/A

DETAILED DESCRIPTION OF THE INVENTION

In general, the invention relates to the use of pharmaceutical compositions having one or more compounds of Formulae I-XVI as the active ingredient, for treating neurodegenerative disorders. When the pharmaceutical composition is administered, according to the treatment regimens of the invention, to an individual desiring or needing such treatment, it provides an improvement or lessening in decline of cognitive function, biochemical disease marker progression, and/or plaque pathology associated with neurodegenerative disorders such as AD. The composition of the invention is formulated with one or more pharmaceutically acceptable excipients, salts, or carriers. The pharmaceutical composition of the invention is delivered orally, preferably in a tablet or capsule dosage form. The pharmaceutical compositions can be used in methods for treating, preventing, and prophylaxis against neurodegenerative disorders such as Alzheimer's disease, and disease characterized by abnormal amyloid precursor protein processing.

The invention therefore provides compounds of Formulae I-XVI as described in the Summary of the Invention (and in more detail below) and pharmaceutical composition having such compounds. In one specific use, the compounds can be used for the treatment and/or prophylaxis of neurodegenerative disorders. The inventors have found that compounds of Formulae I-XVI as described in the summary have an $A\beta_{42}$ lowering effect in cell based assays.

Some of the compounds of Formulae I-XVI, for use in the invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the compounds that are optically active are used in optically pure form. Furthermore, some of the compound for use in the invention can exist as cis and trans geometric isomers all such isomers and mixtures thereof are intended to be within the scope of the present invention.

Additionally, the formulas are intended to cover solvated as well as unsolvated forms of the identified structures. For example, Formulae I-XVI includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formulae I-XVI, the invention includes pharmaceutically acceptable prodrugs, pharmaceutically active metabolites, and pharmaceutically acceptable salts of such compounds.

Prodrugs and active metabolites of compound may be identified using routine techniques known in the art. See, e.g., Bertolini, G et al., *J. Med. Chem.*, 40, 2011-2016 (1997); Shan, D. et al., *J. Pharm. Sci.*, 86 (7), 756-767; Bagshawe K., *Drug Dev. Res.*, 34, 220-230 (1995); Bodor N, *Advance in Drug Res.*, 13, 224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991).

Compounds of the Invention

In general, the invention relates to compounds of Formulae I-XIV, pharmaceutically acceptable salts thereof, and pharmaceutical compositions containing the compounds and salts. The compounds of the invention can be used for the treatment and prophylaxis of neurodegenerative disorders, including Alzheimer's disease.

In a first aspect, the invention provides compounds of Formula I and II, pharmaceutically acceptable salts thereof, and pharmaceutical compositions having such compounds.

FORMULA I

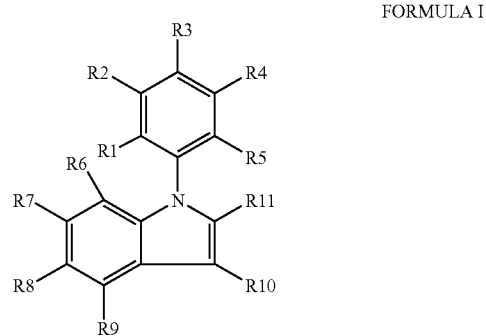

According to the first aspect of the invention, compounds of Formula I have one or more of R1-R5 independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$, with the provision that R3 is not hydroxyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, and wherein each carbon can be optionally substituted with one or more C$_{1-3}$ alkyl or C$_{3-6}$ cycloalkyl.

In one sub-embodiment, with the compound is not 1-[4-(methylsulfonyl)phenyl]-2-phenyl-1H-Indole.

According to one embodiment of the first aspect of the invention, one or more of R1-R5 in the compounds of Formula I, are independently chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$alkyl)$_2$, —S(=O)$_2$NH$_2$, —S(=O)$_2$N(C$_{1-3}$alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is as defined above; and

R11 is an optionally substituted phenyl group.

In one sub-embodiment R3 is not hydroxyl.

According to another embodiment of this first aspect of the invention, in the compounds of Formula I, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R1-R5 independently are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two of R6-R9 can be taken together to form an optionally substituted C$_{4-7}$ aryl or cycloalkyl ring; and R11 is an optionally substituted phenyl.

According to one embodiment of the first aspect of the invention, in the compounds of Formula I, R1 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to one embodiment of the first aspect of the invention, in the compounds of Formula I, R1 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$alkyl)$_2$, —S(=O)$_2$NH$_2$, and —S(=O)$_2$N(C$_{1-3}$alkyl)$_2$.

According to another embodiment of the first aspect of the invention, in the compounds of Formula I, R1 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$alkyl), -L-C(=O)N(C$_{1-3}$alkyl)$_2$, -L-S(=O)$_2$NH$_2$, and -L-S(=O)$_2$N(C$_{1-3}$alkyl)$_2$, with the provision that if R1 is —COOH, or an ester thereof, then R10 is not —COOH, or an ester thereof.

According to one embodiment of the first aspect of the invention, in the compounds of Formula I, R2 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$alkyl)$_2$, —S(=O)$_2$NH$_2$, and —S(=O)$_2$N(C$_{1-3}$alkyl)$_2$.

According to yet another embodiment of the first aspect of the invention, in the compounds of Formula I, R2 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$alkyl)$_2$, —S(=O)$_2$NH$_2$, and —S(=O)$_2$N(C$_{1-3}$alkyl)$_2$.

According to another embodiment of the first aspect of the invention, in the compounds of Formula I, R2 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -L-CH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$alkyl), -L-C(=O)N(C$_{1-3}$alkyl)$_2$, -L-S(=O)$_2$NH$_2$, and -L-S(=O)$_2$N(C$_{1-3}$alkyl)$_2$, with the provision that when R2 is —C(=O)OH, R3 is not —OH or —OC(=O)CH$_3$.

According to another embodiment of the first aspect of the invention, in the compounds of Formula I, R3 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$alkyl)$_2$, —S(=O)$_2$NH$_2$, and —S(=O)$_2$N(C$_{1-3}$alkyl)$_2$.

According to still another embodiment of the first aspect of the invention, in the compounds of Formula I, R3 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -LCH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$alkyl), -L-C(=O)N(C$_{1-3}$alkyl)$_2$, -L-S(=O)$_2$NH$_2$, and -L-S(=O)$_2$N(C$_{1-3}$alkyl)$_2$.

The first aspect of the invention also includes compounds of Formula II.

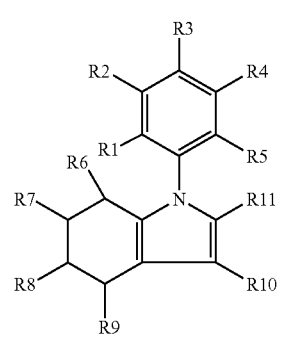

FORMULA II

In the first aspect of the invention, compounds of Formula II are provided having one or more of R1-R5 independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -LC(=O)CH$_2$OH, -L-C(=O)CH$_2$SH, -L-C(=O)

NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more C$_{1-3}$ alkyl or C$_{3-6}$ cycloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is an optionally substituted phenyl group; and

R$_o$ is chosen from haloalkyl and alkyl.

In one sub-embodiment, when R2 is —C(=O)OH, then R3 is not hydroxyl (or —O—C(=O)CH$_3$), —SH, —Cl, —NH$_2$, methoxy, and —NHC(=O)CH$_3$;

In one sub-embodiment, the compound is not 4-(4,5-dihydro-2-phenyl-3H-benz[e]indol-3-yl)-2-hydroxy-benzoic acid, 4-(4,5-dihydro-2-phenyl-3H-benz[e]indol-3-yl)-benzoic acid, 4-(7-chloro-4,5-dihydro-2-phenyl-3H-benz[e]indol-3-yl)-2-hydroxy-benzoic acid, 2-hydroxy-4-(4,5,6,7-tetrahydro-2-phenyl-1H-indol-1-yl)-benzoic acid, 4-(4,5,6,7-tetrahydro-2-phenyl-1H-indol-1-yl)-benzoic acid, 3-(4,5-dihydro-2-phenyl-3H-benz[e]indol-3-yl)-benzamide, 4-(4,5-dihydro-2-phenyl-3H-benz[e]indol-3-yl)-benzamide, 3-(4,5-dihydro-2-phenyl-1H-benz[g]indol-1-yl)-benzoic acid, 2-(4,5-dihydro-2-phenyl-1H-benz[g]indol-1-yl)-benzoic acid, or 3-[2-(4-bromophenyl)-4,5,6,7-tetrahydro-1H-indol-1-yl]-benzoic acid.

In one embodiment of the first aspect of the invention, one of R1-R5 in the compounds of Formula II is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is as defined above; and

R11 is an optionally substituted phenyl.

According to another embodiment of this first aspect of the invention, in the compounds of Formula II, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others of R1-R5 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring; and R11 is an optionally substituted phenyl.

According to another embodiment of the first aspect of the invention, in the compounds of Formula II, R1 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -LCH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$alkyl), -L-C(=O)N(C$_{1-3}$alkyl)$_2$, -L-S(=O)$_2$NH$_2$, and -L-S(=O)$_2$N(C$_{1-3}$alkyl)$_2$. In one sub-embodiment, the compound is not 2-(4,5-dihydro-2-phenyl-1H-benz[g]indol-1-yl)benzoic acid (CAS No. 54670-19-8).

According to yet another embodiment of the first aspect of the invention, in the compounds of Formula II, R1 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to still another embodiment of the first aspect of the invention, in the compounds of Formula II, R2 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -LCH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$alkyl), -L-C(=O)N(C$_{1-3}$alkyl)$_2$, -L-S(=O)$_2$NH$_2$, and -L-S(=O)$_2$N(C$_{1-3}$alkyl)$_2$. In one sub-embodiment, (1) if R2 is —C(=O)NH$_2$, —C(=O)NH(CH$_2$CH$_3$), —C(=O)N(CH$_2$CH$_3$)$_2$, then R3 is not —OH or if R3 is —OH then one or more R1 and R4-R9 has a substituent which is not hydro or a carbon, (2), if R2 is —C(=O)OH, then R3 is not —OH, —SH, —Cl, —NH$_2$, —OCH$_3$, —NHC(=O)CH$_3$, (3) R6 and R7 cannot be taken together to form a 6 member unsubstituted aryl ring, (4) R8 and R9 cannot be taken together to form a 6 member unsubstituted aryl ring, and/or (5) R11 is not para-bromo substituted phenyl.

According to another embodiment of the first aspect of the invention, in the compounds of Formula II, R2 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to still another embodiment of the first aspect of the invention, in the compounds of Formula II, R3 is chosen from -L-C(=O)OH, -L-CH=CHC(=O)OH, -L-CH$_2$CH$_2$C(=O)OH, -L-CH$_2$CH$_2$CH$_2$C(=O)OH, -L-C(CH$_2$CH$_2$)C(=O)OH, -L-CH(CH$_3$)C(=O)OH, -L-CH(CH$_2$CH$_3$)C(=O)OH, -L-C(CH$_3$)(CH$_2$CH$_3$)C(=O)OH, -L-CH=C(CH$_3$)C(=O)OH, -L-C(CH$_2$CH$_3$)$_2$C(=O)OH, -LCH$_2$C(=O)OH, -L-C(CH$_3$)$_2$C(=O)OH, -L-C(=O)NH$_2$, -L-C(=O)NHCH$_3$, -L-C(=O)N(CH$_3$)$_2$, -L-S(=O)$_2$(C$_{1-3}$alkyl), -L-S(=O)$_2$NH$_2$, -L-S(=O)$_2$NHCH$_3$, -L-S(=O)$_2$N(CH$_3$)$_2$, -L-C(=O)NH(C$_{1-3}$alkyl), -L-C(=O)N(C$_{1-3}$alkyl)$_2$, -L-S(=O)$_2$NH$_2$, and -L-S(=O)$_2$N(C$_{1-3}$alkyl)$_2$. In one sub-embodiment, if R3 is —C(=O)OH then R2 is not hydroxyl or if R3 is —C(=O)NH$_2$ or —C(=O)OH, then one or more of a 4-7 member aryl or cycloalkyl formed from two adjacent of R6-R9, R2, R3, R4, R5, R6, R7, R8, R9, R10 and R11, is substituted with one or more non-hydrogen substituents excluding R6-R9 attachments to form another ring system.

According to another embodiment of the first aspect of the invention, in the compounds of Formula II, R3 is chosen from —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to another embodiment of the first aspect of the invention, in the compounds of Formula II, R4 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to yet another embodiment of the first aspect of the invention, in the compounds of Formula II, R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

According to one embodiment of the first aspect of the invention, R8 and R9 in the compounds of Formula I are taken together to form a 6 member aryl ring as in Formula III.

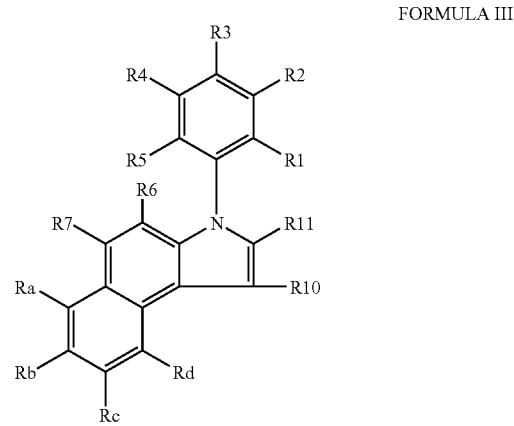

FORMULA III

According to one embodiment of the first aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the first aspect of the invention.

According to one embodiment of the first aspect of the invention, R8 and R9 in the compounds of Formula II are taken together to form a 6 member aryl ring as in Formula IV.

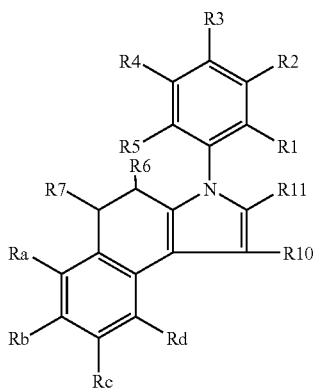

FORMULA IV

According to one embodiment of the first aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the first aspect of the invention.

In a second aspect, the invention provides compounds of Formula I and II:

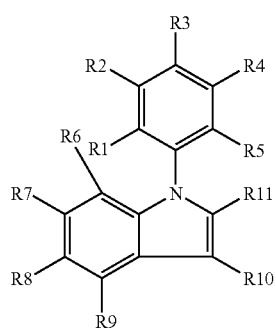

FORMULA I

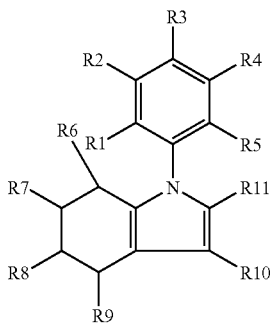

FORMULA II wherein R1-R5 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 are chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$ alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; or two adjacent of R6-R9 can be taken together to form a 4-7 member substituted aryl or cycloalkyl ring wherein the substituent is chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$ alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R10 is chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;
R11 is an optionally substituted phenyl group; and
L is as defined above.

In one sub-embodiment, the compound is not, 1,2-diphenyl-indole-4-acetic acid.

According to one embodiment of the second aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —C(=O)NH($C_{1-3}$ alkyl), —C(=O)N($C_{1-3}$alkyl)$_2$, —S(=O)$_2$NH$_2$, and —S(=O)$_2$N($C_{1-3}$alkyl)$_2$.

In another embodiment of this second aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; or two adjacent of R6-R9 can be taken together to form a 4-7 member aryl or cycloalkyl ring substituted with one or more substituents chosen from —C(=O)OH, —CH=CHC(=O)OH, —CH₂CH₂C(=O)OH, —CH₂CH₂CH₂C(=O)OH, —C(CH₂CH₃)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; and the others of R6-R9 are independently chosen from hydro, hydroxyl, halo, alkyl, alkoxy, haloalkyl, haloalkoxy, —N(C$_{1-3}$ alkyl)₂, —NH(C$_{1-3}$ alkyl), —C(=O)NH₂, —C(=O)NH(C$_{1-3}$ alkyl), —C(=O)N(C$_{1-3}$ alkyl)₂, —S(=O)₂(C$_{1-3}$alkyl), —S(=O)₂NH₂, —S(=O)₂N(C$_{1-3}$ alkyl)₂, —S(=O)₂NH(C$_{1-3}$ alkyl), —CHF₂, —OCF₃, —OCHF₂, —SCF₃, —CF₃, —CN, —NH₂, and —NO₂;

R1-R5 and R10, independent of one another, are chosen from hydro, hydroxyl, halo, alkyl, alkoxy, haloalkyl, haloalkoxy, —N(C$_{1-3}$ alkyl)₂, —NH(C$_{1-3}$ alkyl), —C(=O)NH₂, —C(=O)NH(C$_{1-3}$ alkyl), —C(=O)N(C$_{1-3}$ alkyl)₂, —S(=O)₂(C$_{1-3}$alkyl), —S(=O)₂NH₂, —S(=O)₂N(C$_{1-3}$ alkyl)₂, —S(=O)₂NH(C$_{1-3}$ alkyl), —CHF₂, —OCF₃, —OCHF₂, —SCF₃, —CF₃, —CN, —NH₂, and —NO₂; and R11 is an optionally substituted phenyl.

In one embodiment of the second aspect of the invention, R6 is chosen from -L-C(=O)OH, -L-CH=CHC(=O)OH, -L-CH₂CH₂C(=O)OH, -L-CH₂CH₂CH₂C(=O)OH, -L-C(CH₂CH₃)C(=O)OH, -L-CH(CH₃)C(=O)OH, -L-CH(CH₂CH₃)C(=O)OH, -L-C(CH₃)(CH₂CH₃)C(=O)OH, -L-CH=C(CH₃)C(=O)OH, -L-C(CH₂CH₃)₂C(=O)OH, -L CH₂C(=O)OH, -L-C(CH₃)₂C(=O)OH, -L-C(=O)NH₂, -L-C(=O)NHCH₃, -L-C(=O)N(CH₃)₂, -L-S(=O)₂(C$_{1-3}$ alkyl), -L-S(=O)₂NH₂, -L-S(=O)₂NHCH₃, -L-S(=O)₂N(CH₃)₂, -L-C(=O)NH(C$_{1-3}$alkyl), -L-C(=O)N(C$_{1-3}$alkyl)₂, -L-S(=O)₂NH₂, and -L-S(=O)₂N(C$_{1-3}$alkyl)₂.

In one embodiment of the second aspect of the invention, R6 is chosen from —C(=O)OH, —CH=CHC(=O)OH, —CH₂CH₂C(=O)OH, —CH₂CH₂CH₂C(=O)OH, —C(CH₂CH₃)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH₃, —C(=O)N(CH₃)₂, —S(=O)₂(C$_{1-3}$alkyl), —S(=O)₂NH₂, —S(=O)₂NHCH₃, —S(=O)₂N(CH₃)₂, —C(=O)NH(C$_{1-3}$ alkyl), —C(=O)N(C$_{1-3}$alkyl)₂, —S(=O)₂NH₂, and —S(=O)₂N(C$_{1-3}$alkyl)₂.

In one embodiment of the second aspect of the invention, R7 is chosen from -L-C(=O)OH, -L-CH=CHC(=O)OH, -L-CH₂CH₂C(=O)OH, -L-CH₂CH₂CH₂C(=O)OH, -L-C(CH₂CH₃)C(=O)OH, -L-CH(CH₃)C(=O)OH, -L-CH(CH₂CH₃)C(=O)OH, -L-C(CH₃)(CH₂CH₃)C(=O)OH, -L-CH=C(CH₃)C(=O)OH, -L-C(CH₂CH₃)₂C(=O)OH, -L CH₂C(=O)OH, -L-C(CH₃)₂C(=O)OH, -L-C(=O)NH₂, -L-C(=O)NHCH₃, -L-C(=O)N(CH₃)₂, -L-S(=O)₂(C$_{1-3}$ alkyl), -L-S(=O)₂NH₂, -L-S(=O)₂NHCH₃, -L-S(=O)₂N(CH₃)₂, -L-C(=O)NH(C$_{1-3}$alkyl), -L-C(=O)N(C$_{1-3}$alkyl)₂, -L-S(=O)₂NH₂, and -L-S(=O)₂N(C$_{1-3}$alkyl)₂.

In one embodiment of the second aspect of the invention, R7 is chosen from —C(=O)OH, —CH=CHC(=O)OH, —CH₂CH₂C(=O)OH, —CH₂CH₂CH₂C(=O)OH, —C(CH₂CH₃)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH₃, —C(=O)N(CH₃)₂, —S(=O)₂(C$_{1-3}$alkyl), —S(=O)₂NH₂, —S(=O)₂NHCH₃, —S(=O)₂N(CH₃)₂, —C(=O)NH(C$_{1-3}$alkyl), —C(=O)N(C$_{1-3}$alkyl)₂, —S(=O)₂NH₂, and —S(=O)₂N(C$_{1-3}$alkyl)₂.

In one embodiment of the second aspect of the invention, R8 is chosen from -L-C(=O)OH, -L-CH=CHC(=O)OH, -L-CH₂CH₂C(=O)OH, -L-CH₂CH₂CH₂C(=O)OH, -L-C(CH₂CH₃)C(=O)OH, -L-CH(CH₃)C(=O)OH, -L-CH(CH₂CH₃)C(=O)OH, -L-C(CH₃)(CH₂CH₃)C(=O)OH, -L-CH=C(CH₃)C(=O)OH, -L-C(CH₂CH₃)₂C(=O)OH, -L CH₂C(=O)OH, -L-C(CH₃)₂C(=O)OH, -L-C(=O)NH₂, -L-C(=O)NHCH₃, -L-C(=O)N(CH₃)₂, -L-S(=O)₂(C$_{1-3}$ alkyl), -L-S(=O)₂NH₂, -L-S(=O)₂NHCH₃, -L-S(=O)₂N(CH₃)₂, -L-C(=O)NH(C$_{1-3}$alkyl), -L-C(=O)N(C$_{1-3}$alkyl)₂, -L-S(=O)₂NH₂, and -L-S(=O)₂N(C$_{1-3}$alkyl)₂.

In one embodiment of the second aspect of the invention, R8 is chosen from —C(=O)OH, —CH=CHC(=O)OH, —CH₂CH₂C(=O)OH, —CH₂CH₂CH₂C(=O)OH, —C(CH₂CH₃)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH₃, —C(=O)N(CH₃)₂, —S(=O)₂(C$_{1-3}$ alkyl), —S(=O)₂NH₂, —S(=O)₂NHCH₃, —S(=O)₂N(CH₃)₂, —C(=O)NH(C$_{1-3}$alkyl), —C(=O)N(C$_{1-3}$alkyl)₂, —S(=O)₂NH₂, and —S(=O)₂N(C$_{1-3}$alkyl)₂.

In one embodiment of the second aspect of the invention, R9 is chosen from -L-C(=O)OH, -L-CH=CHC(=O)OH, -L-CH₂CH₂C(=O)OH, -L-CH₂CH₂CH₂C(=O)OH, -L-C(CH₂CH₃)C(=O)OH, -L-CH(CH₃)C(=O)OH, -L-CH(CH₂CH₃)C(=O)OH, -L-C(CH₃)(CH₂CH₃)C(=O)OH, -L-CH=C(CH₃)C(=O)OH, -L-C(CH₂CH₃)₂C(=O)OH, -L CH₂C(=O)OH, -L-C(CH₃)₂C(=O)OH, -L-C(=O)NH₂, -L-C(=O)NHCH₃, -L-C(=O)N(CH₃)₂, -L-S(=O)₂(C$_{1-3}$ alkyl), -L-S(=O)₂NH₂, -L-S(=O)₂NHCH₃, -L-S(=O)₂N(CH₃)₂, -L-C(=O)NH(C$_{1-3}$alkyl), -L-C(=O)N(C$_{1-3}$alkyl)₂, -L-S(=O)₂NH₂, and -L-S(=O)₂N(C$_{1-3}$alkyl)₂.

In one embodiment of the second aspect of the invention, R9 is chosen from —C(=O)OH, —CH=CHC(=O)OH, —CH₂CH₂C(=O)OH, —CH₂CH₂CH₂C(=O)OH, —C(CH₂CH₃)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —C(CH₃)₂C(=O)OH, —C(=O)NH₂, —C(=O)NHCH₃, —C(=O)N(CH₃)₂, —S(=O)₂(C$_{1-3}$alkyl), —S(=O)₂NH₂, —S(=O)₂NHCH₃, —S(=O)₂N(CH₃)₂, —C(=O)NH(C$_{1-3}$ alkyl), —C(=O)N(C$_{1-3}$alkyl)₂, —S(=O)₂NH₂, and —S(=O)₂N(C$_{1-3}$alkyl)₂.

In one embodiment of the second aspect of the invention, R8 and R9 in the compounds of Formula I are taken together to form a 6 member aryl ring as in Formula III.

FORMULA III

According to one embodiment of the second aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the second aspect of the invention.

In one embodiment of the second aspect of the invention, R8 and R9 in the compounds of Formula II are taken together to form a 6 member aryl ring as in Formula IV.

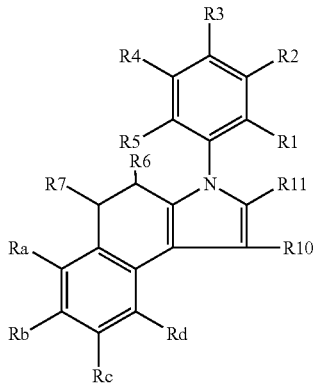

FORMULA IV

According to one embodiment of the second aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the second aspect of the invention.

In a third aspect, the invention provides compounds of Formula I and II:

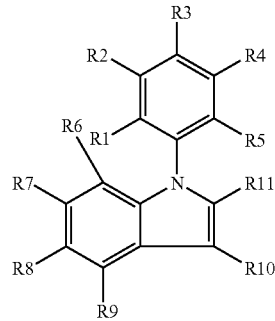

FORMULA I

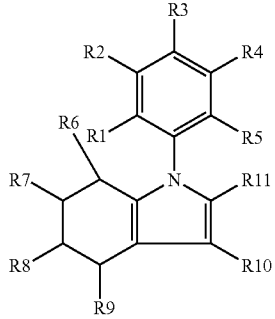

FORMULA II wherein R1-R9 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

In one sub-embodiment, the compound is not 1-(O-carboxyphenyl)-2-phenyl-indole-3-carboxylic acid, or the methyl or ethyl ester thereof.

According to one embodiment of this aspect of the invention, R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$ alkyl), —S(=O)$_2$NH$_2$, —S(=O)$_2$NHCH$_3$, —S(=O)$_2$N (CH₃)₂, —C(=O)NH(C₁₋₃alkyl), —C(=O)N(C₁₋₃alkyl)₂, —S(=O)₂NH₂, and —S(=O)₂N(C₁₋₃alkyl)₂.

In another embodiment of this third aspect of the invention, R10 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; R1-R9 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂; two adjacent of R6-R9 can be taken together to form a 4-7 member optionally substituted aryl or cycloalkyl ring; and R11 is an optionally substituted phenyl.

In one embodiment of the third aspect of the invention, R8 and R9 in the compounds of Formula I are taken together to form a 6 member aryl ring as in Formula III.

FORMULA III

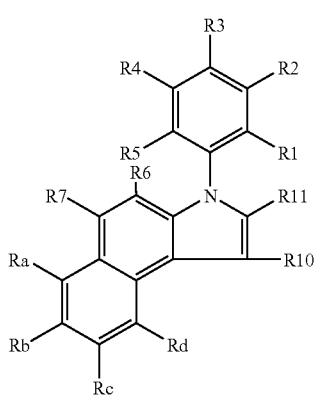

According to one embodiment of the third aspect of the invention, compounds of Formula III are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in the other embodiments of the third aspect of the invention.

In one embodiment of the third aspect of the invention, R8 and R9 in the compounds of Formula II are taken together to form a 6 member aryl ring as in Formula IV

FORMULA IV

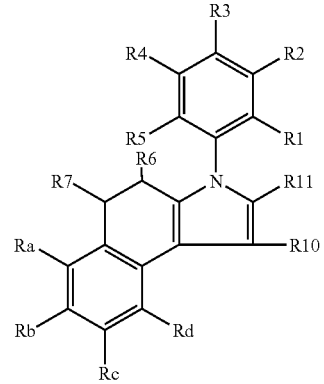

According to one embodiment of the third aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the third aspect of the invention.

In a fourth aspect, the invention provides compounds of Formula I and II:

FORMULA I

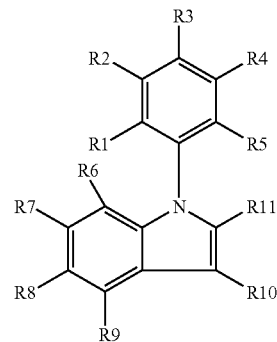

FORMULA II

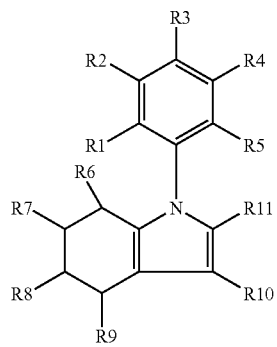

wherein R1-R10 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is a phenyl ring substituted with one or more substituents independently chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$ alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl and the others are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and

L is as defined above.

In one sub-embodiment, the compound is not 5-(4,5-dihydro-3-phenyl-3H-benz[e]indol-2-yl)-2-hydroxy-benzoic acid or 2-hydroxy-5-(4,5,6,7-tetrahydro-1-phenyl-1H-indol-2-yl)-benzoic acid.

According to one embodiment of the fourth aspect of the invention, one substituent on the phenyl of R11 is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, —C(CH$_3$)$_2$C(═O)OH, —C(═O)NH$_2$, —C(═O)NHCH$_3$, —C(═O)N(CH$_3$)$_2$, —S(═O)$_2$(C$_{1-3}$alkyl), —S(═O)$_2$NH$_2$, —S(═O)$_2$NHCH$_3$, —S(═O)$_2$N(CH$_3$)$_2$, —C(═O)NH(C$_{1-3}$ alkyl), —C(═O)N(C$_{1-3}$alkyl)$_2$, —S(═O)$_2$NH$_2$, and —S(═O)$_2$N(C$_{1-3}$alkyl)$_2$.

In another embodiment of fourth aspect of the invention, R11 is a phenyl ring substituted with a substituent chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, and —C(CH$_3$)$_2$C(═O)OH; and the other substituents on the phenyl are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; and two adjacent of R6-R9 can be taken together to form an optionally substituted 4-7 member aryl or cycloalkyl ring.

In one embodiment of the fourth aspect of the invention, R8 and R9 in the compounds of Formula I are taken together to form a 6 member aryl ring as in Formula III.

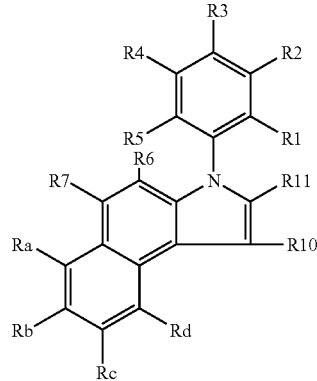

FORMULA III

According to one embodiment of the fourth aspect of the invention, compounds of Formula III are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); and the other variables can be defined as in one of the other embodiments of the fourth aspect of the invention.

In one embodiment of the fourth aspect of the invention, R8 and R9 in the compounds of Formula II are taken together to form a 6 member aryl ring as in Formula IV.

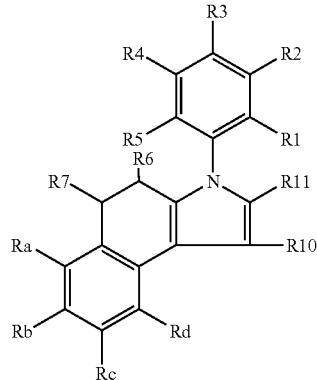

FORMULA IV

According to one embodiment of the fourth aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in the other embodiments of the fourth aspect of the invention.

In a fifth aspect, the invention provides compounds of Formula I and II:

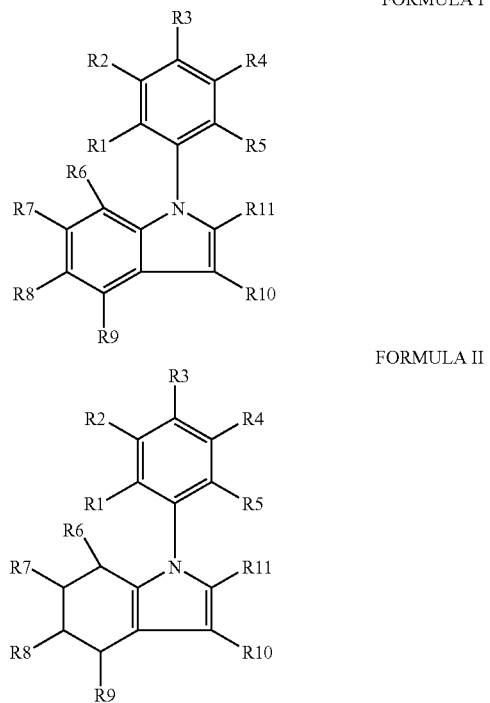

FORMULA I

FORMULA II wherein R1-R9 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is a phenyl ring substituted with one or more substituents independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$ alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and
L is as defined above.

According to one embodiment of this fifth aspect of the invention, one substituent on the phenyl of R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$(C$_{1-3}$alkyl), —S(=O)$_2$NH$_2$, —S(=O)$_2$NH(C$_{1-3}$alkyl), and —S(=O)$_2$N(C$_{1-3}$alkyl)$_2$, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

In another embodiment of this fifth aspect of the invention, the phenyl group of R10 has a substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the other substituents are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R1-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form an optionally substituted 4-7 member aryl or cycloalkyl ring; and R11 is an optionally substituted phenyl.

In one embodiment of the fifth aspect of the invention, R8 and R9 in the compounds of Formula I are taken together to form a 6 member aryl ring as in Formula III.

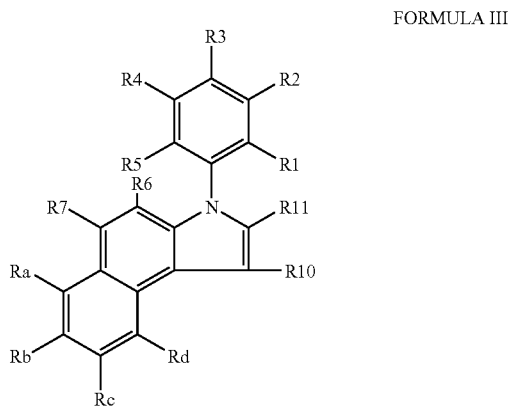

FORMULA III

According to one embodiment of the fifth aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the fifth aspect of the invention.

In one embodiment of the fifth aspect of the invention, R8 and R9 in the compounds of Formula II are taken together to form a 6 member aryl ring as in Formula IV.

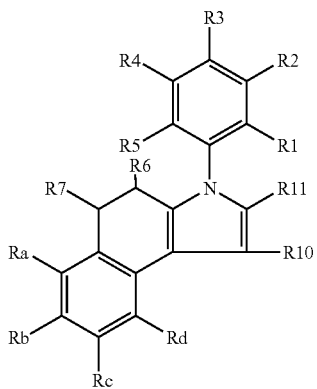

FORMULA IV

According to one embodiment of the fifth aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the fifth aspect of the invention.

In a sixth aspect, the invention provides compounds of Formula I and II:

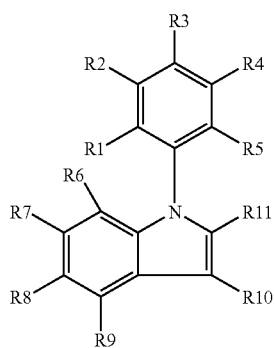

FORMULA I

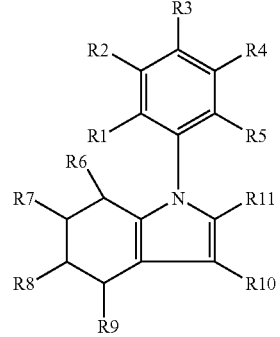

FORMULA II wherein R1-R9 and R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R10 is -L-R12 wherein L is as defined above; and

R12 is a phenyl ring substituted with one or more substituents independently chosen from of -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

According to one embodiment of the sixth aspect of the invention, one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH($C_{1-3}$alkyl), —C(=O)N($C_{1-3}$alkyl)$_2$, —S(=O)$_2$($C_{1-3}$alkyl), —S(=O)$_2$NH$_2$, —S(=O)$_2$NH($C_{1-3}$alkyl), and —S(=O)$_2$N($C_{1-3}$alkyl)$_2$, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$.

In another embodiment of this sixth aspect of the invention, one of the substituents of R12 is chosen from —C(=O)OH, —CH=CHC(=O)OH, —CH$_2$CH$_2$C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; and the others are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R1-R9, and R11, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂; and two adjacent of R6-R9 can be taken together to form an optionally substituted 4-7 member aryl or cycloalkyl ring.

In one embodiment of the sixth aspect of the invention, R8 and R9 in the compounds of Formula I are taken together to form a 6 member aryl ring as in Formula III.

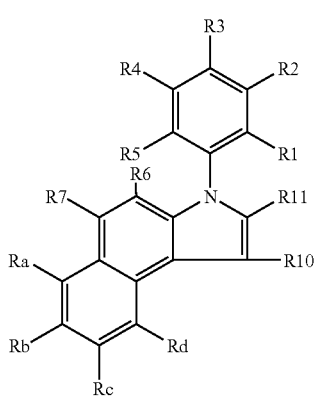

FORMULA III

According to one embodiment of the sixth aspect of the invention, compounds of Formula III are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O) OCH₂CH₃)-phenyl, and —O—Si(CH₃)₂(C(CH₃)₃); and the other variables can be defined as in one of the other embodiments of the sixth aspect of the invention.

In one embodiment of the sixth aspect of the invention, R8 and R9 in the compounds of Formula II are taken together to form a 6 member aryl ring as in Formula IV.

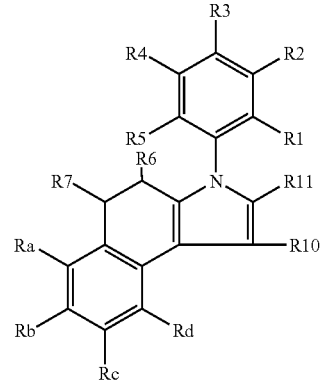

FORMULA IV

According to one embodiment of the sixth aspect of the invention, compounds of Formula IV are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O) OCH₂CH₃)-phenyl, and —O—Si(CH₃)₂(C(CH₃)₃); and the other variables can be defined as in one of the other embodiments of the sixth aspect of the invention.

In a seventh embodiment, the invention provides compounds of Formula I and II:

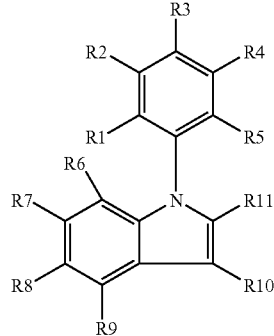

FORMULA I

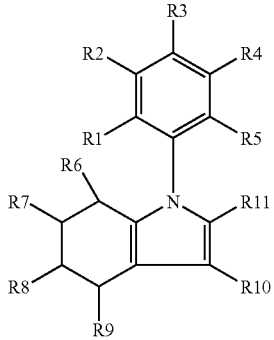

FORMULA II wherein R1-R10 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is -L-R12 wherein L is as defined above; and

R12 is a phenyl ring substituted with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)R$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl; and

L is as defined above.

According to one embodiment of this seventh aspect of the invention, one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —S(=O)$_2$NH($C_{1-3}$ alkyl), —C(=O)N($C_{1-3}$alkyl), —S(=O)$_2$NH$_2$, -and —S(=O)$_2$N($C_{1-3}$alkyl)$_2$, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$.

In another embodiment of this seventh aspect of the invention, one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R1-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form an optionally substituted 4-7 member aryl or cycloalkyl ring; and R11 is an optionally substituted phenyl.

In one embodiment of the seventh aspect of the invention, R8 and R9 in the compounds of Formula I are taken together to form a 6 member aryl ring as in Formula III

FORMULA III

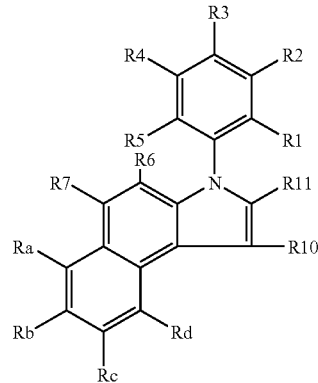

According to one embodiment of the seventh aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the seventh aspect of the invention.

In one embodiment of the seventh aspect of the invention, R8 and R9 in the compounds of Formula II are taken together to form a 6 member aryl ring as in Formula IV.

FORMULA IV

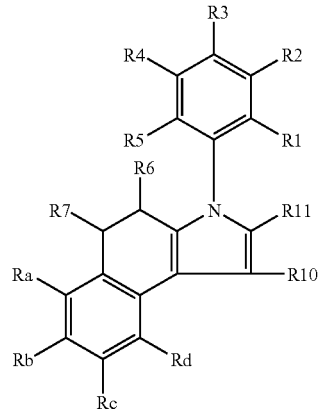

According to one embodiment of the seventh aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the seventh aspect of the invention.

In an eighth embodiment, the invention provides compounds of Formula I and II:

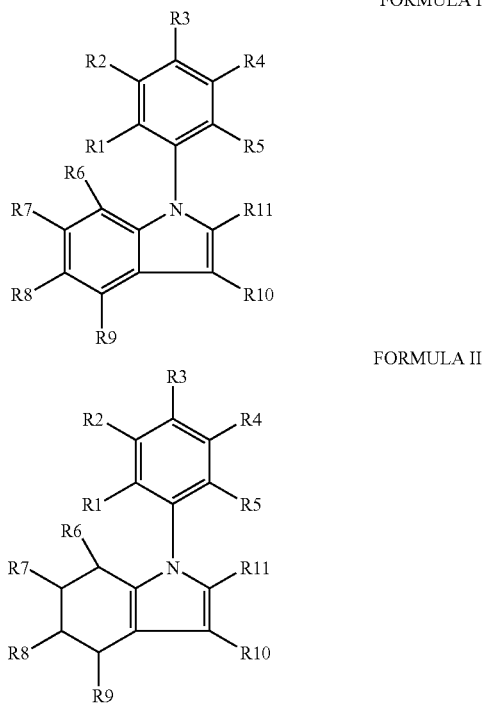

FORMULA I

FORMULA II wherein R1-R9 are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl ring;

R10 and R11 are independently chosen from hydro, hydroxyl, halo, alkyl, alkoxy, haloalkyl, haloalkoxy, —N($C_{1-3}$ alkyl)$_2$, —NH($C_{1-3}$ alkyl), —S(=O)$_2$($C_{1-3}$alkyl), —S(=O)$_2$NH$_2$, —S(=O)$_2$N($C_{1-3}$ alkyl)$_2$, —S(=O)$_2$NH ($C_{1-3}$ alkyl), —CHF$_2$, —OCF$_3$, —OCHF$_2$, —SCF$_3$, —CF$_3$, —CN, —NH$_2$, —NO$_2$, and -L-R12; and R12 is a phenyl ring substituted with one or more substituents independently chosen from -L-C(=O)OH, -L-CH=CHC(=O)OH, -L-C(=O)NH$_2$, -L-C(=O)NH ($C_{1-3}$ alkyl), -L-C(=O)N($C_{1-3}$ alkyl)$_2$, -L-S(=O)$_2$($C_{1-3}$ alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L is as defined above.

According to one embodiment of the eighth of the invention, R12 is present and one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$NH$_2$, —S(=O)$_2$NHCH$_3$, —S(=O)$_2$N(CH$_3$)$_2$, —C(=O)NH($C_{1-3}$ alkyl), —C(=O)N($C_{1-3}$alkyl)$_2$, —S(=O)$_2$($C_{1-3}$alkyl), —S(=O)$_2$NH$_2$, —S(=O)$_2$NH($C_{1-3}$alkyl), and —S(=O)$_2$N($C_{1-3}$alkyl)$_2$, and the others are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$.

In another embodiment of the eighth aspect of the invention, R12 is present and one substituent on the phenyl of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N($C_{1-3}$ alkyl)$_2$, —NH ($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R1-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form an optionally substituted 4-7 member aryl or cycloalkyl ring.

In one embodiment of the eighth aspect of the invention, R8 and R9 in the compounds of Formula I are taken together to form a 6 member aryl ring as in Formula III.

FORMULA III

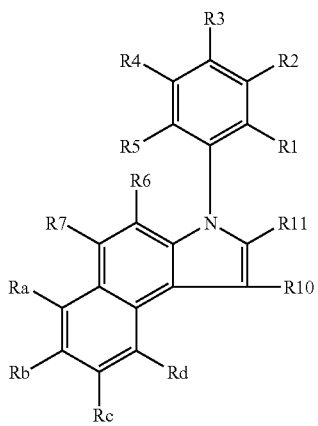

According to one embodiment of the eighth aspect of the invention, compounds of Formula III are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eighth aspect of the invention.

In one embodiment of the eighth aspect of the invention, R8 and R9 in the compounds of Formula II are taken together to form a 6 member aryl ring as in Formula IV.

FORMULA IV

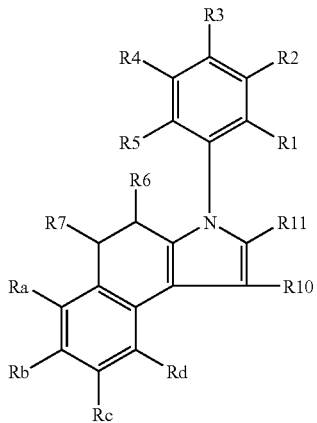

According to one embodiment of the eighth aspect of the invention, compounds of Formula IV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eighth aspect of the invention.

In a ninth aspect, the invention provides compounds of Formula V and VI:

FORMULA V

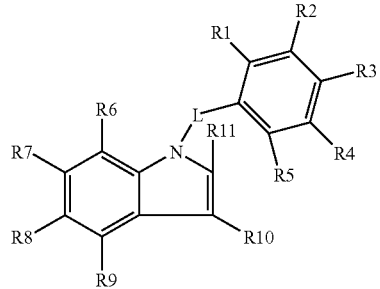

FORMULA VI

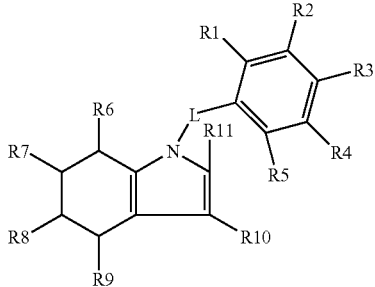

wherein one or more of R1-R5 is independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; the others of R1-R5, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

L is as defined above;

R6-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring; and R11 is an optionally substituted phenyl group.

In one sub-embodiment, R3 is not hydroxyl

According to one embodiment of this ninth aspect of the invention, one of R1-R5 is chosen from —C(=O)OH, —CH$_2$CH$_2$C(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$alkyl), —S(=O)$_2$NH$_2$, —S(=O)$_2$NHCH$_3$, —S(=O)$_2$N(CH$_3$)$_2$, —C(=O)NH(C$_{1-3}$ alkyl), —C(=O)N(C$_{1-3}$alkyl)$_2$, —S(=O)$_2$NH$_2$, —S(=O)$_2$NH(C$_{1-3}$alkyl), and —S(=O)$_2$N(C$_{1-3}$alkyl)$_2$, and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

In another embodiment of this ninth aspect of the invention, L is a bond, one of R1-R5 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH; and the others are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; or two adjacent of R6-R9 can be taken together to form an optionally substituted 4-7 member aryl or cycloalkyl ring.

In one embodiment of the ninth aspect of the invention, R8 and R9 in the compound of Formula V are taken together to form a 6 member aryl ring as in Formula VII.

FORMULA VII

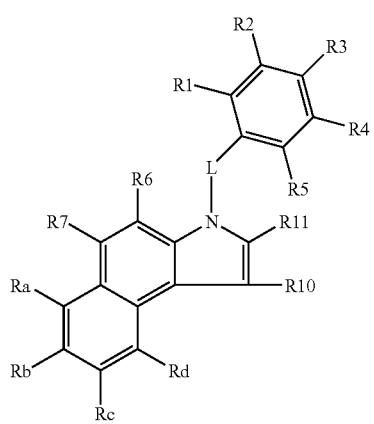

According to one embodiment of the ninth aspect of the invention, compounds of Formula VII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the ninth aspect of the invention.

In one embodiment of the ninth aspect of the invention, R8 and R9 in the compounds of Formula VI are taken together to form a 6 member aryl ring as in Formula VIII.

FORMULA VIII

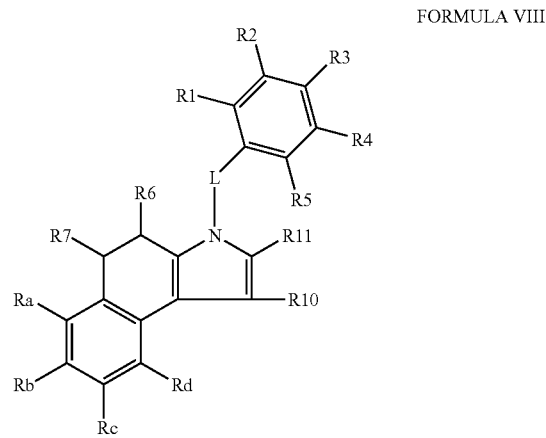

According to one embodiment of the ninth aspect of the invention, compounds of Formula VIII are provided wherein Ra, Rb, Rc, and Rd are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the ninth aspect of the invention.

In a tenth aspect, the invention provides compounds of Formula IX and X:

FORMULA IX

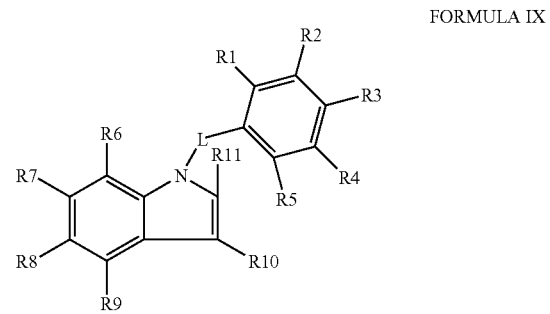

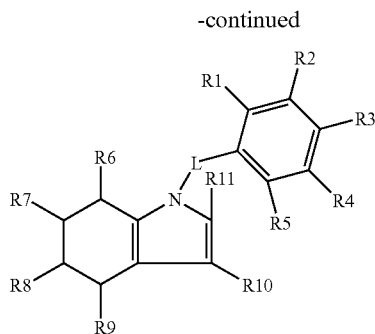

FORMULA X wherein one or more of R1-R11 are chosen from -L-R12, -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR$_o$, -L-C(=O)NHR$_o$, -L-NH(C=O)NHR$_o$, -L-C(=O)N(R$_o$)₂, -L-NH(C=O)N(R$_o$)₂, -L-sulfo, -L-(2,6 difluorophenol), -L-phosphono, and -L-tetrazolyl; wherein R12 is a phenyl ring substituted with one or more substituents independently chosen from -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR$_o$, -L-C(=O)NHR$_o$, -L-NH(C=O)NHR$_o$, -L-C(=O)N(R$_o$)₂, -L-NH(C=O)N(R$_o$)₂, -L-sulfo, -L-(2,6 difluorophenol), -L-phosphono, and -L-tetrazolyl, and the others are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R$_o$ is chosen from alkyl and haloalkyl;

L is as defined above; and the others of R1-R11 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂; and two adjacent of R6-R9 can be taken together to form a 4-7 member optionally substituted aryl or cycloalkyl ring.

In another embodiment of this tenth aspect of the invention, L is a bond, R12 is present and one substituents on the phenyl of R12 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; and the others are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R1-R9, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂; and two adjacent of R6-R9 can be taken together to form an optionally substituted 4-7 member aryl or cycloalkyl ring.

In one embodiment of the tenth aspect of the invention, R8 and R9 in the compounds of Formula IX are taken together to form a 6 member aryl ring as in Formula XI

FORMULA XI

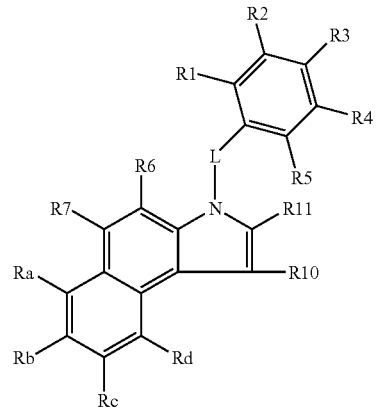

According to one embodiment of the tenth aspect of the invention, compounds of Formula XI are provided wherein Ra, Rb, Rc, and Rd are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); and the other variables can be defined as in one of the other embodiments of the tenth aspect of the invention.

In one embodiment of the tenth aspect of the invention, R8 and R9 in the compounds of Formula X are taken together to form a 6 member aryl ring as in Formula XII.

FORMULA XII

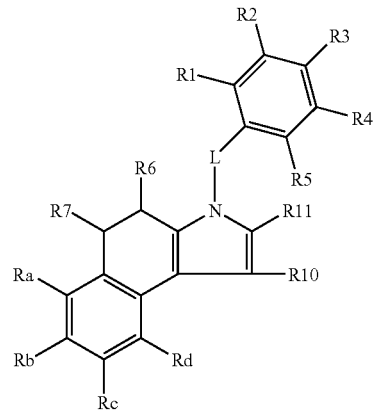

According to one embodiment of the tenth aspect of the invention, compounds of Formula XII are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the tenth aspect of the invention.

In an eleventh aspect, the invention provides compounds of Formula XIII and XIV:

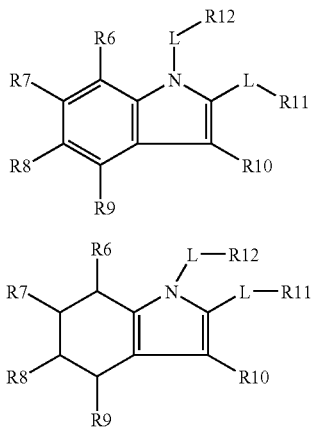

FORMULA XIII

FORMULA XIV wherein L is as defined above or is selected from an optionally substituted, saturated or partially saturated cyclopropyl, cyclobutyl, cyclopentyl, cyclohexyl, cycloheptyl, and $C_{1-12}$ alkyl;

R1-R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl or cycloalkyl ring;

R11 is chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

R12 is chosen from optionally substituted $C_{1-12}$ alkyl, phenyl, and $C_{3-7}$ cycloalkyl.

In one embodiment of the eleventh aspect of the invention, R8 and R9 in the compounds of Formula XIII are taken together to form a 6 member aryl ring as in Formula XV.

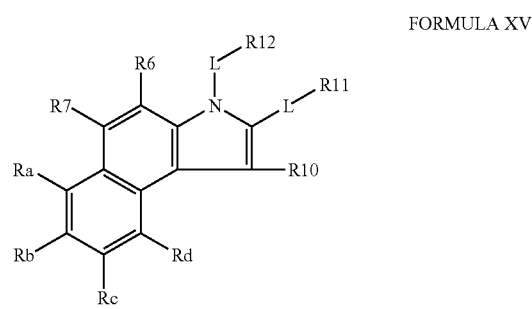

FORMULA XV

According to one embodiment of the eleventh aspect of the invention, compounds of Formula XV are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In one embodiment of the eleventh aspect of the invention, R8 and R9 in the compounds of Formula XIV are taken together to form a 6 member aryl ring as in Formula XVI.

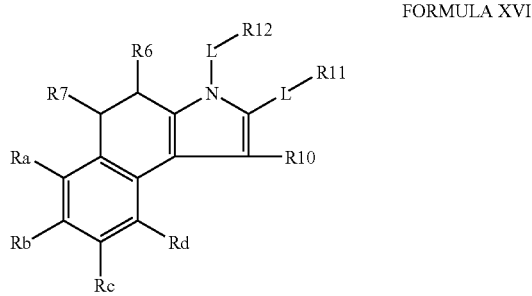

FORMULA XVI

According to one embodiment of the eleventh aspect of the invention, compounds of Formula XVI are provided wherein Ra, Rb, Rc, and Rd are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); and the other variables can be defined as in one of the other embodiments of the eleventh aspect of the invention.

In a twelfth aspect, the invention provides compounds of Formula I and II pharmaceutically acceptable salts thereof, and pharmaceutical compositions having such compounds:

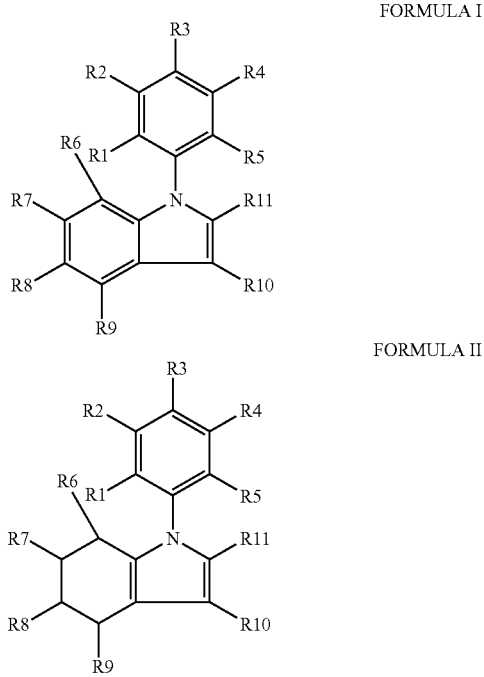

FORMULA I

FORMULA II wherein one or more of R1-R5 is chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$ alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl, and the others of R1-R5, independent of one another, are chosen hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(═O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the twelfth aspect of the invention, one of R1-R5 in the compounds of Formulae I and II, is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, —C(CH$_3$)$_2$C(═O)OH, —C(═O)NH$_2$, —C(═O)NHCH$_3$, —C(═O)N(CH$_3$)$_2$, —S(═O)$_2$(C$_{1-3}$ alkyl), —S(═O)$_2$NH$_2$, —S(═O)$_2$NHCH$_3$, —S(═O)$_2$N(CH$_3$)$_2$, —C(═O)NH(C$_{1-3}$alkyl), —C(═O)N(C$_{1-3}$alkyl)$_2$, —S(═O)$_2$NH$_2$, —S(═O)$_2$N(C$_{1-3}$alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is —(CH$_2$)$_n$—(CH$_2$)$_n$—, with n independently 0, 1, 2, or 3; and

R11 is an optionally substituted heterocyclic group.

In another embodiment of this twelfth aspect of the invention, one of R1-R5 is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, and —C(CH$_3$)$_2$C(═O)OH; and the others of R1-R5 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two of R6-R9 can be taken together to form an optionally substituted C$_{4-7}$ member aryl, heterocyclic, or cycloalkyl ring; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2, 3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a thirteenth aspect, the invention provides compounds of Formula I and II:

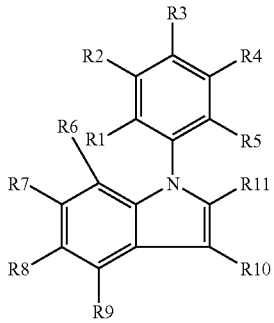

FORMULA I

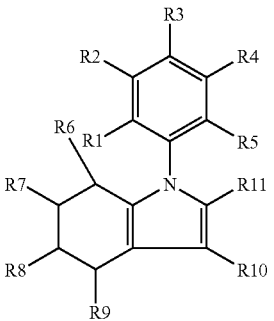

FORMULA II wherein R1-R5, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$NH$_2$, —S(=O)$_2$($C_{1-3}$alkyl), —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

one or more of R6-R9 is independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; or two adjacent of R6-R9 can be taken together to form an optionally substituted 4-7 member aryl, heterocyclic, or cycloalkyl ring substituted with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl; and the others of R6-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently selected from 0, 1, 2, 3, 4, 5, 6, 7, and 8, wherein each carbon can be optionally substituted with one or more $C_{1-3}$ alkyl or $C_{3-6}$ cycloalkyl.

In one embodiment of the thirteenth aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —C(=O)NH($C_{1-3}$ alkyl), —C(=O)N($C_{1-3}$alkyl)$_2$, —S(=O)$_2$NH$_2$, and —S(=O)$_2$N($C_{1-3}$alkyl)$_2$; or two adjacent of R6-R9 can be taken together to form an optionally substituted 4-7 member aryl, heterocyclic, or cycloalkyl ring substituted with one or more substituents chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —C(=O)NH($C_{1-3}$alkyl), —C(=O)N($C_{1-3}$alkyl)$_2$, —S(=O)$_2$NH$_2$, and —S(=O)$_2$N($C_{1-3}$alkyl)$_2$; and the others of R6-R9, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R1-R5, and R10, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R11 is an optionally substituted heterocyclic group.

In another embodiment of this thirteenth aspect of the invention, one of R6-R9 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH₃)C(═O)OH, —CH(CH₂CH₃)C(═O)OH, —C(CH₃)(CH₂CH₃)C(═O)OH, —CH═C(CH₃)C(═O)OH, —C(CH₂CH₃)₂C(═O)OH, —CH₂C(═O)OH, and —C(CH₃)₂C(═O)OH; or two adjacent of R6-R9 can be taken together to form an optionally substituted 4-7 member aryl, heterocyclic, or cycloalkyl ring substituted with one or more substituents chosen from —C(═O)OH, —CH═CHC(═O)OH, —CH₂CH₂C(═O)OH, —CH₂CH₂CH₂C(═O)OH, —C(CH₂CH₂)C(═O)OH, —CH(CH₃)C(═O)OH, —CH(CH₂CH₃)C(═O)OH, —C(CH₃)(CH₂CH₃)C(═O)OH, —CH═C(CH₃)C(═O)OH, —C(CH₂CH₃)₂C(═O)OH, —CH₂C(═O)OH, and —C(CH₃)₂C(═O)OH; and the others of R6-R9 independently are chosen from hydro, hydroxyl, halo, alkyl, alkoxy, haloalkyl, haloalkoxy, —N(C₁₋₃ alkyl)₂, —NH(C₁₋₃ alkyl), —C(═O)NH₂, —C(═O)NH(C₁₋₃ alkyl), —C(═O)N(C₁₋₃ alkyl)₂, —S(═O)₂(C₁₋₃alkyl), —S(═O)₂NH₂, —S(═O)₂N(C₁₋₃ alkyl)₂, —S(═O)₂NH(C₁₋₃ alkyl), —CHF₂, —OCF₃, —OCHF₂, —SCF₃, —CF₃, —CN, —NH₂, and —NO₂;

R1-R5, and R10, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(═O)NH₂, —C(═O)NH(C₁₋₃ alkyl), —C(═O)N(C₁₋₃ alkyl)₂, —S(═O)₂(C₁₋₃alkyl), —S(═O)₂NH₂, —S(═O)₂N(C₁₋₃ alkyl)₂, —S(═O)₂NH(C₁₋₃ alkyl), —CHF₂, —OCF₃, —OCHF₂, —SCF₃, —CF₃, —CN, —NH₂, and —NO₂; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a fourteenth aspect, the invention provides compounds of Formula I and II:

FORMULA I

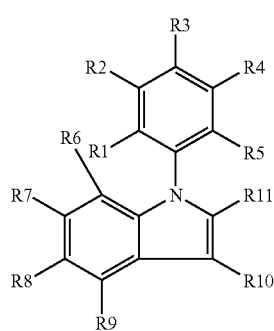

FORMULA II

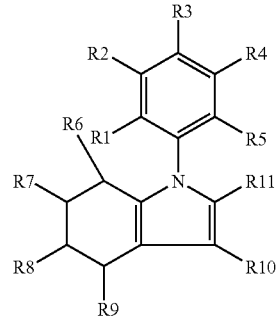

wherein R1-R9 are independently chosen hydro, hydroxyl, halo, alkyl, alkoxy, haloalkyl, haloalkoxy, —N(C₁₋₃ alkyl)₂, —NH(C₁₋₃ alkyl), —C(═O)NH₂, —C(═O)NH(C₁₋₃ alkyl), —C(═O)N(C₁₋₃ alkyl)₂, —S(═O)₂(C₁₋₃alkyl), —S(═O)₂NH₂, —S(═O)₂N(C₁₋₃ alkyl)₂, —S(═O)₂NH(C₁₋₃ alkyl), —CHF₂, —OCF₃, —OCHF₂, —SCF₃, —CF₃, —CN, —NH₂, —NO₂, —C(═O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(═O)OCH₂CH₃ substituted furanyl, para-(C(═O)OCH₂CH₃)-phenyl, and —O—Si(CH₃)₂(C(CH₃)₃); two adjacent of R6-R9 can be taken together to form an optionally substituted C₄₋₇ member aryl, heterocyclic, or cycloalkyl ring;

R10 is chosen from -L-C(═O)OH, -L-CH═CHC(═O)OH, -L-C(═O)NH₂, -L-C(═O)NH(C₁₋₃ alkyl), -L-C(═O)N(C₁₋₃ alkyl)₂, -L-S(═O)₂(C₁₋₃alkyl), -L-S(═O)₂NH₂, -L-S(═O)₂N(C₁₋₃ alkyl)₂, -L-S(═O)₂NH(C₁₋₃ alkyl), -L-C(═O)NHOH, -L-C(═O)CH₂NH₂, -L-C(═O)CH₂OH, -L-C(═O)CH₂SH, -L-C(═O)NHCN, -L-NHC(═O)OR_o, -L-C(═O)NHR_o, -L-NH(C═O)NHR_o, -L-C(═O)N(R_o)₂, -L-NH(C═O)N(R_o)₂, -L-sulfo, -L-(2,6 difluorophenol), -L-phosphono, and -L-tetrazolyl;

R_o is chosen from alkyl and haloalkyl;

R11 is an optionally substituted heterocyclic group; and

L can be saturated, partially saturated, or unsaturated, and is chosen from —(CH₂)ₙ—(CH₂)ₙ—, —(CH₂)ₙC(═O)(CH₂)ₙ—, —(CH₂)ₙNH(CH₂)ₙ—, —(CH₂)ₙO(CH₂)ₙ—, and —(CH₂)ₙS(CH₂)ₙ—, where each n is independently chosen from 0, 1, 2, 3, 4, 5, 6, 7, and 8, wherein each carbon can be optionally substituted with one or more C₁₋₃ alkyl or C₃₋₆ cycloalkyl;

In one embodiment of the fourteenth aspect of the invention, R10 is chosen from —C(═O)OH, —CH═CHC(═O)OH, —CH₂CH₂C(═O)OH, —CH₂CH₂CH₂C(═O)OH, —C(CH₂CH₂)C(═O)OH, —CH(CH₃)C(═O)OH, —CH(CH₂CH₃)C(═O)OH, —C(CH₃)(CH₂CH₃)C(═O)OH, —CH═C(CH₃)C(═O)OH, —C(CH₂CH₃)₂C(═O)OH, —CH₂C(═O)OH, —C(CH₃)₂C(═O)OH, —C(═O)NH₂, —C(═O)NHCH₃, —C(═O)N(CH₃)₂, —S(═O)₂(C₁₋₃ alkyl), —S(═O)₂NH₂, —S(═O)₂NHCH₃, —S(═O)₂N(CH₃)₂, —C(═O)NH(C₁₋₃alkyl), —C(═O)N(C₁₋₃alkyl)₂, —S(═O)₂NH₂, and —S(═O)₂N(C₁₋₃alkyl)₂; and R11 is an optionally substituted heterocyclic group.

In another embodiment of this third aspect of the invention, R10 is chosen from —C(═O)OH, —CH═CHC(═O)OH, —CH₂CH₂C(═O)OH, —CH₂CH₂CH₂C(═O)OH, —C(CH₂CH₂)C(═O)OH, —CH(CH₃)C(═O)OH, —CH(CH₂CH₃)C(═O)OH, —C(CH₃)(CH₂CH₃)C(═O)OH, —CH═C(CH₃)C(═O)OH, —C(CH₂CH₃)₂C(═O)OH, —CH₂C(═O)OH, and —C(CH₃)₂C(═O)OH; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a fifteenth aspect, the invention provides compounds of Formula I and II:

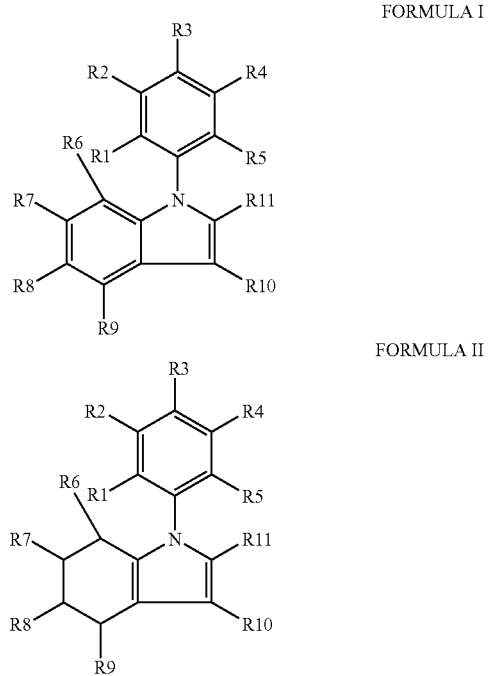

FORMULA I

FORMULA II wherein R1-R10, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(═O)NH₂, —C(═O)NH(C₁₋₃ alkyl), —C(═O)N(C₁₋₃ alkyl)₂, —S(═O)₂(C₁₋₃alkyl), —S(═O)₂NH₂, —S(═O)₂N(C₁₋₃ alkyl)₂, —S(═O)₂NH(C₁₋₃ alkyl), —CHF₂, —OCF₃, —OCHF₂, —SCF₃, —CF₃, —CN, —NH₂, —NO₂, —C(═O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(═O)OCH₂CH₃ substituted furanyl, para-(C(═O) OCH₂CH₃)-phenyl, and —O—Si(CH₃)₂(C(CH₃)₃); two adjacent of R6-R9 can be taken together to form a 4-7 member optionally substituted aryl, heterocyclic, or cycloalkyl ring;

R11 is a heterocyclic group with one or more substituents independently chosen from -L-C(═O)OH, -L-CH═CHC(═O)OH, -L-C(═O)NH₂, -L-C(═O)NH(C₁₋₃ alkyl), -L-C(═O)N(C₁₋₃ alkyl)₂, -L-S(═O)₂(C₁₋₃alkyl), -L-S(═O)₂NH₂, -L-S(═O)₂N(C₁₋₃ alkyl)₂, -L-S(═O)₂NH(C₁₋₃ alkyl), -L-C(═O)NHOH, -L-C(═O)CH₂NH₂, -L-C(═O)CH₂OH, -L-C(═O)CH₂SH, -L-C(═O)NHCN, -L-NHC(═O)OR₀, -L-C(═O)NHR₀, -L-NH(C═O)NHR₀, -L-C(═O)N(R₀)₂, -L-NH(C═O)N(R₀)₂, -L-sulfo, -L-(2,6 difluorophenol), -L-phosphono, and -L-tetrazolyl;

R₀ is chosen from alkyl and haloalkyl; and

L can be saturated, partially saturated, or unsaturated, and is chosen from —(CH₂)ₙ—(CH₂)ₙ—, —(CH₂)ₙC(═O) (CH₂)ₙ—, —(CH₂)ₙNH(CH₂)ₙ—, —(CH₂)ₙO(CH₂)ₙ—, and —(CH₂)ₙ(CH₂)ₙ—, where each n is independently chosen from 0, 1, 2, 3, 4, 5, 6, 7, and 8, wherein each carbon can be optionally substituted with one or more C₁₋₃ alkyl or C₃₋₆ cycloalkyl.

In one embodiment of the fifteenth aspect of the invention, one substituent on the heterocyclic group of R11 is chosen from —C(═O)OH, —CH═CHC(═O)OH, —CH₂CH₂C(═O)OH, —CH₂CH₂CH₂C(═O)OH, —C(CH₂CH₂)C(═O)OH, —CH(CH₃)C(═O)OH, —CH(CH₂CH₃)C(═O)OH, —C(CH₃)(CH₂CH₃)C(═O)OH, —CH═C(CH₃)C(═O)OH, —C(CH₂CH₃)₂C(═O)OH, —CH₂C(═O)OH, —C(CH₃)₂C(═O)OH, —C(═O)NH₂, —C(═O)NHCH₃, —C(═O)N(CH₃)₂, —S(═O)₂(C₁₋₃alkyl), —S(═O)₂NH₂, —S(═O)₂NHCH₃, —S(═O)₂N(CH₃)₂, —C(═O)NH(C₁₋₃ alkyl), —C(═O)N(C₁₋₃alkyl)₂, —S(═O)₂NH₂, and —S(═O)₂N(C₁₋₃alkyl)₂.

In another embodiment of this fifteenth aspect of the invention, one of the substituents on the heterocyclic group of R11 is chosen from —C(═O)OH, —CH═CHC(═O)OH, —CH₂CH₂C(═O)OH, —CH₂CH₂CH₂C(═O)OH, —C(CH₂CH₃)C(═O)OH, —CH(CH₃)C(═O)OH, —CH(CH₂CH₃)C(═O)OH, —C(CH₃)(CH₂CH₃)C(═O)OH, —CH═C(CH₃)C(═O)OH, —C(CH₂CH₃)₂C(═O)OH, —CH₂C(═O)OH, and —C(CH₃)₂C(═O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a sixteenth aspect, the invention provides compounds of Formula I and II:

FORMULA I

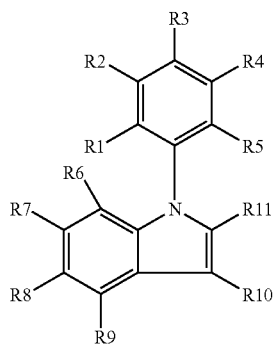

FORMULA II

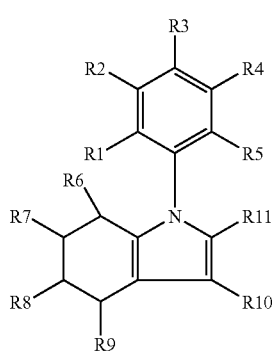

wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In one embodiment of the sixteenth aspect of the invention, one substituent on the heterocyclic group of R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$alkyl), —S(=O)$_2$NH$_2$, —S(=O)$_2$NHCH$_3$, —S(=O)$_2$N(CH$_3$)$_2$, —C(=O)NH($C_{1-3}$ alkyl), —C(=O)N($C_{1-3}$alkyl)$_2$, —S(=O)$_2$NH$_2$, and —S(=O)$_2$N($C_{1-3}$alkyl)$_2$.

In another embodiment of this sixteenth aspect of the invention, one substituent on the heterocyclic group of R10 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a seventeenth aspect, the invention provides compounds of Formula I and II:

FORMULA I

FORMULA II wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is -L-R12;

R12 is a heterocyclic group with one or more substituents chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more $C_{1-3}$ alkyl or $C_{3-6}$ cycloalkyl.

In one embodiment of the seventeenth aspect of the invention, one substituent on the heterocyclic group of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$($C_{1-3}$ alkyl), —S(=O)$_2$NH$_2$, —S(=O)$_2$NHCH$_3$, —S(=O)$_2$N(CH$_3$)$_2$, —C(=O)NH($C_{1-3}$alkyl), —C(=O)N($C_{1-3}$alkyl)$_2$, —S(=O)$_2$NH$_2$, and —S(=O)$_2$N($C_{1-3}$alkyl)$_2$.

In another embodiment of this seventeenth aspect of the invention, one of the substituent on the heterocyclic group of R12 is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In an eighteenth embodiment, the invention provides compounds of Formula I and II:

FORMULA I

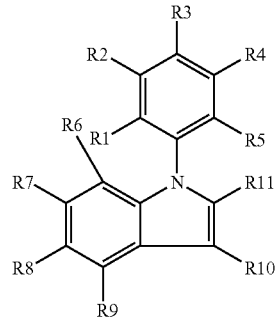

FORMULA II

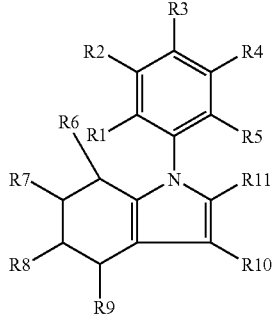

wherein R1-R9 and R11 independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 is a heterocyclic group with one or more substituents independently chosen from -L-C(=O)OH, -L-CH=CHC(=O)OH, -L-C(=O)NH$_2$, -L-C(=O)NH($C_{1-3}$ alkyl), -L-C(=O)N($C_{1-3}$ alkyl)$_2$, -L-S(=O)$_2$($C_{1-3}$alkyl), -L-S(=O)$_2$NH$_2$, -L-S(=O)$_2$N($C_{1-3}$ alkyl)$_2$, -L-S(=O)$_2$NH($C_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(═O)(CH$_2$)$_n$—, —(CH$_2$)$_n$NH(CH$_2$)$_n$—, —(CH$_2$)$_n$O(CH$_2$)$_n$—, and —(CH$_2$)$_n$(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the eighteenth aspect of the invention, one substituent on the heterocyclic group of R10 is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, —C(CH$_3$)$_2$C(═O)OH, —C(═O)NH$_2$, —C(═O)NHCH$_3$, —C(═O)N(CH$_3$)$_2$, —S(═O)$_2$(C$_{1-3}$ alkyl), —S(═O)$_2$NH$_2$, —S(═O)$_2$NHCH$_3$, —S(═O)$_2$N(CH$_3$)$_2$, —C(═O)NH(C$_{1-3}$alkyl), —C(═O)N(C$_{1-3}$alkyl)$_2$, —S(═O)$_2$NH$_2$, and —S(═O)$_2$N(C$_{1-3}$alkyl)$_2$.

In another embodiment of the eighteenth aspect of the invention, one substituent on the heterocyclic group of R10 is chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, and —C(CH$_3$)$_2$C(═O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenoxazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a nineteenth aspect, the invention provides compounds of Formula I and II:

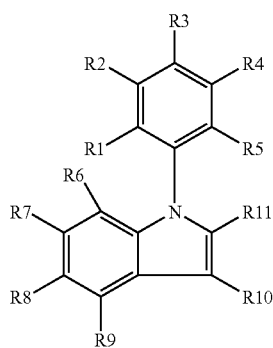

FORMULA I

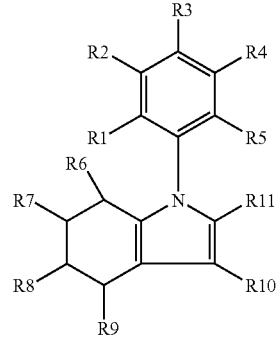

FORMULA II wherein R1-R9, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$(C$_{1-3}$alkyl), —S(═O)$_2$NH$_2$, —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(═O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(═O)OCH$_2$CH$_3$ substituted furanyl, para-(C(═O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R10 and R11 are independently chosen from hydro, hydroxyl, halo, alkyl, alkoxy, haloalkyl, haloalkoxy, —N(C$_{1-3}$ alkyl)$_2$, —NH(C$_{1-3}$ alkyl), —C(═O)NH$_2$, —C(═O)NH(C$_{1-3}$ alkyl), —C(═O)N(C$_{1-3}$ alkyl)$_2$, —S(═O)$_2$NH$_2$, —S(═O)$_2$(C$_{1-3}$alkyl), —S(═O)$_2$N(C$_{1-3}$ alkyl)$_2$, —S(═O)$_2$NH(C$_{1-3}$ alkyl), —CHF$_2$, —OCF$_3$, —OCHF$_2$, —SCF$_3$, —CF$_3$, —CN, —NH$_2$, —NO$_2$, and -L-R12;

R12 is a heterocyclic group with one or more substituents independently chosen from -L-C(═O)OH, -L-CH═CHC(═O)OH, -L-C(═O)NH$_2$, -L-C(═O)NH(C$_{1-3}$ alkyl), -L-C(═O)N(C$_{1-3}$ alkyl)$_2$, -L-S(═O)$_2$(C$_{1-3}$alkyl), -L-S(═O)$_2$NH$_2$, -L-S(═O)$_2$N(C$_{1-3}$ alkyl)$_2$, -L-S(═O)$_2$NH(C$_{1-3}$ alkyl), -L-C(═O)NHOH, -L-C(═O)CH$_2$NH$_2$, -L-C(═O)CH$_2$OH, -L-C(═O)CH$_2$SH, -L-C(═O)NHCN, -L-NHC(═O)OR$_o$, -L-C(═O)NHR$_o$, -L-NH(C═O)NHR$_o$, -L-C(═O)N(R$_o$)$_2$, -L-NH(C═O)N(R$_o$)$_2$, -L-sulfo, -L-(2,6 difluorophenol), -L-phosphono, and -L-tetrazolyl;

R$_o$ is chosen from alkyl and haloalkyl; and

L can be saturated, partially saturated, or unsaturated, and is chosen from —(CH$_2$)$_n$—(CH$_2$)$_n$—, —(CH$_2$)$_n$C(═O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the nineteenth aspect of the invention, R12 is present and has one or more substituents independently chosen from —C(═O)OH, —CH═CHC(═O)OH, —CH$_2$CH$_2$C(═O)OH, —CH$_2$CH$_2$CH$_2$C(═O)OH, —C(CH$_2$CH$_2$)C(═O)OH, —CH(CH$_3$)C(═O)OH, —CH(CH$_2$CH$_3$)C(═O)OH, —C(CH$_3$)(CH$_2$CH$_3$)C(═O)OH, —CH═C(CH$_3$)C(═O)OH, —C(CH$_2$CH$_3$)$_2$C(═O)OH, —CH$_2$C(═O)OH, —C(CH$_3$)$_2$C(═O)OH, —C(═O)NH$_2$, —C(═O)NHCH$_3$, —C(═O)N(CH$_3$)$_2$, —S(═O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In another embodiment of this nineteenth aspect of the invention, R12 is present and has one substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a twentieth aspect, the invention provides compounds of Formula V and VI:

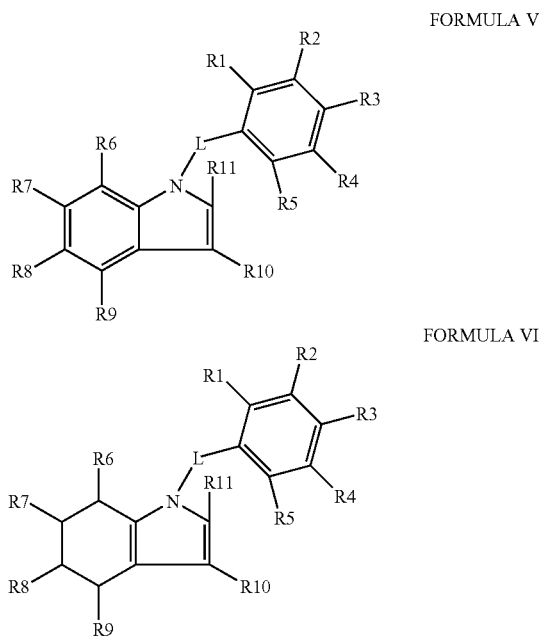

FORMULA V

FORMULA VI wherein one or more of R1-R5 is independently chosen from -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, -L-C(=O)CH$_2$OH, -L-C(=O)CH$_2$SH, -L-C(=O)NHCN, -L-NHC(=O)OR$_o$, -L-C(=O)NHR$_o$, -L-NH(C=O)NHR$_o$, -L-C(=O)N(R$_o$)$_2$, -L-NH(C=O)N(R$_o$)$_2$, -L-sulfo, -L-(2,6 difluorophenol), -L-phosphono, and -L-tetrazolyl, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R$_o$ is chosen from alkyl and haloalkyl;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); two adjacent of R6-R9 can be taken together to form a 4-7 member optionally substituted aryl, heterocyclic, or cycloalkyl ring;

R11 is an optionally substituted heterocyclic group; and

L can be saturated, partially saturated, or unsaturated, and is chosen from —(CH$_2$)$_n$—(CH$_2$)$_n$—, —(CH$_2$)$_n$C(=O)(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, 3, 4, 5, 6, 7, and 8, wherein each carbon can be optionally substituted with one or more C$_{1-3}$ alkyl or C$_{3-6}$ cycloalkyl.

In one embodiment of the twentieth aspect of the invention, one of R1-R5 in the compounds of Formulae I and II, is chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, —C(CH$_3$)$_2$C(=O)OH, —C(=O)NH$_2$, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$, and the others of R1-R5, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6-R10, independent of one another, are chosen from hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$; two adjacent of R6-R9 can be taken together to form a 4-7 member optionally substituted aryl or cycloalkyl ring;

L is —(CH$_2$)$_n$—(CH$_2$)$_n$—, with n independently 0, 1, 2, or 3; and

R11 is an optionally substituted heterocyclic group.

In another embodiment of this twentieth of the invention, L is a bond, one of R1-R5 is chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, and —C(CH₃)₂C(=O)OH; and the others of R1-R5 independently are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂;

R6-R10, independent of one another, are chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, and —NO₂; two of R6-R9 can be taken together to form an optionally substituted 4-7 member aryl, heterocyclic, or cycloalkyl ring; and R11 is an optionally substituted heterocyclic group.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In a twenty-first aspect, the invention provides compounds of Formula V and VI:

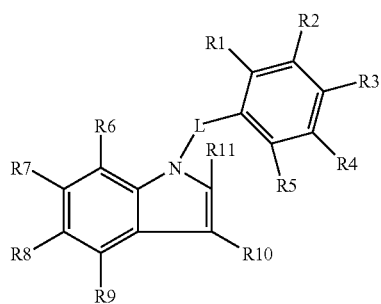

FORMULA V

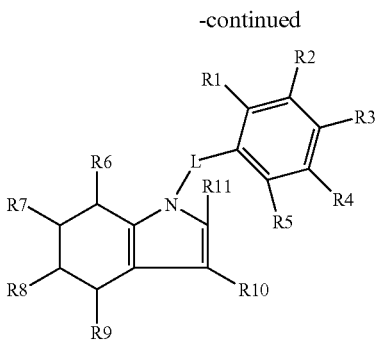

FORMULA VI wherein R1-R11, independent of one another, are chosen from -L-R12, -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR_o, -L-C(=O)NHR_o, -L-NH(C=O)NHR_o, -L-C(=O)N(R_o)₂, -L-NH(C=O)N(R_o)₂, -L-sulfo, -L-(2,6 difluorophenol), -L-phosphono, and -L-tetrazolyl;

R_o is chosen from alkyl and haloalkyl;

R12 is a heterocyclic group with one or more substituents independently chosen -L-C(=O)OH, -L-CH=CHC(=O)OH, -L-C(=O)NH₂, -L-C(=O)NH(C₁₋₃ alkyl), -L-C(=O)N(C₁₋₃ alkyl)₂, -L-S(=O)₂(C₁₋₃alkyl), -L-S(=O)₂NH₂, -L-S(=O)₂N(C₁₋₃ alkyl)₂, -L-S(=O)₂NH(C₁₋₃ alkyl), -L-C(=O)NHOH, -L-C(=O)CH₂NH₂, -L-C(=O)CH₂OH, -L-C(=O)CH₂SH, -L-C(=O)NHCN, -L-NHC(=O)OR_o, -L-C(=O)NHR_o, -L-NH(C=O)NHR_o, -L-C(=O)N(R_o)₂, -L-NH(C=O)N(R_o)₂, -L-sulfo, -L-(2,6 difluorophenol), -L-phosphono, and -L-tetrazolyl; and the others of R1-R11 are independently chosen from hydro, hydroxyl, halo, alkyl, alkoxy, haloalkyl, haloalkoxy, —N(C₁₋₃ alkyl)₂, —NH(C₁₋₃ alkyl), —C(=O)NH₂, —C(=O)NH(C₁₋₃ alkyl), —C(=O)N(C₁₋₃ alkyl)₂, —S(=O)₂(C₁₋₃alkyl), —S(=O)₂NH₂, —S(=O)₂N(C₁₋₃ alkyl)₂, —S(=O)₂NH(C₁₋₃ alkyl), —CHF₂, —OCF₃, —OCHF₂, —SCF₃, —CF₃, —CN, —NH₂, —NO₂, —C(=O)—N-morpholino, -cyclohexyl, -morpholino, -pyrrolidinyl, -piperazinyl, —(N-methyl)-piperazinyl, —OCH₂-phenyl, -pyridinyl, methylenedioxy, ethylenedioxy, —C(=O)OCH₂CH₃ substituted furanyl, para-(C(=O)OCH₂CH₃)-phenyl, and —O—Si(CH₃)₂(C(CH₃)₃); two adjacent of R6-R9 can be taken together to form a 4-7 member optionally substituted aryl, heterocyclic, or cycloalkyl ring; and L can be saturated, partially saturated, or unsaturated, and is chosen from —(CH₂)_n—(CH₂)_n—, —(CH₂)_nC(=O)(CH₂)_n—, —(CH₂)_nNH(CH₂)_n—, —(CH₂)_nO(CH₂)_n—, and —(CH₂)_n(CH₂)_n—, where each n is independently chosen from 0, 1, 2, 3, 4, 5, 6, 7, and 8, wherein each carbon can be optionally substituted with one or more C₁₋₃ alkyl or C₃₋₆ cycloalkyl.

In one embodiment of the twenty-first aspect of the invention, R12 is present and has one or more substituents independently chosen from —C(=O)OH, —CH=CHC(=O)OH, —CH₂CH₂C(=O)OH, —CH₂CH₂CH₂C(=O)OH, —C(CH₂CH₂)C(=O)OH, —CH(CH₃)C(=O)OH, —CH(CH₂CH₃)C(=O)OH, —C(CH₃)(CH₂CH₃)C(=O)OH, —CH=C(CH₃)C(=O)OH, —C(CH₂CH₃)₂C(=O)OH, —CH₂C(=O)OH, —C(CH₃)₂C(=O)OH, —C(=O)NH₂, —C(=O)NHCH$_3$, —C(=O)N(CH$_3$)$_2$, —S(=O)$_2$(C$_{1-3}$ alkyl), —S(=O)$_2$NH$_2$, —S(=O)$_2$NHCH$_3$, —S(=O)$_2$N(CH$_3$)$_2$, —C(=O)NH(C$_{1-3}$alkyl), —C(=O)N(C$_{1-3}$alkyl)$_2$, —S(=O)$_2$NH$_2$, and —S(=O)$_2$N(C$_{1-3}$alkyl)$_2$.

In another embodiment of this twenty-first aspect of the invention, L is a bond, R12 is present and has one substituent chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH.

In one embodiment of this twenty-first aspect, the invention includes analogs where the ring to which R1-R5 are attached is a 4-7 member heterocyclic ring instead a phenyl ring.

In one embodiment of this aspect of the invention the heterocyclic group is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, 2H-pyrrolyl, imidazolyl, pyrazolyl, pyridyl (pyridinyl), 2-pyridyl, 3-pyridyl, 4-pyridyl, pyrazinyl, pyrimidinyl, pyridazinyl, tetrahydrofuranyl, pyranyl, piperidinyl, piperazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, quinuclidinyl, morpholinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, oxazolyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, pyrazolo[1,5-a]pyrimidin-3-yl, 1,2-benzoisoxazol-3-yl, benzimidazolyl, 2-oxindolyl and 2 oxobenzimidazolyl. In one sub-embodiment of this embodiment, the heterocyclic group is chosen from pyridinyl, isoxazolyl, furanyl, thiazolyl, pyrimidinyl, pyrrolyl, thiophenyl, triazolyl, benzo[1,3]dioxolyl, and benzofuranyl.

In another aspect of the invention, one or more of the carbon atoms of the indole core are replaced by a heteroatom independently —N—, —O—, and —S—. In one embodiment, the substituents are as in any one of the other aspects and/or sub-embodiments of the invention.

In another aspect of the invention, the core indole group is replace with a group chosen from 5,7-Dihydro-6H-pyrrolo[2,3-h]cinnoline; 5,7-Dihydro-6H-pyrrolo[2,3-h]quinazoline; 4,5-Dihydro-3H-3,6,7-triaza-cyclopenta[a]naphthalene; 5,7-Dihydro-6H-pyrrolo[3,2-f]quinoxaline; 5,7-Dihydro-6H-pyrrolo[3,2-f]phthalazine; 5,7-Dihydro-6H-pyrrolo[2,3-h]quinoline; 5,7-Dihydro-6H-pyrrolo[3,2-f]quinazoline; 4,5-Dihydro-3H-pyrrolo[3,2-f]isoquinoline; 4,5-Dihydro-3H-pyrrolo[3,2-f]quinoline; and 5,7-Dihydro-6H-pyrrolo[2,3-h]isoquinoline. In one embodiment, the substituents are as in any one of the other aspects and/or sub-embodiments of the invention.

In some aspects of the invention, L is substituted with one or more substituents independently chosen from —C(=O)OH, —CH=CHC(=O)OH, —CH$_2$CH$_2$C(=O)OH, —CH$_2$CH$_2$CH$_2$C(=O)OH, —C(CH$_2$CH$_2$)C(=O)OH, —CH(CH$_3$)C(=O)OH, —CH(CH$_2$CH$_3$)C(=O)OH, —C(CH$_3$)(CH$_2$CH$_3$)C(=O)OH, —CH=C(CH$_3$)C(=O)OH, —C(CH$_2$CH$_3$)$_2$C(=O)OH, —CH$_2$C(=O)OH, and —C(CH$_3$)$_2$C(=O)OH, in lieu of having one of said substituents elsewhere in the compounds of Formulae I-XVI.

In some embodiments, of the first through twenty-first aspects of the invention, if a position in Formulae I-XVI is not specified then it can be specified as in one of the other embodiments of that aspect of the invention. Alternatively, the position can be substituted with one or more substituents independently chosen from the list of optional substituents below.

Optionally substituted, when used herein without reference to further definition, refers to a substituent independently chosen from the group consisting of hydro, hydroxyl, halo, alkyl, alkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$.

Furthermore, the invention provides derivatives or analog of the compounds defined in first through twenty-first aspects of the invention, where the derivative or analog is chosen from an ester (e.g., methyl or ethyl ester), an amide, a carbamate, a urea, an amadine, or a combination thereof. Methods for generating an ester, an amide, a carbamate, a urea, an amadine, or a combination thereof, of the compounds of the first aspect through the twenty-first aspects are known to an ordinary artisan skilled in organic chemical synthesis.

As the skilled artisan readily recognizes, in some of the embodiments of the first twenty-one aspects of the invention, some of the compounds can have more than one -L-group, each of which is independent chosen.

Methods of Prevention and Treatment

In some aspects, the invention provides methods for treating and/or preventing neurodegenerative disorders like AD and MCI, and lowering Aβ$_{42}$ in an individual in need of such treatment. It is believed that by lowering the amounts of Aβ$_{42}$ in an individual by administering an Aβ$_{42}$ lowering effective amount of a composition described herein, that Alzheimer's disease and mild cognitive impairment can be treated or prevented. Generally, the invention relates to the idea that compounds of Formulae I-XVI can be used to lower Aβ$_{42}$ levels. Thus, diseases characterized by increased levels of Aβ$_{42}$, can be treated or prevented with the methods of the invention which are designed to lower Aβ$_{42}$, prevent an increase in Aβ$_{42}$, and/or reduce the rate of increase of Aβ$_{42}$.

The invention is based on the fact that the inventors have discovered that compounds of Formulae I-XVI lower Aβ$_{42}$ levels in in vitro APP processing assays. Furthermore, compounds of Formulae I-XVI, in general, have negligible levels of COX inhibition and therefore are thought to essentially be devoid of the deleterious side-effects associated with COX inhibition. Thus, a preferred embodiment of the invention is the use of a pharmaceutical composition having one or more compounds of Formulae I-XVI, where the compound lowers Aβ$_{42}$ levels and does not substantial inhibit the cyclooxygenases. Preferred compounds of Formulae I-XVI for use in the invention are those that have little or negligible COX-1 and/or COX-2 inhibition at 1 µM, more preferred are those that little or negligible COX-1 and/or COX-2 inhibition at 10 µM, and more preferred are those that little or negligible COX-1 and/or COX-2 inhibition at 100 µM compound. COX-1 and COX-2 inhibition can be determined with a COX inhibitor screening kit from e.g., Cayman Chemical, Ann Arbor, Mich. (Cat. #560131).

In one embodiment of the invention, a method for lowering Aβ$_{42}$ protein levels, in an individual in need of such treatment, is provided that includes the step of administering an effective amount of a compound of Formulae I-XVI as described above.

While not wishing to be bound by theory, it is believed that the compound of Formulae I-XVI acts in vivo to treat and/or prevent Alzheimer's disease and MCI by lowering the amount of $A\beta_{42}$ that is present or would be present in the absence of such treatment. Amyloid β polypeptides are derived from amyloid precursor proteins (APPs). A variety of amyloid β polypeptides are known including $A\beta_{34}$, $A\beta_{37}$, $A\beta_{38}$, $A\beta_{39}$, and $A\beta_{40}$. Increased $A\beta_{42}$ levels are associated with Alzheimer's disease and MCI. Thus, by lowering the amounts of $A\beta_{42}$, a treatment is provided for combating Alzheimer's disease and/or MCI.

In another embodiment, the invention relates to a method of preventing Alzheimer's disease. According to this embodiment, a method for preventing Alzheimer's disease is provided which comprises administering, to an individual in need of such treatment, a composition comprising a compound having Formulae I-XVI. The method of this embodiment is useful for preventing the symptoms of Alzheimer's disease, the onset of Alzheimer's disease, and/or the progression of the disease.

In another embodiment, the invention provides a method of treating a neurodegenerative disorder, by identifying a patient in need of such treatment, and administering to the patient a therapeutically effective amount of a pharmaceutical composition having one or more compounds of Formulae I-XVI. Administration of a compound of Formulae I-XVI for at least 4 weeks, preferably at least 4 months, and more desirably at least 8 months, can provide an improvement or lessening in decline of cognitive function as characterized by cognition tests, biochemical disease marker progression, and/or plaque pathology. It is preferred that the lessening in decline in cognitive function is at least 25% as compared to individuals treated with placebo, more preferably at least 40%, and even more desirably at least 60%. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. The pharmaceutical composition for use in the invention is formulated with one or more pharmaceutically acceptable excipients, salts, or carriers. The pharmaceutical composition for use in the invention is delivered orally, preferably in a tablet or capsule dosage form.

In yet another embodiment, the invention provides a method for prophylaxis against a neurodegenerative disorder, by identifying a patient in need of or desiring such treatment, and administering to the patient a prophylactically effective amount of a pharmaceutical composition having one or more compounds of Formulae I-XVI. Preferred compounds for use in this embodiment of the invention include those in Tables 1-6. Administration of a compound of Formulae I-XVI for at least 4 weeks, preferably at least 4 months, and more desirably at least 8 months, can delay the onset of the neurodegenerative disorder or slow the rate of onset of symptoms of the disorder. Patients having a predisposition to a neurodegenerative disorder or suspected of needing prophylaxis can be identified by any method known to the skilled artisan for diagnosis of such neurodegenerative disorders.

In still another embodiment, the invention provides a method of treating a disease characterized by abnormal amyloid precursor protein processing by (1) identifying a patient in need of such treatment, and (2) administering to the patient a therapeutically effective amount of a pharmaceutical composition having one or more compounds of Formulae I-XVI. Examples of biochemical disease markers include, for example, amyloid beta peptide (Aβ), $A\beta_{42}$, and tau.

In another embodiment, the invention provides a method of prophylaxis or delaying the onset of a disease (or one or more symptoms thereof) characterized by abnormal amyloid precursor protein processing, by identifying a patient in need of such treatment and administering to the patient a prophylactically effective amount of a pharmaceutical composition having one or more compounds of Formulae I-XVI. Oral administration of the pharmaceutical composition for use in the method of this aspect the invention for at least 4 weeks, preferably at least 4 months, and more desirably at least 8 months, prevents or delays the onset of the disease (or symptoms thereof) characterized by abnormal amyloid precursor protein processing.

In another embodiment, the invention provides a method of treating Alzheimer's disease comprising administering to a patient in need of such treatment, a pharmaceutical composition having one or more compounds of Formulae I-XVI. Oral administration of the pharmaceutical composition for use in the method of this aspect of the invention for at least 4 weeks, preferably at least 4 months, and more desirably at least 8 months, provides an improvement or lessening in decline of cognitive function as characterized by cognition tests, biochemical disease marker progression, and/or plaque pathology. Desirably, the oral dose is provided in capsule or tablet form. According to this aspect of the invention, a patient in need of treatment is administered an Alzheimer's disease treating effective amount of a pharmaceutical composition having one or more compounds of Formulae I-XVI and one or more pharmaceutically acceptable salts, excipients and carriers. The method of this aspect of the invention involves identifying an individual likely to have mild-to-moderate Alzheimer's disease. An individual having probable mild-to-moderate Alzheimer's disease can be diagnosed by any method available to the ordinary artisan skilled in such diagnoses. For example, diagnosis can be according to DSM IV (TR) and/or meets NINCDS-ADRDA criteria for probable AD. According to this aspect of the invention, individuals with probable mild-to-moderate AD take an oral dose of a pharmaceutical composition for a specified period of time. Individuals undergoing such treatment are likely to see an improvement or lessening in decline of cognitive function, an improvement or lessening in decline in biochemical disease marker progression, and/or an improvement or lessening of decline in plaque pathology. A lessening in decline in cognitive function can be assessed using tests of cognitive function like the ADAS-cog. For example, an individual treated with placebo having probable mild-to-moderate Alzheimer's disease is expected to score approximately 5.5 points worse on the ADAS-cog test after a specified period of time of treatment (e.g., 1 year) whereas an individual treated with the composition of this aspect of the invention for the same period of time will score approximately 2.2 points worse on the ADAS-cog scale with a 60% decrease in decline or 3.3 points worse with a 40% decrease in decline in cognitive function when treated with the composition for the same specified period of time. In a related aspect, the method involves identifying a patient having moderate-to-severe AD and administering to the patient an Alzheimer's disease treating effective amount of a compound of Formulae I-XVI.

In another embodiment, the invention provides a method of preventing the onset of Alzheimer's disease comprising administering to a patient in need of or desiring such treatment, a pharmaceutical composition having one or more compounds of Formulae I-XVI. Administration of the pharmaceutical composition for use in the method of this aspect of the invention for at least 4 weeks, preferably at least 4 months, and more desirably at least 8 months, delays the onset of decline of cognitive function, biochemical disease marker progression, and/or plaque pathology. According to this embodiment, an individual desiring or needing preventative treatment against the onset of AD is administered a pharmaceutical composition having one or more compounds of Formulae I-XVI. The preventative treatment is preferably maintained as long as the individual continues to desire or need the treatment. Individuals needing or desiring preventative treatment against AD can be those having risk factors for developing AD. For example, risk factors for developing AD can be genetic factors or environmental factors. In one embodiment, the risk factor is age. Genetic risk factors can be assessed in a variety of ways, such as ascertaining the family medical history of the individual, or performing a genetic test to identify genes that confer a predisposition for developing AD. Additionally, risk factors can be assessed by monitoring genetic and biochemical markers. The method of this embodiment involves evaluating risk factors for cognitive decline. Evaluation of risk factors can include genetic testing for predisposing genes, alleles, and polymorphisms. Risk factors also refer to environmental factors like stroke, brain injury, age, and diet. Depending on the risk factor or factors associated with a particular patient a particular treatment regimen is selected for treating cognitive decline. For example, mutations in a Familial Alzheimer's disease gene are a risk factor. Another risk factor for cognitive decline is age. Head trauma is another risk factor for cognitive decline. Based on the patient's risk factors, a physician will prescribe a particular therapeutic treatment or prophylactic treatment suitable for the patient.

In still another embodiment, the invention provides a method of lowering $A\beta_{42}$ levels to a greater extent than inhibiting COX-1, COX-2, or a combination thereof. In particular, the method of this embodiment comprises administering to a patient in need of treatment an effective amount of one or more compounds of Formulae I-XVI. The method of this embodiment involves the lowering of $A\beta_{42}$ levels while not substantial affecting the activity of COX-1, COX-2, or both COX-1, and COX-2. Thus, the amount of the composition administered is effective for lowering $A\beta_{42}$ levels and does not substantially inhibit COX-1, COX-2, or both COX-1 and COX-2. For example, the effective amount can be above the ED50 (the dose therapeutically effective in 50% of the population) for $A\beta_{42}$ lowering, and below the ED50 for COX inhibition. Another example is a sufficiently small amount of compound so that inhibition of at least one COX activity is negligible and $A\beta_{42}$ levels are reduced. The method of this embodiment can be used to treat and/or prevent Alzheimer's disease. The method of this embodiment can also be used to treat and/or prevent MCI and other neurodegenerative disorders.

According to a preferred embodiment, the invention provides a method of lowering $A\beta_{42}$ levels to a greater extent than inhibiting COX-1, COX-2, or a combination thereof. In particular, the method of this embodiment comprises administering, to a patient in need of treatment, an effective amount of one or more compounds of Formulae I-XVI, wherein the effective amount of compound is capable of lowering $A\beta_{42}$, while not substantially affecting or inhibiting the activity of at least one isoform of COX. Thus, the method of this embodiment involves the lowering of $A\beta_{42}$ levels while not substantially inhibiting the activity of COX-1, COX-2, or both COX-1 and COX-2. The method of this embodiment can be used to treat and/or prevent Alzheimer's disease, MCI, and/or other neurodegenerative disorders. In one aspect of this embodiment, the effective amount of compound having Formulae I-XVI reduce $A\beta_{42}$ levels or production of $A\beta_{42}$ by at least 1, 2, 5, 10, 15, 20, 25, 30, 40, or 50 or more percent while inhibiting COX-1, COX-2, or both COX-1 and COX-2 by less than 1, 2, 5, 10, 15, 20, 25, 30, 40, 50, 60, 70, 80, or 90 percent. In a preferred aspect of this embodiment, the effective amount of compound according to Formulae I-XVI lower $A\beta_{42}$ by at least 5 percent while not substantially inhibiting COX-1, COX-2, or both COX-1 and COX-2 activity or levels. In another preferred aspect of this embodiment, the effective amount of the compound having Formulae I-XVI that is administered to an individual is such that it lowers $A\beta_{42}$ levels, and does not inhibit COX activity to a significant extent, e.g., the amount administered is below the in vivo IC50 value for COX-1, COX-2 or both COX-1 and COX-2 and above the in vivo IC50 value for $A\beta_{42}$ lowering activity. As used in this context, IC50 refers to the amount of compound sufficient to inhibit COX activity by 50% (COX-1, COX-2, or both COX-1 and COX-2) or reduce $A\beta_{42}$ levels by 50%. An "effective amount" according to this preferred aspect of this embodiment, can also be viewed in terms of ED50 parameters, binding constants, dissociation constants, and other pharmacological parameters, e.g., the amount administered is below the ED50 value for COX-1, COX-2 or both COX-1 and COX-2 and above the ED50 value for $A\beta_{42}$. It is noted that the effective amount of the compound does not necessarily have to be above an IC50 or ED50 for $A\beta_{42}$ lowering and below the IC50 or ED50 for COX inhibition. That is, the "effective amount" can be at some intermediate value such that $A\beta_{42}$ levels are lowered to a greater extent than inhibition of COX-1, COX-2 or both COX-1 and COX-2.

The skilled artisan readily recognizes that the compounds and pharmaceutical compositions can be used to treat other disease besides those listed herein.

Patient Population

In one aspect of the invention, any individual having, or suspected of having, a neurodegenerative disorder, such as Alzheimer's disease, may be treated using the compositions and methods of the present invention. Individuals who would particularly benefit from the compositions and methods of the invention include those individuals diagnosed as having mild to moderate Alzheimer's disease according to a medically-accepted diagnosis, such as, for example the NINCDS-ADRDA criteria. Progression of the disease may be followed by medically accepted measure of cognitive function, such as, for example, the Mini-Mental State Exam (MMSE; see Mohs et al. *Int. Psychogeriatr.* 8:195-203 (1996)); ADAS-Cog (Alzheimer Disease Assessment Scale-Cognitive; see Galasko et al. *Alzheimer Dis Assoc Disord,* 11 suppl 2:S33-9 (1997)); Behavioral Pathology in Alzheimer's Disease Rating Scale (BEHAVE-AD); Blessed Test; CANTAB—Cambridge Neuropsychological Test Automated Battery; CERAD (The Consortium to Establish a Registry for Alzheimer's Disease) Clinical and Neuropsychological Tests (includes MMSE); Clock Draw Test; Cornell Scale for Depression in Dementia (CSDD); Geriatric Depression Scale (GDS); Neuropsychiatric Inventory (NPI); the 7 Minute Screen; the Alzheimer's Disease Cooperative Study Activities of Daily Living scale (ADCS-ADL; see McKhann et al. *Neurology* 34:939-944 (1984)); the DSM-IV (Diagnostic and Statistical Manual of Mental Disorders—Fourth Edition (DSM-IV), published by the American Psychiatric Association, Washington D.C., 1994); or the NINCDS-ADRDA criteria (see Folstein et al. *J. Psychiatr. Res.* 12:189-198 (1975)). Individuals diagnosed as having probable AD can be identified as having a mild-to-moderate form of the disease by an accepted measure of cognitive function such as the MMSE. In addition, methods that allow for evaluating different regions of the brain and estimating plaque and tangle frequencies can be used. These methods are described by Braak et al. *Acta Neuropathol* 82:239-259 (1991); Khachaturian *Arch. Neuro.* 42:1097-1105 (1985); Mirra et al. (1991) *Neurology* 41:479-486; and Mirra et al. *Arch Pathol Lab Med* 117:132-144 (1993). The severity of AD is generally determined by one of the initial tests provided above. For example, MMSE scores of 26-19 indicate mild AD, while scores from 18-10 indicate moderate AD.

Diagnoses of Alzheimer's disease based on these tests are recorded as presumptive or probable, and may optionally be supported by one or more additional criteria. For example, a diagnosis of Alzheimer's disease may be supported by evidence of a family history of AD; non-specific changes in EEG, such as increased slow-wave activity; evidence of cerebral atrophy on CT with progression documented by serial observation; associated symptoms such as depression, insomnia, incontinence, delusions, illusions, hallucinations, catastrophic verbal, emotional or physical outbursts, sexual disorders, weight loss, and/or attendant neurologic abnormalities, such as increased muscle tone, myoclonus or gait disorder, etc.

Additionally, amyloid deposits, generally associated with AD, may be detected through the use of positron emission tomography (PET) using an amyloid-specific tracer such as Pittsburgh Compound-B (PIB). See Klunk et al., *Ann. Neurol.* 55(3):306-309 (2004). Increased amyloid deposits in the frontal, parietal, temporal and occipital cortices, and in the striatum, relative to normal brain tissue, as visualized, for example by PIB, support a diagnosis of AD. Generally, a greater number and density of amyloid deposits indicates more advanced AD.

The invention encompasses the treatment of an individual preferably having mild to moderate AD, to the extent that individual has AD, whether or not one or more non-AD neurodegenerative diseases or conditions are previously, concurrently or subsequently diagnosed.

The compounds and methods of the present invention are useful for individuals who have received prior medication for AD, as well as individuals who have received no prior medication for AD, and is useful for individuals currently receiving medication for AD other than a compound of Formulae I-XVI, and for individuals not receiving medication for AD other than a compound of Formulae I-XVI.

Individuals of any age may be treated by the methods of the invention, with the pharmaceutical compositions of the invention; however, the invention encompasses a preferred embodiment for treating or preventing Alzheimer's disease in individuals between the ages of 45 and 105. In various embodiments, individuals treated by the therapeutic or prophylactic methods of the invention may be from 55 to 70 years of age, 60 to 80 years of age, 55 to 65 years of age, 60 to 75 years of age, 65 to 80 years of age, 55 to 60 years of age, 60 to 65 years of age, 65 to 70 years of age, 70 to 75 years of age, 75 to 80 years of age, or 80 years old and older.

In yet another embodiment, the invention provides a method of slowing cognitive decline in an individual suspected of having mild cognitive impairment (MCI) comprising administering to the individual an effective amount of a compound of Formulae I-XVI. Mild cognitive impairment is a clinical condition between normal aging and Alzheimer's disease characterized by memory loss greater than expected for the particular age of the individual yet the individual does not meet the currently accepted definition for probable Alzheimer's disease. See, e.g., Petersen et al. *Arch. Neurol.* 58:1985-1992 (2001); Petersen *Nature Rev.* 2:646-653 (2003); and Morris et al. *J Mol. Neuro.* 17:101-118 (2001). Thus, according to this embodiment an individual suspected of having or diagnosed with MCI is treated twice daily with a composition having a compound of Formulae I-XVI per dose for at least 4 weeks, at least 4 months, preferably at least 8 months, and more desirably at least 1 year. Typically, patients having MCI first complain of or have a loss of memory. Preferably an individual associated with the patient can corroborate the memory deficit. Furthermore, general cognition is not sufficiently impaired to cause concern about more widespread cognitive disorder and although daily living activities may be affected that are not significantly impaired and the patients are not demented. Individuals having or suspected of having MCI that are treated according to this embodiment can expect to slow cognitive decline and/or progression to probable AD.

Thus, in one embodiment, the invention provides a method of treating an individual known or suspected of having Alzheimer's disease comprising administering an effective amount of a compound of Formulae I-XVI. In a specific embodiment, the individual is diagnosed as having mild to moderate Alzheimer's disease. In another specific embodiment, the individual is diagnosed by a cognitive test as having mild to moderate AD. In another specific embodiment, the cognitive test is the Mini-Mental State Exam (MMSE). In another specific embodiment, the individual has a score on the MMSE of from 26 to 19, inclusive. In another specific embodiment, the individual has a score on the MMSE of from 18 to 10, inclusive. In another specific embodiment, the individual has a score on the MMSE of 26 to 10, inclusive.

In other embodiments, the invention provides a method of treating an individual known or suspected of having Alzheimer's disease comprising administering an effective amount of a compound of Formulae I-XVI, wherein the individual is concurrently taking a second drug for the treatment of Alzheimer's disease. In a further embodiment, the individual has been diagnosed as having mild to moderate Alzheimer's disease. In a specific embodiment, said second drug is an acetylcholinesterase (AChE) inhibitor. In a more specific embodiment, said AChE inhibitor is Galanthamine (galantamine, Reminyl); E2020 (Donepezil, Aricept); Physostigmine; Tacrine (tetrahydroaminoacridine, THA); Rivastigmine; Phenserine; Metrifonate (Promem); or Huperazine, or a combination of any of the foregoing. In another embodiment, the second drug is a drug other than an acetylcholinesterase inhibitor. In a preferred embodiment, the method or compositions of the invention are used in patients or individuals undergoing therapy with Aricept. The invention also encompasses methods of treating patients refractory to, or who no longer show improvement with, conventional AD therapy.

In another embodiment, the individual is concurrently taking a non-drug substance for the treatment of Alzheimer's disease. In a specific embodiment, said non-drug substance is an anti-oxidant. In another specific example, said anti-oxidant is vitamin C or vitamin E. In another specific embodiment, svitamin C is taken in a dose of 500-1000 mg per dose of a compound of Formulae I-XVI. In another specific embodiment, vitamin E is taken in a dose of 400-800 IU per dose of a compound of Formulae I-XVI. In this regard, the invention encompasses the use of one or more such anti-oxidants as an adjunct to therapy for Alzheimer's disease, and not primarily as a nutritional supplement.

In another embodiment, the invention provides a method of treating an individual diagnosed as having mild to moderate Alzheimer's disease comprising administering an effective amount of a compound of Formulae I-XVI, wherein the individual has, prior to taking a compound of Formulae I-XVI, taken a second drug for the treatment of Alzheimer's disease. In a specific embodiment, the second drug is an acetylcholinesterase (AChE) inhibitor. In a more specific embodiment, the ACE inhibitor is Galanthamine (galantamine, Reminyl); E2020 (Donepezil, Aricept); Physostigmine; Tacrine (tetrahydroaminoacridine, THA); Rivastigmine; Phenserine; Metrifonate (Promem); or Huperazine, or a combination of any of the foregoing. In another embodiment, the second drug is a drug other than an acetylcholinesterase inhibitor.

In another embodiment, the individual has, prior to taking a compound of Formulae I-XVI, taken a non-drug substance for the treatment of Alzheimer's disease. In a specific embodiment, said non-drug substance is an anti-oxidant. In a specific example, the anti-oxidant is vitamin C or vitamin E. In another specific embodiment, the vitamin C is taken in a dose of 500-1000 mg per dose. In another specific embodiment, the vitamin E is taken in a dose of 400-800 IU per dose. In this regard, the invention encompasses the use of one or more such anti-oxidants as an adjunct to therapy for Alzheimer's disease, and not primarily as a nutritional supplement.

The invention further provides a combination therapy strategy for preventing Alzheimer's disease and MCI. According to this aspect of the invention, an individual in need of treatment is administered a compound of Formulae I-XVI, and a compound chosen from NSAIDs (non-steroidal anti-inflammatory drugs), COX-2 inhibitors (cyclooxygenase-2), β-secretase inhibitors, R-flurbiprofen, γ-secretase inhibitors, acetylcholine esterase inhibitors, and NMDA antagonists. Preferably the combination therapy involves treating the individual in need of treatment with a compound of Formulae I-XVI in combination with an acetylcholine esterase inhibitor or an NMDA receptor antagonist. Preferred acetylcholine esterase inhibitors for combination therapy are tacrine, donepezil, rivastigmine, and galantamine. Preferred NMDA receptor antagonists for combination therapy are memantine, adamantane, amantadine, an adamantane derivative, dextromethorphan, dextrorphan, dizocilpine, ibogaine, ketamine, and remacemide. The acetylcholine esterase inhibitor or NMDA receptor antagonists is preferably formulated in a combination dosage form with a compound of Formulae I-XVI.

The treatment regime used in the combination therapy can involve administration of a composition comprising the combination of active ingredients, the concomitant administration of separate compositions, each comprising at least one active ingredient. Furthermore, the administration of the active ingredients can be performed at different times and/or different routes. For example, a composition comprising at least one active ingredient can be administered in the morning, and a composition comprising at least one different active ingredient can be administered in the evening. Another example would involve the administration of a composition having at least one active ingredient orally while the second composition is administered intravenously.

While not wishing to be bound by theory, it is believed that the compounds of Formulae I-XVI are capable of slowing the rate of death of neurons. Accordingly, it is also believed that the compounds of Formulae I-XVI acts in vivo to treat and/or prevent Alzheimer's disease and MCI by slowing the rate of death of neurons that is present or would be present in the absence of such treatment.

The skilled artisan readily recognizes that the invention includes the use of compounds of Formulae I-XVI, pharmaceutically acceptable salts, metabolites and prodrugs thereof in each of the described embodiments.

DEFINITIONS

As used herein, the term "alkyl" refers to a saturated aliphatic hydrocarbon including straight chain and branched chain groups. Preferably, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). More preferably, it is a medium size alkyl having 1 to 10 carbon atoms. Even more preferably, it is a lower alkyl having 1 to 6 carbon atoms, and even more preferably 1 to 4 carbon atoms. The alkyl group may be substituted or unsubstituted. When substituted, the substituent group(s) is preferably one or more individually selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, cyanato, isocyanato, thiocyanato, isothiocyanato, nitro, silyl, and amino.

As used herein, the term "halo" refers to chloro, fluoro, bromo, and iodo.

As used herein, the term "hydro" refers to a hydrogen atom (—H group).

As used herein, the term "hydroxy" refers to an —OH group.

As used herein, the term "alkoxy" refers to both an —O-alkyl and an —O-cycloalkyl group, as defined herein. Lower alkoxy refers to —O-lower alkyl groups.

As used herein, the term "aryloxy" refers to both an —O-aryl and an —O-heteroaryl group, as defined herein.

As used herein, the term "mercapto" group refers to an —SH group.

As used herein, the term "alkylthio" group refers to both an S-alkyl and an —S-cycloalkyl group, as defined herein.

As used herein, the term "arylthio" group refers to both an —S-aryl and an —S-heteroaryl group, as defined herein.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "aldehyde" group refers to a carbonyl group where R" is hydro.

As used herein, the term "cycloketone" refer to a cycloalkyl group in which one of the carbon atoms which form the ring has a "=O" bonded to it; i.e. one of the ring carbon atoms is a —C(=O)— group.

As used herein, the term "thiocarbonyl" group refers to a —C(=S)R" group, with R" as defined herein.

As used herein, the term "O-carboxy" group refers to a R"C(=O)O— group, with R" as defined herein.

As used herein, the term "C-carboxy" group refers to a —C(=O)OR" groups with R" as defined herein.

As used herein, the term "ester" is a C-carboxy group, as defined herein, wherein R" is any of the listed groups other than hydro.

As used herein, the term "C-carboxy salt" refers to a —C(=O)O⁻M⁺ group wherein M⁺ is selected from the group consisting of lithium, sodium, magnesium, calcium, potassium, barium, iron, zinc and quaternary ammonium.

As used herein, the term "acetyl" group refers to a —C(=O)CH₃ group.

As used herein, the term "carboxyalkyl" refers to —(CH₂)$_r$C(=O)OR" wherein r is 1-6 and R" is as defined above.

As used herein, the term "carboxyalkyl salt" refers to a —(CH$_2$)$_r$C(=O)O$^-$M$^+$ wherein M$^+$ is selected from the group consisting of lithium, sodium, potassium, calcium, magnesium, barium, iron, zinc and quaternary ammonium.

As used herein, the term "carboxylic acid" refers to a C-carboxy group in which R" is hydro.

As used herein, the term "haloalkyl" refers to an alkyl group substituted with 1 to 6 halo groups, preferably haloalkyl is a —CX$_3$ group wherein X is a halo group. The halo groups can be independently selected.

As used herein, the term "trihalomethanesulfonyl" refers to a X$_3$CS(=O)$_2$— group with X as defined above.

As used herein, the term "cyano" refers to a —C≡N group.

As used herein, the term "cyanato" refers to a —CNO group.

As used herein, the term "isocyanato" refers to a —NCO group.

As used herein, the term "thiocyanato" refers to a —CNS group.

As used herein, the term "isothiocyanato" refers to a —NCS group.

As used herein, the term "sulfinyl" refers to a —S(=O)R" group, with R" as defined herein.

As used herein, the term "sulfonyl" refers to a —S(=O)$_2$R" group, with R" as defined herein.

As used herein, the term "sulfonamido" refers to a —S(=O)$_2$NR$^{17}$R$^{18}$, with R$^{17}$ and R$^{18}$ as defined herein.

As used herein, the term "trihalomethanesulfonamido" refers to a X$_3$CS(=O)$_2$NR$^{17}$-group with X and R$^{17}$ as defined herein.

As used herein, the term "O-carbamyl" refers to a —OC(=O)NR$^{17}$R$^{18}$ group with R$^{17}$ and R$^{18}$ as defined herein.

As used herein, the term "N-carbamyl" refers to a R$^{18}$OC(=O)NR$^{17}$— group, with R$^{17}$ and R$^{18}$ as defined herein.

As used herein, the term "O-thiocarbamyl" refers to a —OC(=S)NR$^{17}$R$^{18}$ group with R$^{17}$ and R$^{18}$ as defined herein.

As used herein, the term "N-thiocarbamyl" refers to a R$^{17}$OC(=S)NR$^{18}$— group, with R$^{17}$ and R$^{18}$ as defined herein.

As used herein, the term "amino" refers to an —NR$^{17}$R$^{18}$ group, with R$^{17}$ and R$^{18}$ both being hydro.

As used herein, the term "C-amido" refers to a —C(=O)NR$^{17}$R$^{18}$ group with R$^{17}$ and R$^{18}$ as defined herein. An "N-amido" refers to a R$^{17}$C(=O)NR$^{18}$— group with R$^{17}$ and R$^{18}$ as defined herein.

As used herein, the term "nitro" refers to a —NO$_2$ group.

As used herein, the term "quaternary ammonium" refers to a —$^+$NR$^{17}$R$^{18}$R$^{19}$ group wherein R$^{17}$, R$^{18}$, and R$^{19}$ are independently selected from the group consisting of hydro and unsubstituted lower alkyl.

As used herein, the term "methylenedioxy, ethylenedioxy" refers to a —OCH$_2$O— group wherein the oxygen atoms are bonded to adjacent ring carbon atoms.

As used herein, the term "ethylenedioxy" refers to a —OCH$_2$CH$_2$O— group wherein the oxygen atoms are bonded to adjacent ring carbon atoms.

As used herein, the term "cycloalkyl" refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is preferably one or more individually selected from alkyl, aryl, heteroaryl, heterocyclic, hydroxy, alkoxy, aryloxy, mercapto, alkylthio, arylthio, cyano, halo, carbonyl, thiocarbonyl, carboxy, O-carbamyl, N-carbamyl, C-amido, N-amido, nitro, and amino.

As used herein, the term "heterocycle" or heterocyclic" refers to a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Example of "heterocycles" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl. "Heterocycle" can include heteroaryls when the pi-electron system of a heterocycle is completely conjugated.

As used herein, the term "aryl" refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more selected from halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, S-sulfonamido, N-sulfonamido, trihalo-methanesulfonamido, and amino.

As used herein, the term "heteroaryl" refers to groups having 5 to 14 ring atoms; 6, 10 or 14 pi electrons shared in a cyclic array; and containing carbon atoms and 1, 2 or 3 oxygen, nitrogen or sulfur heteroatoms. Non-limiting heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7 aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2 oxobenzimidazolyl. Where the heteroaryl group contains a nitrogen atom in a ring, such nitrogen atom may be in the form of an N-oxide, e.g., a pyridyl N oxide, pyrazinyl N-oxide and pyrimidinyl N-oxide. When substituted, the substituted group(s) is preferably one or more selected from alkyl, cycloalkyl, halo, trihalomethyl, hydroxy, alkoxy, aryloxy, mercapto, alkylthio, arylthio, cyano, nitro, carbonyl, thiocarbonyl, sulfonamido, carboxy, sulfinyl, sulfonyl, O-carbamyl, N-carbamyl, O-thiocarbamyl, N-thiocarbamyl, C-amido, N-amido, and amino.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein. In another example the symptom can be cognitive decline. Preventing an increase, according to the definition provided herein, means that the amount of symptom (e.g., protein or cognitive decline) does not increase or that the rate at which it increases is reduced.

As used herein, the term "treating Alzheimer's disease" refers to a slowing of or a reversal of the progress of the disease. Treating Alzheimer's disease includes treating a symptom and/or reducing the symptoms of the disease.

As used herein, the term "preventing Alzheimer's disease" refers to a slowing of the disease or of the onset of the disease or the symptoms thereof. Preventing Alzheimer's disease can include stopping the onset of the disease or symptoms thereof.

As used herein, the term "$A\beta_{42}$ lowering" refers to the capability to reduce the amount of $A\beta_{42}$ present and/or being produced. Levels of $A\beta_{42}$ can be determined with an ELISA assay configured to detect $A\beta_{42}$. Methods of determining $A\beta_{42}$ levels are described in the examples and references cited therein.

As used herein, the term "unit dosage form" refers to a physically discrete unit, such as a capsule or tablet suitable as a unitary dosage for a human patient. Each unit contains a predetermined quantity of a compound of Formulae I-XVI, which was discovered or believed to produce the desired pharmacokinetic profile which yields the desired therapeutic effect. The dosage unit is composed of a compound of Formulae I-XVI in association with at least one pharmaceutically acceptable carrier, salt, excipient, or combination thereof.

As used herein, the term "dose" or "dosage" refers the amount of active ingredient that an individual takes or is administered at one time. For example, an 800 mg dose of a compound of Formulae I-XVI refers to, in the case of a twice-daily dosage regimen, a situation where the individual takes 800 mg of a compound of Formulae I-XVI twice a day, e.g., 800 mg in the morning and 800 mg in the evening. The 800 mg of a compound of Formulae I-XVI dose can be divided into two or more dosage units, e.g., two 400 mg dosage units of a compound of Formulae I-XVI in tablet form or two 400 mg dosage units of a compound of Formulae I-XVI in capsule form.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

"A pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt.

Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methanesulfonates, propanesulfonates, naphthalene-1-sulfonates, naphthalene-2-sulfonates, and mandelates.

Preparation of the Compounds of the Invention

Representative synthetic schemes and experimental descriptions for the compounds of Formulae I-XVI for use in the methods of the invention are given in the Examples below.

Dosages, Formulations, and Route of Administration

The active compounds of this invention are typically administered in combination with a pharmaceutically acceptable carrier through any appropriate routes such as parenteral, oral, or topical administration, in a therapeutically (or prophylactically) effective amount according to the methods set forth above. A preferred route of administration for use in the invention is oral administration.

Generally, the toxicity profile and therapeutic efficacy of the therapeutic agents can be determined by standard pharmaceutical procedures in suitable cell models or animal models. As is known in the art, the LD50 represents the dose lethal to about 50% of a tested population. The ED50 is a parameter indicating the dose therapeutically effective in about 50% of a tested population. Both LD50 and ED50 can be determined in cell models and animal models. In addition, the IC50 may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the ED50 and/or IC50, but remains significantly below the LD50 dosage level, as determined from cell or animal models.

Typically, the compounds and compositions for use in the invention can be effective at an amount of from about 0.05 mg to about 4000 mg per day, preferably from about 0.1 mg to about 2000 mg per day. However, the amount can vary with the body weight of the patient treated and the state of disease conditions. The active ingredient may be administered at once, or may be divided into a number of smaller doses to be administered at predetermined intervals of time.

In the case of combination therapy, a therapeutically effective amount of another therapeutic compound can be administered in a separate pharmaceutical composition, or alternatively included in the pharmaceutical composition according to the present invention. The pharmacology and toxicology of other therapeutic compositions are known in the art. See e.g., Physicians Desk Reference, Medical Economics, Montvale, N.J.; and The Merck Index, Merck & Co., Rahway, N.J. The therapeutically effective amounts and suitable unit dosage ranges of such compounds used in the art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can also be adjusted as the various factors change over time.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, surfactants, and antioxidants can all be included. For example, useful components include sodium chloride, acetate, citrate or phosphate buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al, *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network that swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.* 73:1718-1720 (1984).

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Soft gelatin capsules can be prepared in which capsules contain a mixture of the active ingredient and vegetable oil or non-aqueous, water miscible materials such as, for example, polyethylene glycol and the like. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size. The operating parameters of the machine may be selected by the skilled artisan.

If the compound for use in the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound for use in the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. These substituents may optionally be further substituted with a substituent selected from such groups.

EXAMPLES

Example 1

Tablets

| Ingredient | Amount | Preferred Ranges |
|---|---|---|
| Compound of Formulae I-XVI | 400 mg | +50% to −50% |
| Microcrystalline Cellulose | 392 mg | +50% to −50% |
| Colloidal Silicon Dioxide | 4 mg | +50% to −50% |
| Magnesium Stearate | 4 mg | +50% to −50% |

The tablets are prepared using art known procedures.

Example 2

Coated Tablets

| Ingredient | Amount | Preferred Ranges |
|---|---|---|
| Compound of Formulae I-XVI | 400 mg | +50% to −50% |
| Microcrystalline Cellulose | 392 mg | +50% to −50% |
| Colloidal Silicon Dioxide | 4 mg | +50% to −50% |
| Magnesium Stearate | 4 mg | +50% to −50% |
| Coated with | | |
| Lactose monohydrate | | |
| Hydroxyl propyl methyl cellulose | | |
| Titanium dioxide | | |
| Tracetin/glycerol triacetate | | |
| Iron oxide | | |

The coated tablets are produced using art known procedures.

Example 3

Capsules

| Ingredient | Amount | Preferred Ranges |
|---|---|---|
| Compound of Formulae I-XVI | 400 mg | +50% to −50% |
| Microcrystalline Cellulose | 392 mg | +50% to −50% |
| Colloidal Silicon Dioxide | 4 mg | +50% to −50% |
| Magnesium Stearate | 4 mg | +50% to −50% |
| Encapsulated in gelatin | | |

The capsules are produced using art known procedures.

Example 4

Tablets

| Ingredient | Amount | Preferred Ranges |
|---|---|---|
| Compound of Formulae I-XVI | 200 mg | +50% to −50% |
| Microcrystalline Cellulose | 196 mg | +50% to −50% |
| Colloidal Silicon Dioxide | 2 mg | +50% to −50% |
| Magnesium Stearate | 2 mg | +50% to −50% |

Example 5

Treatment of Alzheimer's Disease with a Compound of Formulae I-XVI

The compounds of Formulae I-XVI can be administered twice daily as tablets containing 400 mg of active ingredient or as a capsule containing 400 mg of the active ingredient. A higher dose can be administered to the patient in need of such treatment which can involve the patient taking e.g., a 800 mg dose of a compound of Formulae I-XVI in the morning and a 800 mg dose of a compound of Formulae I-XVI in the evening. Typically, for the treatment of mild-to-moderate Alzheimer's disease, an individual is diagnosed by a doctor as having the disease using a suitable combination of observations. One criterion indicating a likelihood of mild-to-moderate Alzheimer's disease is a score of about 15 to about 26 on the MMSE test. Another criteria indicating mild-to-moderate Alzheimer's disease is a decline in cognitive function. Compounds of Formulae I-XVI can also be administered in liquid dosage forms (or any other appropriate route of administration). The dosages can also be divided or modified, and taken with or without food. For example, the 400 mg dose can be divided into two 200 mg tablets or capsules.

Depending on the stage of the disease, the compound (i.e., Formulae I-XVI) can also be administered twice daily in liquid, capsule, or tablet dosage forms where the dose has various amounts (i.e., 850 mg, 750 mg, 700 mg, 650 mg, 600 mg, 550 mg, 500 mg, 450 mg, 350 mg, 300 mg, 250 mg, 200 mg, 150 mg, and 100 mg). Again, the dosages can also be divided or modified, and taken with or without food. The doses can be taken during treatment with other medications for treating Alzheimer's disease or symptoms thereof. For example, the compound can be administered in the morning as a tablet containing 400 mg of active ingredient (i.e., a compound of Formulae I-XVI) and an acetylcholine esterase inhibitor (i.e., tacrine (Cognex®), donepezil (Aricept®), rivastigmine (Exelon®), and galantamine (Reminyl®)), and/or an NMDA antagonist (i.e., memantine). It may be desirable to lower the amount of acetylcholine esterase inhibitor (and/or NMDA antagonist) and/or the compound of Formulae I-XVI to avoid adverse side effects associated with higher doses of these compounds. Alternatively, the acetylcholine esterase inhibitor (and/or NMDA antagonist) and compound of Formulae I-XVI can be co-formulated into a single dosage form, i.e., liquid, tablet, capsule, etc.

Patients having mild-to-moderate Alzheimer's disease undergoing the treatment regimen of this example with a compound of Formulae I-XVI in doses of about 20 mg to 1600 mg per day can experience a lessening in decline of cognitive function (as measured by the ADAS-cog or CDR sum of boxes), plaque pathology, and/or biochemical disease marker progression.

Example 6

Detection of Amyloid Beta with Biosource Elisa Kit (Camarillo, Calif.)

The present invention provides compositions and methods for lowering $A\beta_{42}$ levels. To test whether compounds and compositions are capable of modulating $A\beta$ levels, a sandwich enzyme-linked immunosorbent assay (ELISA) is employed to measure secreted $A\beta$ ($A\beta42$ and/or $A\beta40$) levels. In this example, H4 cells expressing wide type APP695 are seeded at 200,000 cells/per well in 6 well plates, and incubated at 37 degree C. with 5% $CO_2$ overnight. Cells are treated with 1.5 ml medium containing vehicle (DMSO) or a test compound at 1.25 μM, 2.5 μM, 5.0 μM and 10.0 μM (as well as other concentration if desirable) concentration for 24 hours or 48 hours. The supernatant from treated cells is collected into eppendorf tubes and frozen at −80 degree C. for future analysis.

The amyloid peptide standard is reconstituted and frozen samples are thawed. The samples and standards are diluted with appropriate diluents and the plate is washed 4 times with Working Wash Buffer and patted dry on a paper towel. 100 μL per well of peptide standards, controls, and dilutions of samples to be analyzed is added. The plate is incubated for 2 hours while shaking on an orbital plate shaker at RT. The plate is then washed 4 times with Working Wash Buffer and patted dry on a paper towel. Detection Antibody Solution is poured into a reservoir and 100 μL/well of Detection Antibody Solution is immediately added to the plate. The plate is incubated at RT for 2 hours while shaking and then washed four times with Working Wash Buffer and patted dry on a paper towel. Secondary Antibody Solution is then poured into a reservoir and 100 μL/well of Secondary Antibody Solution is immediately added to the plate. The plate is incubated at RT for 2 hours with shaking, washed 5 times with Working Wash Buffer, and patted dry on a paper towel.

100 μL of stabilized chromogen is added to each well and the liquid in the wells begins to turn blue. The plate is incubated for 30 minutes at room temperature and in the dark. 100 μL of stop solution is added to each well and the plate is tapped gently to mix resulting in a change of solution color from blue to yellow. The absorbance of each well is read at 450 nm having blanked the plate reader against a chromogen blank composed of 100 μL each of stabilized chromogen and stop solution. The plate is read within 2 hours of adding the stop solution. The absorbance of the standards is plotted against the standard concentration and the concentrations of unknown samples and controls are calculated.

Example 7

Synthesis of Compounds

General: Chemicals were purchased from standard commercial vendors and used as received unless otherwise noted. "Degassed" means reduced pressure then nitrogen gas for three cycles. Abbreviations are consistent with those in the ACS Style Guide, plus: satd (saturated), DCM (dichloromethane), pRPLC (preparative HPLC), "dry" glassware means oven/desiccator dried. Solvents were ACS grade unless otherwise noted. Analytical TLC plates (Silica Gel 60 F254, EM Science, Gibbstown, N.J., or Merck #5715) were used to follow the course of reactions, and the MPLC system used for purifications was from Isco (Foxy Jr fraction collector, UA-6 detector), using Isco silica gel flash columns (10 or 40 g). $^1$H NMR spectra in CDCl$_3$, CD$_3$OD, and/or d6-DMSO were recorded on either a Varian Mercury 400 MHz or Brucker ARX-300 MHz instrument and chemical shifts are expressed in parts per million (ppm, δ) relative to TMS as the internal standard. Mass spectra were obtained on a Thermo Finnigan LCQ-Deca (injection volume 5 uL, XTerra MS-C$_{18}$ 3.5 μm 2.1×50 mm column, XTerra MS-C$_{18}$ 5 μm 2.1×20 mm guard column), ESI source, analytical HPLC was performed on an HP1050 (injection volume 5 μl, XTerra RP-C$_{18}$ 5 μm 4.6×250 mm column, with an XTerra MS-C$_{18}$ 5 μm 2.1×20 mm guard column), and preparative HPLC was performed on an Agilent 1100 Prep-LC with various columns and conditions depending on the compound. GCMS was performed on either an Agilent Technology 6890N or Shimadzu QP5000/17A instrument. Yields are unoptimized.

1-(2-Oxo-2-phenyl-ethyl)-3,4-dihydro-1H-naphthalen-2-one (3)

A solution of phenacylbromide (5.21 g, 26.1 mmol) in toluene (16 mL) was added over 15 minutes to a boiling, stirred solution of 1-(3,4-dihydro-2-naphthyl)pyrrolidine (5.21 g, 26.2 mmol) in toluene (17 mL). The reaction was refluxed 3 hours, diluted with water (15 mL) and refluxed for 4 hours then cooled. The layers were separated and the aqueous phase was extracted with toluene and dried over MgSO$_4$ and concentrated. The material was purified by MPLC using a gradient from 0 to 20% ethyl acetate/hexanes to afford 4.85 g (70% yield) title product as a yellow oil.

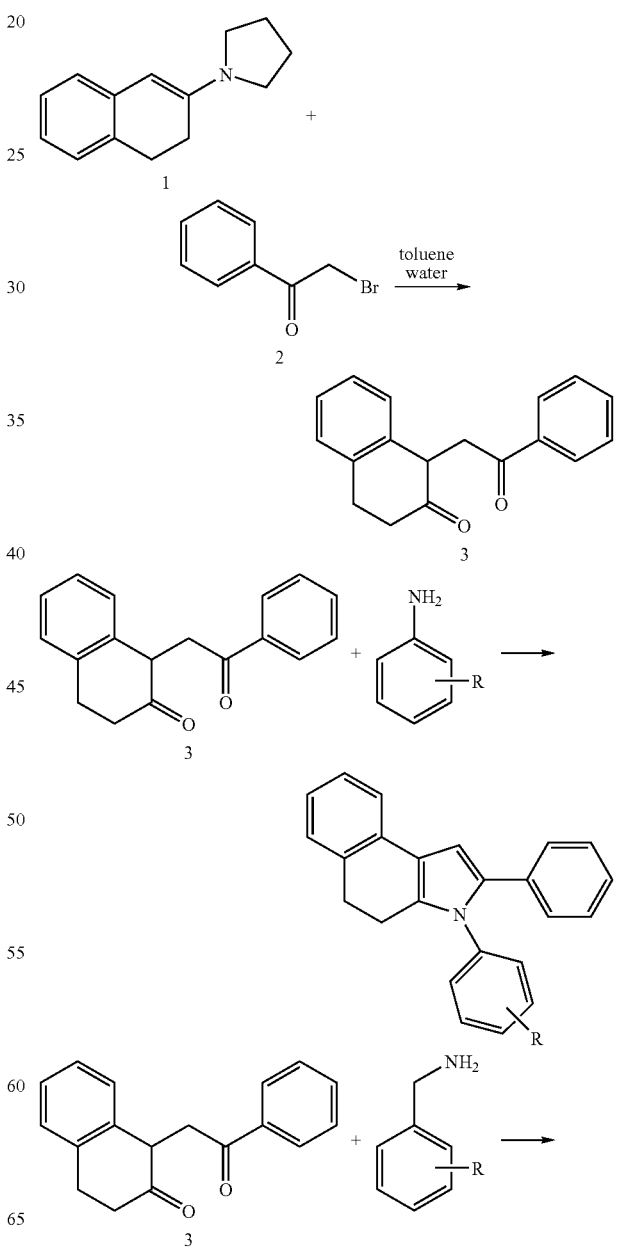

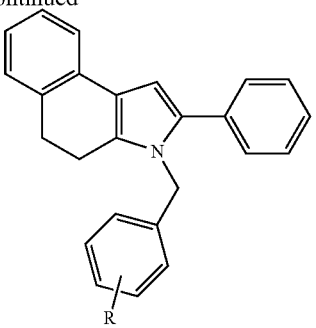

(4) R = 3-COOH, 4-OH
(5) R = 4-CH$_2$CH$_2$COOH
(6) R = 4-CH$_2$COOH
(7) R = 3-OH
(8) R = 4-OH
(9) R = 3-COOH
(10) R = 3-CH$_2$COOH
(11) R = 3-CH$_2$CH$_2$COOH
(12) R = 4-CH$_2$CH$_2$CH$_2$COOH
(13) R = 4-COOH
(14) R = 4-OH

Compounds 4-14 were prepared in the same way. Compound 4 is given as an example.

[2-Hydroxy-5-(2-phenyl-4,5-dihydro-benzo[e]indol-3-yl)-phenyl]-methanediol (4)

A mixture of 3 (2.41 g, 9.1 mmol), 5-aminosalicylic acid (1.40 g, 9.1 mmol) and glacial acetic acid (9 mL) was heated under reflux for 2 hours. After cooling, the precipitate was filtered and washed with acetic acid and water. The solid was recrystallized from acetic acid to afford 1.75 g (50% yield) title product as a yellow solid; MS m/z 380 (M$^-$–H) 9.92 min; $^1$H NMR (DMSO-d$_6$) δ 2.63 (t, 2H), 2.94 (t, 2H), 4.89 (s, 1H), 7.16 (m, 13H).

3-[4-(2-Phenyl-4,5-dihydro-benzo[e]indol-3-yl)-phenyl]-propionic acid (5)

MS m/z 392 (M$^-$–H) 6.99 min; $^1$H NMR (CDCl$_3$) δ 2.7 (d, 8H), 7.18 (m, 15H).

[4-(2-Phenyl-4,5-dihydro-benzo[e]indol-3-yl)-phenyl]-acetic acid (6)

MS m/z 380 (M$^+$+H) 6.90 min; $^1$H NMR (CDCl$_3$) δ 2.75 (d, 2H), 3.74 (d, 2H), 7.40 (m, 17H).

3-(2-Phenyl-4,5-dihydro-benzo[e]indol-3-yl)-phenol (7)

MS m/z 336 (M$^-$–H), 6.97 min, 338 (M$^+$+H) 6.95 min; $^1$H NMR (CDCl$_3$) δ 2.75 (d, 4H), 7.08 (m, 15H).

4-(2-Phenyl-4,5-dihydro-benzo[e]indol-3-yl)-phenol (8)

MS m/z 336 (M$^-$–H) 6.85 min, 338 (M$^+$+H) 6.86 min; $^1$H NMR (CDCl$_3$) δ 2.60 (s, 2H), 2.87 (s, 2H), 3.89 (s, 2H), 6.91 (m, 13H).

3-(2-Phenyl-4,5-dihydro-benzo[e]indol-3-yl)-benzoic acid (9)

MS m/z 364 (M$^-$–H) 6.97 min, 366 (M$^+$+H) 6.97 min; $^1$H NMR (CDCl$_3$) δ 2.66 (t, 2H), 2.94 (t, 2H), 7.12 (m, 15H).

[3-(2-Phenyl-4,5-dihydro-benzo[e]indol-3-yl)-phenyl]-acetic acid (10)

MS m/z 378 (M$^-$–H) 6.92 min; $^1$H NMR (DMSO-d$_6$) δ 2.50 (s, 1H), 3.29 (s, 4H), 3.68 (s, 2H), 7.35 (m, 14H).

3-[3-(2-Phenyl-4,5-dihydro-benzo[e]indol-3-yl)-phenyl]-propionic acid (11)

MS m/z 392 (M$^-$–H) 7.33 min; $^1$H NMR (CDCl$_3$) δ 2.12 (t, 3H), 2.47 (t, 4H) 2.80 (t, 2H), 7.08 (m, 14H).

4-[4-(2-Phenyl-4,5-dihydro-benzo[e]indol-3-yl)-phenyl]-butyric acid (12)

MS m/z 406 (M$^-$–H) 8.22 min; $^1$H NMR (C$_6$D$_6$) δ 1.99 (m, 10H), 7.07 (m, 15H).

4-(2-Phenyl-4,5-dihydro-benzo[e]indol-3-ylmethyl)-benzoic acid (13)

MS m/z 378 (M$^-$–H) 6.81 min, 380 (M$^+$+H) 6.81 min; δ 2.66 (t, 2H), 2.98 (t, 2H), 6.61 (s, 2H), 7.22 (m, 15H).

4-(2-Phenyl-4,5-dihydro-benzo[e]indol-3-ylmethyl)-phenol (14)

MS m/z 352 (M$^+$+H) 6.83 min; $^1$H NMR (CDCl$_3$) δ 2.68 (t, 2H), 2.97 (t, 2H), 5.09 (s, 2H), 7.21 (m, 15H).

3-[3-(2-Phenyl-benzo[e]indol-3-yl)-phenyl]-propionic acid (15)

MS m/z 390 (M$^-$–H) 7.45 min; $^1$H NMR (CDCl$_3$) δ 2.15 (m, 4H), 7.07 (m, 15H).

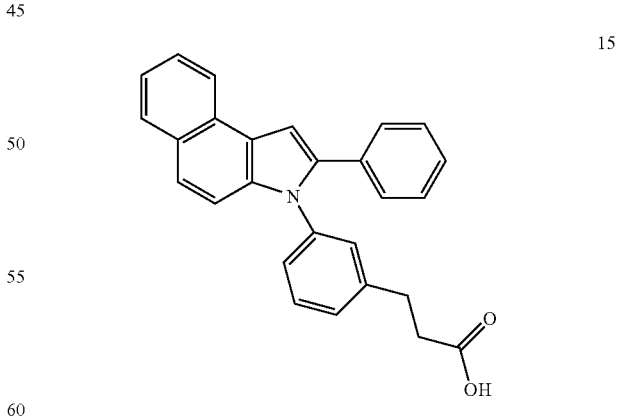

15

Example 8

The following synthetic routes can be employed to make the compounds of Formulae I-XVI (e.g., those in the Tables below).

Route A: Allen, et al, J. Med. Chem. 1976, 19 (2), 318-325.
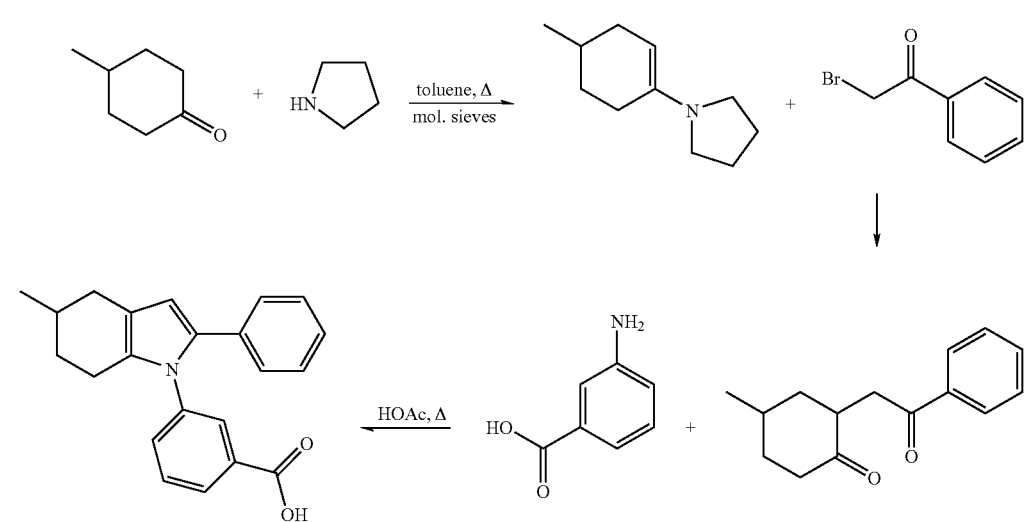
Route B: Murakami, et al, Chem. Pharm. Bull. 1995, 43 (8), 1281-1286.
Route C: Allen, et al, J. Med. Chem. 1976, 19 (2), 318-325.
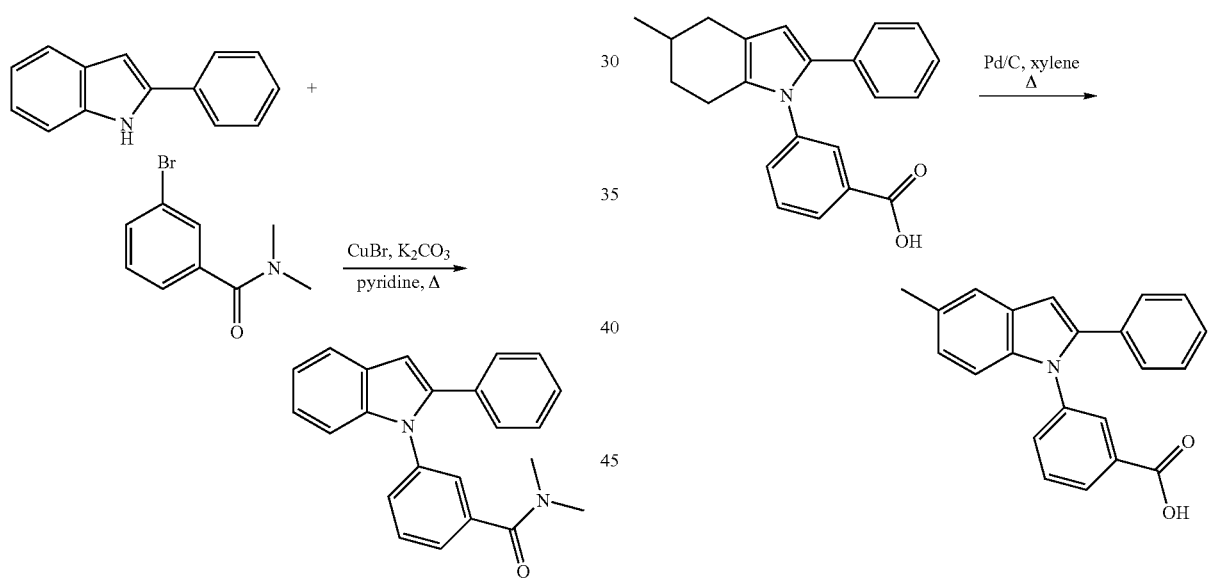
Compounds 16-90 below in Table 1, can be prepared in a similar manner as described for Compounds 4-14.
TABLE 1
| product structure | SM ketone |
|---|---|

TABLE 1-continued
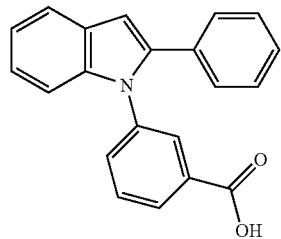 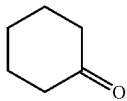
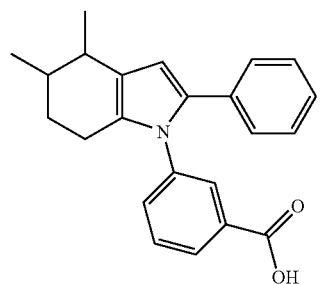 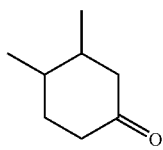
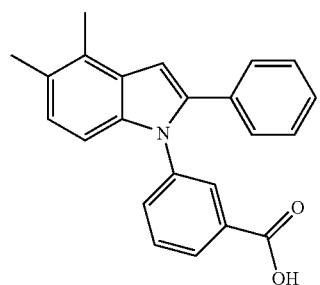 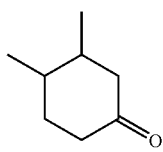
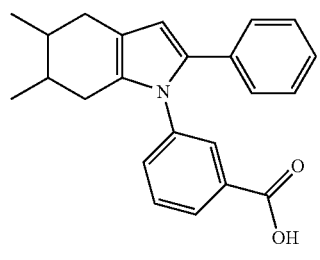 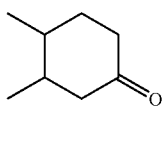
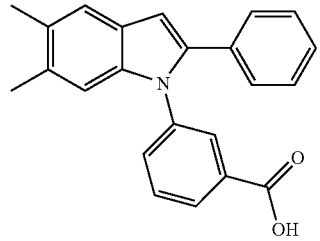 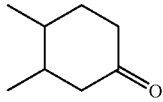
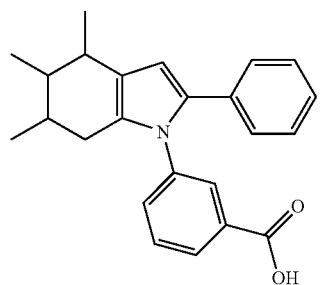 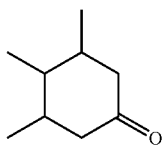

TABLE 1-continued
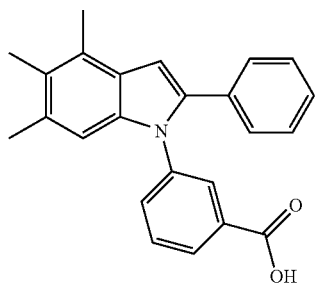 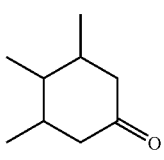
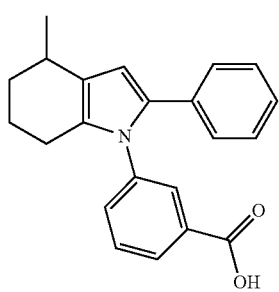 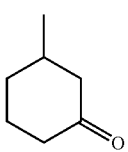
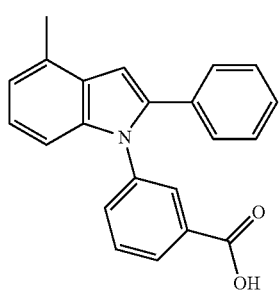 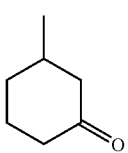
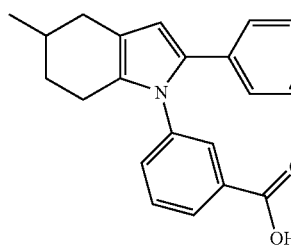 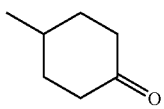
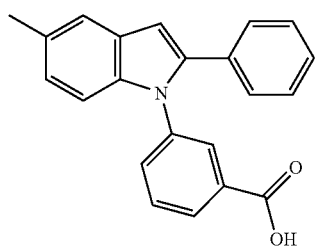 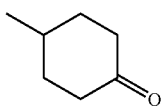

TABLE 1-continued
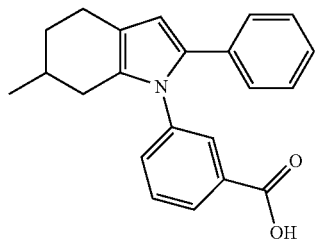 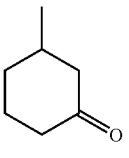
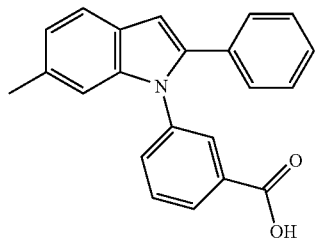 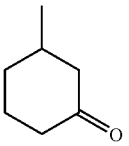
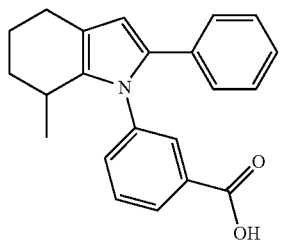 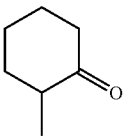
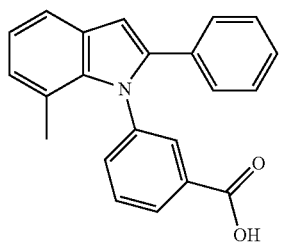 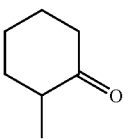
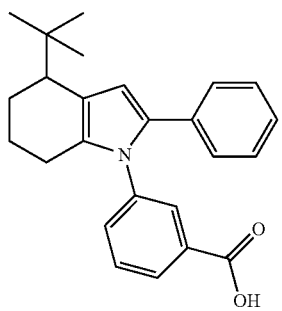 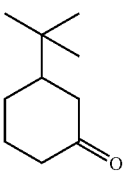
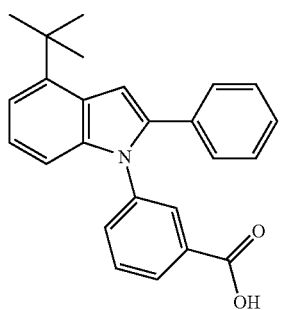 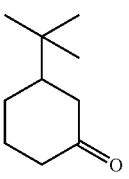

TABLE 1-continued
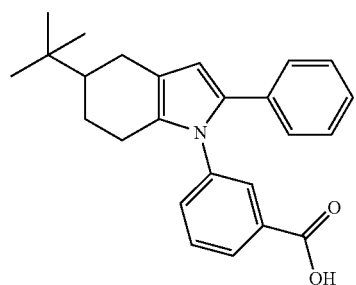 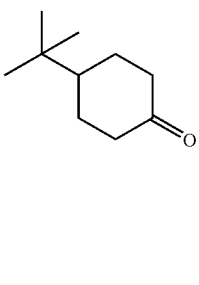
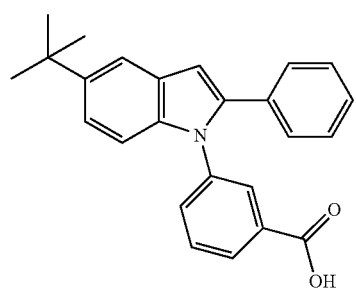 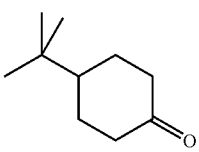
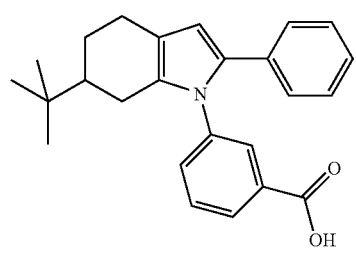 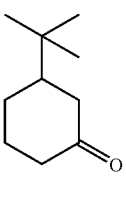
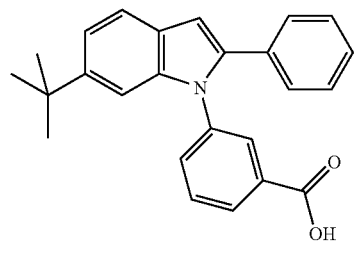 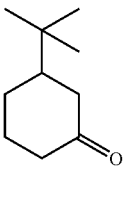
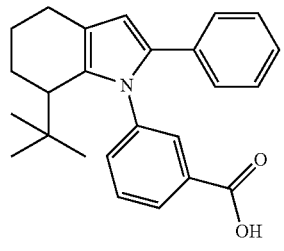 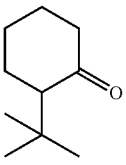
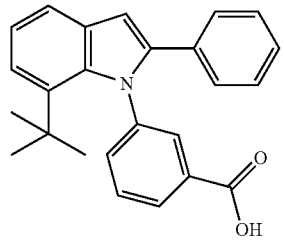 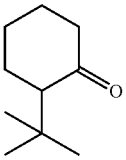

TABLE 1-continued
| | |
|---|---|
| 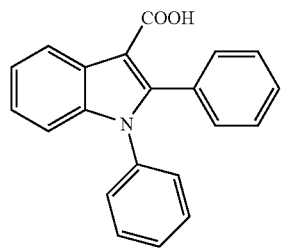 | 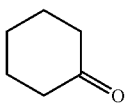 |
| 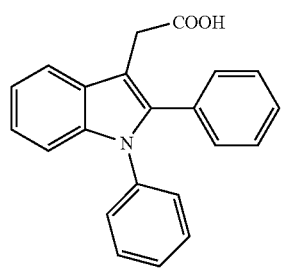 | 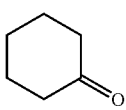 |
| 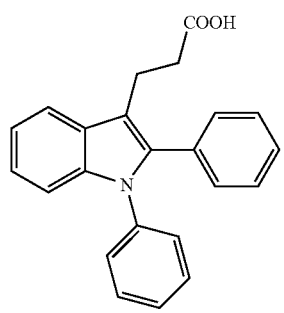 | 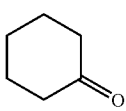 |
| 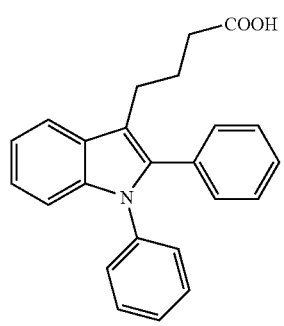 | 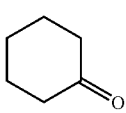 |
| 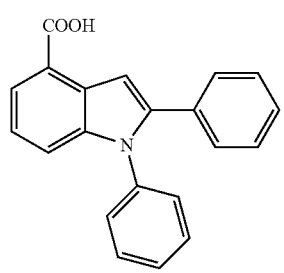 | 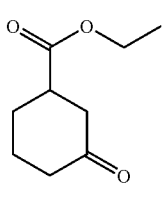 |

TABLE 1-continued
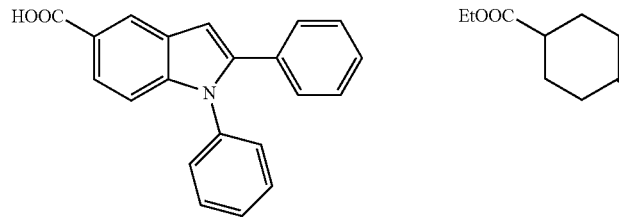
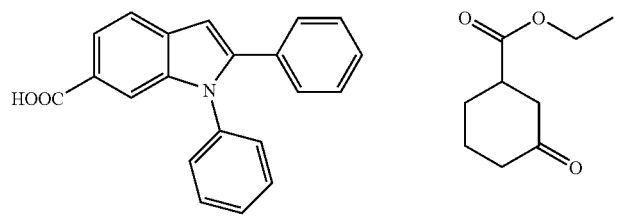
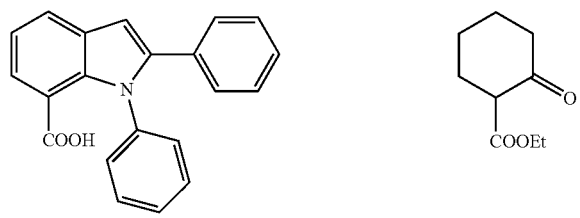
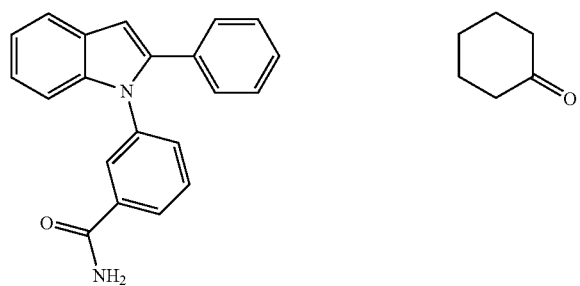
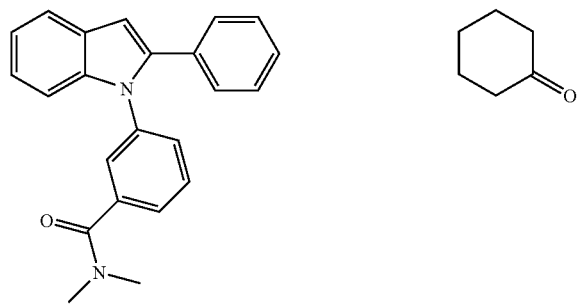
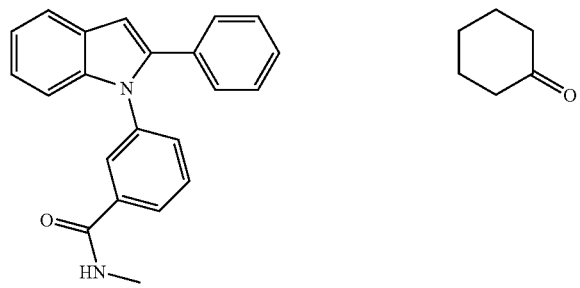

TABLE 1-continued
| | |
|---|---|
| 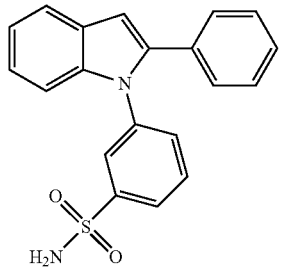 | 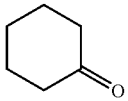 |
| 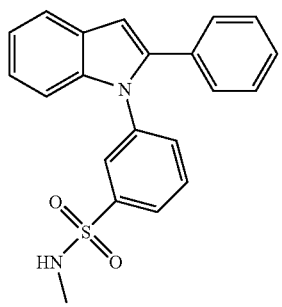 | 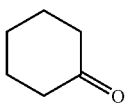 |
| 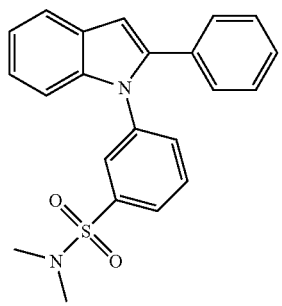 | 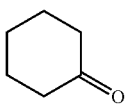 |
| 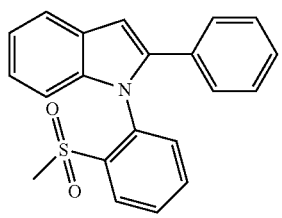 | 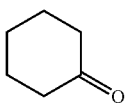 |
| 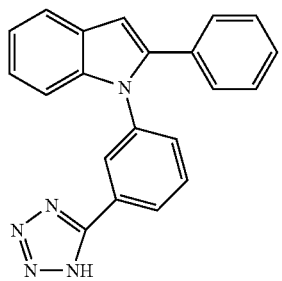 | 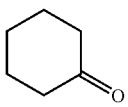 |

TABLE 1-continued
| product structure | SM ketone/enamine |
|---|---|
| 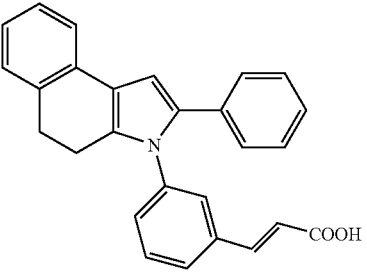 | 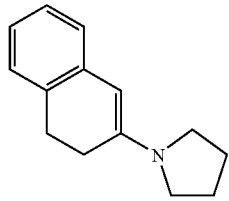 |
| 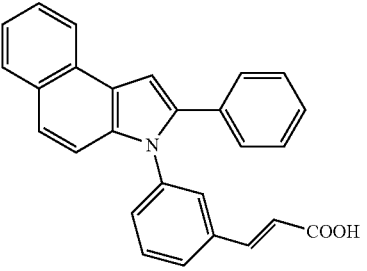 | 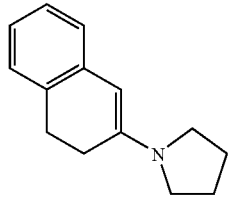 |
| 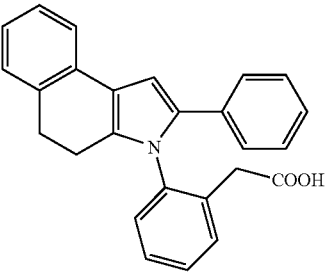 | 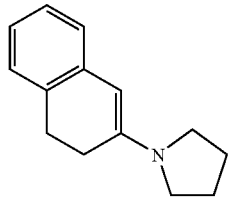 |
| 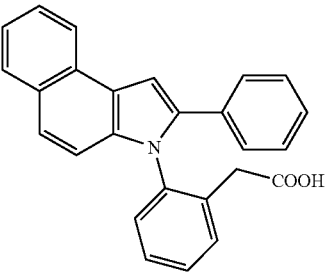 | 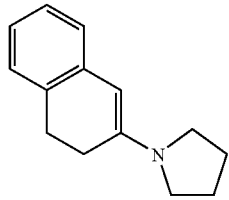 |
| 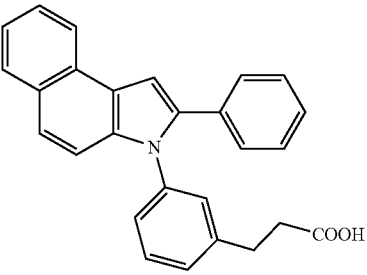 | 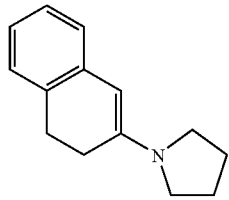 |

TABLE 1-continued
| | |
|---|---|
| 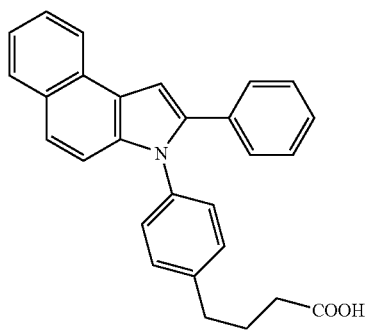 | 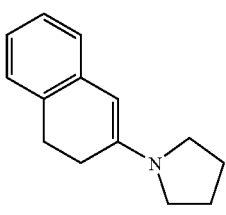 |
| 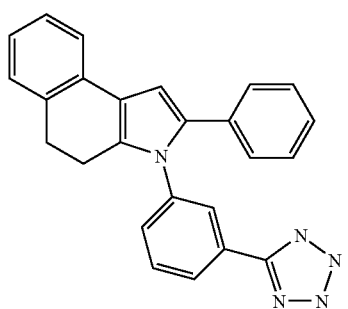 | 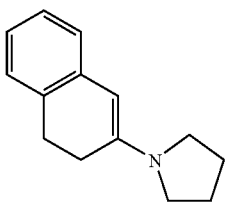 |
| 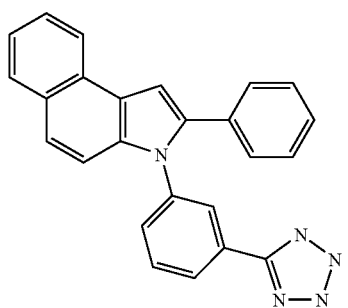 | 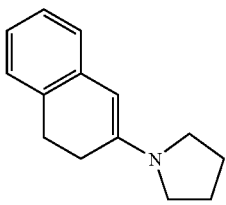 |
| 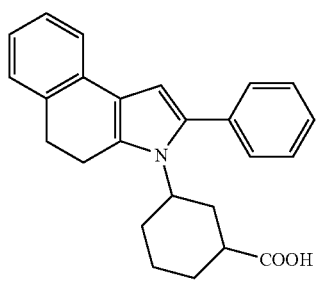 | 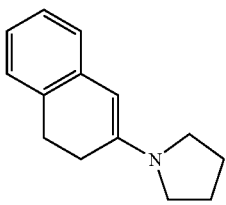 |
| 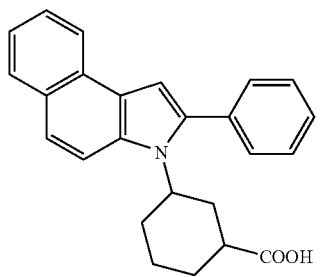 | 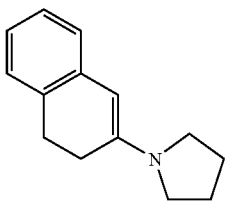 |

TABLE 1-continued
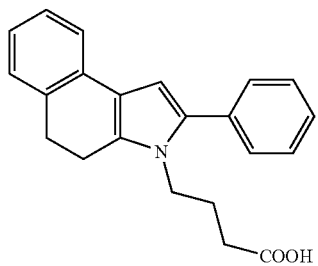 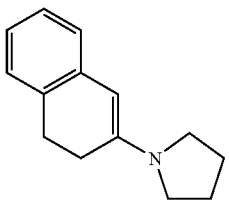
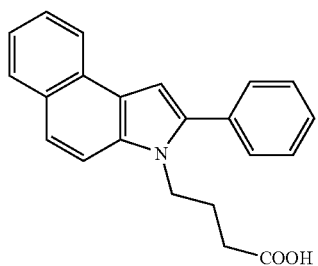 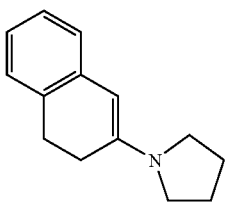
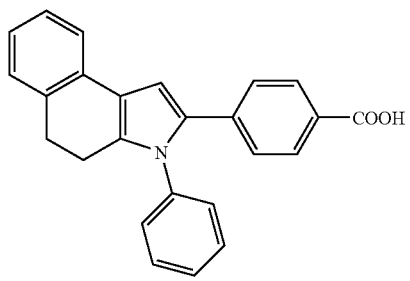 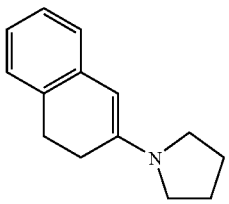
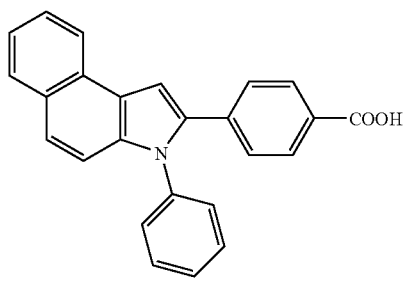 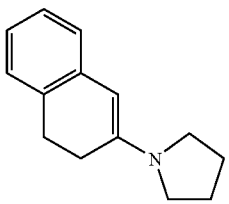
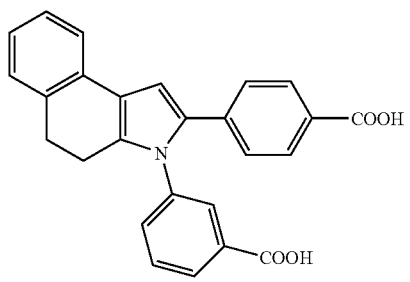 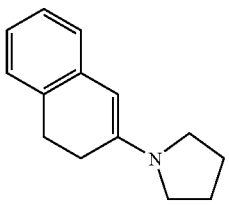

TABLE 1-continued
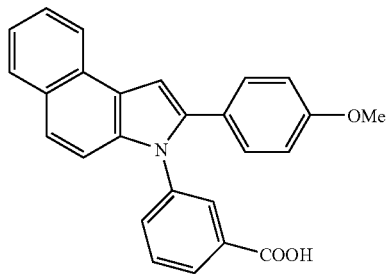 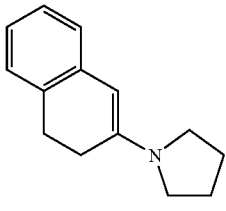
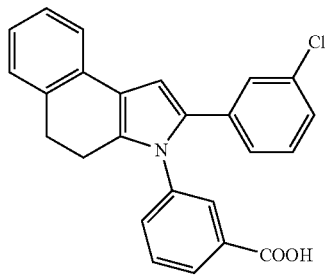 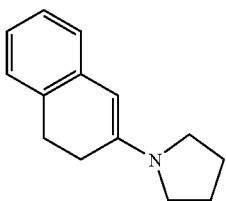
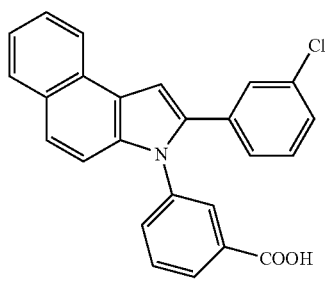 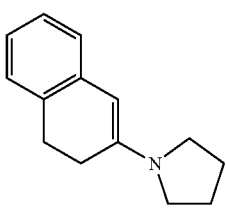
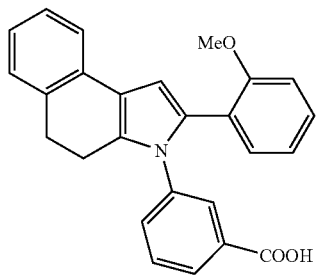 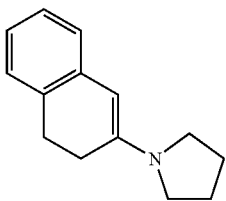
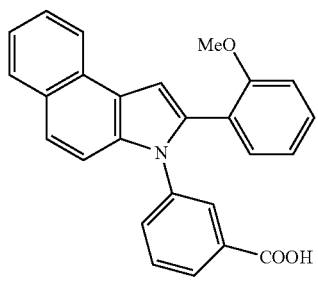 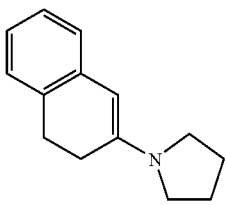

TABLE 1-continued
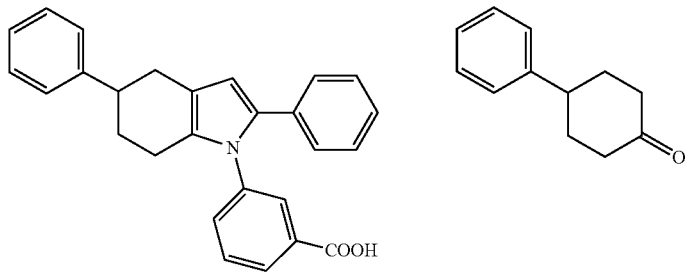
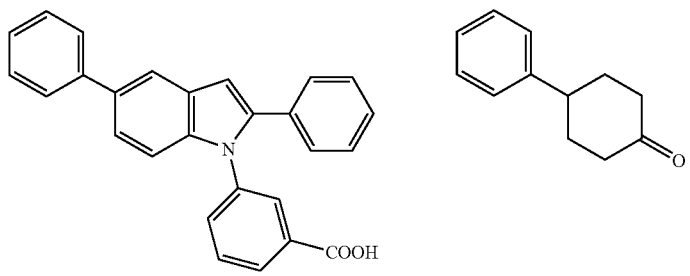
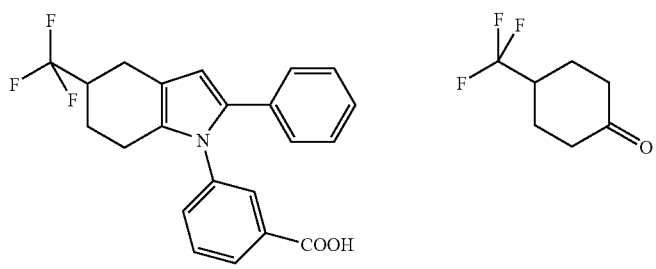
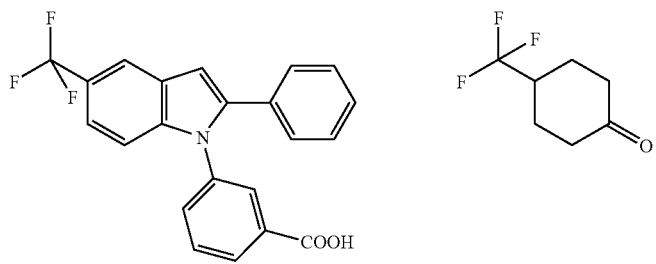
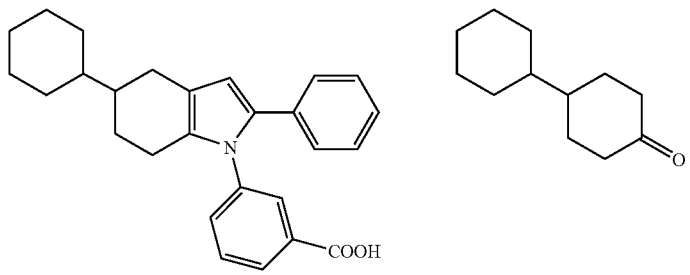

TABLE 1-continued
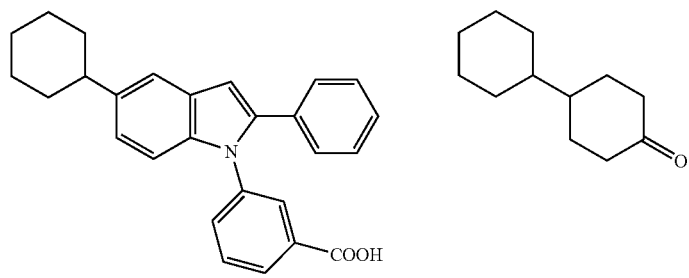
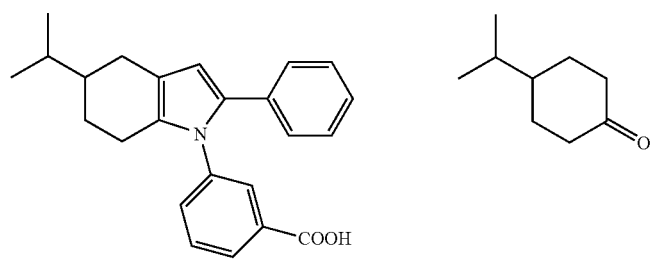
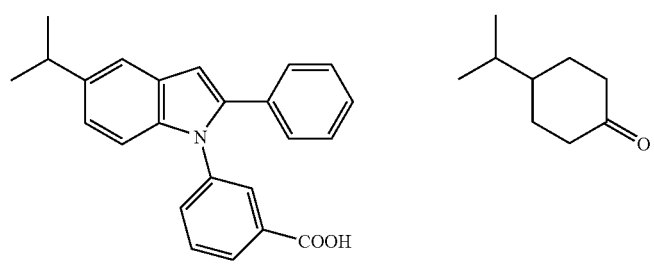
| alpha-bromo ketone | aniline | synthetic route |
|---|---|---|
| 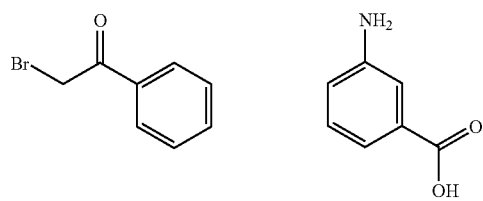 | 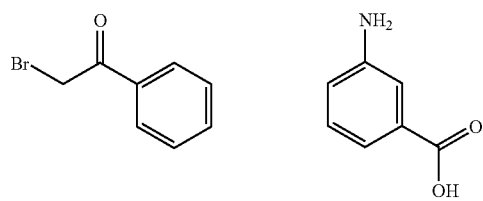 | A |
| 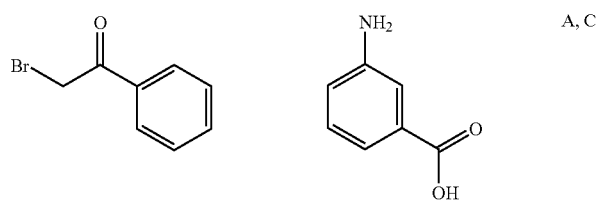 | 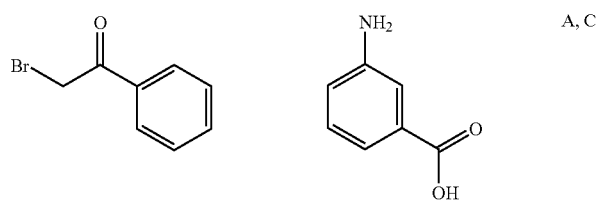 | A, C |
| 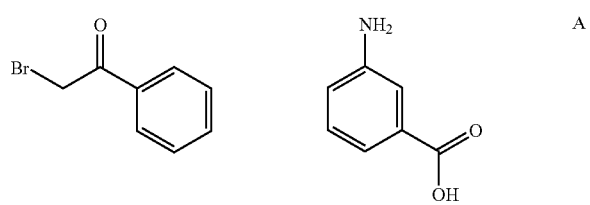 | 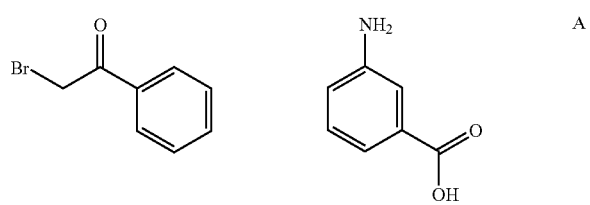 | A |

TABLE 1-continued
| | | |
|---|---|---|
| 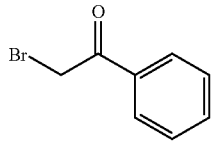 | 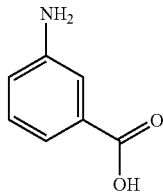 | A, C |
| 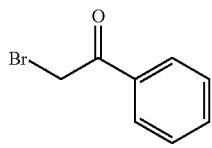 | 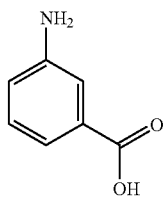 | A |
| 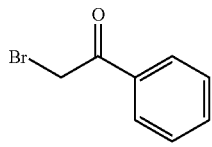 | 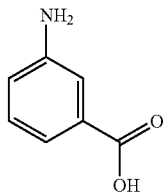 | A, C |
| 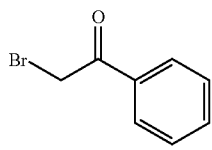 | 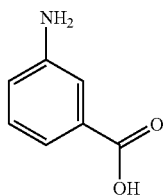 | A |
| 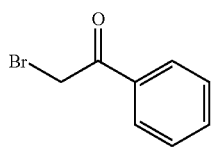 | 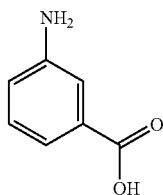 | A, C |
| 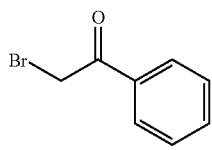 | 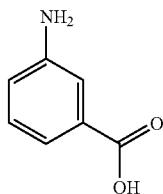 | A |
| 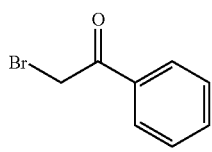 | 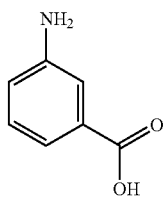 | A, C |

TABLE 1-continued
| | | |
|---|---|---|
| 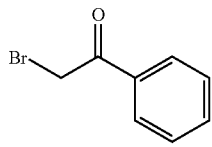 | 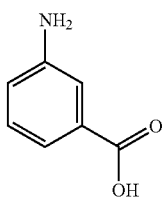 | A |
| 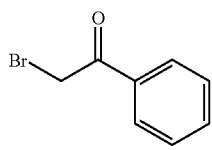 | 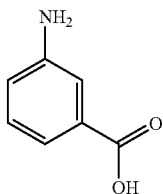 | A, C |
| 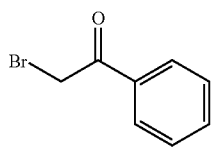 | 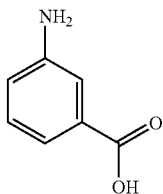 | A |
| 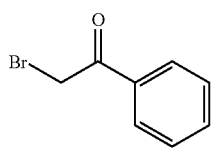 | 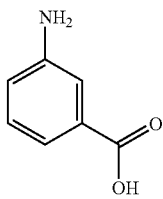 | A, C |
| 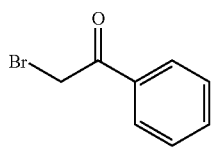 | 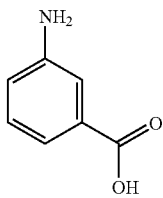 | A |
| 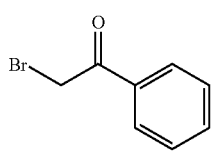 | 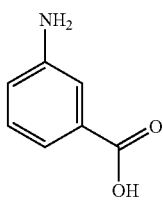 | A, C |
| 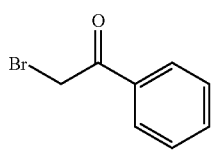 | 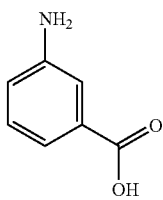 | A |

TABLE 1-continued
| | | |
|---|---|---|
| 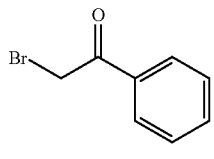 | 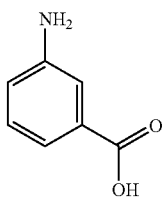 | A, C |
| 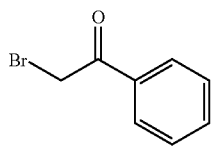 | 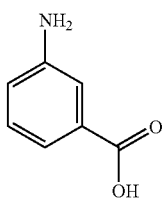 | A |
| 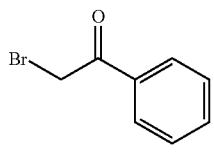 | 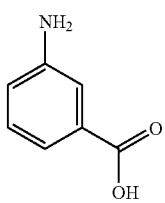 | A, C |
| 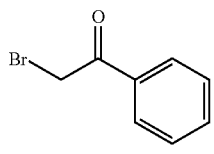 | 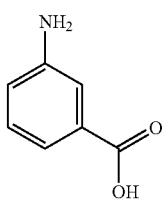 | A |
| 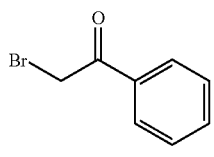 | 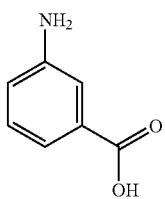 | A, C |
| 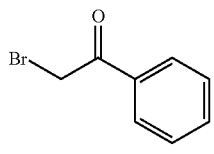 | 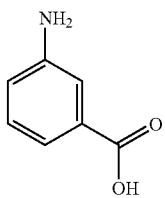 | A |
| 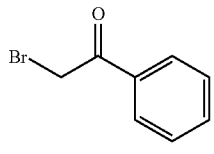 | 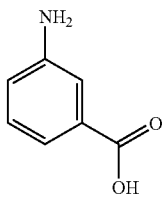 | A, C |
| 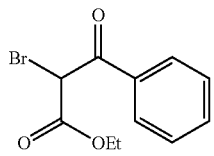 | 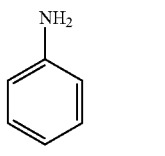 | A, C, B |

TABLE 1-continued

| Reactant 1 | Reactant 2 | Methods |
|---|---|---|
| EtOOC-CH(Br)-CH2-C(O)-Ph | aniline | A, C, B |
| EtOOC-CH2-CH2-CH(Br)-C(O)-Ph | aniline | A, C, B |
| EtOOC-CH2-CH2-CH2-CH(Br)-C(O)-Ph | aniline | A, C, B |
| BrCH2-C(O)-Ph | aniline | A, C, B |
| BrCH2-C(O)-Ph | aniline | A, C, B |
| BrCH2-C(O)-Ph | aniline | A, C, B |
| BrCH2-C(O)-Ph | aniline | A, C, B |
| BrCH2-C(O)-Ph | 3-aminobenzamide | A, C |
| BrCH2-C(O)-Ph | 3-amino-N,N-dimethylbenzamide | A, C |

TABLE 1-continued

| alpha-bromo ketone | aniline | synthetic route |
|---|---|---|
| BrCH₂C(O)-phenyl | 3-amino-N-methylbenzamide | A, C |
| BrCH₂C(O)-phenyl | 3-aminobenzenesulfonamide | A, C |
| BrCH₂C(O)-phenyl | 3-amino-N-methylbenzenesulfonamide | A, C |
| BrCH₂C(O)-phenyl | 3-amino-N,N-dimethylbenzenesulfonamide | A, C |
| BrCH₂C(O)-phenyl | 3-(methylsulfonyl)aniline | A, C |
| BrCH₂C(O)-phenyl | 3-(1H-tetrazol-5-yl)aniline | A, C |

| alpha-bromo ketone | aniline | synthetic route |
|---|---|---|
| BrCH₂C(O)-phenyl | 3-aminocinnamic acid | A |
| BrCH₂C(O)-phenyl | 3-aminocinnamic acid | A, C |

TABLE 1-continued

TABLE 1-continued

TABLE 1-continued

| | | |
|---|---|---|
| (2-methoxyphenyl bromoacetyl) | 3-aminobenzoic acid | A, C |
| (phenyl bromoacetyl) | 3-aminobenzoic acid | A |
| (phenyl bromoacetyl) | 3-aminobenzoic acid | A, C |
| (phenyl bromoacetyl) | 3-aminobenzoic acid | A |
| (phenyl bromoacetyl) | 3-aminobenzoic acid | A, C |
| (phenyl bromoacetyl) | 3-aminobenzoic acid | A |
| (phenyl bromoacetyl) | 3-aminobenzoic acid | A, C |
| (phenyl bromoacetyl) | 3-aminobenzoic acid | A |
| (phenyl bromoacetyl) | 3-aminobenzoic acid | A, C |

Example 9

Synthesis of Compound 34

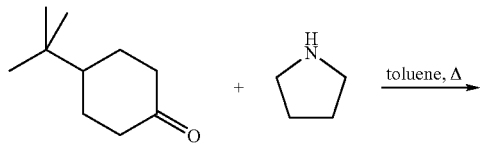

1-(4-tert-butylcyclohex-1-enyl)pyrrolidine: A 50 mL round-bottomed flask containing 4-tert-butylcyclohexanone (6.01 gm) in anhydrous toluene (20 mL) was fitted with a Dean-Stark trap containing 3 A molecular sieves, reflux condenser and a heating mantle. Pyrrolidine (6.00 mL) was added, and the solution heated to reflux for 18 hr. The solvent was evaporated and the crude product was used directly for the next reaction.

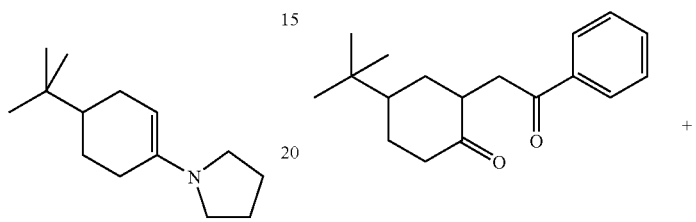

4-tert-butyl-2-(2-oxo-2-phenylethyl)-cyclohexanone: To a 250-mL round-bottomed flask containing 3.3 mL of 1-(4-tert-butylcyclohex-1-enyl)pyrrolidine was added 100 mL anhydrous DMF, under nitrogen. The flask was fitted with an addition funnel containing 2-bromoacetophenone (4.12 gm) in 35 mL anhydrous DMF, which was dripped into the enamine solution over 60 min. This solution was stirred at ambient temperature for 10 hr, then 90 mL water was added to the solution and it was stirred for another 11 hr, under nitrogen. The solution was then extracted twice with ethyl acetate and water, the organic layers combined and further washed with water (3×), dried over sodium sulfate, filtered and rotovapped down to give a yellow oil. The oil was purified by MPLC using 10% ethyl acetate/hexanes.

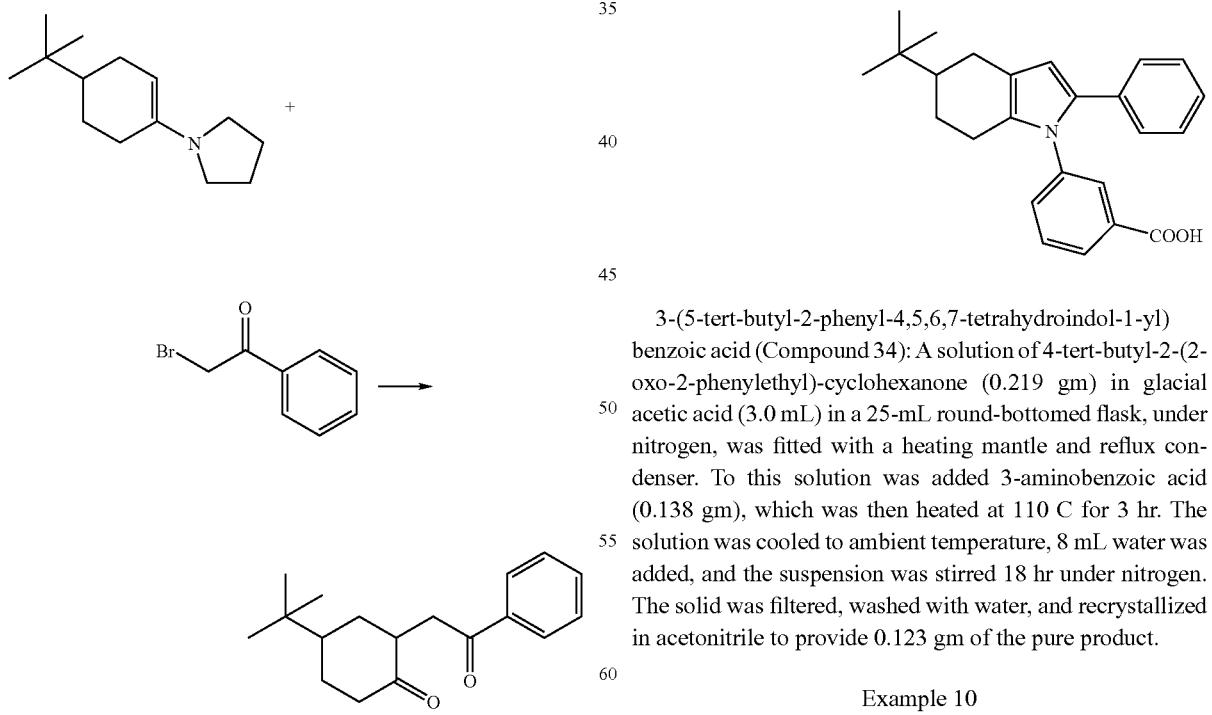

3-(5-tert-butyl-2-phenyl-4,5,6,7-tetrahydroindol-1-yl) benzoic acid (Compound 34): A solution of 4-tert-butyl-2-(2-oxo-2-phenylethyl)-cyclohexanone (0.219 gm) in glacial acetic acid (3.0 mL) in a 25-mL round-bottomed flask, under nitrogen, was fitted with a heating mantle and reflux condenser. To this solution was added 3-aminobenzoic acid (0.138 gm), which was then heated at 110 C for 3 hr. The solution was cooled to ambient temperature, 8 mL water was added, and the suspension was stirred 18 hr under nitrogen. The solid was filtered, washed with water, and recrystallized in acetonitrile to provide 0.123 gm of the pure product.

Example 10

Analytical data for compounds of Formulae I and II. These compounds were synthesized via the indicated synthetic route. Ab42 IC50 (uM) refers to IC50 value for Ab42 lowering in e.g., the assay described in Example 6.

TABLE 2

| Compound Number | product structure | 1H NMR, δ | MS | name | Syn. route used | Ab42 IC50 (uM) |
|---|---|---|---|---|---|---|
| 17 | | CDCl3; 8.1(m, 2H); 7.7(m, 1H); 7.5(t, 1H); 7.4(m, 1H); 7.2-7.3(m, 8H, ArH); 6.8(s, 1H). | pos. mode 314(M + H); neg. mode 312(M − H) | 3-(2-phenylindol-1-yl) benzoic acid | A, C | 55 |
| 34 | | CDCl3/d3-MeOD; 8.0(m, 2H); 7.4(t, 1H); 7.2(m, 1H); 7.0-7.2(m, 5H, ArH); 6.2(s, 1H); 2.7(m, 1H); 2.5(s, 1H); 2.4(m, 2H); 2.0(m, 1H); 1.5(m, 1H); 1.4(m, 1H); 0.9(s, 9H). | pos. mode 374(M + H); neg. mode 372(M − H) | 3-(5-tert-Butyl-2-phenyl-4,5,6,7-tetrahydro-indol-1-yl) benzoic acid | A | 8 |
| 85 | | CDCl3; 7.2(m, 1H); 6.9-7.1(m, 8H, ArH); 6.2(s, 1H); 2.9(t, 2H); 2.7(m, 1H); 2.5(m, 3H); 2.4(m, 2H); 2.0(m, 1H); 1.5(m, 1H); 1.4(m, 1H); 0.9(s, 9H). | pos. mode 402(M + H); neg. mode 400(M − H) | 3-[3-(5-tert-Butyl-2-phenyl-4,5,6,7-tetrahydro-indol-1-yl)-phenyl] propionic acid | A | 20 |
| 63 | | DMSO-d6; 7.0-8.4(13H, ArH); 6.9(1H), 2.9(2H, CH2), 2.5(2H, CH2). | pos. mode 342(M + H); neg. mode 340(M − H) | 2-phenyl-3-[3-(2H-tetrazol-5-yl)-phenyl]-4,5-dihydro-3H-benzo[e]indole | A | 24 |
| 69 | | DMSO-d6; 6.8-7.9(14H, ArH), 3.0(2H, CH2) 2.7(2H, CH2). | neg. mode 364(M − 1) | 4-(3-phenyl-4,5-dihydro-3H-benzo[e]indol-2-yl) benzoic acid | A | 45 |

TABLE 2-continued

| Compound Number | product structure | 1H NMR, δ | MS | name | Syn. route used | Ab42 IC50 (uM) |
|---|---|---|---|---|---|---|
| 86 | | DCDl3; 7.0-7.2 (m, 9H, ArH); 6.2(s, 1H); 2.6 (m, 4H); 2.4(m, 4H); 2.0(m, 3H); 1.8(s, 3H). | neg. mode 358(M − H) | 4-[4-(2-phenyl-4,5,6,7-tetrahydro-indol-1-yl)-phenyl] butyric acid | A | 30 |
| 87 | | DMSO-d6; 7.2-8.4(16H, ArH). | pos. mode 364(M + 1); neg. mode 362(M − 1) | 3-(2-phenylbenzo[e]indol-3-yl) benzoic acid | A, C | 12 |
| 88 | | CDCl3; 7.3(t, 1H); 6.9-7.1 (m, 8H, ArH); 6.2(s, 1H); 2.9 (t, 2H); 2.7(m, 1H); 2.5(m, 3H); 2.4(m, 1H); 2.2(m, 1H); 1.9(m, 2H); 1.4(m, 1H); 1.0(d, 3H). | pos. mode 360(M + H); neg. mode 358(M − H) | 3-[3-(5-methyl-2-phenyl-4,5,6,7-tetrahydro-indol-1-yl)-phenyl] propionic acid | A | 27 |
| 89 | | DMSO-d6; 7.2-8.4(16H, ArH); 2.7(2H, CH2); 2.3(2H, CH2); 1.9(2H, CH2). | pos. mode 406(M + 1); neg. mode 404(M − 1) | 4-[4-(2-phenyl-benzo[e]indol-3-yl)-phenyl] butyric acid | A, C | 8 |

TABLE 2-continued

| Compound Number | product structure | 1H NMR, δ | MS | name | Syn. route used | Ab42 IC50 (uM) |
|---|---|---|---|---|---|---|
| 90 | | CDCl3; 7.3(t, 1H); 6.9-7.2 (m, 8H, ArH); 6.2(s, 1H); 2.9 (t, 2H); 2.6(br. s, 2H); 2.5(t, 2H); 2.4(br. s, 2H); 1.8(br. s, 4H). | pos. mode 346(M + H) | 3-[3-(2-phenyl-4,5,6,7-tetrahydro-indol-1-yl)-phenyl] propionic acid | A | 54 |
| 66 | | CDCl3; 7.1-8.4 (11H, ArH), 6.4 (1H, ArH), 4.4 (1H, CH) 1.4-2.7 (9H, CH2). | pos. mode 372(M + 1) | 3-(2-phenylbenzo [e]indol-3-yl) cyclohexane carboxylic acid | A, C | 54 |
| 67 | | CD3OD-d4; 7.1-8.2(10H, ArH), 4.0(2H, CH2), 3.0(2H, CH2), 2.9(2H, CH2), 2.1(2H, CH2), 1.9(2H, CH2). | pos. mode 332(M + 1) | 4-(2-phenyl-4,5-dihydrobeno [e]indol-3-yl) butyric acid | A | 35 |
| 68 | | CD3OD-d4; 7.1-8.2(12H, ArH) 4.4(2H, CH2) 2.1(2H, CH2) 1.9(2H, CH2). | pos. mode 330(M + 1) | 4-(2-phenyl-benzo[e]indol-3-yl) butyric acid | A, C | 31 |

TABLE 2-continued

| Compound Number | product structure | 1H NMR, δ | MS | name | Syn. route used | Ab42 IC50 (uM) |
|---|---|---|---|---|---|---|
| 71 | | DMSO-d6; 7.0-7.9(14H, ArH), 6.3(1H, ArH), 3.0(1H, CH), 2.8(1H, CH2), 2.7(2H, CH2), 2.4(1H, CH2), 1.9(2H, CH2). | pos. mode 394(M + 1) | 3-(2,5-diphenyl-4,5,6,7-tetrahydro-indol-1-yl) benzoic acid | A | 50 |
| 91 | | CDCl3; 8.0(m, 1H); 7.9(m, 1H); 7.4(t, 1H); 7.0-7.3(m, 6H, ArH); 6.2(s, 1H); 2.6(m, 1H); 2.5(br. s, 1H); 2.4(m, 1H); 2.1(m, 1H); 1.9(m, 2H); 1.4(m, 1H); 1.0(d, 3H). | pos. mode 332(M + H) | 3-(4-methyl-2-phenyl-4,5,6,7-tetrahydro-indol-1-yl) benzoic acid | A | 3 |
| 92 | | acetone-d6; 7.5 (m, 5H); 7.2(m, 7H); 7.0(t, 1H); 6.8(s, 1H); 3.2 (s, 2H, CH2); 2.9(m, 2H); 2.6 (m, 1H); 2.4(m, 1H). | pos. mode 380(M + H) | [2-(2-phenyl-4,5-dihydrobenzo [e]indol-3-yl)-phenyl] acetic acid | A | 27 |

Example 11

The following synthetic routes can be used to make the compounds of Formulae I-XVI.

Synthetic Routes for Heteroaromatics

Route A: Allen, et al, J. Med. Chem. 1976, 19 (2), 318-325.

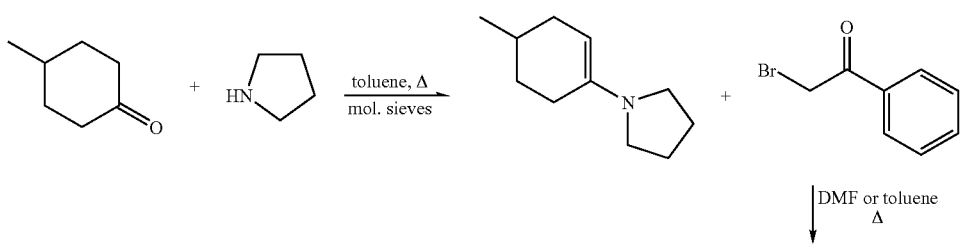

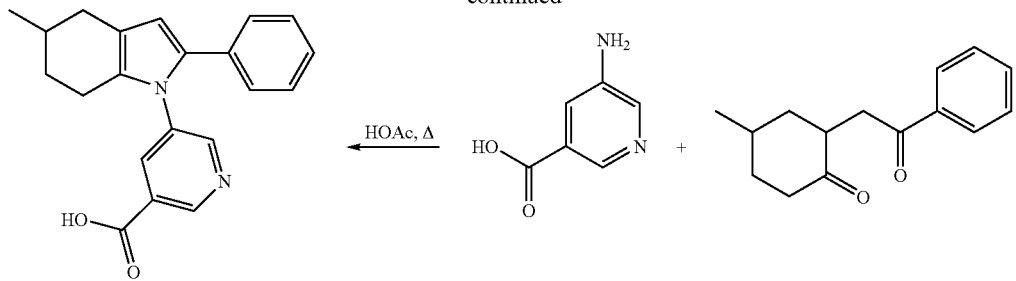
Route B: Murakami, et al, Chem. Pharm. Bull. 1995, 43 (8), 1281-1286.
Route C: Allen, et al, J. Med. Chem. 1976, 19 (2), 318-325.
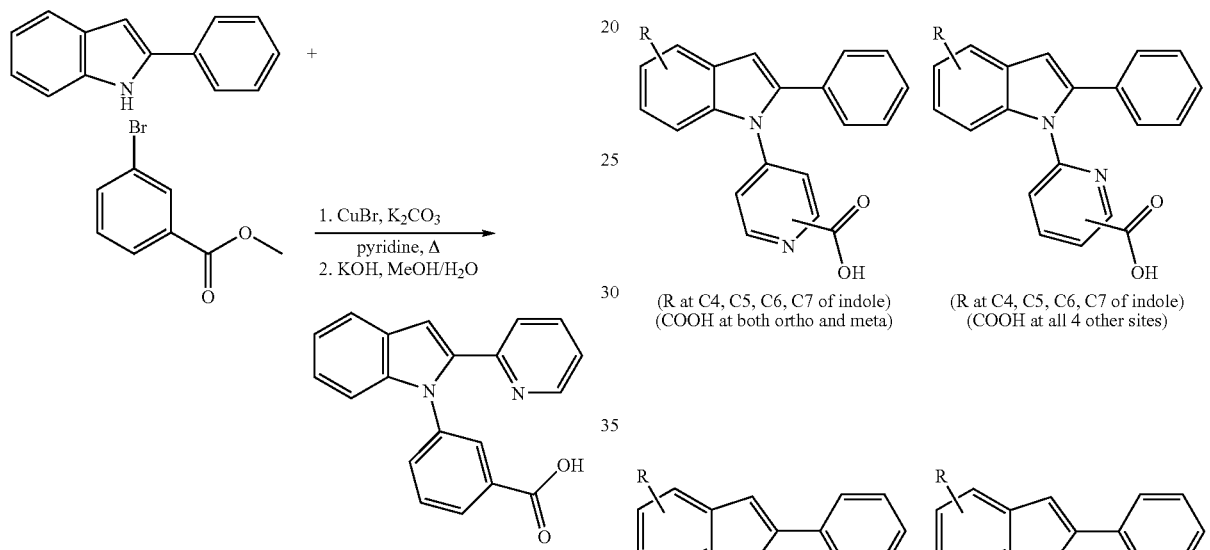
Compounds for Heteroaromatics
Heteroaromatic N-Alkylated Analogs:
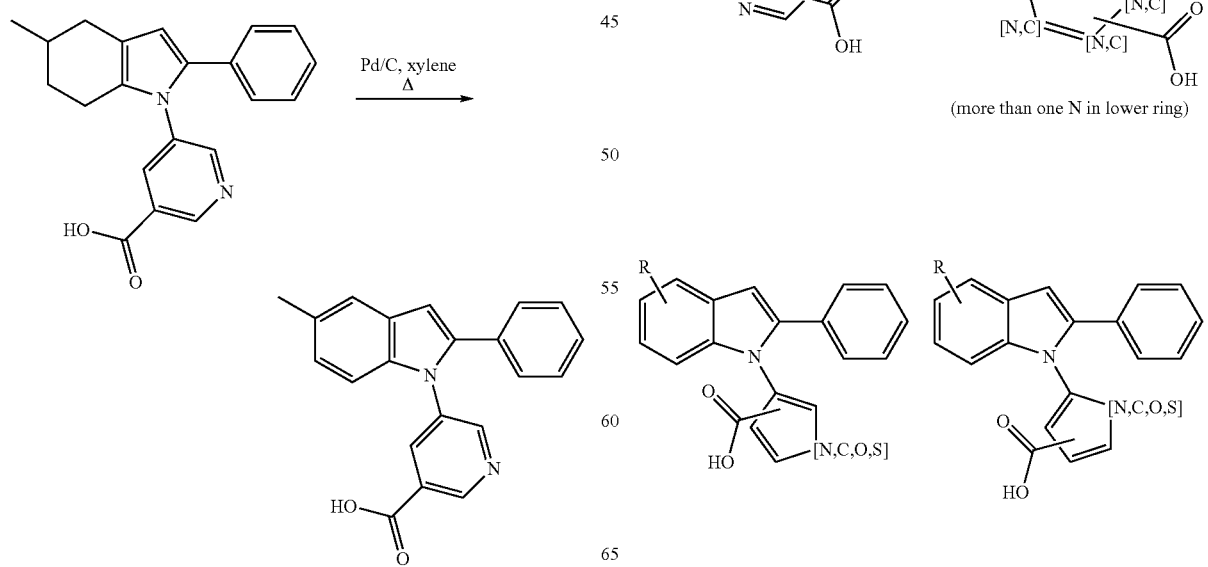
(R at C4, C5, C6, C7 of indole)
(COOH at both ortho and meta)
(R at C4, C5, C6, C7 of indole)
(COOH at all 4 other sites)
(more than one N in lower ring)
also, all of the above with a partially saturated ring (4,5,6,7-tetrahydroindoles):

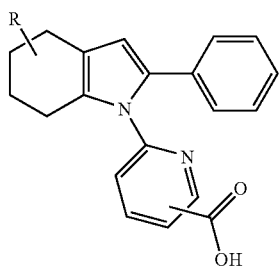
(etc, as above)
rearranging the acid group placement:
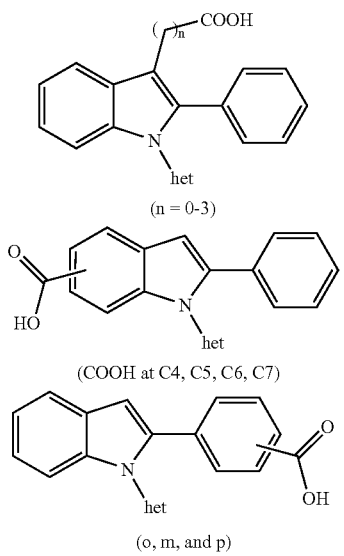
placing the heterocycle at the indole C-1 or C-2 position:
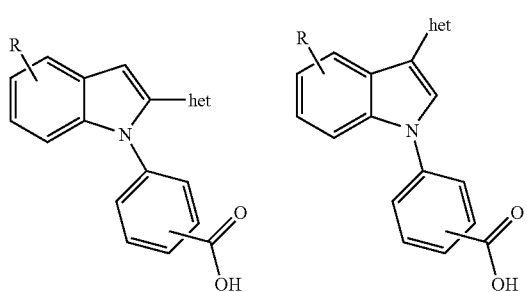
changing the acid group moiety:
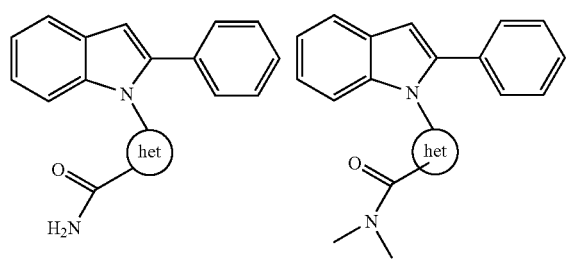
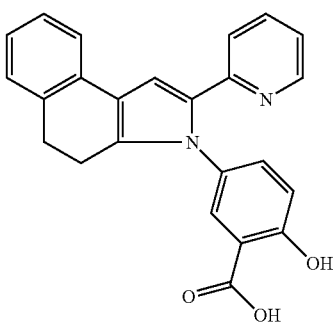
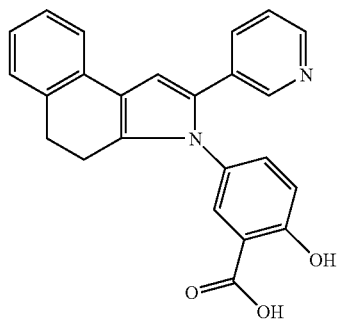
Compounds of Formulae I-XVI include, but are not limited to:
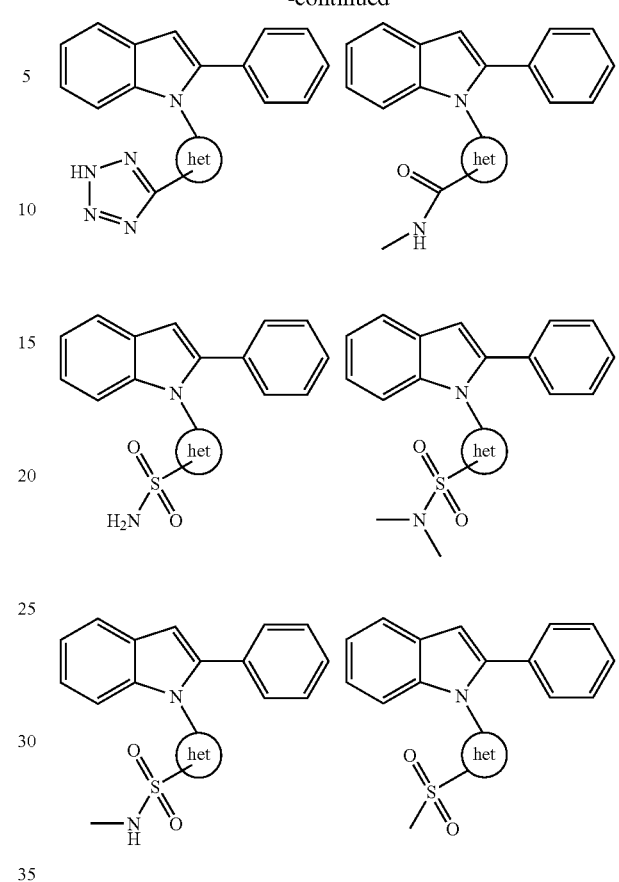

-continued
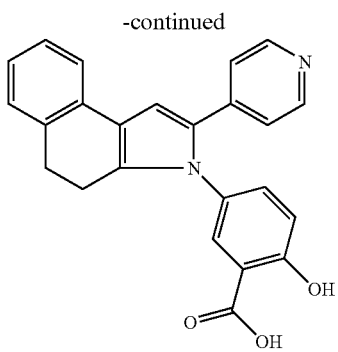
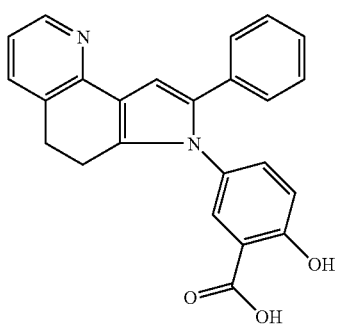
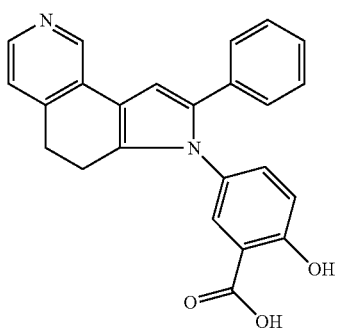
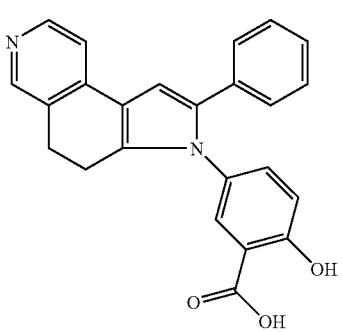
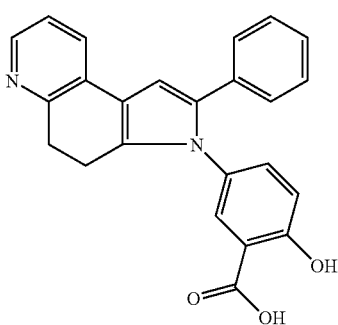
-continued
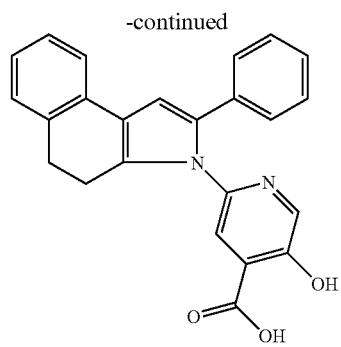
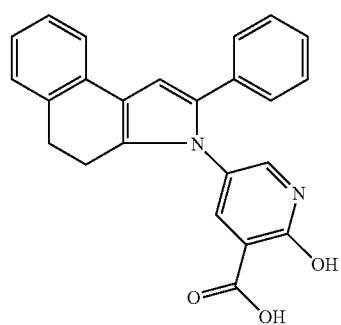
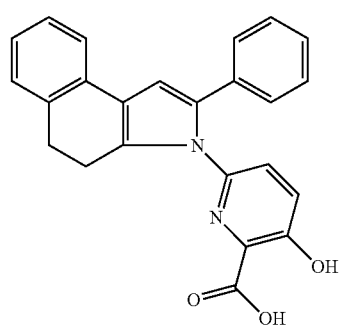
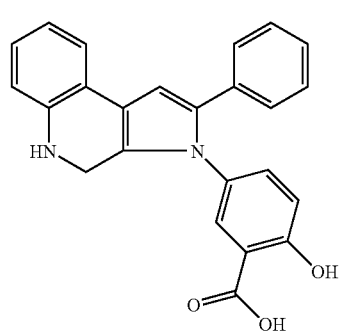
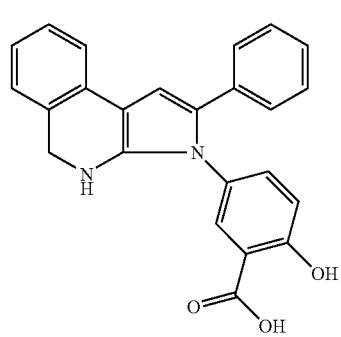

-continued
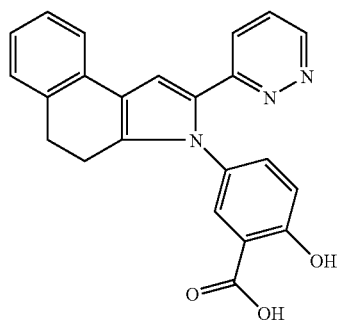
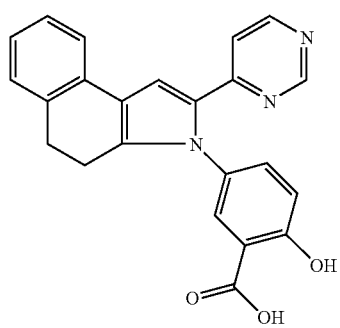
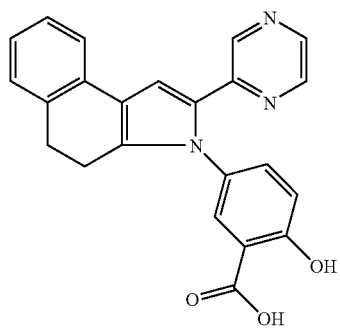
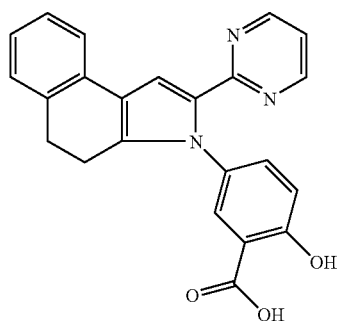
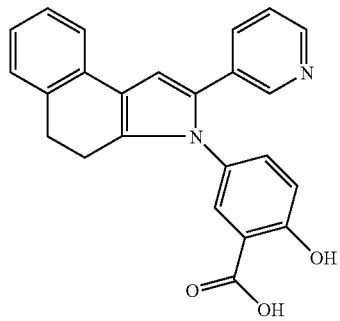
-continued
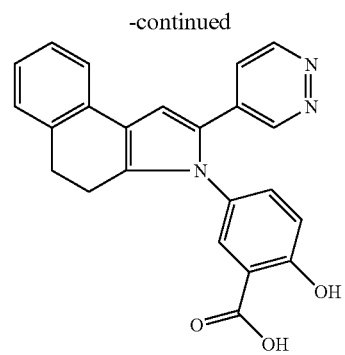
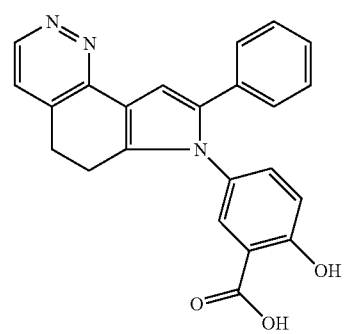
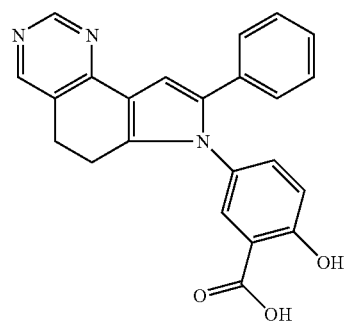
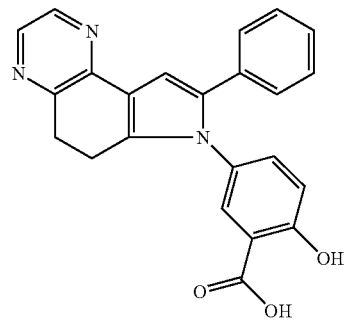
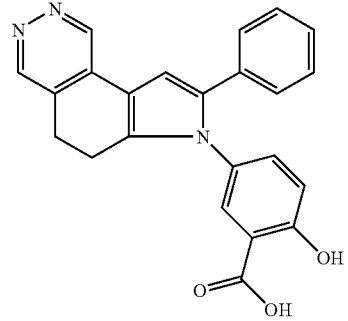

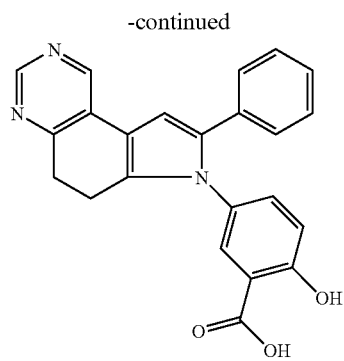
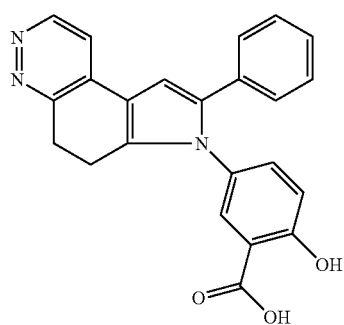
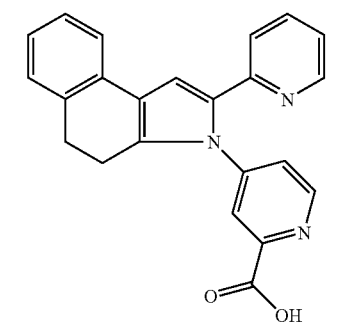
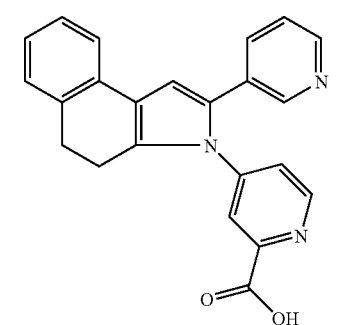
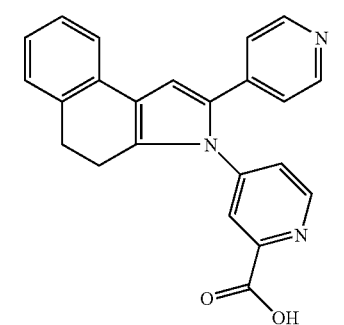
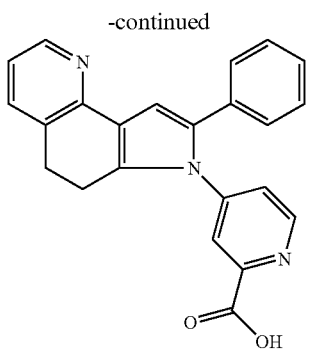
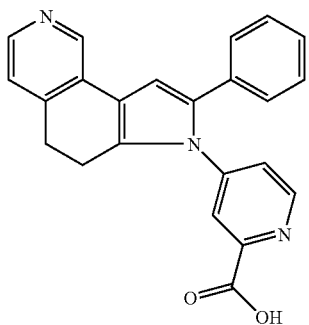
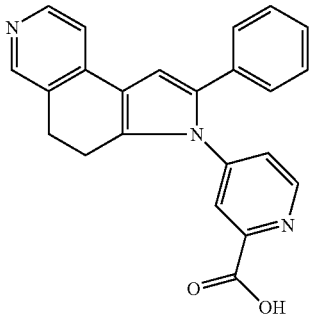
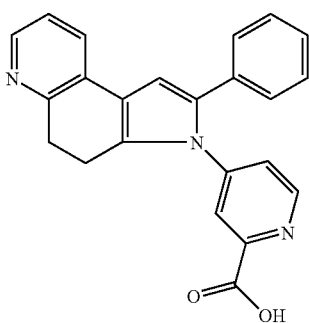

TABLE 3

Exemplary Compounds of the Invention

| product structure | SM ketone | alpha-bromo ketone | aniline | synthetic route |
| --- | --- | --- | --- | --- |
| (4,5,6,7-tetrahydroindole, 2-phenyl, N-pyridine-COOH) | cyclohexanone | bromoacetophenone | 6-aminopyridine-2-carboxylic acid | A |
| (indole, 2-phenyl, N-pyridine-COOH) | cyclohexanone | bromoacetophenone | 6-aminopyridine-2-carboxylic acid | A, C |
| (4,5,6,7-tetrahydroindole, 2-phenyl, N-4-pyridine-2-COOH) | cyclohexanone | bromoacetophenone | 4-aminopyridine-2-carboxylic acid | A |
| (indole, 2-phenyl, N-4-pyridine-2-COOH) | cyclohexanone | bromoacetophenone | 4-aminopyridine-2-carboxylic acid | A, C |
| (4,5,6,7-tetrahydroindole, 2-phenyl, N-5-pyridine-3-COOH) | cyclohexanone | bromoacetophenone | 5-aminopyridine-3-carboxylic acid | A |
| (indole, 2-phenyl, N-5-pyridine-3-COOH) | cyclohexanone | bromoacetophenone | 5-aminopyridine-3-carboxylic acid | A, C |

TABLE 3-continued
Exemplary Compounds of the Invention
| product structure | SM ketone | alpha-bromo ketone | aniline | synthetic route |
|---|---|---|---|---|
| 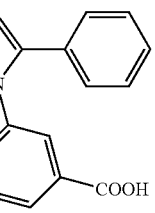 | 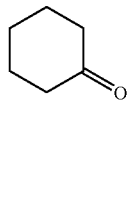 | 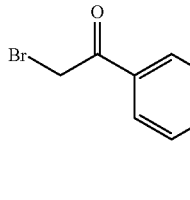 | 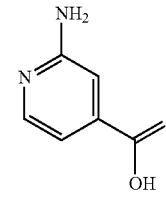 | A |
| 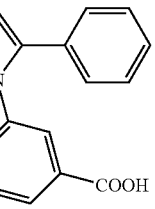 | 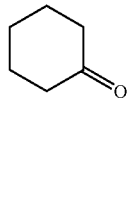 | 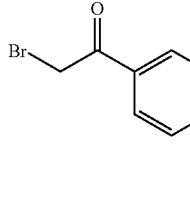 | 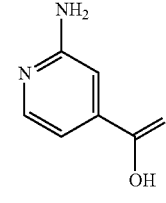 | A, C |
| 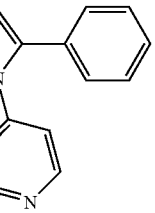 | 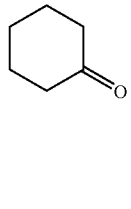 | 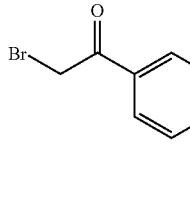 | 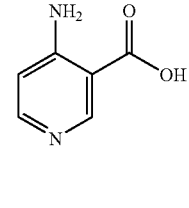 | A |
| 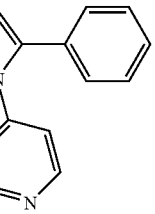 | 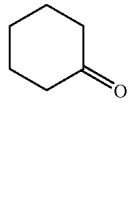 | 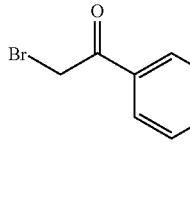 | 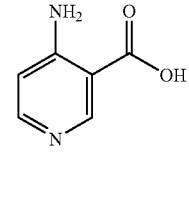 | A, C |
| 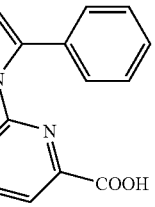 | 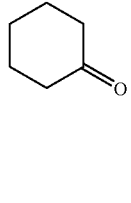 | 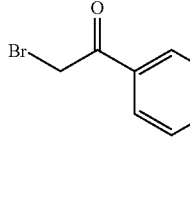 | 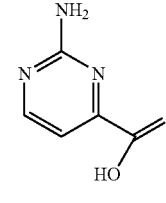 | A |
| 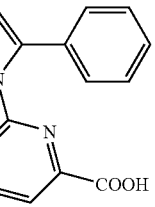 | 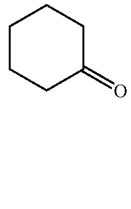 | 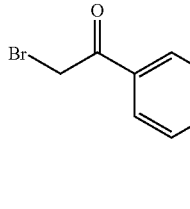 | 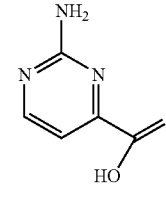 | A, C |

TABLE 3-continued

Exemplary Compounds of the Invention

| product structure | SM ketone | alpha-bromo ketone | aniline | synthetic route |
|---|---|---|---|---|
| | cyclohexanone | 2-bromo-1-phenylethanone | 5-amino-1H-pyrrole-2-carboxylic acid | A |
| | cyclohexanone | 2-bromo-1-phenylethanone | 5-amino-1H-pyrrole-2-carboxylic acid | A, C |
| | cyclohexanone | 2-bromo-1-phenylethanone | 4-aminofuran-2-carboxylic acid | A |
| | cyclohexanone | 2-bromo-1-phenylethanone | 4-aminofuran-2-carboxylic acid | A, C |
| | cyclohexanone | ethyl 2-bromo-3-oxo-3-phenylpropanoate | pyridin-3-amine | A, C |
| | cyclohexanone | ethyl 2-bromo-4-oxo-4-phenylbutanoate | pyridin-3-amine | A, C |

TABLE 3-continued

Exemplary Compounds of the Invention

| product structure | SM ketone | alpha-bromo ketone | aniline | synthetic route |
|---|---|---|---|---|
| | | | | A, C |
| | | | | A, C |
| | | | | A, C |
| | | | | A, C |
| | | | | A, C |

TABLE 3-continued
Exemplary Compounds of the Invention
| product structure | SM ketone | alpha-bromo ketone | aniline | synthetic route |
|---|---|---|---|---|
| 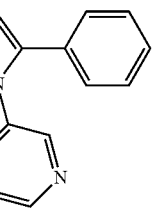 | 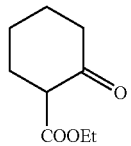 | 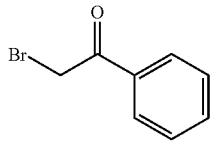 | 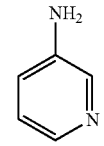 | A, C |
| 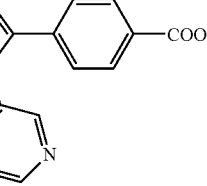 | 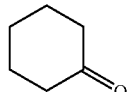 | 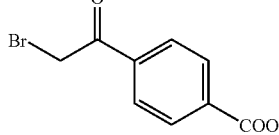 | 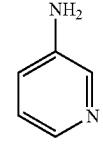 | A, C |
| 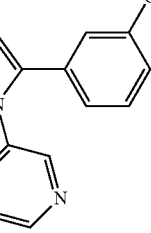 | 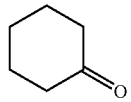 | 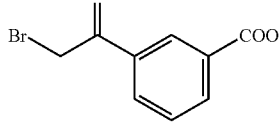 | 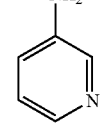 | A, C |
| 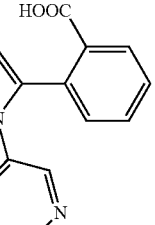 | 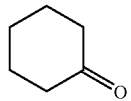 | 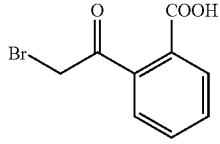 | 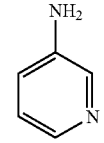 | A, C |
| 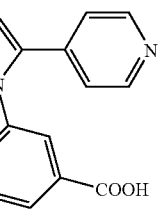 |  | 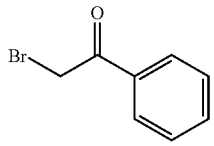 | 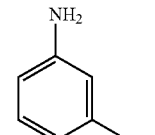 | A, C, B |
| 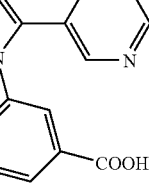 | 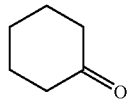 | 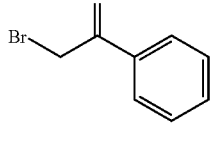 | 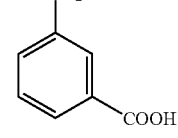 | A, C, B |

TABLE 3-continued

Exemplary Compounds of the Invention

| product structure | SM ketone | alpha-bromo ketone | aniline | synthetic route |
|---|---|---|---|---|
| | cyclohexanone | 2-bromo-1-phenylethanone | 3-aminobenzoic acid | A, C, B |
| | cyclohexanone | 2-bromo-1-phenylpropan-... (α-bromo phenyl ketone) | 3-aminobenzoic acid | A, C |
| | cyclohexanone | α-bromo phenyl ketone | 3-aminobenzoic acid | A, C |
| | cyclohexanone | α-bromo phenyl ketone | 3-aminobenzoic acid | A, C |

TABLE 3-continued

Exemplary Compounds of the Invention

| product structure | SM ketone | alpha-bromo ketone | aniline | synthetic route |
|---|---|---|---|---|
| | cyclohexanone | bromoacetophenone | 5-amino-nicotinamide | A, C |
| | cyclohexanone | bromoacetophenone | N,N-dimethyl 5-amino-nicotinamide | A, C |
| | cyclohexanone | bromoacetophenone | N-methyl 5-amino-nicotinamide | A, C |
| | cyclohexanone | bromoacetophenone | 5-amino-pyridine-3-sulfonamide | A, C |
| | cyclohexanone | bromoacetophenone | N-methyl 5-amino-pyridine-3-sulfonamide | A, C |

TABLE 3-continued

Exemplary Compounds of the Invention

| product structure | SM ketone | alpha-bromo ketone | aniline | synthetic route |
|---|---|---|---|---|
| (indole with 2-phenyl and N-pyridyl-sulfonamide structure) | cyclohexanone | 2-bromo-1-phenylethanone | 5-amino-N,N-dimethylpyridine-3-sulfonamide | A, C |
| (indole with 2-phenyl and N-pyridyl-methylsulfonyl structure) | cyclohexanone | 2-bromo-1-phenylethanone | 3-amino-5-(methylsulfonyl)pyridine | A, C |

TABLE 4

Exemplary Compounds of the Invention

| Compound Number | product structure | ketone/diketone SM | a-bromo ketone SM | aniline |
|---|---|---|---|---|
| 133 | (tert-butyl tetrahydroindole with 2-phenyl, N-furan-COOMe) | 4-tert-butylcyclohexanone | 2-bromo-1-phenylethanone | methyl 5-aminofuran-2-carboxylate |
| 134 | (benzo-fused pyrrole with 2-thienyl, N-phenyl-COOH) | 3,4-dihydronaphthalen-2(1H)-one | 2-bromo-1-(thiophen-3-yl)ethanone | 3-aminobenzoic acid |

TABLE 4-continued

Exemplary Compounds of the Invention

| Compound Number | product structure | ketone/diketone SM | a-bromo ketone SM | aniline |
|---|---|---|---|---|
| 135 | | | | |
| 136 | | | | |
| 137 | | | | |
| 138 | | | | |

TABLE 4-continued

Exemplary Compounds of the Invention

| Compound Number | product structure | ketone/diketone SM | a-bromo ketone SM | aniline |
|---|---|---|---|---|
| 139 | | | | |
| 140 | | | | |
| 141 | | | | |
| 142 | | | | |

US 7,678,823 B2
187                                                                                                                 188
TABLE 4-continued
Exemplary Compounds of the Invention
| Compound Number | product structure | ketone/diketone SM | a-bromo ketone SM | aniline |
|---|---|---|---|---|
| 143 | 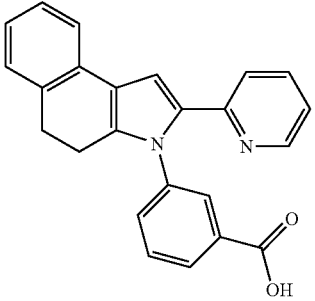 | 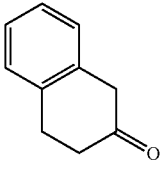 | 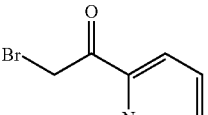 | 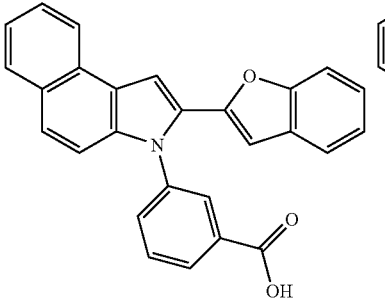 |
| 144 | 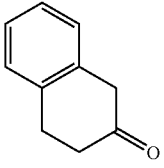 | 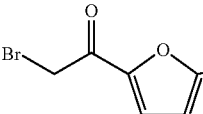 | 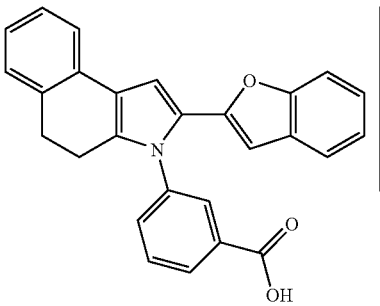 | 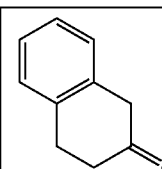 |
| 145 | 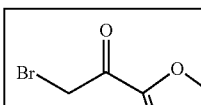 | | | |
| 146 | 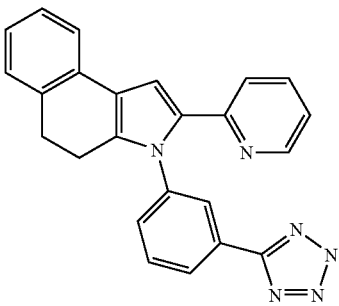 | 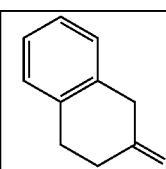 | | 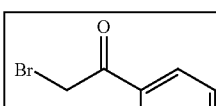 |

TABLE 4-continued

Exemplary Compounds of the Invention

| Compound Number | product structure | ketone/diketone SM | a-bromo ketone SM | aniline |
|---|---|---|---|---|
| 147 | | | | |
| 148 | | | | |

TABLE 5

Analytical data for the Compounds in Table 4

| Compound Number | 1H NMR, δ | MS | Name | Synthetic route used |
|---|---|---|---|---|
| 133 | CDCl3; 7.1-7.3 (m, 6H, ArH); 6.2 (s, 1H); 6.0 (d, 1H); 3.9 (s, 3H); 2.6 (m, 3H); 2.3 (m, 1H); 2.o (m, 1H); 1.3-1.5 (m, 2H); 1.0 (s, 9H). | pos. mode 378 (M + H). | 5-(5-tertButyl-2-phenyl-4,5,6,7-tetrahydroindol-1-yl) furan-2-carboxylic acid methyl ester | A |
| 134 | DMSO-d6; 6.6-8.4 (14H, ArH), | pos. mode 370 (M + 1) | 3-(2-thiophen-3-yl-benzo[e]indol-3-yl) benzoic acid | A, C |
| 135 | DMSO-d6; 6.6-8.4 (13H, ArH), 2.9 (2H, CH2), 2.6 (2H, CH2) | pos. mode 396 (M + 1); 394 (M − 1). | 3-[3-(2H-tetrazol-5-yl)-phenyl]-2-thiophen-3-yl-3H benzo[e]indole | A, C |
| 136 | CDCl3; 7.1-7.3 (m, 6H, ArH); 6.2 (s, 1H); 6.0 (d, 1H); 2.6 (m, 2H); 2.4-2.5 (m, 2H); 2.0 (m, 1H); 1.5 (m, 2H); 1.0 (s, 9H). | pos. mode 364 (M + H); neg. mode 362 (M − H) | 5-(5-tertButyl-2-phenyl-4,5,6,7-tetrahydroindol-1-yl) furan-2-carboxylic acid | A |

TABLE 5-continued

Analytical data for the Compounds in Table 4

| Compound Number | 1H NMR, δ | MS | Name | Synthetic route used |
|---|---|---|---|---|
| 137 | DMSO-d6; 7.1-8.5 (14H, ArH/NH); 5.8 (1H); 2.9 (2H, CH2); 2.6 (2H, CH2). | pos.mode 430 (M + 1); neg. mode 429 (M − 1). | 2-benzofuran-2-yl-3-[3-(2H-tetrazol-5-yl)-phenyl]-4,5-dihydro-3H-benzo[e]indole | A |
| 138 | DMSO-d6; 7.0-8.2 (15H, ArH/NH); 6.3 (1H); 2.9 (2H, CH2); 2.6 (2H, CH2). | pos. mode 457 (M + 1); neg mode 455 (M − 1). | 2-(3-phenylisoxazol-5-yl)-3-[3-(2H-tetrazol-5-yl)-phenyl]-4,5-dihydro-3H-benzo[e]indole | A |
| 139 | DMSO d6; 7.0-8.1 (14H, ArH); 6.2 (1H); 2.9 (2H, CH2); 2.6 (2H, CH2). | pos.mode 433 (M + 1); heg.mode 431 (M − 1). | 3-(2-phenylisoxazol-5-yl)-4,5-dihydrobenzo[e]indol-3-yl] benzoic acid | A |
| 140 | DMSO-d6; 7.3-8.8 (15H, ArH). | pos. mode 365 (M + 1). | 3-(2-pyridin-3-yl-benzo[e]indol-3-yl) benzoic acid | A, C |
| 141 | DMSO-d6; 7.0-8.6 (13H, ArH), 2.9 (2H, CH2), 2.6 (2H, CH2). | pos. mode 367 (M + 1). | 3-(2-pyridin-3-yl-4,5-dihydrobenzo[e]indol-3-Yl) benzoic acid | A |
| 142 | DMSO-d6; 7.2-8.5 (15H, ArH). | pos. mode 365 (M + 1). | 3-(2-pyridin-2-yl-benzo[e]indol-3-yl) benzoic acid | A, C |
| 143 | DMSO-d6; 6.9-8.5 (13H, ArH), 2.9 (2H, CH2), 2.6 (2H, CH2). | pos. mode 367 (M + 1); 365 (M + 1). | 3-(2-pyridin-2-yl-4,5-dihydrobenzo[e]indol-3-yl) benzoic acid | A |
| 144 | DMSO-d6; 7.1-8.2 (16H, ArH). | pos. mode 404 (M + 1). | 3-(2-benzofuran-2-yl-benzo[e]indol-3-yl) benzoic acid | A, C |
| 145 | DMSO-d6; 7.0-8.1 (14H, ArH), 2.9 (2H, CH2), 2.6 (2H, CH2). | pos. mode 406 (M + 1). | 3-(2-benzofuran-2-yl-4,5-dihydrobenzo[e]indol-3-yl) benzoic acid | A |
| 146 | DMSO-d6; 7.0-8.6 (14H, ArH), 2.9 (2H, CH2), 2.6 (2H, CH2). | pos. mode 391 (M + 1). | 2-pyridin-2-yl-3-[3-(2H-tetrazol-5-yl)-phenyl]-4,5-dihydro-3H-benzo[e]indole | A |
| 147 | DMSO-d6; 7.4-8.6 (16H, ArH). | pos. mode 389 (M + 1). | 2-pyridin-3-yl-3-[3-(2H-tetrazol-5-yl)-phenyl]-3H-benzo[e]indole | A, C |
| 148 | DMSO-d6; 7.2-8.4 (16H, ArH). | pos. mode 389 (M + 1). | 2-pyridin-2-yl-3-[3-(2H-tetrazol-5-yl)-phenyl]-3H-benzo[e]indole | A, C |

Compounds of Formulae I and II, e.g., those disclosed in Table 4 and 5, are capable of modulating APP processing and lower Ab42 in the cell based assay described in Example 6. Compounds 138 and 139 have an Ab42 lowering IC50 of 10 μM and 2 μM, respectively.

Example 12
More Compounds of the Invention

Additional compounds of the invention, synthesized according to the above described routes are given below along with relevant characterization data. These compounds exemplify the compounds of the invention including those of aspects 1-21 of the invention.

TABLE 6
Compounds of the Invention and Starting Materials
| product structure | ketone SM | α-bromo ketone SM | aniline/amine |
|---|---|---|---|
| 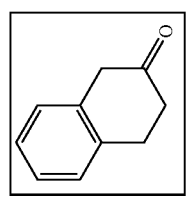 | 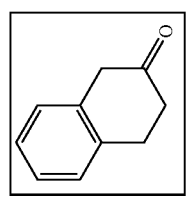 | 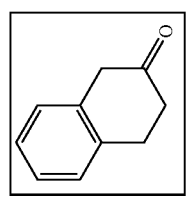 | 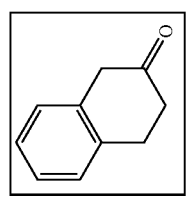 |
| 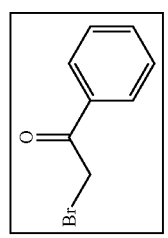 | 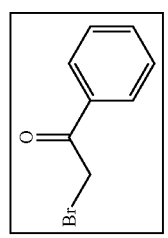 | 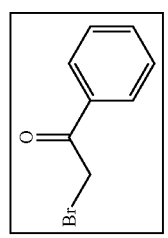 | 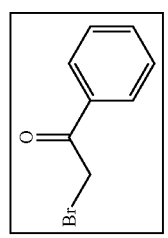 |

TABLE 6-continued
Compounds of the Invention and Starting Materials
| product structure | ketone SM | α-bromo ketone SM | aniline/amine |
|---|---|---|---|
| 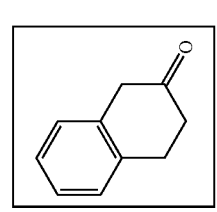 | 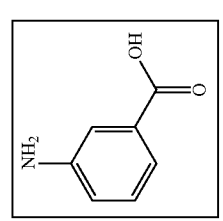 | 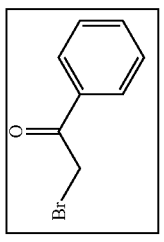 | 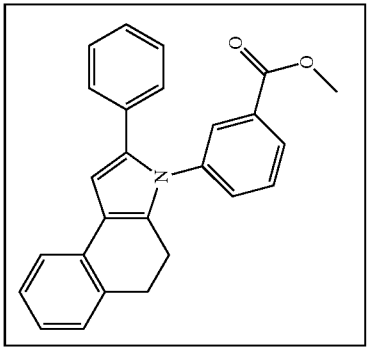 |
| 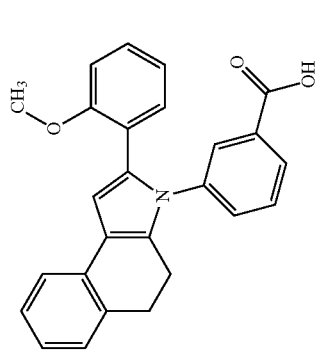 | 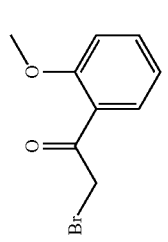 | 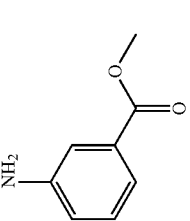 | 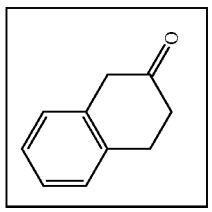 |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|
| 201 | β-tetralone | phenacyl bromide | 2-amino-phenylpropanoic acid (COOH) |
| 202 | β-tetralone | phenacyl bromide | 2-amino-phenylpropanoic acid (COOH) |
| | 4-tert-butylcyclohexanone | phenacyl bromide | 3-amino-N-methylbenzamide |

TABLE 6-continued
Compounds of the Invention and Starting Materials
| product structure | ketone SM | α-bromo ketone SM | aniline/amine |
|---|---|---|---|
| 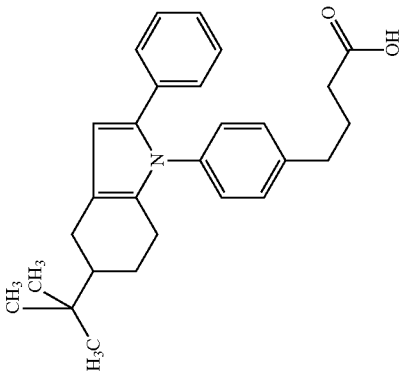 | | | |
| 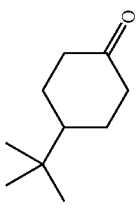 | | | |

TABLE 6-continued
Compounds of the Invention and Starting Materials
| product structure | ketone SM | α-bromo ketone SM | aniline/amine |
|---|---|---|---|
| 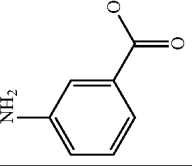 | 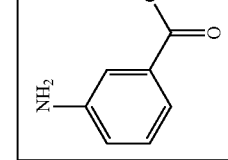 | 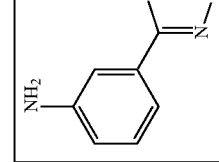 | 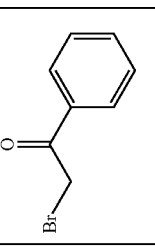 |
| 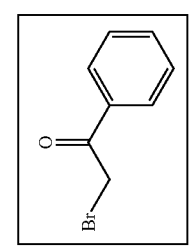 | 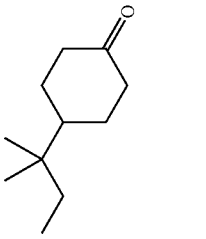 | 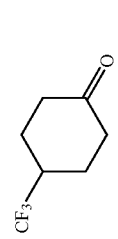 | 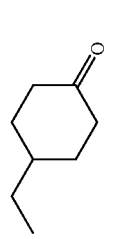 |
| 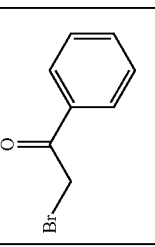 | 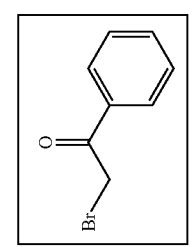 | 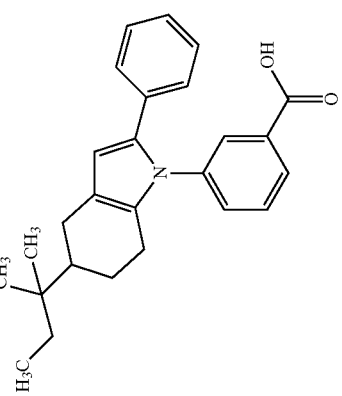 | 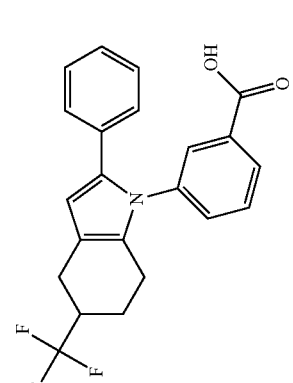 |

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| product structure | ketone SM | α-bromo ketone SM | aniline/amine |
|---|---|---|---|
| 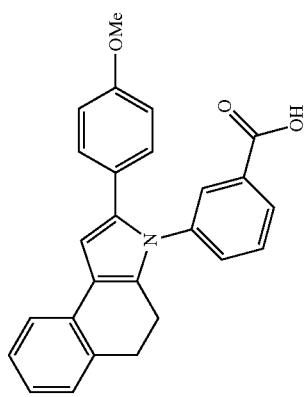 | 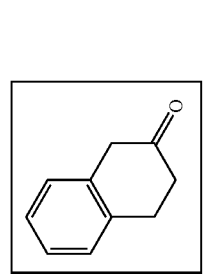 | 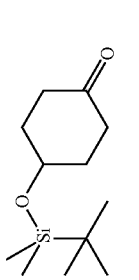 | 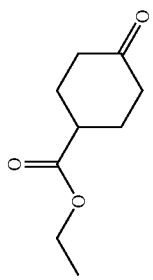 |
| 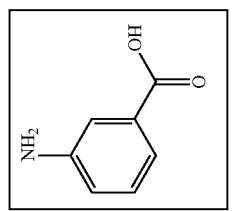 | 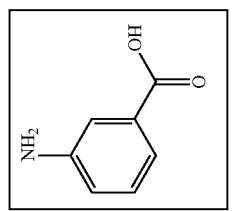 | 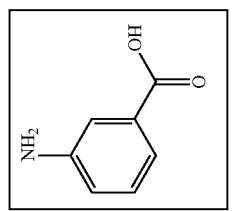 | 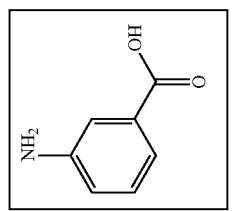 |
| 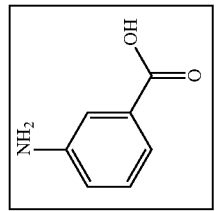 | 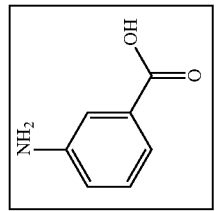 | 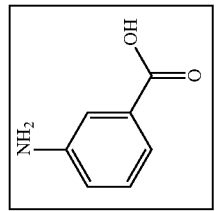 | 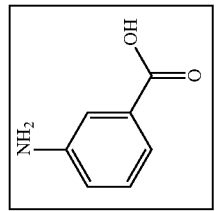 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| ketone SM | α-bromo ketone SM | aniline/amine | product structure |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

TABLE 6-continued

Compounds of the Invention and Starting Materials

| ketone SM | α-bromo ketone SM | aniline/amine | product structure |
|---|---|---|---|

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| ketone SM | α-bromo ketone SM | aniline/amine |
|---|---|---|
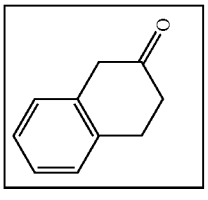

TABLE 6-continued
Compounds of the Invention and Starting Materials
| product structure | ketone SM | α-bromo ketone SM | aniline/amine |
|---|---|---|---|
| 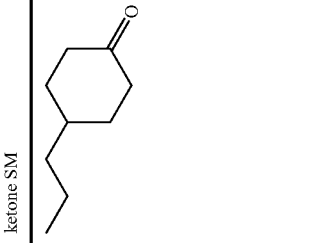 | 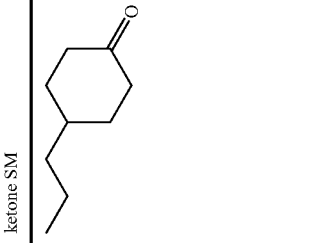 | 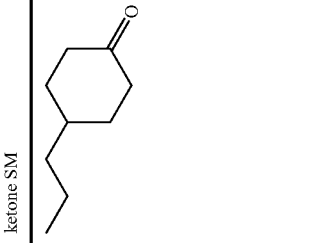 | 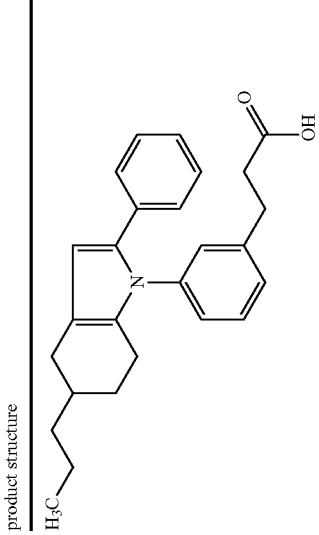 |
| 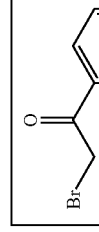 | 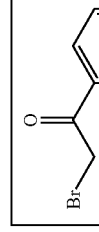 | 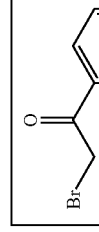 | 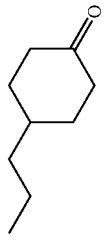 |
| 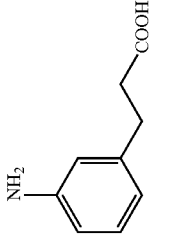 |  |  | 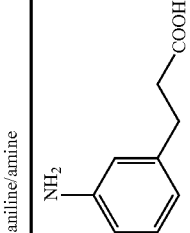 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

TABLE 6-continued

Compounds of the Invention and Starting Materials

| ketone SM | α-bromo ketone SM | aniline/amine |
|---|---|---|
| 2-tetralone | 2-bromo-1-(4-fluorophenyl)ethanone | 3-aminobenzoic acid |
| 2-tetralone | 2-bromo-1-(3,5-bis(trifluoromethyl)phenyl)ethanone | 3-aminobenzoic acid |
| 2-tetralone | 2-bromo-1-(3-chlorophenyl)ethanone | 3-aminobenzoic acid | product structure: corresponding 2-aryl-1-(3-carboxyphenyl)-benzo[g]indoles

TABLE 6-continued
Compounds of the Invention and Starting Materials
| ketone SM | α-bromo ketone SM | aniline/amine | product structure |
|---|---|---|---|
| 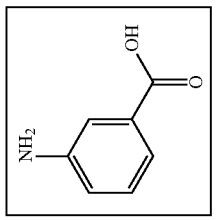 |  | 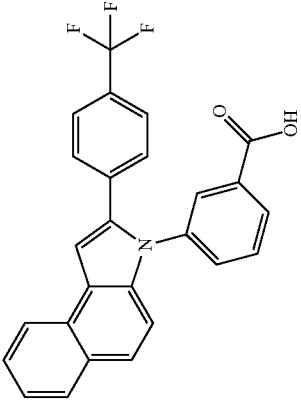 | 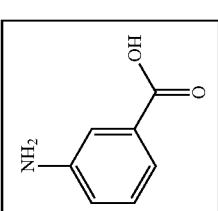 |
| 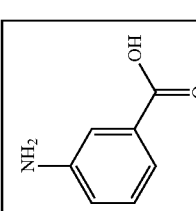 |  | 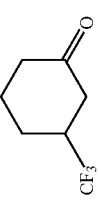 | 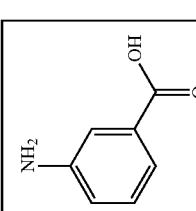 |
| 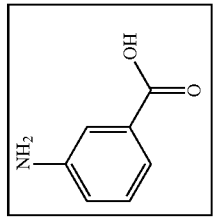 | 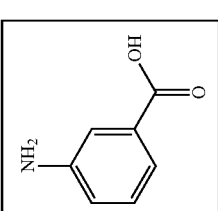 | 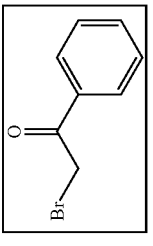 |  |

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| ketone SM | α-bromo ketone SM | aniline/amine | product structure |
|---|---|---|---|
| 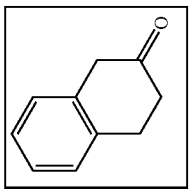 | 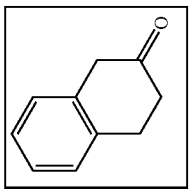 | 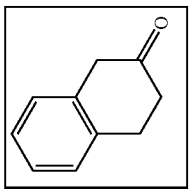 | 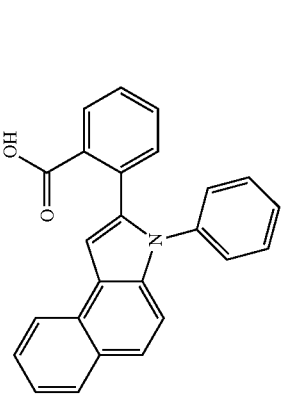 |
| 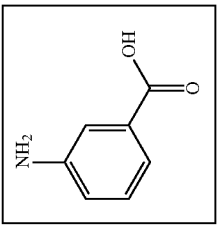 | 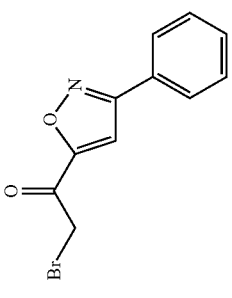 | 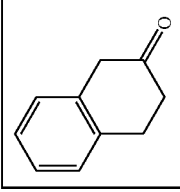 | 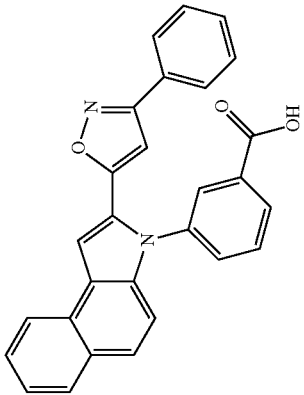 |
| 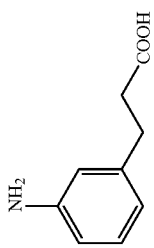 | 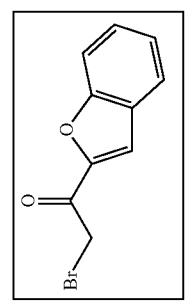 | 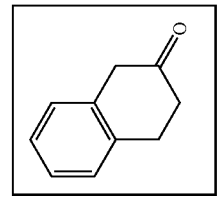 | 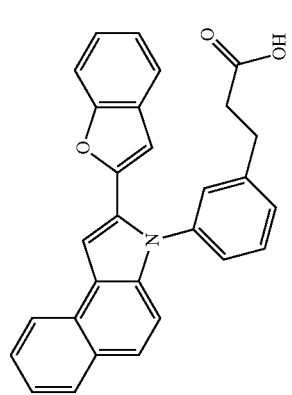 |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| product structure | ketone SM | α-bromo ketone SM | aniline/amine |
|---|---|---|---|

TABLE 6-continued
Compounds of the Invention and Starting Materials
| product structure | ketone SM | α-bromo ketone SM | aniline/amine |
|---|---|---|---|
| 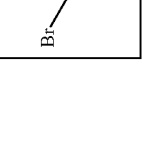 | 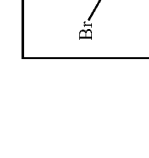 | 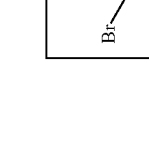 | 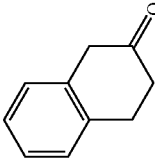 |
| 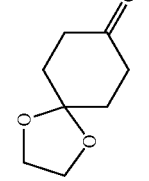 | 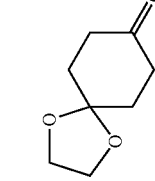 | 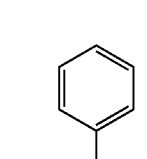 | 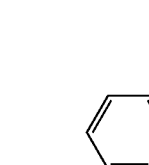 |
| 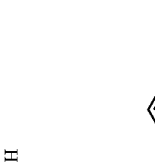 | 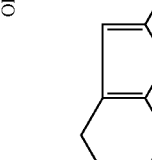 | | |

TABLE 6-continued

Compounds of the Invention and Starting Materials

TABLE 6-continued

Compounds of the Invention and Starting Materials

| ketone SM | α-bromo ketone SM | aniline/amine |
|---|---|---|

TABLE 6-continued

Compounds of the Invention and Starting Materials

TABLE 6-continued

Compounds of the Invention and Starting Materials

| ketone SM | α-bromo ketone SM | aniline/amine |

TABLE 6-continued
Compounds of the Invention and Starting Materials
| ketone SM | α-bromo ketone SM | aniline/amine | product structure |
|---|---|---|---|
| 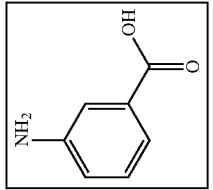 |  | 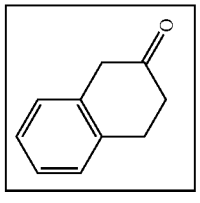 |  |
|  | 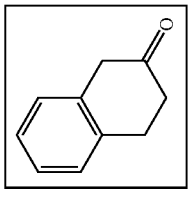 | 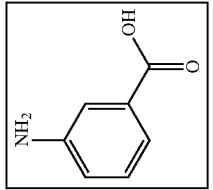 | 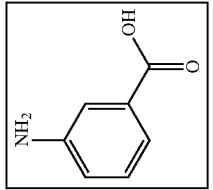 |
|  | 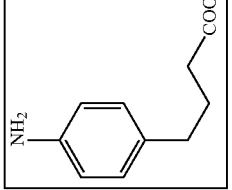 | 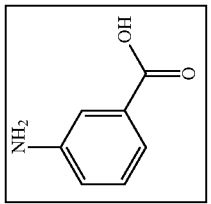 |  |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| ketone SM | α-bromo ketone SM | aniline/amine | product structure |
|---|---|---|---|

TABLE 6-continued
Compounds of the Invention and Starting Materials
| product structure | ketone SM | α-bromo ketone SM | aniline/amine |
|---|---|---|---|
| 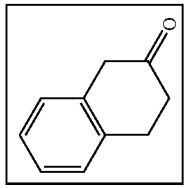 | 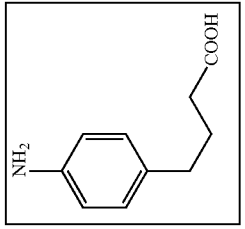 | 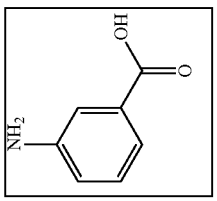 | 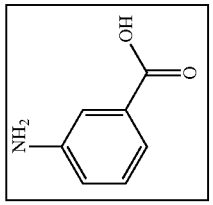 |
| 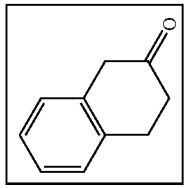 | 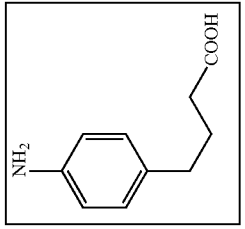 | 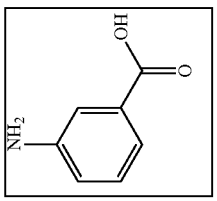 | 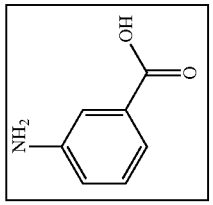 |
| 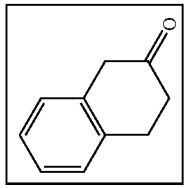 | 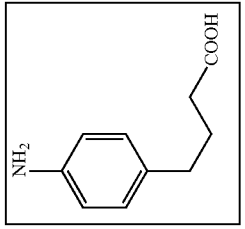 | 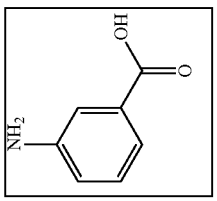 | 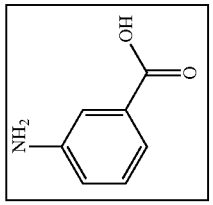 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

TABLE 6-continued
Compounds of the Invention and Starting Materials
| ketone SM | α-bromo ketone SM | aniline/amine | product structure |
|---|---|---|---|
| 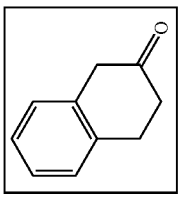 | 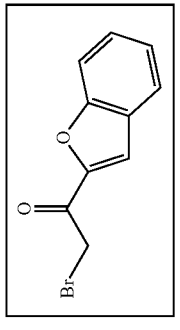 | 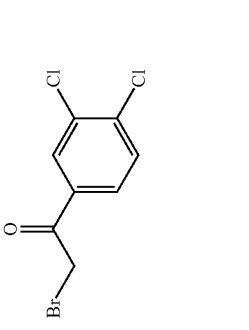 | 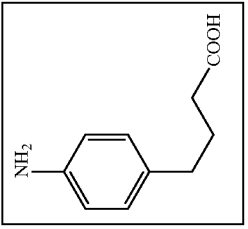 |
| 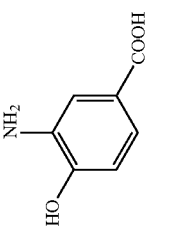 | 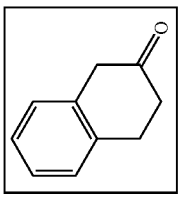 | 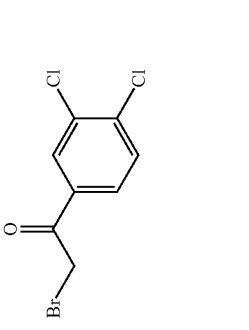 | 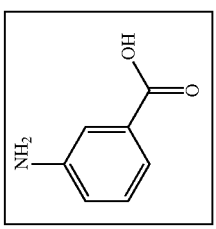 |
| 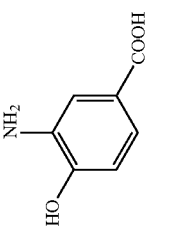 | 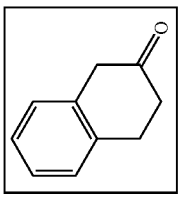 | 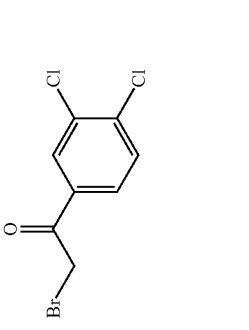 | 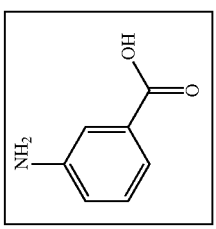 |

TABLE 6-continued

Compounds of the Invention and Starting Materials

| product structure | ketone SM | α-bromo ketone SM | aniline/amine |

TABLE 6-continued
Compounds of the Invention and Starting Materials
| product structure | ketone SM | α-bromo ketone SM | aniline/amine |
|---|---|---|---|
| 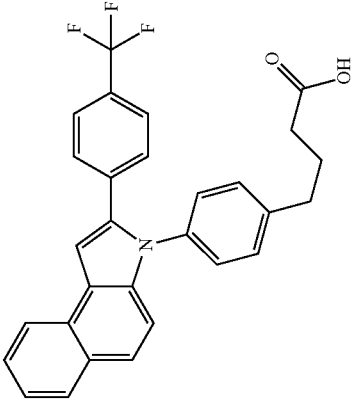 | 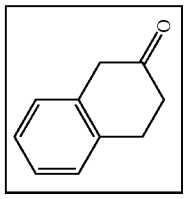 | 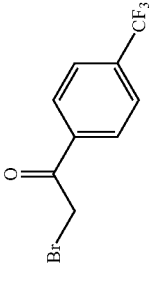 | 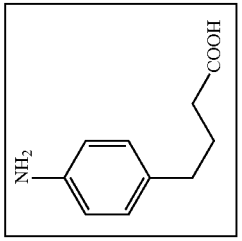 |

TABLE 6-continued

Compounds of the Invention and Starting Materials

| ketone SM | α-bromo ketone SM | aniline/amine | product structure |
|---|---|---|---|

TABLE 6-continued

Compounds of the Invention and Starting Materials

| ketone SM | α-bromo ketone SM | aniline/amine |
|---|---|---|

TABLE 6-continued

Compounds of the Invention and Starting Materials

TABLE 6-continued
Compounds of the Invention and Starting Materials
| ketone SM | α-bromo ketone SM | aniline/amine | product structure |
|---|---|---|---|
| 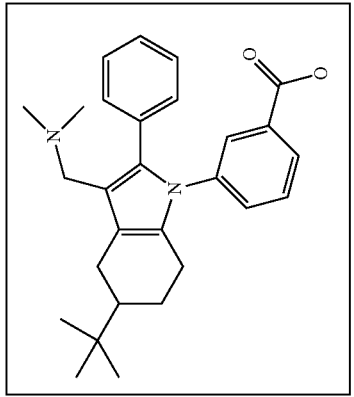 | 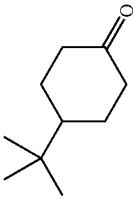 | 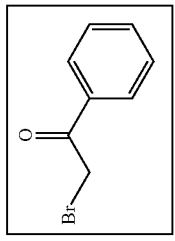 | 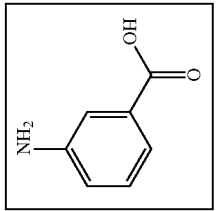 |

TABLE 6-continued
Compounds of the Invention and Starting Materials
| product structure | ketone SM | α-bromo ketone SM | aniline/amine |
|---|---|---|---|
| 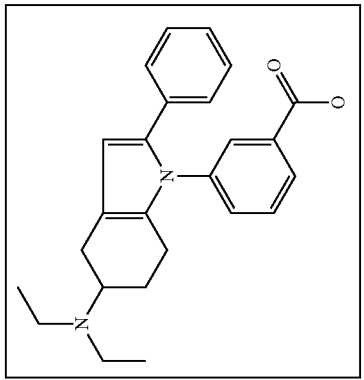 | 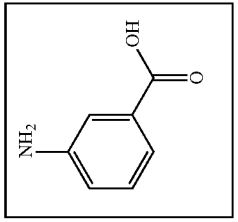 | 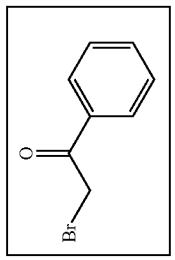 | 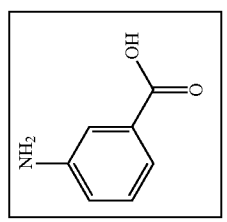 |

TABLE 6-continued

Compounds of the Invention and Starting Materials

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| ketone SM | α-bromo ketone SM | aniline/amine | product structure |
|---|---|---|---|

TABLE 6-continued

Compounds of the Invention and Starting Materials

| ketone SM | α-bromo ketone SM | aniline/amine |
|---|---|---|
| 4-(trifluoromethyl)cyclohexanone | 2-bromo-1-(4-nitrophenyl)ethanone | 3-aminobenzoic acid |
| 3,4-dihydronaphthalen-2(1H)-one | 2-bromo-1-(3-methoxyphenyl)ethanone | 3-aminobenzoic acid |
| 3,4-dihydronaphthalen-2(1H)-one | 2-bromo-1-(4-hydroxyphenyl)ethanone | 3-aminobenzoic acid | product structure

TABLE 6-continued
Compounds of the Invention and Starting Materials
| product structure | ketone SM | α-bromo ketone SM | aniline/amine |
|---|---|---|---|
| 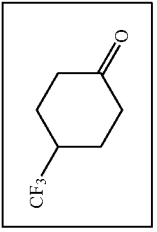 | 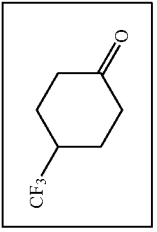 | 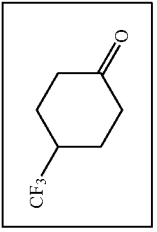 | 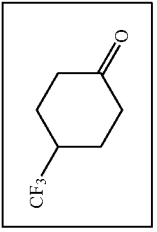 |
| 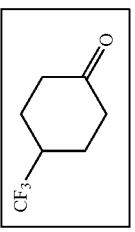 | 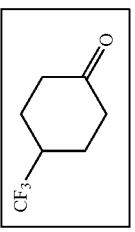 | 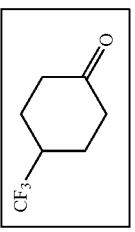 | 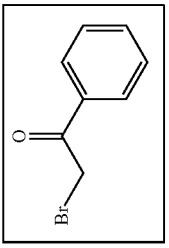 |
| 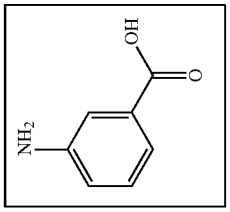 | 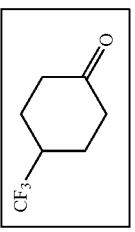 | 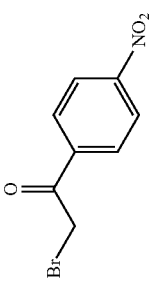 | 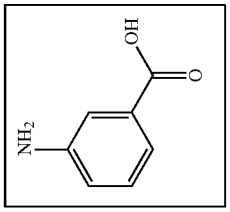 |

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| ketone SM | α-bromo ketone SM | aniline/amine | product structure |
|---|---|---|---|
| cyclohexanone | 2-bromo-1-phenylethanone | 4-(4-aminophenyl)butanoic acid | 4-(4-(2-phenyl-4,5,6,7-tetrahydro-1H-indol-1-yl)phenyl)butanoic acid |
| 3,4-dihydronaphthalen-2(1H)-one | 2-bromo-1-phenylethanone | 3-aminobenzoic acid | 3-(2-phenyl-1H-benzo[g]indol-1-yl)benzoic acid |
| 4-methylcyclohexanone | 2-bromo-1-phenylethanone | 3-(3-aminophenyl)propanoic acid | 3-(3-(5-methyl-2-phenyl-4,5,6,7-tetrahydro-1H-indol-1-yl)phenyl)propanoic acid |

TABLE 6-continued

Compounds of the Invention and Starting Materials

| ketone SM | α-bromo ketone SM | aniline/amine |
|---|---|---|

TABLE 6-continued

Compounds of the Invention and Starting Materials

| product structure | ketone SM | α-bromo ketone SM | aniline/amine |
|---|---|---|---|

TABLE 6-continued

Compounds of the Invention and Starting Materials

| ketone SM | α-bromo ketone SM | aniline/amine | product structure |
|---|---|---|---|
| 3-methylcyclohexanone | 2-bromo-1-phenylethanone | 3-aminobenzoic acid | 1-(3-carboxyphenyl)-4-methyl-2-phenyl-4,5,6,7-tetrahydro-1H-indole |
| 4-tert-butylcyclohexanone | 2-bromo-1-phenylethanone | methyl 5-amino-furan-2-carboxylate | 5-[5-tert-butyl-2-phenyl-4,5,6,7-tetrahydroindol-1-yl]-furan-2-carboxylic acid |

TABLE 6-continued
Compounds of the Invention and Starting Materials
| product structure | ketone SM | α-bromo ketone SM | aniline/amine |
|---|---|---|---|
| 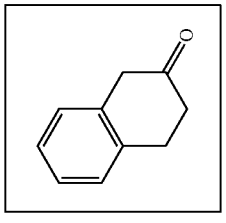 | 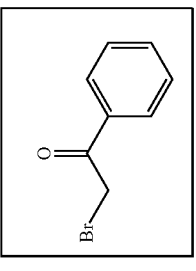 | 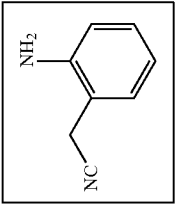 |  |
| 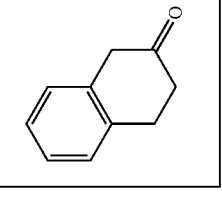 | 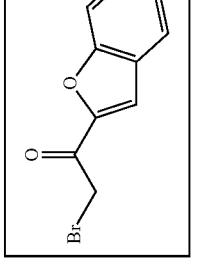 | 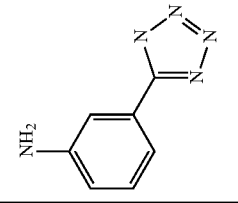 |  |

TABLE 6-continued

Compounds of the Invention and Starting Materials

| ketone SM | α-bromo ketone SM | aniline/amine |
|---|---|---|

TABLE 7

Compounds from Table 6 and Characterization Data

| product structure | 1H NMR, d | MS | name |
| --- | --- | --- | --- |
| 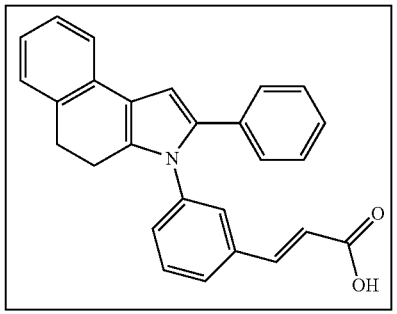 | DMSO-d6; 7.1-7.3(m, 16H); 6.8(s, 1H); 2.9(t, 2H); 2.6(t, 2H). | pos. mode 392 (M + H), neg. mode 390(M − 1). | 3-[3-(2-phenyl-4,5-dihydrobenzo[e]indol-3-yl)-phenyl]acrylic acid |
| 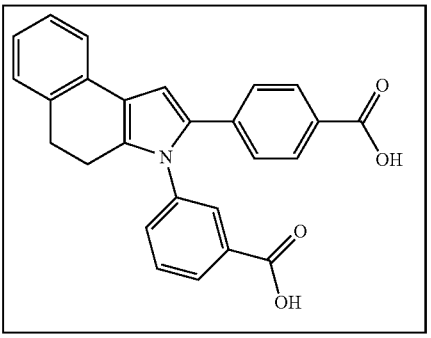 | DMSO-d6; 8.03(d, 1H), 7.82-7.73(m, 3H), 7.68-7.52(m, 3H), 7.26-7.19 (m, 4H), 7.12-7.07 (m, 2H), 2.98(t, 2H), 2.70 (t, 2H). | pos. mode 410 (M + H); neg. mode 408(M − H). | 3-[2-(4-carboxyphenyl)-4,5-dihydrobenzo[e]indol-3-yl]benzoic acid |
| 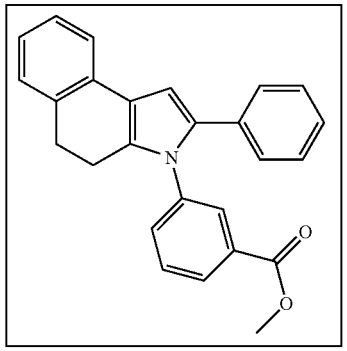 | CDCl3; 8.02(tt, 1H), 7.93 (t, 1H); 7.46(d, 1H), 7.42 (t, 1H), 7.28(d, 1H); 7.24 (m, 1H), 7.21-7.05(m, 7H), 6.74(s, 1H), 3.92(s, 3H), 3.0(t, 2H), 2.72(t, 2H). | pos. mode 380 (M + H). | methyl 3-(2-phenyl-4,5-dihydrobenzo[e]indol-3-yl)benzoate |
| 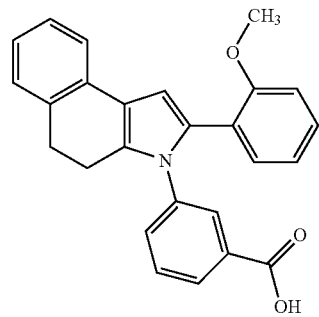 | MeOH-d4; 7.75(t, 1H), 7.42-7.36(m, 3H), 7.32-7.14(m, 5H), 7.0(t, 1H), 6.91(t, 1H), 6.73(d, 1H), 6.5(s, 1H), 3.33(s, 3H) 2.96(t, 2H), 2.71(t, 2H). | pos. mode 396 (M + H). | 3-[2-(2-methoxyphenyl)-4,5-dihydrobenzo[e]indol-3-yl]benzoic acid |

TABLE 7-continued

Compounds from Table 6 and Characterization Data

| product structure | 1H NMR, d | MS | name |
|---|---|---|---|
| | MeOH-d4; 8.3(d, 1H); 7.99-7.94(m, 2H); 7.88 (d, 1H); 7.59-7.38 (m, 7H); 7.33-7.28(m, 1H); 7.21(s, 1H); 6.99(t, 1H); 6.81(s, 1H); 3.38(s, 3H). | pos. mode 394 (M + H). | 3-[2-(2-methoxyphenyl)-benzo[e]indol-3-yl] benzoic acid |
| | CDCl3: 8.0(d, 1H); 7.9 (br. s, 1H); 7.5(t, 1H); 7.2 (m, 1H); 7.1(m, 5H); 6.3 (s, 1H); 2.7(m, 1H); 2.5 (m, 1H); 2.3-2.4(m, 2H); 2.0(m, 1H); 1.5(m, 1H); 1.4(m, 1H); 1.0(s, 9H). | pos. mode 398 (M + H). | 5-tButyl-2-phenyl-1-[3-(1H-tetrazol-5-yl)phenyl]-4,5,6,7-tetrahydro-1H-indole |
| | DMSO-d6; 7.2-8.4 (m, 16H). | pos. mode 388 (M + H). | 2-phenyl-3-[3-(2H-tetrazol-5-yl)-phenyl] 3H-benzo[e]indole |
| | CDCl3: 7.7(dm, 1H); 7.5 (br. s, 1H); 7.4(t, 1H); 7.3 (m, 1H); 7.0-7.2(m, 5H); 6.2(s, 1H); 2.7(m, 1H); 2.6(m, 1H); 2.4(m, 1H); 2.2(m, 1H); 1.9(m, 2H); 1.4(m, 1H); 1.1(d, 3H). | pos. mode 331 (M + H). | 3-(5-methyl-2-phenyl-4,5,6,7-tetrahydroindol-1-yl)benzamide |

TABLE 7-continued

Compounds from Table 6 and Characterization Data

| product structure | 1H NMR, d | MS | name |
| --- | --- | --- | --- |
| 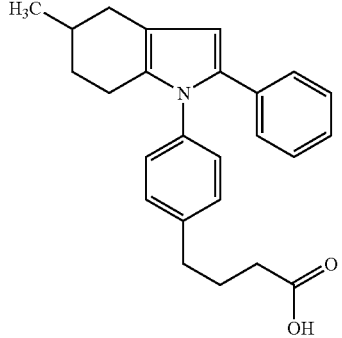 | CDCl3: 7.0-7.2(m, 9H); 6.2(s, 1H); 2.7(m, 3H); 2.5(m, 1H); 2.4(m, 3H); 2.2(m, 1H); 2.0(m, 2H); 1.9(m, 2H); 1.4(m, 1H); 1.0(d, 3H). | pos. mode 374 (M + H). | 4-[4-(5-methyl-2-phenyl-4,5,6,7-tetrahydroindol-1-yl)phenyl]butyric acid |
| 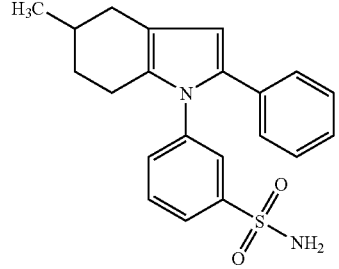 | CDCl3: 7.8(dm, 1H); 7.7 (br. s, 1H); 7.5(t, 1H); 7.3 (m, 1H); 7.0-7.2(m, 5H); 6.2(s, 1H); 2.7(m, 1H); 2.6(m, 1H); 2.4(m, 1H); 2.2(t, 1H); 1.9(m, 2H); 1.4(m, 1H); 1.1(d, 3H). | pos. mode 367 (M + H). | 3-(5-methyl-2-phenyl-4,5,6,7-tetrahydroindol-1-yl)benzenesulfonamide |
| 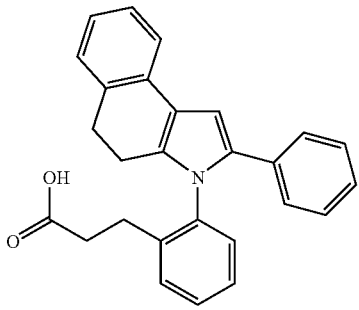 | CD3OD: 7.44(m, 1H), 7.41-7.36(m, 3H), 7.30 (m, 1H), 7.20-7.08(m, 7H), 7.00(m, 1H), 6.77 (s, 1H); 2.97-2.92(m, 2H), 2.67-2.48(m, 2H), 2.44-2.34(m, 2H), 2.25 (m, 1H), 2.04(m, 1H). | neg. mode 392 (M − H) | 3-[2-(2-phenyl-4,5-dihydro-benzo[e]indol-3-yl)-phenyl]propionic acid |
| 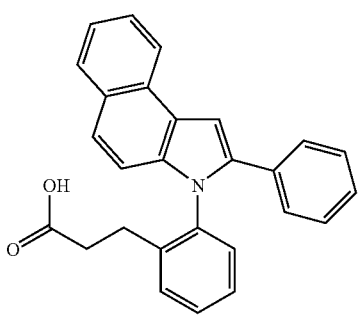 | CD3OD: 8.34(m, 1H), 7.88(m, 1H), 7.58-7.52 (m, 2H), 7.50-7.34(m, 8H), 7.26-7.20(m, 3H), 7.04(m, 1H), 2.44(m, 1H), 2.37(m, 1H), 2.09 (m, 1H), 1.98(m, 1H). | neg. mode 390 (M − H) | 3-[2-(2-phenyl-benzo[e]indol-3-yl)-phenyl]propionic acid |

TABLE 7-continued

Compounds from Table 6 and Characterization Data

| product structure | 1H NMR, d | MS | name |
|---|---|---|---|
| | CDCl3: 7.7(dm, 1H); 7.5 (br. s, 1H); 7.4(t, 1H); 7.2 (m, 1H); 7.0-7.1(m, 5H); 6.2(s, 1H); 5.9(br. s, 1H); 3.0(d, 3H); 2.7(d, 1H); 2.6(m, 1H); 2.4(m, 2H); 2.0(m, 1H); 1.5(m, 1H); 1.4(m, 1H); 1.0(s, 9H). | pos. mode 387 (M + H). | 3-(5-tButyl-2-phenyl-4,5,6,7-tetrahydroindol-1-yl)N-methyl benzamide |
| | CDCl3: 7.0-7.2(m, 9H); 6.2(s, 1H); 2.5(m, 3H); 2.4-2.5(m, 4H); 2.0(m, 3H); 1.5(m, 2H); 1.4(m, 1H); 0.9(s, 9H). | pos. mode 416 (M + H). | 4-[4-(5-tButyl-2-phenyl-4,5,6,7-tetrahydroindol-1-yl)phenyl]butyric acid |
| | CDCl3: 8.0(d, 1H); 7.9 (br. s, 1H); 7.4(m, 2H); 7.0-7.2(m, 6H); 6.2(s, 1H); 2.6(m, 1H); 2.5(m, 1H); 2.2(m, 2H); 1.9(m, 1H); 1.4(m, 2H); 1.0(d, 3H). | pos. mode 356 (M + H); neg. mode 354(M − H). | 4-methyl-2-phenyl-1-[3-(1H-tetrazol-5-yl)phenyl]-4,5,6,7-tetrahydro-1H-indole |
| | CDCl3; 8.00(dt, 1H), 7.94(br s, 1H), 7.39(t, 1H), 7.26-7.28(m, 1H), 7.05-7.18(m, 5H), 6.27 (s, 1H), 2.50-2.70(m, 2H), 2.30-2.45(m, 2H), 1.95-2.05(m, 1H), 1.55-1.70(m, 1H), 1.30-1.45 (m, 3H), 0.90(s, 3H), 0.89(s, 3H), 0.85(t, 3H). | pos. mode 388 (M + H). | 3-[5-(1,1-dimethylpropyl)-2-phenyl-4,5,6,7-tetrahydroindol-1-yl] benzoic acid |

TABLE 7-continued

Compounds from Table 6 and Characterization Data

| product structure | 1H NMR, d | MS | name |
|---|---|---|---|
| | CDCl3; 8.03(dt, 1H), 7.93(br s,1H), 7.43(t, 1H), 7.26-7.30(m, 1H), 7.08-7.20(m, 3H), 7.04-7.06(m, 2H), 6.28(s, 1H), 2.91(dd, 1H), 2.55-2.74 (m, 2H), 2.45-2.55 (m, 2H), 2.15-2.25(m, 1H), 1.75(qd, 1H). | pos. mode 386 (M + H). | 3-(2-phenyl-5-trifluoromethyl-4,5,6,7-tetrahydroindol-1-yl) benzoic acid |
| | CDCl3; 8.02(d, 1H), 7.84(br s, 1H), 7.50(t, 1H), 7.05-7.20(m, 6H), 6.28(s, 1H), 2.76(dd, 1H), 2.52-2.64(m, 1H), 2.40-2.50(m, 1H), 2.17-2.27(m, 1H), 1.88-1.98 (m, 1H), 1.67(br s, 1H), 1.32-1.50(m, 3H), 0.99(t, 3H). | pos. mode 370 (M + H). | 5-ethyl-2-phenyl-1-[3-(1H-tetrazol-5-yl)phenyl]-4,5,6,7-tetrahydro-1H-indole |
| | CDCl3; 8.01(dt, 1H), 7.97(br s, 1H), 7.40(t, 1H), 7.28(br d, 1H), 7.03-7.19(m, 5H), 6.26(s, 1H), 3.51(dd, 1H), 2.54 (br s, 1H), 2.41(br d, 1H), 2.22(dd, 1H), 1.93(br d, 1H), 1.67(br s, 1H), 1.33-1.49(m, 3H), 0.99(t, 3H). | pos. mode 346 (M + H). | 3-(5-ethyl-2-phenyl-4,5,6,7-tetrahydroindol-1-yl)benzoic acid |
| | CDCl3; 8.06(dt, 1H), 7.90(br s, 1H), 7.50(t, 1H), 7.10-7.20(m, 6H), 6.29(s, 1H), 2.76(dd, 1H), 2.60-2.75(m, 2H), 2.53(br dd, 2H), 2.21(br d, 1H), 1.74(qd, 1H). | pos. mode 410 (M + H). | 2-phenyl-1-[3-(1H-tetrazol-5-yl)-phenyl]-5-trifluoromethyl-4,5,6,7-tetrahydro-1H-indole |

TABLE 7-continued

Compounds from Table 6 and Characterization Data

| product structure | 1H NMR, d | MS | name |
|---|---|---|---|
| | CDCl3; 7.26(t, 1H), 6.95-7.20 (m, 7H), 6.93(br s, 1H), 6.23(s, 1H), 2.88(t, 2H), 2.75(dd, 1H), 2.48-2.59 (m, 3H), 2.41(br d, 1H), 2.22(dd, 1H), 1.91 (br d, 1H), 1.65(br s, 1H), 1.35-1.50(m, 3H), 0.98 (t, 3H). | pos. mode 374 (M + H). | 3-[3-(5-ethyl-2-phenyl-4,5,6,7-tetrahydroindol-1-yl)-phenyl]propionic acid |
| | CDCl3; 8.03(d, 1H), 7.95(br s, 1H), 7.42(t, 1H), 7.28(d, 1H), 7.05-7.20 (m, 5H), 6.28(s, 1H), 4.19(q, 2H), 2.94 (dd, 1H), 2.85(d, 1H), 2.72-2.81(m, 1H), 2.59 (br s, 1H), 2.48(br d, 1H), 2.23(br d, 1H), 1.82-1.90 (m, 1H), 1.30(t, 3H). | pos. mode 390 (M + H). | 3-(5-ethyoxycarbonyl-2-phenyl-4,5,6,7-tetrahydroindol-1-yl) benzoic acid |
| | CDCl3; 8.01(dt, 1H), 7.97(br s, 1H), 7.41(t, 1H), 7.25-7.30(m, 1H), 7.08-7.18(m, 3H), 7.02-7.06 (m, 2H), 6.23(s, 1H), 2.87(dd, 1H), 2.46-2.64(m, 3H), 1.92-2.02 (m, 1H), 1.78-1.88(m, 2H), 0.93(s, 9H), 0.12(s, 3H), 0.11(s, 3H). | pos. mode 448 (M + H); neg. mode 446(M − H). | 3-[5-(tButyldimethylsilyl)-2-phenyl-4,5,6,7-tetrahydroindol-1-yl] benzoic acid |
| | MeOH-d4; 7.95(t, 1H), 7.67(t, 1H), 7.58(t, 1H), 7.51-7.44(m, 2H), 7.18 (d, 2H), 7.01(d, 3H), 6.8 (d, 2H), 6.74(s, 1H), 3.35 (s, 3H), 2.92(t, 2H), 2.62 (t, 2H). | pos. mode 396 (M + H). | 3-[2-(4-methoxyphenyl)-4,5-dihydrobenzo[e]indol-3-yl]benzoic acid |

TABLE 7-continued

Compounds from Table 6 and Characterization Data

| product structure | 1H NMR, d | MS | name |
|---|---|---|---|
| | MeOH-d4; 8.4(d, 1H), 8.03(tt, 1H), 7.95(d, 1H), 7.84(t, 1H), 7.7-7.58 (m, 4H), 7.49-7.43(m, 2H), 7.32-7.24(m, 3H), 6.9(m, 2H), 3.74(s, 3H). | pos. mode 394 (M + H). | 3-[2-(4-methoxyphenyl)-benzo[e]indol-3-yl] benzoic acid |
| | CDCl3; 8.35(d, 1H), 7.96-7.92(m, 2H), 7.79(t, 1H), 7.63-7.56(m, 3H), 7.50-7.35(m, 4H), 7.27 (s, 1H), 6.59(dd, 1H), 6.43(d, 1H), 3.76(s, 3H), 3.34(s, 3H). | pos. mode 424 (M + H). neg. mode 422(M − H). | 3-[2,(2,4-dimethoxyphenyl)-benzo[e]indol-3-yl] benzoic acid |
| | MeOH-d4; 7.96(dt, 1H), 7.75(br s, 1H), 7.46(t, 1H), 7.27-7.33(m, 1H), 7.09-7.15(m, 2H), 7.01-7.09(m, 3H), 6.22(s, 1H), 2.80-2.90(m, 1H), 2.70-2.80(m, 2H), 2.40-2.60(m, 2H), 2.15-2.25 (m, 1H), 1.80-1.90 (m, 1H). | pos. mode 362 (M + H); neg. mode 360(M − H). | 3-(5-carboxy-2-phenyl-4,5,6,7-tetrahydroindol-1-yl)benzoic acid |
| | DMSO-d6; 7.99(tt, 1H), 7.70(t, 1H), 7.61(t, 1H), 7.54-7.47(m, 2H), 7.29 (d, 2H), 7.19(d, 2H), 7.11-7.05(m, 3H), 6.92(s, 1H), 2.94(t, 2H), 2.64(t, 2H). | pos. mode 400 (M + H). | 3-[2-(4-chlorophenyl)-4,5-dihydrobenzo[e]indol-3-yl] benzoic acid |

TABLE 7-continued

Compounds from Table 6 and Characterization Data

| product structure | 1H NMR, d | MS | name |
|---|---|---|---|
| | DMSO-d6; 7.71-7.48 (m, 5H), 7.22-7.18(m, 5H), 7.07-6.95(m, 3H), 2.94(t, 2H), 2.64(t, 2H). | pos. mode 400 (M + H). | 3-[2-(3-chlorophenyl)-4,5-dihydrobenzo[e]indol-3-yl] benzoic acid |
| | DMSO-d6; 6.9-7.4(m, 9H), 6.3(s, 1H), 4.4(t, 1H), 2.9(t, 2H), 2.6(t, 2H), 3.3(t, 2H), 1.8-0.4 (m, 10H). | pos. mode 400 (M + H); neg. mode 398(M − 1). | 3-cyclohexyl-3-(2-phenyl-4,5-dihydrobenzo[e]indol-3-yl)propionic acid |
| | DMSO-d6; 7.4-8.2(m, 11H), 7.0(s, 1H), 4.6(s, 1H), 3.3(t, 2H), 2.1-0.3 (m, 10H). | pos. mode 398 (M + H), neg. mode 396(M − 1). | 3-cyclohexyl-3-(2-phenylbenzo[e]indol-3-yl) propionic acid |
| | CDCl3; 7.3(m, 1H); 7.0-7.2 (m, 7H); 6.9(br. s, 1H); 6.2(s, 1H); 2.9(t, 2H); 2.6(m, 2H); 2.5(m, 2H); 2.4(m, 1H); 2.1(m, 1H); 1.9(m, 2H); 1.4(m, 1H); 1.0(d, 3H). | pos. mode 360 (M + H). | 3-[3-(4-methyl-2-phenyl 4,5,6,7-tetrahydroindol-1-yl)phenyl]propionic acid |
| | CDCl3; 8.03(d, 1H), 7.93(br s, 1H), 7.42(t, 1H), 7.29(d, 1H), 7.00-7.17 (m, 5H), 6.27(s, 1H), 2.61(br s, 2H), 2.21 (br s, 2H), 1.56(t, 2H), 1.00(s, 6H). | pos. mode 346 (M + H); neg. mode 344(M − H). | 3-(6,6-dimethyl-2-phenyl-4,5,6,7-tetrahydroindol-1-yl)benzoic acid |

TABLE 7-continued

Compounds from Table 6 and Characterization Data

| product structure | 1H NMR, d | MS | name |
|---|---|---|---|
| Chiral | CDCl3; 7.27(t, 1H), 7.10-7.16(m, 3H), 7.02-7.10 (m, 4H), 6.92(br s, 1H), 6.25(s, 1H), 2.88(t, 2H), 2.60-2.70(m, 2H), 2.53(t, 2H), 2.43(dd, 1H), 2.05-2.20(m, 1H), 1.80-1.90(m, 2H), 1.35-1.50(m, 1H), 1.04(d, 3H). | pos. mode 360 (M + H); neg. mode 358(M − H). | 3-[3-((R)-6-methyl-2-phenyl-4,5,6,7-tetrahydroindol-1-yl)phenyl]propionic acid |
| Chiral | CDCl3; 8.03(d, 1H), 7.96(br s, 1H), 7.42(t, 1H), 7.29(br d, 1H), 7.00-7.20(m, 5H), 6.27(s, 1H), 2.60-2.70(m, 2H), 2.42(dd, 1H), 2.14(t, 1H), 1.88(br d, 2H), 1.40-1.50(m, 1H), 1.05(d, 3H). | pos. mode 332 (M + H); neg. mode 330(M − H). | 3-((R)-6-methyl-2-phenyl-4,5,6,7-tetrahydroindol-1-yl)benzoic acid |
| | CDCl3; 7.28(t, 1H), 7.10-7.16(m, 3H), 6.99-7.09 (m, 4H), 6.90(t, 1H), 6.25(s, 1H), 2.88(t, 2H), 2.60(t, 2H), 2.52(t, 2H), 2.22(s, 2H), 1.55(t, 2H), 0.99(s, 6H). | pos. mode 374 (M + H); neg. mode 372(M − H). | 3-[3-(6,6-dimethyl-2-phenyl-4,5,6,7-tetrahydroindol-1-yl)phenyl]priopionic acid |
| | DMSO-d6; 7.2-8.2(m, 17H), 6.6(s, 1H). | pos. mode 390 (M + H), neg. mode 388(M − 1). | 3-[3-(2-phenylbenzo[e]indol-3-yl)-phenyl]acrylic acid |
| | CDCl3; 8.0(d, 1H); 7.9 (br. s, 1H); 7.4(t, 2H); 7.0-7.2(m, 6H); 6.2(s, 1H); 2.7(m, 1H); 2.5(m, 1H); 2.4(m, 1H); 2.2(m, 1H); 1.8(m, 2H); 1.4(m, 1H); 1.0(d, 3H). | pos. mode 356 (M + H); neg. mode 354(M − H). | 5-methyl-2-phenyl-1-[3-(1H-tetrazol-5-yl)phenyl]-4,5,6,7-tetrahydro-1H-indole |

TABLE 7-continued

Compounds from Table 6 and Characterization Data

| product structure | 1H NMR, d | MS | name |
|---|---|---|---|
| | CDCl3: 7.7(dm, 1H); 7.5 (br. s, 1H); 7.4(t, 1H); 7.2 (m, 1H); 7.0-7.1(m, 5H); 6.2(s, 1H); 5.9(br. s, 1H); 3.0(d, 3H); 2.7(dd, 1H); 2.5(m, 1H); 2.4(m, 1H); 2.2(m, 1H); 1.9(m, 2H); 1.4(m, 1H); 1.1(d, 3H). | pos. mode 345 (M + H). | N-methyl-3-(5-methyl-2-phenyl-4,5,6,7-tetrahydroindol-1-yl) benzamide |
| | CDCl3; 8.07(d, 1H), 7.82(br s, 1H), 7.50(t, 1H), 7.05-7.18(m, 6H), 6.25(s, 1H), 4.20(q, 2H), 2.75-2.95(m, 3H), 2.45-2.65(m, 2H), 2.15-2.25 (m, 1H), 1.85-1.95 (m, 1H), 1.30(t, 3H). | neg. mode 412 (M − H). | 3-[3-(5-ethoxycarbonyl-2-phenyl-4,5,6,7-tetrahydroindol-1-yl)-phenyl]propionic acid |
| | CDCl3; 7.24-7.30(m, 1H), 7.00-7.20(m, 7H), 6.93(br s, 1H), 6.26(s, 1H), 4.19(q, 2H), 2.79-3.00 (m, 4H), 2.68-2.78 (m, 1H), 2.20-2.45(m, 5H), 2.15-2.25(m, 1H), 1.29(t, 3H). | pos. mode 418 (M + H); neg. mode 416(M − H). | 1-[3-(2-carboxy-ethyl)-phenyl]-2-phenyl-4,5,6,7-tetrahydro-1H-indole-5-carboxylic acid ethyl ester |
| | DMSO-d6; 7.2-8.2(m, 11H), 6.6(s, 1H), 4.6(s, 2H), 2.2(s, 2H), 1.2-1.1 (m, 10H). | EM 397. | [1-(2-phenylbenzo[e]indol-3-ylmethyl)-cyclohexyl] acetic acid |

TABLE 7-continued

Compounds from Table 6 and Characterization Data

| product structure | 1H NMR, d | MS | name |
|---|---|---|---|
| 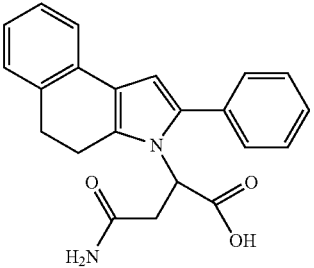 | DMSO-d6; 7.2-8.3(m, 10H), 5.5(s, 1H), 2.9(t, 2H), 2.6(t, 2H), 2.5(br. s, 2H). | pos. mode 361 (M + 1), neg. mode 359(M − 1). | 2-(2-phenyl-4,5-dihydrobenzo[e]indol-3-yl)succinamic acid |
| 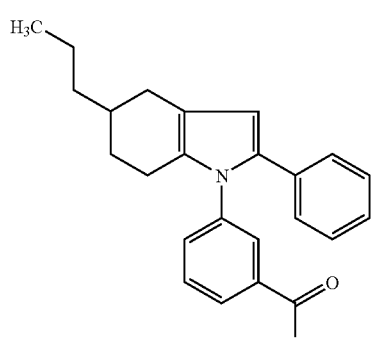 | CDCl3; 8.01(dt, 1H), 7.96(br s, 1H), 7.40(t, 1H), 7.28(br d, 1H), 7.05-7.20(m, 5H), 6.25(s, 1H), 2.74(dd, 1H), 2.50-2.60 (m, 1H), 2.41(br d, 1H), 2.22(dd, 1H), 1.92 (br d, 1H), 1.77(br s, 1H), 1.30-1.50(m, 5H), 0.94 (t, 3H). | neg. mode 358 (M − H). | 3-(2-phenyl-5-propyl-4,5,6,7-tetrahydroindol-1-yl)benzoic acid |
| 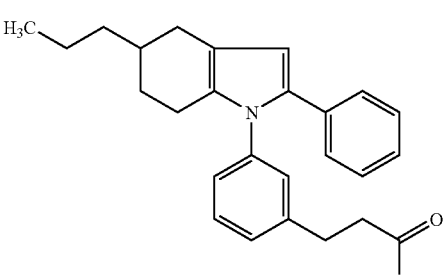 | CDCl3; 7.26(t, 1H), 6.98-7.18(m, 7H), 6.93(br s, 1H), 6.23(s, 1H), 2.88(t, 2H), 2.74(dd, 1H), 2.45-2.60 (m, 3H), 2.41(br d, 1H), 2.21(dd, 1H), 1.91 (br d, 1H), 1.72(br s, 1H), 1.30-1.50(m, 5H), 0.93 (t, 3H). | pos. mode 388 (M + H); neg. mode 386(M − H). | 3-[3-(2-phenyl-5-propyl-4,5,6,7-tetrahydroindol-1-yl)phenyl]propionic acid |
| 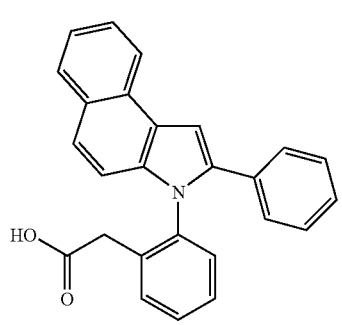 | acetone-d6: 8.41(m, 1H), 7.94(m, 1H), 7.62-7.37 (m, 10H), 7.31-7.22(m, 3H), 7.11(m, 1H), 3.33 (s, 2H). | pos. mode 378 (M + H) | [2-(2-phenyl-benzo[e]indol-3-yl)-phenyl]acetic acid |

TABLE 7-continued

Compounds from Table 6 and Characterization Data

| product structure | 1H NMR, d | MS | name |
|---|---|---|---|
| | CDCl3; 8.14(dt, 1H), 8.09(t, 1H), 8.00(t, 1H), 7.54(t, 1H), 7.37-7.46 (m, 2H), 7.33(d, 1H), 7.20-7.32(m, 5H), 6.89 (d, 1H). | neg. mode 380 (M − H). | 3-(2-phenyl-5-trifluoromethyl-indol-1-yl) benzoic acid |
| | CDCl3; 8.10(s, 1H), 8.08(t, 1H), 7.51(s, 1H), 7.48(t, 1H), 7.37(d, 1H), 7.18-7.28(m, 6H), 7.07 (dd, 1H), 6.77(s, 1H), 2.77(t, 2H), 1.31(t, 3H). | pos. mode 342 (M + H); neg. mode 340(M − H). | 3-(5-ethyl-2-phenyl-indol-1-yl)benzoic acid |
| | MeOH-d4; 8.02(dt, 1H), 7.86-7.92(m, 1H), 7.48-7.57(m, 2H), 7.36-7.45 (m, 1H), 7.20-7.30 (m, 5H), 6.98-7.05(m, 2H), 6.75(d, 1H), 2.39(s, 3H). | pos. mode 328 (M + H); neg. mode 326(M − H). | 3-(6-methyl-2-phenyl-indol-1-yl)benzoic acid |
| | MeOH-d4; 7.48(d, 1H), 7.36(t, 1H), 7.18-7.29 (m, 6H), 7.11(t, 1H), 7.00-7.08(m, 2H), 6.95(ddd, 1H), 6.71(d, 1H), 2.90(t, 2H), 2.51(t, 2H), 2.39(s, 3H). | pos. mode 356 (M + H); neg. mode 354(M − H). | 3-[3-(6-methyl-2-phenyl-indol-1-yl)-phenyl] propionic acid |
| | CDCl3; 8.03(dt, 1H), 7.97(t, 1H), 7.42(t, 1H), 7.28(ddd, 1H), 7.07-7.18 (m, 3H), 7.01-7.06 (m, 2H), 6.26(s, 1H), 4.30-4.40(m 1H), 3.00 (dd, 1H), 2.50-2.70(m, 3H), 1.85-2.05(m, 2H). | pos. mode 334 (M + H); neg. mode 332(M − H). | 3-(5-hydroxy-2-phenyl-4,5,6,7-tetrahydroindol-1-yl)benzoic acid |

TABLE 7-continued

Compounds from Table 6 and Characterization Data

| product structure | 1H NMR, d | MS | name |
|---|---|---|---|
| | CDCl3; 7.5(m, 1H); 7.4 (m, 2H); 7.0-7.2(m, 5H); 6.8(br. s, 1H); 6.2(s, 1H); 3.6(br. s, 4H); 3.2 (br. s, 2H); 2.8(br. s, 2H); 2.7(m, 1H); 2.5(m, 2H); 2.2(m, 1H); 1.9(m, 2H); 1.4(m, 1H); 1.1(d, 3H). | pos. mode 401 (M + H). | [3-(5-methyl-2-phenyl-4,5,6,7-tetrahydroindol-1-yl)phenyl]morpholin-4-yl-methanone |
| | DMSO-d6; 7.2-8.3(m, 5H), 5.6(s, 1H), 3.8(dd, 2H), 2.9(t, 2H), 2.6(t, 2H). | neg. mode 392 (M − 1). | 3-phenyl-3-(2-phenyl-4,5-dihydrobenzo[e]indol-3-yl) propionic acid |
| | DMSO-d6; 7.1-8.3(m, 17H), 6.1(s, 1H), 3.8-3.4(dd, 2H). | neg. mode 390 (M − 1). | 3-phenyl-3-(2-phenylbenzo[e]indol-3-yl) propionic acid |
| | MeOH-d4; 8.3(d, 1H), 8.08-8.06(tt, 1H), 7.96 (d, 1H), 7.87(m, 1H), 7.6-7.2(m, 9H), 6.82(m, 2H), 3.75(s, 3H). | pos. mode 394 (M + H); neg. mode 392(M − H). | 3-[2-(3-methoxyphenyl)-benzo[e]indol-3-yl] benzoic acid |
| | MeOH-d4; 8.3(d, 1H), 8.01-7.97(m, 2H), 7.88 (d, 1H), 7.58-7.37(m, 6H), 7.26-7.24(m, 2H), 7.15-7.11(t, 1H), 6.81 (t, 1H), 6.71(d, 1H). | pos. mode 380 (M + H); neg. mode 378(M − H). | 3-[2-(3-hydroxyphenyl)-benzo[e]indol-3-yl] benzoic acid |

TABLE 7-continued

Compounds from Table 6 and Characterization Data

| product structure | 1H NMR, d | MS | name |
| --- | --- | --- | --- |
| | DMSO-d6; 7.56(d, 1H), 7.32(d, 1H), 7.2(s, 1H), 7.13(d, 1H), 6.8-6.5(m, 10H), 6.28-6.23(m, 1H). | pos. mode 382 (M + H); neg. mode 380(M − H). | 3-[2-(4-fluorophenyl)-benzo[e]indol-3-yl] benzoic acid |
| | DMSO-d6; 8.48(d, 1H), 8.1(tt, 1H), 8.08(s, 1H), 8.04-8.02(m, 2H), 7.97-7.93(m, 3H). 7.77-7.67(m, 4H), 7.55-7.51 (m, 1H), 7.40(d, 1H). | pos. mode 500 (M + H); neg. mode 498(M − H). | 3-[2-(3,5-bistrifluoromethylphenyl)-benzo[e]indol-3-yl] benzoic acid |
| | DMSO-d6; 8.4(d, 1H), 8.07(d, 1H), 8.0(d, 1H), 7.87(s, 1H), 7.72-7.60 (m, 5H), 7.5-7.44(m, 2H), 7.4-7.33(d, 3H), 7.2(s, 1H). | pos. mode 398 (M + H); neg. mode 396(M − H). | 3-[2-(3-chlorophenyl)-benzo[e]indol-3-yl] benzoic acid |
| | DMSO-d6; 8.45(d, 1H), 8.07(tt, 1H), 8.0(d, 1H), 7.9(t, 1H), 7.8(s, 1H), 7.7-7.6(m, 6H), 7.54-7.47(m, 3H), 7.35(d, 1H). | pos. mode 432 (M + H); neg. mode 430(M − H). | 3-[2-(4-trifluoromethylphenyl)-benzo[e]indol-3-yl] benzoic acid |

TABLE 7-continued

Compounds from Table 6 and Characterization Data

| product structure | 1H NMR, d | MS | name |
|---|---|---|---|
| | CDCl3; 8.05(dt, 1H), 7.98(br s, 1H), 7.44(t, 1H), 7.37(br d, 1H), 7.10-7.20(m, 3H), 7.05-7.10 (m, 2H), 6.45(s, 1H), 3.50(sext, 1H), 2.45-2.60(m, 1H), 2.35-2.45 (m, 1H), 1.95-2.15 (m, 2H), 1.85-1.95(m, 1H), 1.68-1.80(m, 1H). | pos. mode 386 (M + H); neg. mode 384(M − H). | 3-(2-phenyl-4-trifluoromethyl-4,5,6,7-tetrahydroindol-1-yl) benzoic acid |
| | CDCl3; 8.06(d, 1H), 7.92(br s, 1H), 7.46(t, 1H), 7.33(br s, 1H), 7.08-7.20(m, 3H), 7.02-7.08 (m, 2H), 6.27(s, 1H), 2.80(dd, 1H), 2.40-2.74 (m, 4H), 2.21(br d, 1H), 1.75(qd, 1H). | pos. mode 386 (M + H); neg. mode 384(M − H). | 3-(2-phenyl-6-trifluoromethyl-4,5,6,7-tetrahydroindol-1-yl) benzoic acid |
| | CDCl3; 7.95-8.10(m, 4H), 7.45(t, 1H), 7.27-7.42 (m, 3H), 7.05-7.18 (m, 3H), 6.95-7.05(m, 2H), 6.01(s, 1H), 4.38(q, 2H), 4.07-4.14(m, 1H), 2.64(br s, 1H), 2.45(br d, 1H), 2.10-2.23(m, 1H), 1.90-2.00(m, 1H), 1.70-1.85(m, 2H), 1.39 (t, 3H). | pos. mode 466 (M + H); neg. mode 464(M − H). | 3-{4-[4-(ethoxycarbonyl)phenyl]-2-phenyl-4,5,6,7-tetrahydroindol-1-yl} benzoic acid |
| | CDCl3; 7.95-8.05(m, 3H), 7.92(s, 1H), 7.40(t, 1H), 7.25-7.35(m, 3H), 7.05-7.20(m, 5H), 6.32 (s, 1H), 4.35(q, 2H), 3.00-3.13(m, 1H), 2.79(br s, 2H), 2.62(br s, 2H), 1.95-2.20(m, 2H), 1.37(t, 3H). | pos. mode 466 (M + H); neg. mode 464(M − H). | 3-{6-[4-(ethoxycarbonyl)phenyl]-2-phenyl-4,5,6,7-tetrahydroindol-1-yl} benzoic acid |

TABLE 7-continued

Compounds from Table 6 and Characterization Data

| product structure | 1H NMR, d | MS | name |
| --- | --- | --- | --- |
|  | MeOH-d4; 8.3(d, 1H), 7.9(d, 1H), 7.75(d, 1H), 7.56-7.26(d, 12H), 7.18 (s, 1H). | neg. mode 362 (M − H). | 2-(3-phenyl-3H-benzo[e]indol-2-yl) benzoic acid |
|  | DMSO-d6; 7.1-8.3(m, 16H), 6.1(s, 1H). | pos. mode 431 (M + 1), neg. mode 429(M − 1). | 3-[2-(3-phenylisoxazol-5-yl)-benzo[e]indol-3-yl] benzoic acid |
|  | DMSO-d6; 7.1-8.4(m, 15H), 6.1(s, 1H), 3.1(t, 2H), 2.7(t, 2H). | pos. mode 432 (M + 1), neg. mode 430(M − 1). | 3-[3-(2-benzofuran-2-yl-benzo[e]indol-3-yl)-phenyl]propionic acid |
|  | CDCl3; 8.22(dt, 1H), 8.07(t, 1H), 7.61(t, 1H), 7.55(ddd, 1H), 7.33-7.37 (m, 1H), 7.28-7.31 (m, 1H), 7.07-7.19(m, 2H), 6.68(s, 1H), 5.60(s, 1H), 2.93(dd, 1H), 2.65-2.75 (m, 1H), 2.40-2.58 (m, 3H), 2.19(br d, 1H), 1.76(qd, 1H). | neg. mode 424 (M − H). | 3-(2-benzofuran-2-yl-5-trifluoromethyl-4,5,6,7-tetrahydroindol-1-yl) benzoic acid |

TABLE 7-continued

Compounds from Table 6 and Characterization Data

| product structure | 1H NMR, d | MS | name |
|---|---|---|---|
| | DSMO-d6; 12.9(br s, 1H), 7.97(dt, 1H), 7.67 (br s, 1H), 7.59(t, 1H), 7.42(d, 1H), 7.40-7.50 (m, 1H), 7.25(d, 1H), 6.89(dd, 1H), 6.48(s, 1H), 2.81(dd, 1H), 2.65-2.78 (m, 1H), 2.50-2.65 (m, 2H), 2.38(dd, 1H), 2.10(br d, 1H), 1.63(qd, 1H). | pos. mode 454 (M + H); neg. mode 452(M − H). | 3-[2-(3,4-dichlorophenyl)-5-trifluoromethyl-4,5,6,7-tetrahydroindol-1-yl] benzoic acid |
| | DMSO-d6; 7.1-8.3(m, 13H), 6.2(s, 1H), 2.9(t, 2H), 2.6(t, 2H). | pos. mode 433 (M + 1), neg. mode 431(M − 1). | 3-[2-(3-phenylisoxazol-5-yl)-4,5-dihydrobenzo[e]indol-3-yl] benzoic acid |
| | CDCl3: 7.7(m, 1H); 7.1-7.3 (m, 11H); 6.8(s, 1H); 2.7(t, 2H); 2.4(t, 2H); 2.0 (m, 2H); 1.4(m, 9H). | pos. mode 412 (M + H); neg. mode 410(M − H). | 4-[4-(5-tButyl-2-phenyl-indol-1-yl)phenyl]butyric acid |
| | DMSO-d6; 8.4(d, 1H), 8.1(tt, 1H), 8.0(d, 1H), 7.9(t, 1H), 7.8(s, 1H), 7.7-7.57(m, 6H), 7.50-7.46(t, 1H), 7.3(d, 1H), 7.2(dd, 1H). | pos. mode 433 (M + H); neg. mode 431(M − H). | 3-[2-(3,4-dichlorophenyl)-benzo[e]indol-3-yl] benzoic acid |

TABLE 7-continued

Compounds from Table 6 and Characterization Data

| product structure | 1H NMR, d | MS | name |
|---|---|---|---|
| | DMSO-d6; 6.6-8.2(m, 16H), 4.6(dd, 2H), 3.3 (dd, 2H), 2.07(s, 1H). | pos. mode 430 (M + 1). | 3-(4-chlorophenyl)-4-(2-phenylbenzo[e]indol-3-yl) butyric acid |
| | CDCl3; 8.05(d, 1H), 7.94(s, 1H), 7.45(t, 1H), 7.31(d, 1H), 7.12-7.20 (m, 3H), 7.04-7.10(m, 2H), 6.27(s, 1H), 3.53(s, 2H), 2.88(t, 2H), 2.70(t, 2H). | 331.8(M dot) | 3-(5-oxo-2-phenyl-4,5,6,7-tetrahydroindol-1-yl)benzoic acid |
| | CDCl3; 8.02(d, 1H), 7.99 (s, 1H), 7.40(t, 1H), 7.29 (t, 1H), 7.08-7.25(m, 3H), 7.00-7.06(m, 2H), 6.24(s, 1H), 4.03-4.10 (m, 4H), 2.89(s, 2H), 2.70-2.60(m, 2H), 2.02-1.95(m, 2H). | pos. mode 376 (M + H). | 3-[2'-phenyl-4',5',6',7'-tetrahydrospiro(1,3-dioxolane-2,5'-indol)-1'-yl] benzoic acid |
| | MeOH-d4; 8.3(d, 1H), 8.04(t, 1H), 7.88(m, 2H), 7.6-7.3(m, 12H). | 363(M dot). | 3-(3-phenyl-3H-benzo[e]indol-2-yl) benzoic acid |
| | DMSO-d6; 8.41(d, 1H), 8.06(tt, 1H), 7.97(d, 1H), 7.86(t, 1H), 7.71-7.6 (m, 5H), 7.5-7.46(m, 1H), 7.43-7.40(m, 2H), 7.32-7.35(m, 3H). | 397(M dot). | 3-[2-(4-chlorophenyl)-benzo[e]indol-3-yl] benzoic acid |

TABLE 7-continued

Compounds from Table 6 and Characterization Data

| product structure | 1H NMR, d | MS | name |
|---|---|---|---|
| | CDCl3: 8.1(m, 2H); 7.7 (s, 1H); 7.5(t, 1H); 7.2-7.3 (m, 9H); 6.8(s, 1H); 0.9(m, 9H). | pos. mode 394 (M + H). | 5-tButyl-2-phenyl-1-[3-(1H-tetrazol-5-yl)phenyl]-1H-indole |
| | DMSO-d6; 8.4(d, 1H), 8.0-7.91(m, 2H), 7.78 (s, 1H), 7.68-7.38(m, 11H), 3.37(s, 3H). | pos. mode 422 (M + H). | 3-[2-(2-carbomethoxyphenyl)-benzo[e]indol-3-yl]benzoic acid |
| | DMSO-d6; 8.3(d, 1H), 8.1(m, 1H), 8.04(m, 1H), 7.92(m, 1H), 7.6(m, 2H), 7.46(m, 5H), 7.3(m, 3H), 6.8(s, 1H). | neg. mode 396 (M − H). | 3-[2-(2-chlorophenyl)-benzo[e]indol-3-yl]benzoic acid |
| | CDCl3; 8.01(dt, 1H), 7.96(br s, 1H), 7.40(t, 1H), 7.27(d, 1H), 7.12-7.18(m, 2H), 7.03-7.12 (m, 3H), 6.26(s, 1H), 2.67(dd, 1H), 2.50-2.62 (m, 1H), 2.32-2.46(m, 2H), 1.96(br d, 1H), 1.72-1.84(m, 4H), 1.68(br d, 1H), 1.55-1.63(m, 1H), 1.45(quint., d, 1H), 1.00-1.36(m, 6H). | 3.99(M Dot) | 3-(5-cyclohexyl-2-phenyl-4,5,6,7-tetrahydroindol-1-yl)benzoic acid |

TABLE 7-continued

Compounds from Table 6 and Characterization Data

| product structure | 1H NMR, d | MS | name |
|---|---|---|---|
| | CDCl3; 8.05(dt, 1H), 8.00(br s, 1H), 7.44(t, 1H), 7.32(br d, 1H), 7.00-7.17(m, 6H), 6.31(s, 1H), 6.21(dd, 1H), 4.37 (qd, 2H), 4.22(br t, 1H), 2.50-2.60(m, 1H), 2.37-2.48(m, 1H), 2.15-2.27 (m, 1H), 1.96-2.07 (m, 1H), 1.85-1.95(m, 1H), 1.72-1.85(m, 1H), 1.38(t, 3H) | pos. mode 456 (M + H). | 5-[1-(3-carboxyphenyl)-2-phenyl-4,5,6,7-tetrahydro-1H-indol-4-yl]-furan-2-carboxylic acid ethyl ester |
| | CDCl3; 8.03(dt, 1H), 7.93(br s, 1H), 7.43(t, 1H), 7.32(br d, 1H), 7.03-7.20(m, 6H), 6.28(s, 1H), 6.14(dd, 1H), 4.33 (q, 2H), 3.15-3.27(m, 1H), 2.63-2.85(m, 4H), 2.28-2.35(m, 1H), 1.88-2.03(m, 1H), 1.35(t, 3H). | pos. mode 456 (M + H). | 5-[1-(3-carboxyphenyl)-2-phenyl-4,5,6,7-tetrahydro-1H-indol-6-yl]-furan-2-carboxylic acid ethyl ester |
| | CDCl3; 8.10(dt, 1H), 7.94(br s, 1H), 7.50(t, 1H), 7.27-7.37(m, 1H), 7.22(d, 1H), 7.18(d, 1H), 6.76(dd, 1H), 6.47(s, 1H), 3.40-3.60(m, 1H), 2.43-2.60(m, 1H), 2.30-2.43(m, 1H), 1.95-2.15 (m, 2H), 1.82-1.95 (m, 1H), 1.65-1.80(m, 1H). | pos. mode 454 (M + H). | 3-[2-(3,4-dichlorophenyl)-4-trifluoromethyl-4,5,6,7-tetrahydroindol-1-yl] benzoic acid |
| | CDCl3; 8.11(dt, 1H), 7.88(br s, 1H), 7.52(t, 1H), 7.33(br s, 1H), 7.15 (d, 1H), 7.17(d, 1H), 6.59 (dd, 1H), 6.29(s, 1H), 2.78(dd, 1H), 2.40-2.70 (m, 4H), 2.15-2.25(m, 1H), 1.73(qd, 1H). | pos. mode 454 (M + H). | 3-[2-(3,4-dichlorophenyl)-6-trifluoromethyl-4,5,6,7-tetrahydroindol-1-yl] benzoic acid |

TABLE 7-continued

Compounds from Table 6 and Characterization Data

| product structure | 1H NMR, d | MS | name |
|---|---|---|---|
| | DMSO-d6; 8.45(d, 1H), 8.1-7.9(m, 8H), 7.74-7.63 (m, 4H), 7.5(t, 1H), 7.37(d, 1H). | pos. mode 432 (M + H). | 3-[2-(3-trifluoromethylphenyl)-benzo[e]indol-3-yl] benzoic acid |
| | DMSO-d6; 8.5(d, 1H), 8.1(tt, 1H), 8.0(d, 1H), 7.9(t, 1H), 7.74-7.64 (m, 5H), 7.53-7.46(m, 3H), 7.3(m, 3H). | pos. mode 448 (M + H). | 3-[2-(4-trifluoromethoxyphenyl)-benzo[e]indol-3-yl] benzoic acid |
| | DMSO-d6; 8.45(d, 1H), 8.10(tt, 1H), 8.01(d, 1H), 7.92(t, 1H), 7.86-7.83 (m, 3H), 7.76-7.72(m, 2H), 7.70-7.65(m, 2H), 7.54-7.5(m, 3H), 7.38 (d, 1H). | pos. mode 389 (M + H). | 3-[2-(4-cyanophenyl)-benzo[e]indol-3-yl] benzoic acid |
| | DMSO-d6; 7.1-8.4(m, 15H), 5.8(s, 1H), 2.7(t, 2H), 2.06(t, 2H), 1.8(t, 2H). | pos. mode 446 (M + 1), neg. mode 444(M − 1). | 4-[4-(2-benzofuran-2-ylbenzo[e]indol-3-yl)-phenyl]butyric acid |

TABLE 7-continued

Compounds from Table 6 and Characterization Data

| product structure | 1H NMR, d | MS | name |
|---|---|---|---|
| | CDCl3; 7.10-7.17(m, 4H), 7.01-7.09(m, 5H), 6.24(s, 1H), 2.58-2.72 (m, 3H), 2.47-2.58(m, 1H), 2.30-2.46(m, 4H), 1.90-2.05(m, 3H), 1.62 (td, 1H), 1.23-1.45(m, 3H), 0.89(s, 3H), 0.88(s, 3H), 0.84(t, 3H). | neg. mode 428 (M − H). | 4-{4-[5-(1,1-dimethylpropyl)-2-phenyl-4,5,6,7-tetrahydroindol-1-yl]-phenyl}butyric acid |
| | CDCl3: 7.0-7.2(m, 9H); 6.2(s, 1H); 2.7(m, 3H); 2.4(m, 3H); 2.1(m, 1H); 2.0(m, 2H); 1.9(m, 2H); 1.4(m, 2H); 1.0(d, 3H). | pos. mode 374 (M + H); neg. mode 372(M − H). | 4-[4-(6-methyl-2-phenyl-4,5,6,7-tetrahydroindol-1-yl)phenyl] butyric acid |
| | CDCl3; 8.02(dt, 1H), 7.97(t, 1H), 7.40(t, 1H), 7.28(ddd, 1H), 7.07-7.18 (m, 3H), 7.01-7.06 (m, 2H), 6.26(s, 1H), 3.45-3.80(m, 1H), 3.46 (s, 3H), 2.99(dd, 1H), 2.65(dd, 1H), 2.40-2.65 (m, 2H), 2.00-2.15(m, 1H), 1.80-2.00(m, 1H). | pos. mode 348 (M + H); neg. mode 346(M − H). | 3-(5-methoxy-2-phenyl-4,5,6,7-tetrahydroindol-1-yl)benzoic acid |
| | 2 rotamers, 1:1, MeOH-d4; 7.87(dd, 0.5H), 7.85 (dd, 0.5H), 7.55(d, 0.5H), 7.44(d, 0.5H), 7.10(s, 2H), 7.09(s, 2H), 7.00-7.03 (m, 1H), 6.98(d, 0.5H), 6.95(d, 0.5H), 6.18(s, 0.5H), 6.17(s, 0.5H), 2.59(dt, 1H), 2.20-2.50 (m, 3H), 1.85-2.00 (m, 1H), 1.45-1.62 (m, 1H), 1.25-1.45(m, 3H), 0.92(s, 3H), 0.91(s, 3H), 0.87(t, 3H). | pos. mode 404 (M + H); neg. mode 402(M − H). | 3-[5-(1,1-dimethylpropyl)-2-phenyl-4,5,6,7-tetrahydroindol-1-yl]4-hydroxybenzoic acid |

TABLE 7-continued

Compounds from Table 6 and Characterization Data

| product structure | 1H NMR, d | MS | name |
|---|---|---|---|
| | CDCl3; 7.87(d, 1H), 7.39(d, 1H), 7.16-7.23 (m, 2H), 7.09-7.16(m, 2H), 7.04-7.09(m, 2H), 6.26(s, 1H), 2.63(dd, 1H), 2.55(br d, 1H), 2.32-2.48 (m, 2H), 1.99(br d, 1H), 1.63(td, 1H), 1.26-1.46(m, 3H), 0.90(s, 3H), 0.89(s, 3H), 0.86(t, 3H) | pos. mode 422 (M + H); neg. mode 420(M − H). | 2-chloro-5-[5-(1,1-dimethylpropyl)-2-phenyl-4,5,6,7-tetrahydroindol-1-yl]benzoic acid |
| | DMSO-d6; 7.0-8.3(m, 14H), 6.4(s, 1H), 3.1(q, 4H),2.6(t, 2H), 2.04(t, 2H), 1.9(q, 4H), 1.8(t, 2H). | pos. mode 475 (M + 1), neg. mode 473(M − 1). | 4-{4-[2-(4-pyrrolidin-1-ylphenyl)-benzo[e]indol-3-yl]-phenyl}butyric acid |
| | CDCl3; 8.02(dt, 1H), 7.94(br s, 1H), 7.42(t, 1H), 7.30(br d, 1H), 7.11-7.18(m, 2H), 7.02-7.11 (m, 3H), 6.26(s, 1H), 2.54-2.74(m, 2H), 2.44(dd, 1H), 2.10-2.20 (m, 1H), 1.94(br d, 1H), 1.65(br s, 1H), 1.30-1.50 (m, 3H), 0.91(t, 3H). | pos. mode 346 (M + H); neg. mode 344(M − H). | 3-(6-ethyl-2-phenyl-4,5,6,7-tetrahydroindol-1-yl)benzoic acid |
| | DMSO-d6; 7.1-8.4(m, 13H), 7.05(s, 1H), 1.5 (dd, 4H), 1.21(s, 6H), 0.93(s, 6H). | pos. mode 474 (M + 1). | 3-[2-(5,5,8,8-tetramethyl-5,6,7,8-tetrahydronapthalen-2-yl)-benzo[e]indol-3-yl] benzoic acid |

TABLE 7-continued

Compounds from Table 6 and Characterization Data

| product structure | 1H NMR, d | MS | name |
|---|---|---|---|
| | DMSO-d6; 7.2-8.3(m, 13H), 6.9(s, 1H), 2.6(t, 2H), 1.9(t, 2H), 1.7(t, 2H), 1.5(q, 4H), 1.21(s, 6H), 0.9(s, 6H). | pos. mode 516 (M + 1). | 4-{4-[2-(5,5,8,8-tetramethyl-5,6,7,8-tetrahydronaphthalen-2-yl)-benzo[e]indol-3-yl]-phenyl}butyric acid |
| | DMSO-d6; 7.1-8.3(m, 4H), 6.4(s, 1H), 3.2(q, 4H), 1.9(q, 4H). | pos. mode 433 (M + 1), neg. mode 431(M − 1). | 3-[2-(4-pyrrolidin-1-ylphenyl)-benzo[e]indol-3-yl]benzoic acid |
| | CDCl3: 8.0(d, 1H); 7.9 (br. s, 1H); 7.4(t, 1H); 7.2 (m, 2H); 7.1(d, 1H); 6.7 (dd, 1H); 6.2(s, 1H); 2.7 (m, 1H); 2.5(m, 1H); 2.3-2.4 (m, 2H); 2.0(m, 1H); 1.4(m, 1H); 1.3(m, 1H); 1.0(s, 9H). | pos. mode 442 (M + H); neg. mode 440(M − H). | 3-[5-tButyl-2-(3,4-dichlorophenyl)-4,5,6,7-tetrahydroindol-1-yl]benzoic acid |
| | DMSO-d6; 8.38(d, 1H), 7.98-7.92(m, 2H), 7.84 (m, 1H), 7.7-7.66(m, 2H), 7.62-7.56(m, 3H), 7.51(s, 1H), 7.48-7.4 (m, 4H). | neg. mode 430 (M − H). | 3-[2-(2,5-dichlorophenyl)-benzo[e]indol-3-yl]benzoic acid |

TABLE 7-continued

Compounds from Table 6 and Characterization Data

| product structure | 1H NMR, d | MS | name |
| --- | --- | --- | --- |
| | DMSO-d6; 7.1-8.4(m, 14H), 6.09(s, 1H). | pos. mode 438 (M + 1). | 5-(2-benzofuran-2-ylbenzo[e]indol-3-yl)2-chlorobenzoic acid |
| | DMSO-d6; 7.1-8.4(m, 14H), 5.9(s, 1H). | pos. mode 420 (M + 1). | 3-(2-benzofuran-2-ylbenzo[e]indol-3-yl)4-hydroxybenzoic acid |
| | DMSO-d6; 8.4(d, 1H), 7.96(d, 1H), 7.73(s, 1H), 7.66-7.56(m, 3H), 7.5-7.44 (m, 2H), 7.4(d, 2H), 7.34-7.28(m, 3H), 7.26 (dd, 1H), 2.65(t, 2H), 2.3 (t, 2H), 1.9(t, 2H). | pos. mode 474 (M + H). | 4-{4-[2-(3,4-dichlorophenyl)-benzo[e]indol-3-yl]-phenyl}butyric acid |
| | CDCl3: 8.0(d, 1H); 7.9 (br. s, 1H); 7.4(m, 3H); 7.2(m, 1H); 7.1(d, 2H); 6.4(s, 1H); 2.7(m, 1H); 2.5(m, 1H); 2.3-2.4(m, 2H); 2.0(m, 1H); 1.5(m, 1H); 1.4(m, 1H); 1.0(s, 9H). | TOF pos. mode 442 (M + H), EM 442.1994. | 3-[5-tButyl-2-(4-trifluoromethylphenyl)-4,5,6,7-tetrahydroindol-1-yl]benzoic acid |

TABLE 7-continued

Compounds from Table 6 and Characterization Data

| product structure | 1H NMR, d | MS | name |
|---|---|---|---|
| | CDCl3: 8.02(d, 1H), 7.96(s, 1H), 7.33-7.45 (m, 5H), 7.25-7.32(m, 2H), 7.08-7.18(m, 3H), 7.00-7.08(m, 2H), 6.25 (s, 1H), 4.67(s, 2H), 3.86-3.92(m, 1H), 3.02(dd, 1H), 2.71(dd, 1H), 2.48-2.58 (m, 2H), 2.05-2.18 (m, 1H), 1.88-2.04(m, 1H). | pos. mode 424 (M + H); neg. mode 422(M − H). | 3-(5-benzyloxy-2-phenyl-4,5,6,7-tetrahydroindol-1-yl)benzoic acid |
| | DMSO-d6; 8.43(d, 1H), 7.99-7.95(m, 2H), 7.87 (s, 2H), 7.69(d, 1H), 7.64 (t, 1H), 7.49(t, 1H), 7.43-7.34(m, 6H), 2.7(t, 2H), 2.25(t, 2H), 1.84(t, 2H). | pos. mode 542 (M + H); neg. mode 540(M − H). | 4-{4-[2-(3,5-bistrifluoromethylphenyl)-benzo[e]indol-3-yl]-phenyl}butyric acid |
| | CDCl3; 8.32(d, 1H), 7.91 (d, 1H), 7.6-7.2(m, 13H), 2.8(t, 2H); 2.4(t, 2H); 2.0(t, 2H). | pos. mode 474 (M + H); neg. mode 472(M − H). | 4-{4-[2-(4-trifluoromethylphenyl)-benzo[e]indol-3-yl]-phenyl}butyric acid |
| | DMSO-d6; 6.8-8.7(m, 15H), 3.9(s, 2H), 2.27(s, 6H). | neg. mode 459 (M − 1). | 3-(2-benzofuran-2-yl-1-dimethylaminomethylbenzo[e]indol-3-yl)benzoic acid |

TABLE 7-continued

Compounds from Table 6 and Characterization Data

| product structure | 1H NMR, d | MS | name |
|---|---|---|---|
| | CDCl3; 8.03(d, 1H), 7.96(s, 1H), 7.42(t, 1H), 7.30(d, 1H), 7.00-7.20 (m, 5H), 6.31(s, 1H), 2.70-2.85(m, 1H), 2.30-2.58(m, 4H), 1.75-2.05 (m, 5H), 1.60-1.85 (m, 2H), 1.40-1.50(m, 1H). | pos. mode 385 (M + H). | 3-[4-(3-cyanopropyl)-2-phenyl-4,5,6,7-tetrahydroindol-1-yl] benzoic acid |
| | CDCl3; 8.04(dt, 1H), 7.94(br s, 1H), 7.43(t, 1H), 7.29(br d, 1H), 7.08-7.20(m, 3H), 7.02-7.08 (m, 2H), 6.26(s, 1H), 2.56-2.74(m, 2H), 2.45(dd, 1H), 2.33(t, 2H), 2.12-2.23(m, 1H), 1.90-1.98(m, 1H), 1.75-1.85(m, 1H), 1.62-1.75 (m, 2H), 1.40-1.61 (m, 3H) | pos. mode 385 (M + H). | 3-[6-(3-cyanopropyl)-2-phenyl-4,5,6,7-tetrahydroindol-1-yl]-benzoic acid |
| | DMSO-d6; 7.8(d, 1H), 7.56(s, 1H), 7.42(t, 1H), 7.24(d, 1H), 7.09(d, 1H), 6.46(d, 1H), 6.32(s, 1H), 5.99(s, 1H), 3.7(s, 3H), 3.3(s, 3H), 2.8-2.55(m, 4H), 2.39(d, 1H), 2.10(d, 1H), 1.66-1.61(m, 1H). | pos. mode 446 (M + H); neg. mode 444(M − H). | 3-[2-(3,4-dimethoxyphenyl)-5-trifluoromethyl-4,5,6,7-tetrahydroindol-1-yl]-benzoic acid |
| | DMSO-d6; 7.91(d, 1H), 7.63(s, 1H), 7.56(t, 1H), 7.44(d, 1H), 6.78(d, 1H), 6.57(d, 1H), 6.51(s, 1H), 6.24(s, 1H), 3.67(s, 3H), 3.35(s, 3H), 2.81-2.55 (m, 4H), 2.36(d, 1H), 2.10(m, 1H), 1.66-1.61 (m, 1H). | pos. mode 446 (M + H); neg. mode 444(M − H). | 3-[2-(2,4-dimethoxyphenyl)-5-trifluoromethyl-4,5,6,7-tetrahydroindol-1-yl] benzoic acid |

TABLE 7-continued

Compounds from Table 6 and Characterization Data

| product structure | 1H NMR, d | MS | name |
|---|---|---|---|
| | DMSO-d6; 8.38(d, 1H), 7.96(d, 1H), 7.64-7.3 (m, 12H), 7.1-7.07(tt, 1H), 2.89(t, 2H), 2.55(t, 2H). | pos. mode 426 (M + H); neg. mode 424(M − H). | 3-{3-[2-(4-chlorophenyl)-benzo[e]indol-3-yl]-phenyl}propionic acid |
| | DMSO-d6; 8.39(d, 1H), 7.97(d, 1H), 7.73(s, 1H), 7.67-7.33(m, 9H); 7.19-7.12(m, 2H); 2.9(t, 2H); 2.55(t, 2H). | pos. mode 460 (M + H). | 3-{3-[2-(3,4-dichlorophenyl)-benzo[e]indol-3-yl]-phenyl}propionic acid |
| | DMSO-d6; 7.92-7.89(tt, 1H), 7.62(s, 1H), 7.54(t, 1H), 7.4(d, 1H), 6.87(d, 2H), 6.75(d, 2H), 6.16(s, 1H), 3.68(t, 4H), 3.34(s, 2H), 3.01(t, 4H), 2.8-2.76 (dd, 1H), 2.6(dd, 1H), 2.34(m, 1H), 2.1(m, 1H), 1.63(m, 1H). | pos. mode 471 (M + H); neg. mode 469(M − H). | 3-[2-(4-morpholin-4-yl-phenyl)-5-trifluoromethyl-4,5,6,7-tetrahydroindol-1-yl]benzoic acid |
| | CDCl3; 7.95-7.88(m, 2H), 7.34(t, 1H), 7.22(d, 1H), 6.87(d, 1H), 6.56(d, 1H), 6.15(s, 1H); 3.83(s, 3H)3.65(s, 3H); 3.51(s, 3H); 2.93-2.88(dd, 1H); 2.71(t, 2H) 2.54-2.51 (m, 2H); 2.21(m, 1H) 1.77-1.72(m, 1H). | pos. mode 476 (M + H); neg. mode 474(M − H). | 3-[5-trifluoromethyl-2-(2,3,4-trimethoxyphenyl)-4,5,6,7-tetrahydroindol-1-yl]benzoic acid |
| | DMSO-d6; 6.9-7.8(m, 9H), 3.4(s, 2H), 2.2(s, 3H), 1.9(s, 3H), 1.4-1.5 (m, 2H), 0.9(s, 9H). | neg. mode 429 (M − 1). | 3-(5-tButyl-3-dimethylaminomethyl-2-phenyl-4,5,6,7-tetrahydroindol-1-yl) benzoic acid |

TABLE 7-continued

Compounds from Table 6 and Characterization Data

| product structure | 1H NMR, d | MS | name |
| --- | --- | --- | --- |
| | DMSO-d6; 8.4(d, 1H); 7.97(d, 1H); 7.85(d, 1H); 7.76-7.46(m, 9H); 7.39-7.33 (dd, 1H); 7.2-7.15 (td, 1H). | pos. mode 432 (M + H). | 2-chloro-5-[2-(4-chlorophenyl)-benzo[e]indol-3-yl] benzoic acid |
| | MeOH-d4; 7.99(d, 1H), 7.77(s, 1H), 7.48(t, 1H), 7.28-7.33(m, 1H), 7.10-7.20(m, 3H), 7.00-7.10 (m, 2H), 6.28(s, 1H), 3.75-3.88(m, 1H), 3.37-3.50(m, 2H), 3.23-3.35(m, 2H), 3.07(dd, 1H), 2.93(dd, 1H), 2.65-2.82 (m, 1H), 2.59(br d, 1H), 2.27(br d, 1H), 2.03 (qd, 1H), 1.40(t, 6H). | pos. mode 389 (M + H); neg. mode 387(M − H). | 3-(5-diethylamino-2-phenyl-4,5,6,7-tetrahydroindol-1-yl) benzoic acid |
| | MeOH-d4; 7.99(dt, 1H), 7.77(br s, 1H), 7.48(t, 1H), 7.31(br d, 1H), 7.08-7.20(m, 3H), 7.00-7.06 (m, 2H), 6.27(s, 1H), 3.75-4.12(m, 4H), 3.58-3.72(m, 1H), 3.20-3.57(m, 4H), 3.10-3.20 (m, 1H), 2.82-2.95 (m, 1H), 2.68-2.79(m, 1H), 2.61(br d, 1H), 2.40 (br d, 1H), 1.98(qd, 1H). | pos. mode 403 (M + H); neg. mode 401(M − H). | 3-(5-morpholin-4-yl-2-phenyl-4,5,6,7-tetrahydroindol-1-yl) benzoic acid |
| | DMSO-d6; 7.87(d, 1H), 7.59(br s, 1H), 7.47(t, 1H), 7.32(br d, 1H), 7.11-7.20(m, 2H), 7.03-7.10 (m, 1H), 6.94-7.02 (m, 2H), 6.23(s, 1H), 2.55-2.90(m, 6H), 2.30-2.40(m, 2H), 2.05-2.18 (m, 2H), 1.75(br s, 4H), 1.57-1.70(m, 1H). | pos. mode 387 (M + H); neg. mode 385(M − H). | 3-(2-phenyl-5-pyrrolidin-1-yl-4,5,6,7-tetrahydroindol-1-yl) benzoic acid |

TABLE 7-continued

Compounds from Table 6 and Characterization Data

| product structure | 1H NMR, d | MS | name |
|---|---|---|---|
| | DMSO-d6; 7.91(d, 1H), 7.60-7.41(m, 3H); 7.25-7.21(m, 2H); 7.0-6.96 (m, 2H); 6.27(s, 1H); 2.54-2.44(m, 1H), 2.31-2.25(m, 2H); 1.91(m, 1H); 1.56-1.50(m, 1H) 1.37-1.24(m, 4H); 0.86-0.80(m, 9H). | pos. mode 422 (M + H), neg. mode 420(M − 1). | 3-[2-(4-chlorophenyl)-5-(1,1,-dimethylpropyl)-4,5,6,7-tetrahydroindol-1-yl]benzoic acid |
| | DMSO-d6; 7.94-7.92(dt, 1H), 7.65-7.38(m, 5H); 7.17(d, 2H); 6.42(s, 1H); 2.51-2.48(m, 1H), 2.31-2.21 (m, 2H); 1.95-1.90 (m, 1H); 1.59-1.51(m, 1H)1.39-1.23(m, 4H); 0.87-0.81(m, 9H). | pos. mode 456 (M + H), neg. mode 454(M − 1). | 3-[5-(1,1-dimethylpropyl)-2-(3-trifluoromethylphenyl)-4,5,6,7-tetrahydro-indol-1-yl]benzoic acid |
| | CDCl3; 8.02-7.93(m, 2H), 7.41(t, 1H); 7.23(m, 1H); 7.03-6.99(m, 2H), 6.87-6.83(m, 2H)6.22(s, 1H); 2.66-2.53(m, 2H), 2.42-2.35(m, 2H); 1.99-1.96(m, 1H); 1.66-1.60 (m, 1H)1.43-1.33(m, 3H); 0.90-0.83(m, 9H). | pos. mode 406 (M + H), neg. mode 404(M − 1). | 3-[5-(1,1-dimethylpropyl)-2-(4-fluorophenyl)-4,5,6,7-tetrahydroindol-1-yl] benzoic acid |
| | CDCl3; 8.05-7.95(m, 2H), 7.44(t, 1H); 7.33-7.13 (m, 5H), 6.34(s, 1H); 2.67-2.53(m, 2H), 2.45-2.35(m, 2H); 2.0-1.97 (m, 1H); 1.66-1.59(m, 1H)1.43-1.35(m, 3H); 0.90-0.84(m, 9H). | pos. mode 456 (M + H), neg. mode 454(M − 1). | 3-[5-(1,1-dimethylpropyl)-2-(4-trifluoromethyl-phenyl)-4,5,6,7-tetrahydro-indol-1-yl] benzoic acid |
| | CDCl3; 7.27-7.38(m, 3H), 7.01-7.18(m, 7H), 6.25(s, 1H), 3.72-3.80 (m, 4H), 2.75-2.90(m, 2H), 2.46-2.74(m, 7H), 2.07-2.17(m, 1H), 1.70 (qd, 1H). | pos. mode 359 (M + H). | 5-morpholin-4-yl-1,2-diphenyl-4,5,6,7-tetrahydro-1H-indole |

TABLE 7-continued

Compounds from Table 6 and Characterization Data

| product structure | 1H NMR, d | MS | name |
|---|---|---|---|
| | CDCl3; 8.04(dd, 1H), 7.94(br s, 1H), 7.44(t, 1H), 7.25-7.30(m, 1H), 7.08-7.15(m, 1H), 6.98-7.06 (m, 2H), 6.81(dt, 1H), 6.29(s, 1H), 2.63 (dd, 1H), 2.48-2.58(m, 1H), 2.30-2.46(m, 2H), 1.98-2.20(m, 1H), 1.56-1.68(m, 1H), 1.30-1.44 (m, 3H), 0.90(s, 3H), 0.89(s, 3H), 0.85(t, 3H). | pos. mode 422 (M + H). | 3-[2-(3-chlorophenyl)-5-(1,1-dimethylpropyl)-4,5,6,7-tetrahydroindol-1-yl]benzoic acid |
| | CDCl3; 8.08-8.05; (dt, 1H); 7.94(s, 1H), 7.46(t, 1H); 7.29-7.27(m, 1H), 7.21-7.15(m, 2H); 6.76-6.73(dd, 1H), 6.29(s, 1H), 2.65-2.60(m, 1H), 2.44-2.32(m, 2H), 1.98 (m, 1H), 1.66-1.56(m, 1H), 1.42-1.33(m, 4H), 0.89-0.83(m, 9H). | pos. mode 457 (M + H). | 3-[2-(3,4-dichlorophenyl)-5-(1,1-dimethylpropyl)-4,5,6,7-tetrahydroindol-1-yl]benzoic acid |
| | CDCl3; 8.16-8.14;(m, 1H); 8.05(m, 1H), 7.55-7.52 (m, 2H); 5.90(s, 1H); 2.43-2.39(m, 2H); 2.06-2.01(m, 1H); 1.59-1.43 (m, 2H); 1.34-1.29 (m, 5H); 1.13(s, 9H); 0.87-0.79(m, 9H). | pos. mode 368 (M + H). | 3-[2-tert-butyl-5-(1,1-dimethylpropyl)-4,5,6,7-tetrahydroindol-1-yl] benzoic acid |
| | CDCl3; 8.03-8.09(m, 2H), 7.42-7.52(m, 3H), 7.30-7.42(m, 4H), 7.17-7.29 (m, 7H), 6.94(dd, 1H), 6.74(d, 1H), 5.15(s, 2H). | pos. mode 420 (M + H). | 3-(5-benzyloxy-2-phenylindol-1-yl)benzoic acid |
| | CDCl3; 8.11(d, 1H), 8.01(d, 2H), 7.93(br s, 1H), 7.52(t, 1H), 7.34(br s, 1H), 7.14(d, 2H), 6.48 (s, 1H), 2.92(dd, 1H), 2.40-2.78(m, 4H), 2.16-2.24(m, 1H), 1.64-1.82 (m, 1H). | pos. mode 431 (M + H). | 3-[2-(4-nitrophenyl)-5-trifluoromethyl-4,5,6,7-tetrahydroindol-1-yl] benzoic acid |

TABLE 7-continued

Compounds from Table 6 and Characterization Data

| product structure | 1H NMR, d | MS | name |
|---|---|---|---|
| | 7.95(tt, 1H), 7.7(t, 1H), 7.62(t, 1H), 7.58-7.46 (m, 2H), 7.22(d, 2H), 7.08-7.04(m, 3H), 6.86-6.82(m, 2H), 6.75(s, 1H), 3.70(s, 3H), 2.93(t, 2H), 2.62(t, 2H) | pos. mode 396 (M + H); neg. mode 394(M − H). | 3-[2-(3-methoxyphenyl)-4,5-dihydrobenzo[e]indol-3-yl]benzoic acid |
| | DMSO-d6; 8.3(d, 1H), 7.9(d, 1H), 7.75(d, 1H), 7.56-7.26(m, 11H), 7.18 (s, 1H). | pos. mode 382 (M + H); neg. mode 380(M − H). | 3-[2-(4-hydroxyphenyl)-benzo[e]indol-3-yl] benzoic acid |
| | CDCl3; 7.63(s, 1H), 7.51(s, 1H), 7.03-7.20 (m, 5H), 6.94(s, 1H), 6.27(s, 1H), 2.90(dd, 1h), 2.38-2.78(m, 4H), 2.20(d, 1H), 1.74(qd, 1H). | pos. mode 401 (M + H) | 3-amino-5-(2-phenyl-5-trifluoromethyl-4,5,6,7-tetrahydroindol-1-yl) benzoic acid |
| | CDCl3; 8.02(d, 1H), 7.93(s, 1H), 7.41(t, 1H), 7.25-7.30(m, 1H), 6.80-6.90(m, 2H), 6.44-6.52 (m, 2H), 6.16(s, 1H), 2.89(dd, 1H), 2.58-2.76 (m, 2H), 2.42-2.52 (m, 2H), 2.19(br d, 1H), 1.64(qd, 1H). | pos. mode 401 (M + H) | 3-[2-(4-aminophenyl)-5-trifluoromethyl-4,5,6,7-tetrahydroindol-1-yl] benzoic acid |

TABLE 7-continued

Compounds from Table 6 and Characterization Data

| product structure | 1H NMR, d | MS | name |
| --- | --- | --- | --- |
| | DMSO-d6; 7.95(tt, 1H), 7.7(t, 1H), 7.59(t, 1H), 7.51-7.44(m, 2H), 7.18 (d, 2H), 7.05-7.0(m, 3H), 6.8(m, 1H), 6.7(s, 1H), 3.7(s, 3H), 3.3(s, 3H), 2.9(t, 2H), 2.6(t, 2H). | pos. mode 426 (M + H). neg. mode 424(M − H). | 3-[2-(2,4-dimethoxyphenyl)-4,5-dihydrobenzo[e]indol-3-yl] benzoic acid |
| | MeOH-d4 (mixture 55%:45% saturated:unsaturated); 8.22(d, 2H); 7.94(d, 2H), 7.85-7.83(d, 2H), 7.75-7.67 (m, 4H), 7.60-7.56 (m, 4H), 7.49-7.45(m, 1H), 7.35-7.28(m, 4H), 7.20-7.17(m, 5H), 7.1-7.07 (m, 2H), 7.0(s, 2H), 3.1(t, 2H), 2.93(t, 2H), 2.4(s, 3H), 2.33(s, 3H). | neg. mode 378 (M − H). | 3-(2-p-tolyl-4,5-dihydrobenzo[e]indol-3-yl) benzoic acid |
| | CDCl3; 8.1(m, 2H); 7.7 (m, 1H); 7.5(t, 1H); 7.4 (m, 1H); 7.2-7.3(m, 8H, ArH); 6.8(s, 1H). | pos. mode 314 (M + H); neg. mode 312(M − H). | 3-(2-phenylindol-1-yl) benzoic acid |
| | CDCl3/d3-MeOD; 8.0(m, 2H); 7.4(t, 1H); 7.2(m, 1H); 7.0-7.2(m, 5H, ArH); 6.2(s, 1H); 2.7(m, 1H); 2.5(s, 1H); 2.4(m, 2H); 2.0(m, 1H); 1.5(m, 1H); 1.4(m, 1H); 0.9(s, 9H). | pos. mode 374 (M + H); neg. mode 372(M − H). | 3-(5-tert-Butyl-2-phenyl-4,5,6,7-tetrahydroindol-1-yl)benzoic acid |

TABLE 7-continued

Compounds from Table 6 and Characterization Data

| product structure | 1H NMR, d | MS | name |
|---|---|---|---|
| 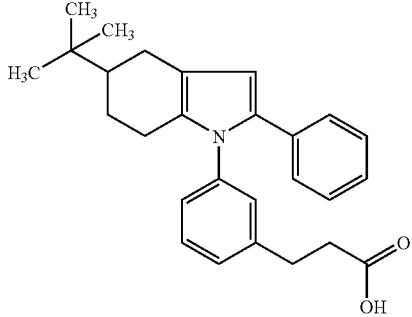 | CDCl3; 7.2(m, 1H); 6.9-7.1 (m, 8H, ArH); 6.2(s, 1H); 2.9(t, 2H); 2.7(m, 1H); 2.5(m, 3H); 2.4(m, 2H); 2.0(m, 1H); 1.5(m, 1H); 1.4(m, 1H); 0.9(s, 9H). | pos. mode 402 (M + H); neg. mode 400(M − H) | 3-[3-(5-tert-Butyl-2-phenyl-4,5,6,7-tetrahydroindol-1-yl)-phenyl]propionic acid |
| 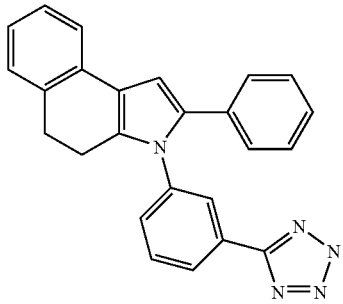 | DMSO-d6; 7.0-8.4(13H, ArH); 6.9(1H); 2.9(2H, CH2), 2.5(2H, CH2). | pos. mode 342 (M + H); neg. mode 340(M − H) | 2-phenyl-3-[3-(2H-tetrazol-5-yl)-phenyl]-4,5-dihydro-3H-benzo[e]indole |
| 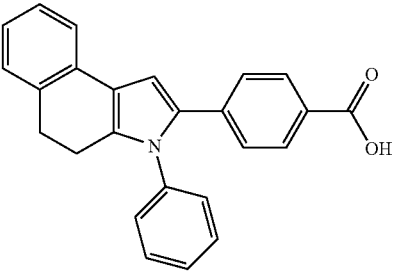 | DMSO-d6; 6.8-7.9(14H, ArH), 3.0(2H, CH2)2.7 (2H, CH2). | neg. mode 364 (M − 1) | 4-(3-phenyl-4,5-dihydro-3H-benzo[e]indol-2-yl) benzoic acid |
| 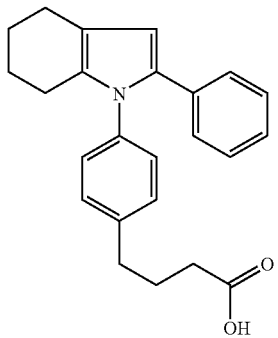 | CDCl3; 7.0-7.2(m, 9H, ArH); 6.2(s, 1H); 2.6(m, 4H); 2.4(m, 4H); 2.0(m, 3H); 1.8(s, 3H). | neg. mode 358 (M − H) | 4-[4-(2-phenyl-4,5,6,7-tetrahydroindol-1-yl)-phenyl]butyric acid |

TABLE 7-continued

Compounds from Table 6 and Characterization Data

| product structure | 1H NMR, d | MS | name |
|---|---|---|---|
| | DMSO-d6; 7.2-8.4 (16H, ArH). | pos. mode 364 (M + 1); neg. mode 362(M − 1) | 3-(2-phenylbenzo[e]indol-3-yl)benzoic acid |
| | CDCl3; 7.3(t, 1H); 6.9-7.1 (m, 8H, ArH); 6.2(s, 1H); 2.9(t, 2H); 2.7(m, 1H); 2.5(m, 3H); 2.4(m, 1H); 2.2(m, 1H); 1.9(m, 2H); 1.4(m, 1H); 1.0(d, 3H). | pos. mode 360 (M + H); neg. mode 358(M − H) | 3-[3-(5-methyl-2-phenyl-4,5,6,7-tetrahydroindol-1-yl)-phenyl]propionic acid |
| | DMSO-d6; 7.2-8.4 (16H, ArH); 2.7(2H, CH2); 2.3(2H, CH2); 1.9 (2H, CH2). | pos. mode 406 (M + 1); neg. mode 404(M − 1) | 4-[4-(2-phenyl-benzo[e]indol-3-yl)-phenyl]butyric acid |
| | CDCl3; 7.3(t, 1H); 6.9-7.2 (m, 8H, ArH); 6.2(s, 1H); 2.9(t, 2H); 2.6(br. s, 2H); 2.5(t, 2H); 2.4(br. s, 2H); 1.8(br. s, 4H). | pos. mode 346 (M + H) | 3-[3-(2-phenyl-4,5,6,7-tetrahydroindol-1-yl)-phenyl]propionic acid |

TABLE 7-continued

Compounds from Table 6 and Characterization Data

| product structure | 1H NMR, d | MS | name |
|---|---|---|---|
| | CDCl3; 7.1-8.4(11H, ArH), 6.4(1H, ArH), 4.4 (1H, CH)1.4-2.7(9H, CH2). | pos. mode 372 (M + 1) | 3-(2-phenylbenzo[e]indol-3-yl) cyclohexanecarboxylic acid |
| | CD3OD-d4; 7.1-8.2(10H, ArH), 4.0(2H, CH2), 3.0 (2H, CH2), 2.9(2H, CH2), 2.1(2H, CH2), 1.9 (2H, CH2). | pos. mode 332 (M + 1) | 4-(2-phenyl-4,5-dihydrobenzo[e]indol-3-yl) butyric acid |
| | CD3OD-d4; 7.1-8.2(12H, ArH)4.4(2H, CH2)2.1 (2H, CH2)1.9(2H, CH2). | pos. mode 330 (M + 1) | 4-(2-phenyl-benzo[e]indol-3-yl)butyric acid |
| | DMSO-d6; 7.0-7.9(14H, ArH), 6.3(1H, ArH), 3.0 (1H, CH), 2.8(1H, CH2), 2.7(2H, CH2), 2.4(1H, CH2), 1.9(2H, CH2). | pos. mode 394 (M + 1) | 3-(2,5-diphenyl-4,5,6,7-tetrahydroindol-1-yl) benzoic acid |

TABLE 7-continued

Compounds from Table 6 and Characterization Data

| product structure | 1H NMR, d | MS | name |
|---|---|---|---|
| | CDCl3; 8.0(m, 1H); 7.9 (m, 1H); 7.4(t, 1H); 7.0-7.3 (m, 6H, ArH); 6.2(s, 1H); 2.6(m, 1H); 2.5(br. s, 1H); 2.4(m, 1H); 2.1 (m, 1H); 1.9(m, 2H); 1.4 (m, 1H); 1.0(d, 3H). | pos. mode 332 (M + H) | 3-(4-methyl-2-phenyl-4,5,6,7-tetrahydroindol-1-yl)benzoic acid |
| | CDCl3; 7.1-7.3(m, 6H, ArH); 6.2(s, 1H); 6.0(d, 1H); 2.6(m, 2H); 2.4-2.5 (m, 2H); 2.0(m, 1H); 1.5 (m, 2H); 1.0(s, 9H). | pos. mode 364 (M + H); neg. mode 362(M − H) | 5-(5-tertButyl-2-phenyl-4,5,6,7-tetrahydroindol-1-yl)furan-2-carboxylic acid |
| | acetone-d6; 7.5(m, 5H); 7.2(m, 7H); 7.0(t, 1H); 6.8(s, 1H); 3.2(s, 2H, CH2); 2.9(m, 2H); 2.6 (m, 1H); 2.4(m, 1H). | pos. mode 380 (M + H) | [2-(2-phenyl-4,5-dihydrobenzo[e]indol-3-yl)-phenyl]acetic acid |

TABLE 7-continued

Compounds from Table 6 and Characterization Data

| product structure | 1H NMR, d | MS | name |
|---|---|---|---|
| | DMSO-d6; 7.1-8.5 (14H, ArH/NH); 5.8(1H); 2.9(2H, CH2); 2.6(2H, CH2). | pos. mode 430 (M + 1); neg. mode 429(M − 1). | 2-benzofuran-2-yl-3-[3-(2H-tetrazol-5-yl)-phenyl]-4,5-dihydro-3H-benzo[e]indole |
| | DMSO-d6; 7.0-8.2 (15H, ArH/NH); 6.3(1H); 2.9(2H, CH2); 2.6(2H, CH2). | pos. mode 457 (M + 1); neg. mode 455(M − 1). | 2-(3-phenylisoxazol-5-yl)-3-[3-(2H-tetrazol-5-yl)-phenyl]-4,5-dihydro-3H-benzo[e]indole |
| | DMSO d6; 7.0-8.1(14H, ArH); 6.2(1H); 2.9(2H, CH2); 2.6(2H, CH2). | pos. mode 433 (M + 1); heg. mode 431(M − 1). | 3-(2-phenylisoxazol-5-yl)-4,5-dihydrobenzo[e]indol-3-yl]benzoic acid |

TABLE 8
Compounds of the Invention and Starting Materials
| product structure | ketone/enamine SM | α-bromo ketone SM | aniline |
|---|---|---|---|
| 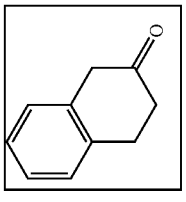 | 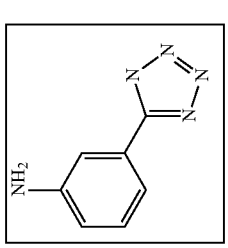 | 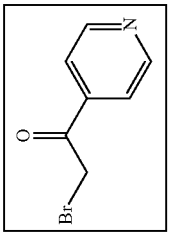 | 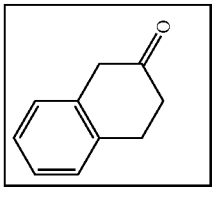 |
| 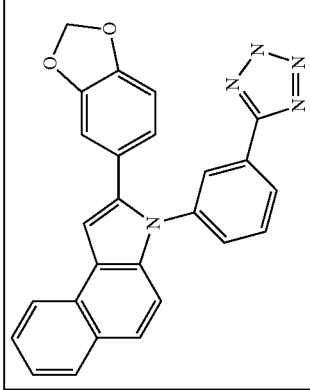 | 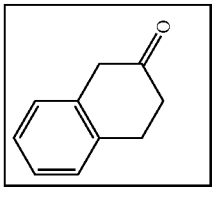 | 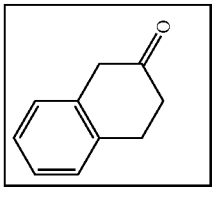 | 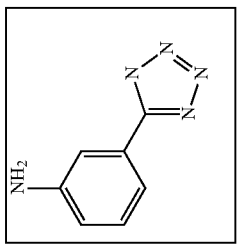 |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 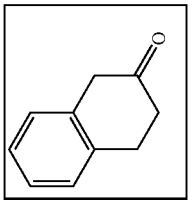 | 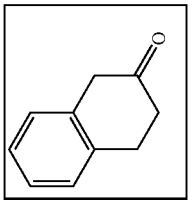 | 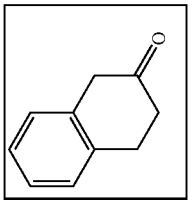 | 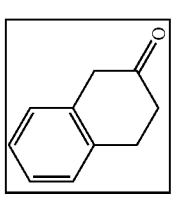 |
| 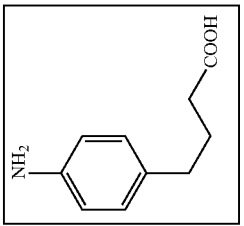 | 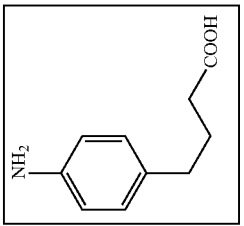 | 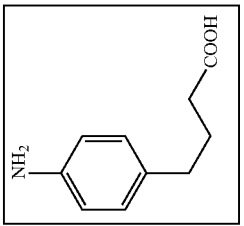 | 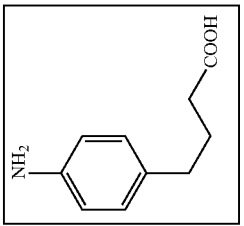 |

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 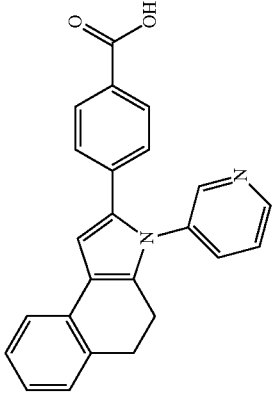 | 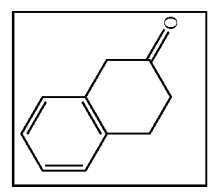 | 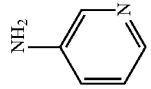 | 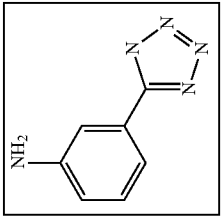 |
| 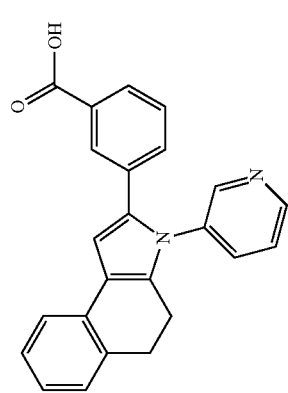 | 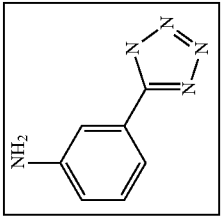 | 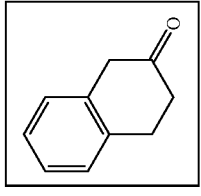 | 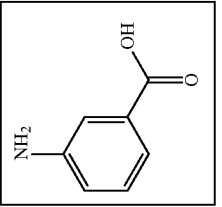 |
| 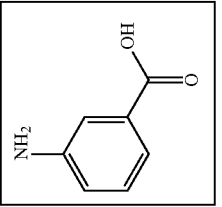 | 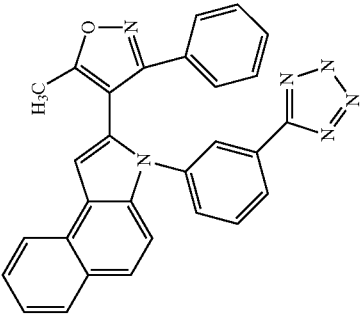 | 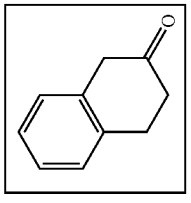 | 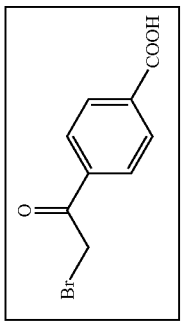 |

TABLE 8-continued

Compounds of the Invention and Starting Materials

| ketone/enamine SM | α-bromo ketone SM | aniline | product structure |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 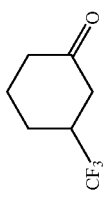 | 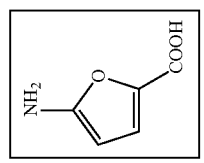 | 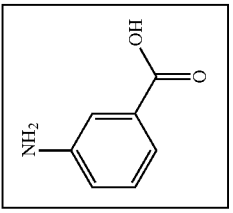 | 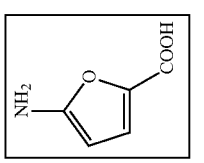 |
| 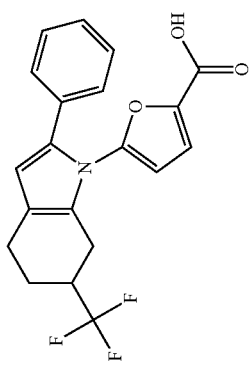 | 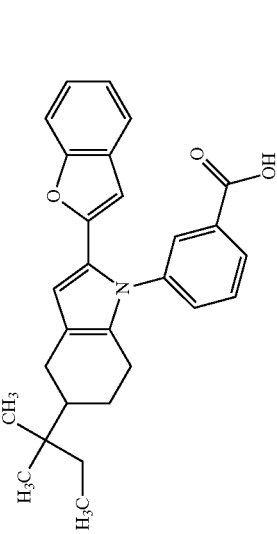 | 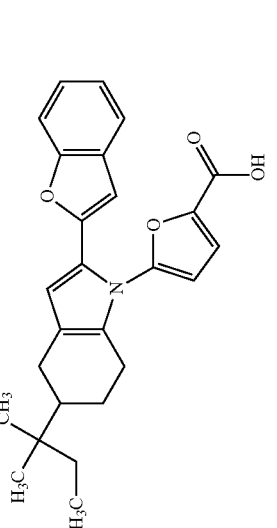 | 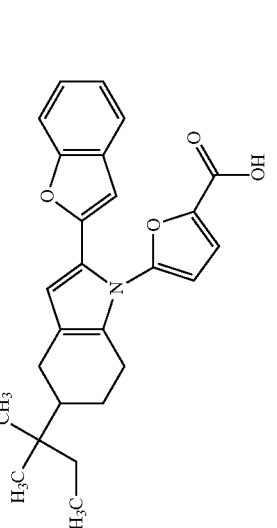 |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|
| 411 | | | |
| 412 | | | |

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 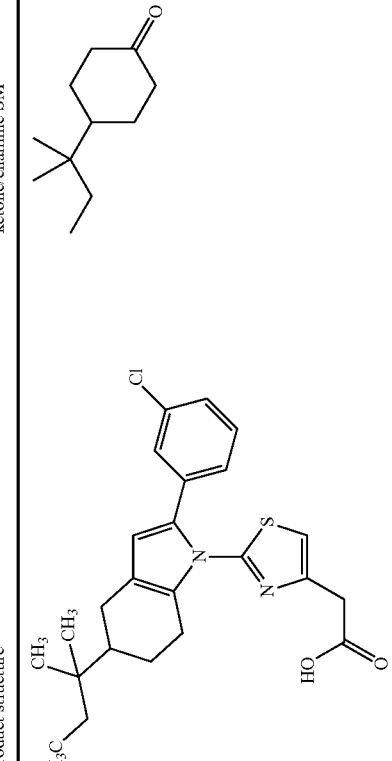 | 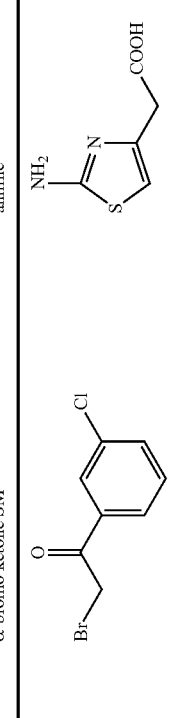 | 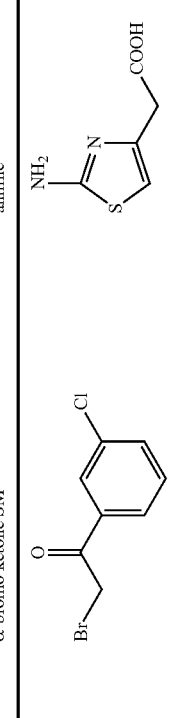 | 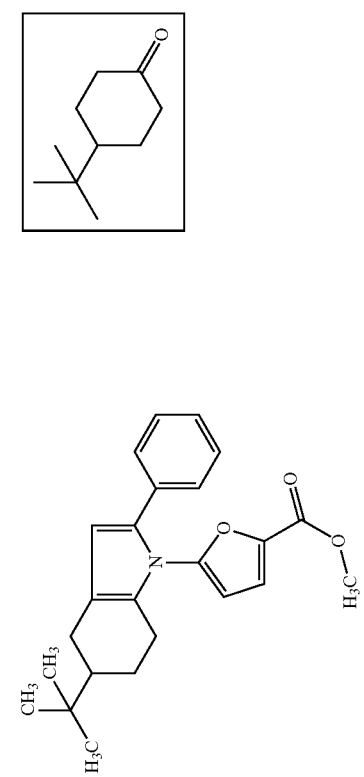 |
| 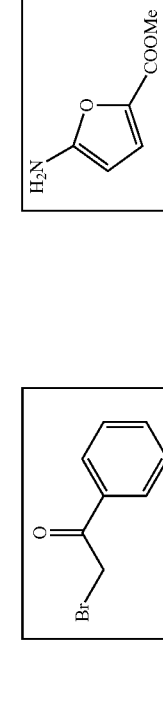 | | 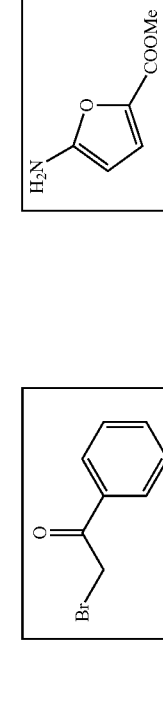 | |

TABLE 8-continued
Compounds of the Invention and Starting Materials
| product structure | ketone/enamine SM | α-bromo ketone SM | aniline |
|---|---|---|---|
| 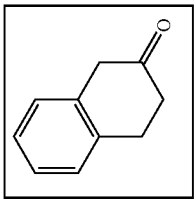 | 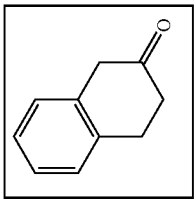 | 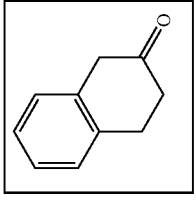 | 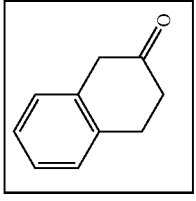 |
| 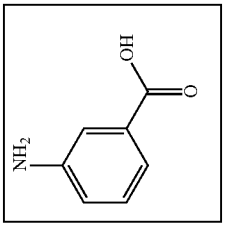 | 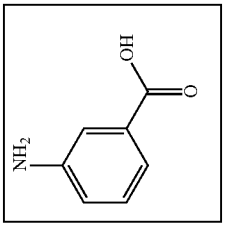 | 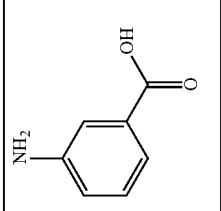 | 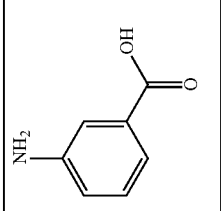 |

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 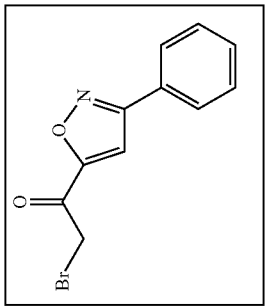 | 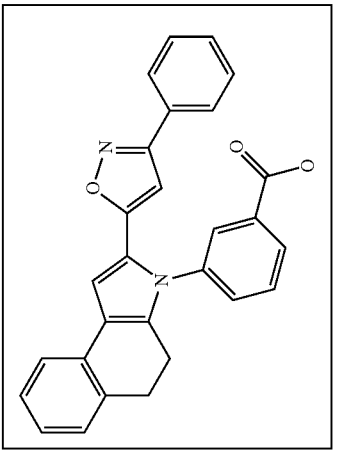 | 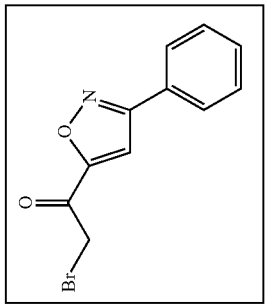 | 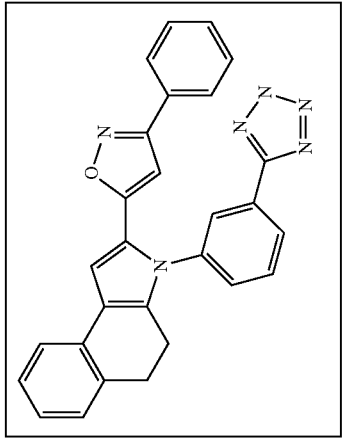 |
| 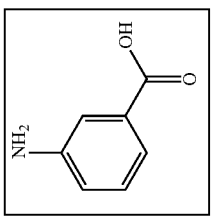 | 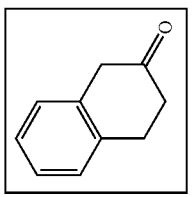 | 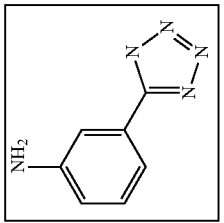 | 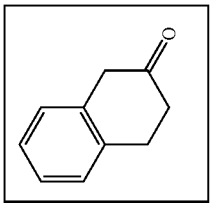 |

TABLE 8-continued

Compounds of the Invention and Starting Materials

| aniline | α-bromo ketone SM | ketone/enamine SM | product structure |
|---|---|---|---|
| 3-aminobenzoic acid | 2-bromo-1-(pyridin-3-yl)ethanone | 3,4-dihydronaphthalen-2(1H)-one | |
| 3-aminobenzoic acid | 2-bromo-1-(pyridin-3-yl)ethanone | 3,4-dihydronaphthalen-2(1H)-one | |
| 3-aminobenzoic acid | 2-bromo-1-(pyridin-2-yl)ethanone | 3,4-dihydronaphthalen-2(1H)-one | |

TABLE 8-continued

Compounds of the Invention and Starting Materials

| product structure | ketone/enamine SM | α-bromo ketone SM | aniline |
|---|---|---|---|

TABLE 8-continued
Compounds of the Invention and Starting Materials
| product structure | ketone/enamine SM | α-bromo ketone SM | aniline |
|---|---|---|---|
| 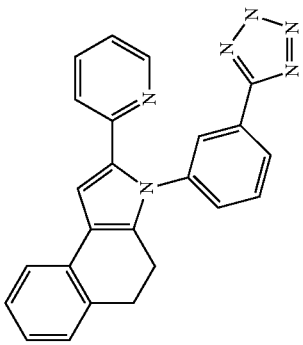 | 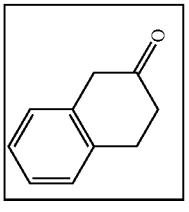 | 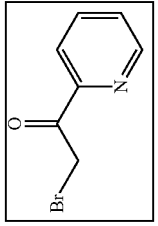 | 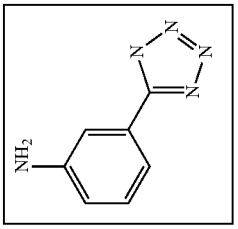 |
| 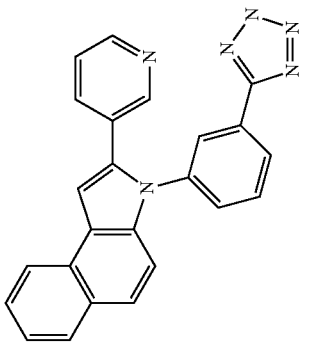 | 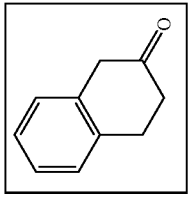 | 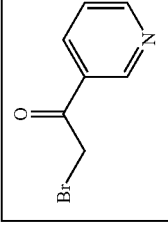 | 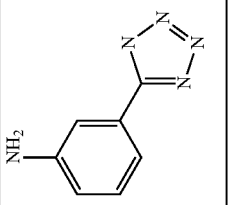 |
| 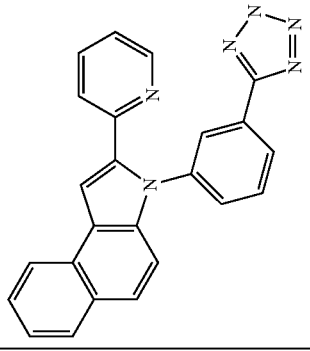 | 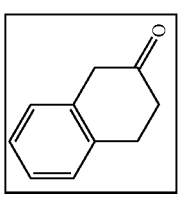 | 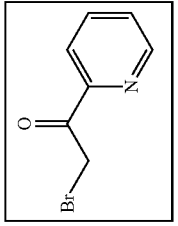 | 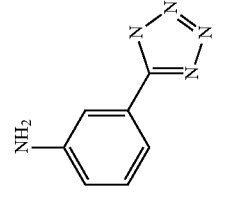 |

TABLE 8-continued
Compounds of the Invention and Starting Materials
| product structure | ketone/enamine SM | α-bromo ketone SM | aniline |
|---|---|---|---|
| 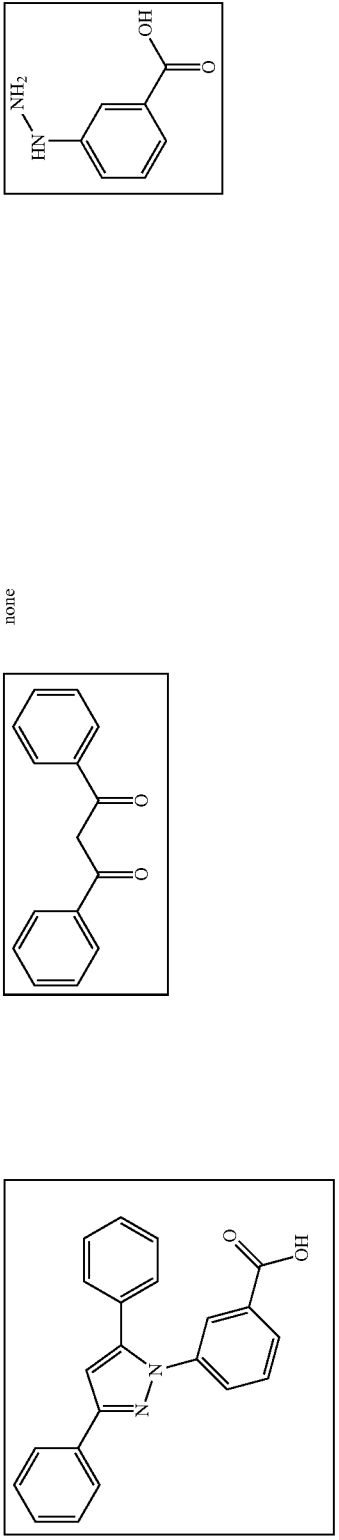 | 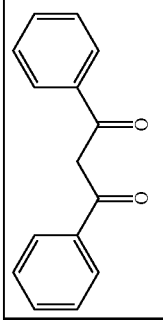 | none | 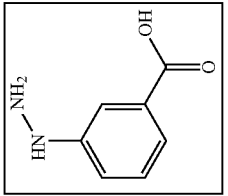 |
| 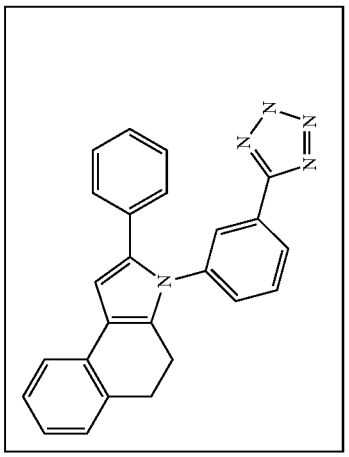 | 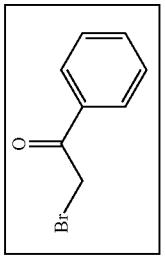 | 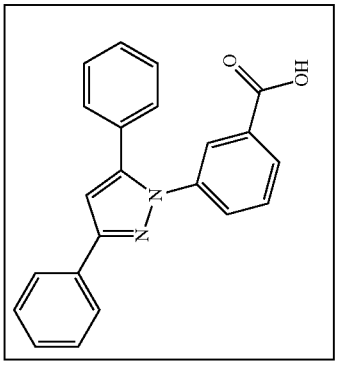 | 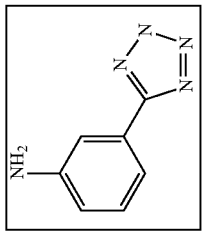 |
| 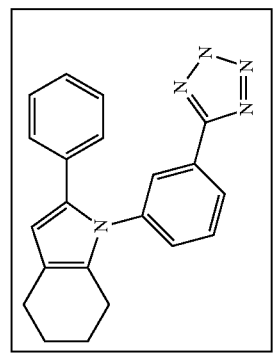 | 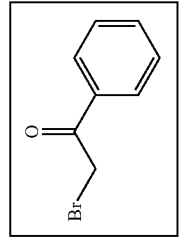 |  | 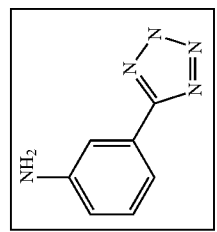 |

TABLE 9

Compounds from Table 8 and Characterization Data

| product structure | 1H NMR, d | MS | name | Ab42 IC50 (uM) |
|---|---|---|---|---|
| 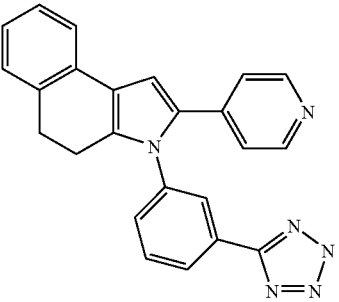 | DMSO-d6; 7.1-8.6 (m, 14H), 6.2(t, 2H), 2.9(t, 2H). | pos. mode 391 (M + 1), neg. mode 389 (M − 1). | 2-pyridin-4-yl-3-[3-(2H-tetrazol-5-yl)-phenyl]-4,5-dihydro-3H-benzo[e]indole | 73 |
| 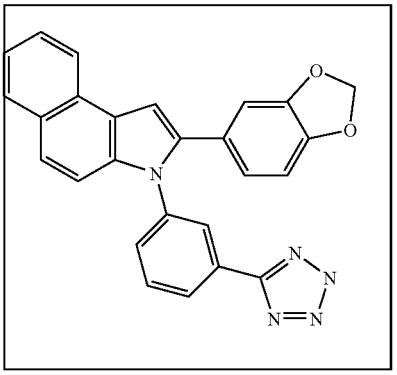 | DMSO-d6; 6.5-8.4 (m, 13H), 5.9(s, 2H), 2.9(t, 2H), 2.6(t, 2H). | pos. mode 434 (M + 1), neg. mode 432 (M − 1). | 2-benzo[1,3]dioxol-5-yl-3-[3-(2H-tetrazol-5-yl)-phenyl]-3H-benzo[e]indole | 56 |
| 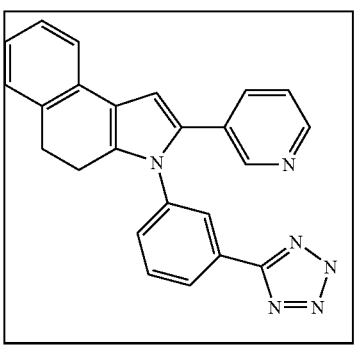 | DMSO-d6; 7.3-8.6 (m, 14H), 2.9(t, 2H), 2.7(t, 2H). | pos mode 391 (M + 1), neg. mode 389 (M − 1). | 2-pyridin-3-yl-3-[3-(2H-tetrazol-5-yl)-phenyl]-4,5-dihydro-3H-benzo[e]indole | >100 |
| 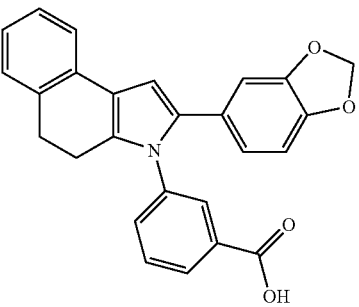 | DMSO-d6; 6.7-8.3 (m, 12H), 6.2(s, 2H), 2.9(t, 2H), 2.6(t, 2H). | pos mode 410 (M + 1). | 3-(2-benzo[1,3]dioxol-5-yl-4,5-dihydrobenzo[e]indol-3-yl) benzoic acid | 18 |

TABLE 9-continued

Compounds from Table 8 and Characterization Data

| product structure | 1H NMR, d | MS | name | Ab42 IC50 (uM) |
|---|---|---|---|---|
| | DMSO-d6; 6.7-8.3 (m, 14H), 6.2(s, 2H). | pos mode 408 (M + 1). | 3-(2-benzo[1,3]dioxol-5-yl-benzo[e]indol-3-yl) benzoic acid | 20 |
| | DMSO-d6; 6.7-8.3 (m, 14H), 5.9(s, 2H), 2.6(t, 2H), 2.0(t, 2H), 1.8(t, 2H). | pos. mode 450 (M + 1). | 4-[4-(2-benzo[1,3]dioxol-5-yl-benzo[e]indol-3-yl)-phenyl] butyric acid | 8.9 |
| | DMSO-d6; 6.5-7.5 (m, 12H), 5.9(s, 2H), 2.8(t, 2H), 2.66(t, 2H), 2.6(t, 2H), 2.04 (t, 2H), 1.8(t, 2H). | pos. mode 452 (M + 1). | 4-[4-(2-benzo[1,3]dioxol-5-yl-4,5-dihydrobenzo[e]indol-3-yl)-phenyl] butyric acid | 8.8 |
| | DMSO-d6; 7.0-6.7 (m, 14H), 2.9(t, 2H), 2.6(t, 2H), 2.43(s, 3H), 2.5(t, 2H), 2.1 (t, 2H), 1.73(t, 2H). | pos. mode 489 (M + 1), neg. mode 487 (M − 1). | 4-{4-[2-(5-methyl-3-phenylisoxazol-4-yl)-4,5-dihydrobenzo[e]indol-3-yl]-phenyl} butyric acid | 1.5 |

TABLE 9-continued

Compounds from Table 8 and Characterization Data

| product structure | 1H NMR, d | MS | name | Ab42 IC50 (uM) |
|---|---|---|---|---|
| | DMSO-d6; 7.0-6.7 (m, 16H), 2.56(t, 2H), 2.43(s, 3H), 2.17(t, 2H), 1.7(t, 2H). | pos. mode 487 (M + 1). | 4-{4-[2-(5-methyl-3-phenylisoxazol-4-yl)-benzo[e]indol-3-yl]-phenyl} butyric acid | 1 |
| | DMSO; 7.1-8.5(m, 13H), 2.9(t, 2H), 2.6 (t, 2H). | pos. mode 367 (M + 1). | 3-(2-pyridin-4-yl-4,5-dihydrobenzo[e]indol-3-yl) benzoic acid | 65 |
| | DMSO-d6; 7.1-8.5 (m, 15H). | pos. mode 365 (M + 1). | 3-(2-pyridin-4-yl-benzo[e]indol-3-yl) benzoic acid | 81 |
| | DMSO-d6; 7.1-6.8 (m, 16H), 2.41(s, 3H). | pos. mode 445 (M + 1), neg. mode 443 (M − 1). | 3-[2-(5-methyl-3-phenylisoxazol-4-yl)-benzo[e]indol-3-yl] benzoic acid | 40 |

TABLE 9-continued

Compounds from Table 8 and Characterization Data

| product structure | 1H NMR, d | MS | name | Ab42 IC50 (uM) |
|---|---|---|---|---|
| | DMSO-d6; 6.6-7.4 (m, 16H), 2.50(s, 3H). | pos. mode 469 (M + 1). | 2-(5-methyl-3-phenylisoxazol-4-yl)-3-[3-(2H-tetrazol-5-yl)-phenyl] 3H-benzo[e]indole | 31 |
| | DMSO-d6; 8.6(d, 1H), 8.5(s, 1H), 7.8 (d, 3H), 7.59-7.53 (m, 2H), 7.27-7.21 (m, 4H), 7.12-7.08 (m, 2H), 3.0(t, 2H), 2.7(t, 2H). | pos. mode 367 (M + H). | 4-(3-pyridin-3-yl-4,5-dihydro-3H-benzo[e]indol-2-yl) benzoic acid | >100 |
| | DMSO-d6; 8.4(s, 1H), 7.84-7.74(m, 4H), 7.6-7.55(m, 2H), 7.4(t, 1H), 7.3 (d, 1H), 7.25(d, 2H), 7.1(t, 1H), 7.0(s, 1H), 2.99(t, 2H), 2.71 (t, 2H). | pos. mode 367 (M + H); neg. mode 365 (M − H). | 3-(3-pyridin-3-yl-4,5-dihydro-3H-benzo[e]indol-2-yl) benzoic acid | >100 |
| | DMSO-d6; 7.1-8.3 (m, 15H), 5.5(s, 2H). | pos. mode 435 (M + 1), neg. mode 433 (M − 1). | 5-[2-(3-phenylisoxazol-5-yl)-benzo[e]indol-3-ylmethyl] furan-3-carboxylic acid | >100 |

TABLE 9-continued

Compounds from Table 8 and Characterization Data

| product structure | 1H NMR, d | MS | name | Ab42 IC50 (uM) |
|---|---|---|---|---|
| | DMSO-d6; 7.1-8.3 (m, 13H), 5.5(s, 2H), 2.9(t, 2H), 2.6(t, 2H). | pos. mode 437 (M + 1), neg. mode 435 (m − 1). | 5-[2-(3-phenylisoxazol-5-yl)-4,5-dihydrobenzo[e]indol-3-ylmethyl] furan-3-carboxylic acid | >100 |
| | DMSO-d6; 6.8-8.5 (m, 15H). | pos. mode 421 (M + 1), neg. mode 419 (M − 1). | 5-[2-(3-phenylisoxazol-5-yl)-benzo[e]indol-3-yl] furan-2-carboxylic acid | 33 |
| | DMSO-d6; 7.2-8.4 (m, 16H), 6.1(s, 1H), 2.7(t, 2H), 2.08(t, 2H), 1.8(t, 2H). | pos. mode 473 (M + 1), neg. mode 471 (M − 1). | 4-{4-[2-(3-phenylisoxazol-5-yl)-benzo[e]indol-3-yl]-phenyl} butyric acid | 4.5 |
| | CDCl3; 7.10-7.30 (m, 6H), 6.21(s, 1H), 5.95(d, 1H), 2.56-2.64(m, 2H), 2.54(d, 1H), 2.32(t, 1H), 2.00(br d, 1H), 1.59 (td, 1H), 1.30-1.48 (m, 3H), 0.89(s, 3H), 0.86(s, 3H), 0.84(t, 3H). | pos. mode 378 (M + H); neg. mode 376 (M − H). | 5-[5-(1,1-dimethylpropyl)-2-phenyl-4,5,6,7-tetrahydroindol-1-yl]-furan-2-carboxylic acid | 5.1 |

TABLE 9-continued

Compounds from Table 8 and Characterization Data

| product structure | 1H NMR, d | MS | name | Ab42 IC50 (uM) |
|---|---|---|---|---|
| | CDCl3; 7.20-7.32 (m, 4H), 7.14(d, 2H), 6.23(s, 1H), 5.99(d, 1H), 2.84(dd, 1H), 2.58-2.73(m, 3H), 2.46(br s, 1H), 2.20-2.38(m, 1H), 1.70-1.85(m, 1H). | pos. mode 376 (M + H). | 5-(2-phenyl-5-trifluoromethyl-4,5,6,7-tetrahydroindol-1-yl)-furan-2-carboxylic acid | 16.5 |
| | DMSO-d6; 9.2(s, 1H), 8.8(s, 1H), 8.4 (d, 1H), 8.1-7.4(m, 9H), 6.92(s, 1H), 6.6 (s, 1H). | pos. mode 354 (M + H). | 3-(3-furan-3-yl-3H-benzo[e]indol-2-yl) benzoic acid | >100 |
| | DMSO-d6; 8.8(s, 1H), 8.4(d, 1H), 8.0-7.92(m, 3H), 7.78-7.67(m, 3H), 7.62-7.49(m, 4H), 6.9(s, 1H), 6.6 (s, 1H). | pos. mode 354 (M + H). | 4-(3-furan-3-yl-3H-benzo[e]indol-2-yl) benzoic acid | >100 |
| | DMSO-d6; 6.7-8.4 (m, 13H), 6.5(s, 1H). | 353(M dot). | 5-(2-phenylbenzo[e]indol-3-yl) furan-2-carboxylic acid | 22 |

TABLE 9-continued

Compounds from Table 8 and Characterization Data

| product structure | 1H NMR, d | MS | name | Ab42 IC50 (uM) |
|---|---|---|---|---|
| | CDCl3; 7.40-7.48 (m, 2H), 7.38(d, 1H), 7.12-7.24(m, 2H), 6.62(s, 1H), 6.49(d, 1H), 5.97(s, 1H), 2.45-2.82(m, 5H), 2.15-2.30(m, 1H), 1.72(qd, 1H). | pos. mode 416 (M + H). | 5-(2-benzofuran-2-yl-6-trifluoromethyl-4,5,6,7-tetrahydroindol-1-yl)-furan-2-carboxylic acid | 23 |
| | CDCl3; 7.19-7.32 (m, 4H), 7.05-7.18 (m, 2H), 6.22(s, 1H), 6.07(d, 1H), 2.45-2.80 (m, 5H), 2.20(br d, 1H), 1.72(qd, 1H). | pos. mode 376 (M + H). | 5-(2-phenyl-6-trifluoromethyl-4,5,6,7-tetrahydroindol-1-yl)-furan-2-carboxylic acid | 25 |
| | CDCl3; 8.20(dt, 1H), 8.09(t, 1H), 7.52-7.62 (m, 2H), 7.32-7.36 (m, 1H), 7.26-7.30 (m, 1H), 6.60-7.17 (m, 2H), 6.66(s, 1H), 5.60(s, 1H), 2.65(dd, 1H), 2.25-2.45(m, 3H), 1.96(br d, 1H), 1.60 (td, 1H), 1.22-1.44(m, 3H), 0.90(s, 6H), 0.85(t, 3H). | pos. mode 428 (M + H). | 3-[2-benzofuran-2-yl-5-(1,1-dimethylpropyl)-4,5,6,7-tetrahydroindol-1-yl] benzoic acid | 3.7 |
| | CDCl3; 7.35-7.44 (m, 3H), 7.12-7.22 (m, 2H), 6.60(s, 1H), 6.41(d, 1H), 5.97(d, 1H), 2.58(dd, 1H), 2.51(br d, 2H), 2.27-2.35(m, 1H), 1.99(br d, 1H), 1.58(td, 1H), 1.25-1.47(m, 3H), 0.90(s, 3H), 0.89(s, 3H), 0.84(t, 3H). | pos. mode 418 (M + H). | 5-[2-benzofuran-2-yl-5-(1,1-dimethylpropyl)-4,5,6,7-tetrahydroindol-1-yl]-furan-2-carboxylic acid | 18 |
| | CDCl3; 7.15-7.28 (m, 6H), 6.20(s, 1H), 5.97(d, 1H), 2.54-2.60 (m, 2H), 2.20-2.40 (m 1H), 1.80-2.00 (m 1H), 1.35-1.85 (m, 8H), 0.95-1.35 (m, 6H). | pos. mode 390 (M + H). | 5-(5-cyclohexyl-2-phenyl-4,5,6,7-tetrahydroindol-1-yl)-furan-2-carboxylic acid | 40 |

TABLE 9-continued

Compounds from Table 8 and Characterization Data

| product structure | 1H NMR, d | MS | name | Ab42 IC50 (uM) |
|---|---|---|---|---|
| | CDCl3; 7.24-7.33 (m, 3H), 6.89(dd, 1H), 6.26(s, 1H), 6.10(d, 1H), 2.83 (dd, 1H), 2.55-2.70 (m, 3H), 2.37-2.53 (m, 1H), 2.23(br d, 1H), 1.70-1.83 (m, 1H) | pos. mode 444 (M + H). | 5-[2-(3,4-dichlorophenyl)-5-trifluoromethyl-4,5,6,7-tetrahydroindol-1-yl]-furan-2-carboxylic acid | 1.6 |
| | DMSO-d6; 8.44(d, 1H), 8.03(d, 1H), 7.98(tt, 1H), 7.9(t, 1H), 7.76-7.74(m, 2H), 7.66-7.61(m, 3H), 7.57(s, 1H), 7.52(m, 2H), 7.46 (d, 1H). | 421(M dot). | 5-[2-(4-trifluoromethylphenyl)-benzo[e]indol-3-yl]-furan-2-carboxylic acid | 21 |
| | CDCl3; 7.36-7.47 (m, 3H), 7.13-7.24 (m, 2H), 6.63(s, 1H), 6.45(d, 1H), 6.00(d, 1H), 2.86(dd, 1H), 2.55-2.70(m, 3H), 2.40-2.55(br s, 1H), 2.23(br d, 1H), 1.70-1.85(m, 1H). | pos. mode 416 (M + H). | 5-(2-benzofuran-2-yl-5-trifluoromethyl-4,5,6,7-tetrahydroindol-1-yl)-furan-2-carboxylic acid | 44 |
| | CDCl3; 7.1-7.3(m, 6H); 6.2(s, 1H); 6.0 (d, 1H); 2.5-2.6(m, 3H); 2.2(m, 1H); 1.9 (m, 2H); 1.4(m, 1H); 1.1(d, 3H). | pos. mode 322 (M + H), TOF EM 322. 1449 (M + H). | 5-(6-methyl-2-phenyl-4,5,6,7-tetrahydroindol-1-yl) furan-2-carboxylic acid | >100 |

TABLE 9-continued

Compounds from Table 8 and Characterization Data

| product structure | 1H NMR, d | MS | name | Ab42 IC50 (uM) |
|---|---|---|---|---|
| | DMSO-d6; 7.2-8.5 (m, 13H), 6.0(s, 1H). | pos. mode 394 (M + 1), neg. mode 392 (M − 1). | 5-(2-benzofuran-2-yl-benzo[e]indol-3-yl) furan-2-carboxylic acid | 22 |
| | CDCl3; 7.22-7.30 (m, 3H), 7.16-7.22 (m, 2H), 6.96(X of ABX, 1H), 6.22(s, 1H), 3.83(A of ABX, 1H), 3.81(B of ABX, 1H), 2.64-2.74(m, 2H), 2.57(dd, 1H), 2.28-2.38(m, 1H), 1.98-2.06(m, 1H), 1.60(tdd, 1H), 1.30-1.46(m, 3H), 0.89(s, 3H), 0.89(s, 3H), 0.84(t, 3H). | pos. mode 409 (M + H); neg. mode 407 (M − H). | {2-[5-(1,1-dimethylpropyl)-2-phenyl-4,5,6,7-tetrahydroindol-1-yl]-thiazol-4-yl} acetic acid | 6.5 |
| | DMSO-d6; 7.1-8.4 (m, 15H), 6.0(s, 1H), 2.7(t, 2H), 2.03(t, 2H), 1.8(t, 2H). | pos. mode 541 (M + 1), neg. mode 539 (M − 1). | 4-(4-{2-[5-(2,4-dichlorophenyl)-furan-2-yl]-benzo[e]indol-3-yl}-phenyl) butyric acid | 17 |
| | DMSO-d6; 7.1-8.4 (m, 15H), 6.0(s, 1H). | pos. mode 499 (M + 1), neg. mode 497 (M − 1). | 3-{2-[5-(2,4-dichlorophenyl)-furan-2-yl]-benzo[e]indol-3-yl} benzoic acid | 33 |

TABLE 9-continued

Compounds from Table 8 and Characterization Data

| product structure | 1H NMR, d | MS | name | Ab42 IC50 (uM) |
|---|---|---|---|---|
| | MeOH-d4; 8.32(d, 1H), 7.92(d, 1H), 7.7 (d, 1H), 7.62-7.44 (m, 6H), 7.38(d, 1H), 7.3(dd, 1H), 6.55 (d, 1H). | pos. mode 422 (M + H). | 5-[2-(3,4-dichlorophenyl)-benzo[e]indol-3-yl]-furan-2-carboxylic acid | 7 |
| | CDCl3: 7.3(m, 2H); 6.9(dd, 2H), 6.2(s, 1H), 6.0(d, 1H); 2.5-2.6(m, 4H); 2.3(m, 1H); 2.0(m, 1H); 1.4 (m, 1H); 1.0(s, 9H). | pos. mode 432 (M + H); TOF EM 432.1122 (M + H). | 5-[5-tButyl-2-(3,4-dichlorophenyl)-4,5,6,7-tetrahydroindol-1-yl] furan-2-carboxylic acid | 11.7 |
| | CDCl3: 7.1-7.3(m, 6H); 6.1(s, 1H); 6.0 (d, 1H); 2.5-2.7(m, 3H); 2.1(m, 1H); 1.9 (m, 2H); 1.4(m, 1H); 1.0(d, 3H). | pos. mode 322 (M + H); TOF EM 322.1476 (M + H). | 5-(5-methyl-2-phenyl-4,5,6,7-tetrahydroindol-1-yl) furan-2-carboxylic acid | >100 |
| | CDCl3; 8.86-8.92 (m, 1H), 8.15-8.22 (m, 1H), 7.75-8.10 (m, 3H), 7.55-7.68 (m, 2H), 7.35(t, 1H), 7.02-7.23(m, 5H), 6.28(s, 1H), 3.60-3.73(m, 1H), 2.65-3.03(m, 4H), 2.20-2.30(m, 1H), 2.05-2.20(m, 1H). | pos. mode 395 (M + H). | 3-(2-phenyl-6-pyridin-2-yl-4,5,6,7-tetrahydroindol-1-yl) benzoic acid | 70.8 |

TABLE 9-continued

Compounds from Table 8 and Characterization Data

| product structure | 1H NMR, d | MS | name | Ab42 IC50 (uM) |
|---|---|---|---|---|
| | CDCl3; 7.26-7.34 (m, 3H), 6.90(dd, 1H), 6.43(s, 1H), 6.17(d, 1H), 3.40-3.50(m, 1H), 2.45-2.65(m, 2H), 1.95-2.15(m, 2H), 1.70-1.95(m, 2H). | pos. mode 444 (M + H). | 5-[2-(3,4-dichlorophenyl)-4-trifluoromethyl-4,5,6,7-tetrahydroindol-1-yl]-furan-2-carboxylic acid | 7.36 |
| | DMSO-d6; 13.4(br s, 1H), 7.54(d, 1H), 7.30-7.38(m, 2H), 7.02(dd, 1H), 6.73 (d, 1H), 6.56(s, 1H), 2.81(br s, 1H), 2.45-2.70(m, 4H), 2.05-2.15(m, 1H), 1.63(qd, 1H) | pos. mode 444 (M + H). | 5-[2-(3,4-dichlorophenyl)-6-trifluoromethyl-4,5,6,7-tetrahydroindol-1-yl]-furan-2-carboxylic acid | 8.9 |
| | CDCl3: 8.0(s, 1H); 7.2-7.3(m, 5H); 6.2 (s, 1H); 2.7(m, 2H); 2.6(m, 1H); 2.2(m, 1H); 1.9(m, 2H); 1.5 (m, 1H); 1.0(d, 3H). | TOF pos. mode 339(M + H); EM 339.1175 (M + H). | 2-(5-methyl-2-phenyl-4,5,6,7-tetrahydroindol-1-yl) thiazole-4-carboxylic acid | >100 |
| | CDCl3: 7.5(d, 2H); 7.1-7.3(m, 3H); 6.3 (s, 1H); 6.0(d, 1H); 2.5-2.6(m, 3H); 2.3 (m, 1H); 2.0(m, 1H); 1.4(m, 1H); 1.0 (s, 9H). | TOF pos. mode 432(M + H); EM 432.1783 (M + H). | 5-[5-tButyl-2-(4-trifluoromethylphenyl)-4,5,6,7-tetrahydroindol-1-yl] furan-2-carboxylic acid | 14 |

TABLE 9-continued

Compounds from Table 8 and Characterization Data

| product structure | 1H NMR, d | MS | name | Ab42 IC50 (uM) |
|---|---|---|---|---|
| | CDCl3: 8.1(br. s., 1H); 8.0(m, 0.4H); 7.7(tt, 0.2H); 7.5(tt, 0.3H); 7.1-7.2(m, 5H); 6.2(s, 1H); 2.5-2.6(m, 3H); 2.3 (m, 1H); 2.0(m, 1H); 1.4-1.5(m, 2H); 1.0 (d, 9H). | pos. mode 321 (M + H); neg. mode 319 (M − H). | 5-tButyl-2-phenyl-1-(4H-[1,2,4]triazol-3-yl)-4,5,6,7-tetrahydro-1H-indole | 63 |
| | DMSO-d6; 7.27(s, 1H), 6.87(d, 1H), 6.68(m, 2H), 6.25(s, 1H), 3.7(s, 3H), 3.6 (s, 3H), 2.79-2.55 (m, 5H), 2.36(s, 1H), 2.12(d, 1H). | neg mode 452 (M dot). | 2-[2-(2,4-dimethoxyphenyl)-5-trifluoromethyl-4,5,6,7-tetrahydroindol-1-yl]-thiazole-4-carboxylic acid | >100 |
| | CDCl3; 7.18(d, 1H), 6.54(d, 1H); 6.48 (dd, 1H), 6.35(d, 1H), 6.1(s, 1H), 3.82 (s, 3H), 3.5(s, 3H), 2.96-2.8(m, 4H), 2.68-2.60(m, 1H), 2.24-2.18(m, 1H), 1.8-1.68(m, 1H). | pos. mode 423 (M + H − OMe). | 2-[2-(3,4-dimethoxyphenyl)-5-trifluoromethyl-4,5,6,7-tetrahydroindol-1-yl]-thiazole-4-carboxylic acid | >100 |
| | DMSO-d6; 7.27(s, 1H); 6.97(d, 2H); 6.84(d, 2H); 6.51(s, 1H); 6.22(s, 1H); 3.7 (t, 4H); 3.1(t, 4H); 2.73(m, 2H); 2.5(m, 3H); 2.12(m, 1H); 1.64(m, 1H). | pos. mode 461 (M + H); neg. mode 459 (M − H). | 5-[2-(4-morpholin-4-yl-phenyl)-5-trifluoromethyl-4,5,6,7-tetrahydroindol-1-yl]-furan-2-carboxylic acid | 68 |

TABLE 9-continued

Compounds from Table 8 and Characterization Data

| product structure | 1H NMR, d | MS | name | Ab42 IC50 (uM) |
|---|---|---|---|---|
| | CDCl3; 7.10-7.22 (m, 3H), 7.02(s, 1H), 6.60-7.01(m, 1H), 6.24(s, 1H), 3.83(s, 2H), 2.60-2.70(m, 2H), 2.54(dd, 1H), 2.20-2.38(m, 1H), 1.96-2.08(m, 1H), 1.55-1.65(m, 1H), 1.32-1.46(m, 3H), 0.89(s, 3H), 0.88(s, 3H), 0.84(t, 3H). | pos. mode 443 (M + 1). | {2-[2-(3-chlorophenyl)-5-(1,1-dimethylpropyl)-4,5,6,7-tetrahydroindol-1-yl]-thiazol-4-yl} acetic acid | na |
| | CDCl3; 7.1-7.3(m, 6H, ArH); 6.2(s, 1H); 6.0(d, 1H); 3.9(s, 3H); 2.6(m, 3H); 2.3 (m, 1H); 2.o(m, 1H); 1.3-1.5(m, 2H); 1.0 (s, 9H). | pos. mode 378 (M + H). | 5-(5-tertButyl-2-phenyl-4,5,6,7-tetrahydroindol-1-yl) furan-2-carboxylic acid methyl ester | >100 |
| | DMSO - d6; 6.6-8.4 (14H, ArH), | pos. mode 370 (M + 1) | 3-(2-thiophen-3-yl-benzo[e]indol-3-yl) benzoic acid | 13.2 |
| | DMSO - d6; 6.6-8.4 (13H, ArH), 2.9 (2H, CH2), 2.6 (2H, CH2) | pos. mode 396 (M + 1); 394(M − 1). | 3-[3-(2H-tetrazol-5-yl)-phenyl]-2-thiophen-3-yl-3H benzo[e]indole | 31 |

TABLE 9-continued

Compounds from Table 8 and Characterization Data

| product structure | 1H NMR, d | MS | name | Ab42 IC50 (uM) |
|---|---|---|---|---|
| | CDCl3; 7.1-7.3(m, 6H, ArH); 6.2(s, 1H); 6.0(d, 1H), 2.6(m, 2H); 2.4-2.5(m, 2H); 2.0(m, 1H); 1.5(m, 2H); 1.0(s, 9H). | pos. mode 364 (M + H); neg. mode 362 (M − H) | 5-(5-tertButyl-2-phenyl-4,5,6,7-tetrahydroindol-1-yl) furan-2-carboxylic acid | 3.7 |
| | DMSO - d6; 7.1-8.5 (14H, ArH/NH); 5.8 (1H); 2.9(2H, CH2); 2.6(2H, CH2). | pos. mode 430 (M + 1); neg. mode 429 (M − 1). | 2-benzofuran-2-yl-3-[3-(2H-tetrazol-5-yl)-phenyl]-4,5-dihydro-3H-benzo[e]indole | 9.3 |
| | DMSO - d6; 7.0-8.2 (15H, ArH/NH); 6.3 (1H); 2.9(2H, CH2); 2.6(2H, CH2). | pos. mode 457 (M + 1); neg mode 455 (M − 1). | 2-(3-phenylisoxazol-5-yl)-3-[3-(2H-tetrazol-5-yl)-phenyl]-4,5-dihydro-3H-benzo[e]indole | 9.6 |
| | DMSO d6; 7.0-8.1 (14H, ArH); 6.2(1H); 2.9(2H, CH2); 2.6 (2H, CH2). | pos. mode 433 (M + 1); heg. mode 431 (M − 1). | 3-(2-phenylisoxazol-5-yl)-4,5-dihydrobenzo[e]indol-3-yl] benzoic acid | 2.2 |

TABLE 9-continued

Compounds from Table 8 and Characterization Data

| product structure | 1H NMR, d | MS | name | Ab42 IC50 (uM) |
|---|---|---|---|---|
| | DMSO - d6; 7.3-8.8 (15H, ArH). | pos. mode 365 (M + 1). | 3-(2-pyridin-3-yl-benzo[e]indol-3-yl) benzoic acid | >100 |
| | DMSO - d6; 7.0-8.6 (13H, ArH), 2.9(2H, CH2), 2.6(2H, CH2). | pos. mode 367 (M + 1). | 3-(2-pyridin-3-yl-4,5-dihydrobenzo[e]indol-3-yl) benzoic acid | >100 |
| | DMSO - d6; 7.2-8.5 (15H, ArH). | pos. mode 365 (M + 1). | 3-(2-pyridin-2-yl-benzo[e]indol-3-yl) benzoic acid | 79 |
| | DMSO - d6; 6.9-8.5 (13H, ArH), 2.9(2H, CH2), 2.6(2H, CH2). | pos. mode 367 (M + 1); 365 (M + 1). | 3-(2-pyridin-2-yl-4,5-dihydrobenzo[e]indol-3-yl) benzoic acid | 70 |

TABLE 9-continued

Compounds from Table 8 and Characterization Data

| product structure | 1H NMR, d | MS | name | Ab42 IC50 (uM) |
|---|---|---|---|---|
| | DMSO - d6; 7.1-8.2 (16H, ArH). | pos. mode 404 (M + 1). | 3-(2-benzofuran-2-yl-benzo[e]indol-3-yl) benzoic acid | 1.17 |
| | DMSO - d6; 7.0-8.1 (14H, ArH), 2.9(2H, CH2), 2.6(2H, CH2). | pos. mode 406 (M + 1). | 3-(2-benzofuran-2-yl-4,5-dihydrobenzo[e]indol-3-yl) benzoic acid | 0.56 |
| | DMSO - d6; 7.0-8.6 (14H, ArH), 2.9(2H, CH2), 2.6(2H, CH2). | pos. mode 391 (M + 1). | 2-pyridin-2-yl-3-[3-(2H-tetrazol-5-yl)-phenyl]-4,5-dihydro-3H-benzo[e]indole | 43 |
| | DMSO - d6; 7.4-8.6 (16H, ArH). | pos. mode 389 (M + 1). | 2-pyridin-3-yl-3-[3-(2H-tetrazol-5-yl)-phenyl]-3H-benzo[e]indole | 46 |

TABLE 9-continued

Compounds from Table 8 and Characterization Data

| product structure | 1H NMR, d | MS | name | Ab42 IC50 (uM) |
|---|---|---|---|---|
| | DMSO - d6; 7.2-8.4 (16H, ArH). | pos. mode 389 (M + 1). | 2-pyridin-2-yl-3-[3-(2H-tetrazol-5-yl)-phenyl]-3H-benzo[e]indole | 32 |
| | DMSO - d6; 13.27 (s(br), CO2H), 7.98-7.90(m, 4H, Ar-H), 7.58-7.50(m, 2H, Ar-H), 7.47(m, 2H, Ar-H), 7.44-7.31(m, 6H, Ar-H), 7.23(s, 1H, pyr-H). | pos. mode 341 (M + H); neg. mode 339 (M − H) | 3-(3,5-diphenyl-pyrazol-1-yl)-benzoic acid | >100 |
| | DMSO-d6; 7.0-8.4 (13H, ArH); 6.9(1H), 2.9(2H, CH2), 2.52 (2H, CH2). | neg. mode 388 (M − H) | 2-phenyl-3-[3-(2H-tetrazol-5-yl)-phenyl]-4,5-dihydro-3H-benzo[e]indole | 24 |
| | CDCl3; 8.0(d, 1H); 7.9(s, 1H); 7.5(t, 1H); 7.0-7.3(7H, ArH); 6.3(1H), 2.6 (2H, CH2), 2.5(2H, CH2); 1.5-1.9(4H). | pos. mode 342 (M + H); neg. mode 340 (M − H) | 2-phenyl-1-[3-(1H-tetrazol-5-yl)-phenyl]-4,5,6,7-tetrahydro-1H-indole | 100 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A compound of Formula II, a pharmaceutically acceptable salt thereof, or a pharmaceutical composition having such a compound,

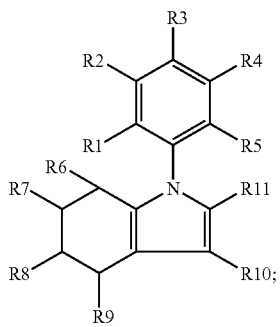

FORMULA II

Wherein one of R2 and R4 is —COOH, while the other is —H;

R1, R3, and R5, independent of one another, are chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$;

R6 is hydro;

one of R7, R8 or R9 is haloalkyl, while the other two are, independent of one another, chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, —C(=O)—N-morpholino, -cyclohexyl, -morpholino, -pyrrolidinyl, -piperazinyl, —(N-methyl)-piperazinyl, —OCH$_2$-phenyl, -pyridinyl, methylenedioxy, ethylenedioxy, —C(=O)OCH$_2$CH$_3$ substituted furanyl, para-(C(=O)OCH$_2$CH$_3$)-phenyl, and —O—Si(CH$_3$)$_2$(C(CH$_3$)$_3$); or optionally two adjacent of R6-R9 can be taken together to form a 4-7 member optionally substituted aryl or cycloalkyl ring;

R10 is hydro; and

R11 is an optionally substituted phenyl or heterocyclic group.

2. The compound of claim 1 wherein R1, R3, and R5, are independently chosen from hydro, hydroxyl, halo, alkyl, alkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, and —NO$_2$; and R11 is an optionally substituted phenyl group.

3. The compound of claim 1 wherein one of R7, R8 or R9 is trifluoromethyl.

4. The compound of claim 3, wherein R7 is trifluoromethyl.

5. The compound of claim 1, wherein R8 is trifluoromethyl.

6. The compound of claim 3, wherein R9 is trifluoromethyl.

7. The compound of claim 3, wherein R11 is a halo-substituted phenyl group.

8. The compound of claim 7, wherein R11 is a 3,4-dichloro-substituted phenyl group.

9. An orally available unit dosage form having a compound according to claim 1.

10. The unit dosage form of claim 9 having from 1 mg to 2000 mg of said compound.

11. The unit dosage form of claim 9 having from 1 mg to 1000 mg of said compound.

12. The unit dosage form of claim 9 having from 1 mg to 800 mg of said compound.

* * * * *